US009156840B2

United States Patent
Luehr et al.

(10) Patent No.: US 9,156,840 B2
(45) Date of Patent: *Oct. 13, 2015

(54) D₂ ANTAGONISTS, METHODS OF SYNTHESIS AND METHODS OF USE

(71) Applicant: ALTOS THERAPEUTICS, LLC, Los Altos, CA (US)

(72) Inventors: Gary W. Luehr, Hayward, CA (US); Arathi Sundaram, Fremont, CA (US); Priyadarshini Jaishankar, Newark, CA (US); Philip W Payne, Sunnyvale, CA (US); Pascal Druzgala, Santa Rosa, CA (US)

(73) Assignee: ALTOS THERAPEUTICS, LLC, Los Altos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/184,615

(22) Filed: Feb. 19, 2014

(65) Prior Publication Data

US 2014/0350005 A1 Nov. 27, 2014

Related U.S. Application Data

(63) Continuation of application No. 13/163,592, filed on Jun. 17, 2011, now Pat. No. 8,691,836.

(60) Provisional application No. 61/356,096, filed on Jun. 18, 2010.

(51) Int. Cl.
| | |
|---|---|
| C07D 471/10 | (2006.01) |
| A61K 31/5377 | (2006.01) |
| A61K 31/438 | (2006.01) |
| C07D 519/00 | (2006.01) |
| A61K 31/435 | (2006.01) |
| A61K 31/439 | (2006.01) |
| A61K 31/4545 | (2006.01) |
| A61K 31/496 | (2006.01) |
| A61K 31/538 | (2006.01) |
| A61K 45/06 | (2006.01) |

(52) U.S. Cl.
CPC ............ *C07D 471/10* (2013.01); *A61K 31/435* (2013.01); *A61K 31/438* (2013.01); *A61K 31/439* (2013.01); *A61K 31/4545* (2013.01); *A61K 31/496* (2013.01); *A61K 31/538* (2013.01); *A61K 31/5377* (2013.01); *A61K 45/06* (2013.01); *C07D 519/00* (2013.01)

(58) Field of Classification Search
CPC ... C07D 519/00; C07D 471/10; A61K 31/438
USPC .......................................... 514/278; 546/16
See application file for complete search history.

(56) References Cited

U.S. PATENT DOCUMENTS

| | | | |
|---|---|---|---|
| 3,155,670 A | 11/1964 | Janssen et al. | |
| 3,238,216 A | 3/1966 | Janssen et al. | |
| 5,182,397 A | 1/1993 | Condon et al. | |
| 6,277,991 B1 * | 8/2001 | Hohlweg et al. ................ | 546/20 |

FOREIGN PATENT DOCUMENTS

| | | |
|---|---|---|
| CN | 101652351 | 2/2010 |
| CN | 101815519 | 8/2010 |
| WO | WO-99/59997 A1 | 11/1999 |
| WO | WO-2011/160084 | 12/2011 |

OTHER PUBLICATIONS

Robert Mach et al , 1992, Effect of n-alkylation on the affinities of analoguous of Spirerone for Dopamine De and Seratonn 5-HT2 Receptors.*
Bakthavachalan et al 1991, Fluoroscent probes for Dopamine Receptors.*
Tein Lu Tai et al, 2003, Increased dopamine D2 receptor binding and enhanced apomorphine-induced locomotor activity in mu-opioid receptor knockout mice.*
Cheng et al., "Relationship between the inhibition constant (K1) and the concentration of inhibitor which causes 50 per cent inhibition (I50) of an enzymatic reaction" Biochem. Pharmacol., 1973, 22(23):3099-3108.
Darmani et al., "The role of D2 and D3 dopamine receptors in the mediation of emesis in Cryptotis parva (the least shrew)", J Neural Transm., 1999, 106(11-12):1045-1061.
Depoortère et al., "Apomorphine-induced emesis in dogs: differential sensitivity to established and 1 novel dopamine D2/5-HT1A antipsychotic compounds", Eur J Pharmacol., 597 (2008) 34-38.
Forest et al., "A novel class of cardiotonic agents: synthesis and biological evaluation of 5-substituted 3,6-dihydrothiadiazin-2-ones with cyclic AMP phosphodiesterase inhibiting and myofibrillar calcium sensitizing properties", J Med Chem., 35 (1992) 163-172.

(Continued)

Primary Examiner — Rita Desai
(74) Attorney, Agent, or Firm — Foley & Lardner LLP

(57) ABSTRACT

Provided are $D_2$ or $D_3$ antagonist compounds and pharmaceutical compositions of formula I (I)

and pharmaceutically acceptable salts thereof, or isomers thereof, wherein $R_1$, $R_2$ and $R_3$ are as defined herein. The invention further comprises methods for making the compounds of the invention and methods for the treatment of conditions mediated by the dopamine $D_2$ or $D_3$ receptor from the compounds of the invention.

13 Claims, No Drawings

(56) References Cited

OTHER PUBLICATIONS

International Preliminary Report on Patentability and Written Opinion dated Jan. 3, 2013 for PCT Application Serial No. PCT/US2011/040983.

International Search Report and Written Opinion for PCT/US2011/040983, dated Sep. 2, 2011.

Jin et al., "Practical synthesis of p-aminophenethylspiperone (NAPS), a high-affinity, selective D2-dopamine receptor antagonist", Synthetic Communications, 2008, 38(5):816-823.

Kirsch et al., "Variability in the measurement of hERG potassium channel inhibition: effects of temperature and stimulus pattern", J Pharmacol Toxicol Methods., 50 (2004) 93-101.

Levant, "The D3 dopamine receptor: neurobiology and potential clinical relevance", Pharmacol Rev., 49(3) (1997) 231-252.

MacKenzie et al., "Characterization of the human dopamine D3 receptor expressed in transfected cell lines", Eur J Pharmacol., 1994, 266(1):79-85.

Metwally et al., "Spiperone: influence of spiro ring substituents on 5-HT2A serotonin receptor binding", Journal of Medicinal Chemistry, 1998, 41(25):5084-5093.

Orjales et al., "New 2-piperazinylbenzimidazole derivatives as 5-HT3 antagonists. Synthesis and pharmacological evaluation", J Med Chem., 40 (1997) 586-593.

Quinn et al., "Studies in postoperative sequelae. Nausea and vomiting—still a problem", Anaesthesia., 1994, 49(1):62-65.

Robertston et al., "Dihydropyridazinone cardiotonics: synthesis and inotropic activity of 5'-(1,4,5,6- tetrahydro-6-oxo-3-pyridazinyl)-spiro[cycloalkane-1,3'-[3H]indol]-2'(1'H)-ones", J. Med. Chem., 1987, 30(5):824-829.

Yan et al., "Characteristics and distribution of M cells in arterially perfused canine left ventricular wedge preparations", Circulation., 1998, 98(18):1921-1927.

Yu et al., "A novel liquid chromatography/tandem mass spectrometry based depletion method for measuring red blood cell partitioning of pharmaceutical compounds in drug discovery", Rapid Commun Mass Spectrom., 2005, 19(2):250-254.

Zhang et al., "Dynorphin A as a potential endogenous ligand for four members of the opioid receptor gene family", J Pharmacol Exp Ther., 286 (1998) 136-141.

* cited by examiner

SEQUENCE LISTING

<160> NUMBER OF SEQ ID NOS: 2

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
caccatggat ccactgaatc tgtcctg     27

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gcagcagagt cagcagtgga     20

D₂ ANTAGONISTS, METHODS OF SYNTHESIS AND METHODS OF USE

CROSS REFERENCE TO RELATED APPLICATIONS

This application is a continuation of application Ser. No. 13/163,592, filed Jun. 17, 2011, which claims priority to provisional application No. 61/356,096, filed Jun. 18, 2010, both of which are incorporated in their entirety by reference herein.

FIELD OF THE INVENTION

This invention relates to novel dopamine $D_2$ and $D_3$ antagonists that are useful as anti-nausea medicaments. The compounds are 1,3,8-triazinspiro[4,5]decane-4-ones that are substituted at the N1, N3, or the N8 positions with various substituents discussed in detail in this application.

SUMMARY

One aspect of the subject invention is a compound of formula I

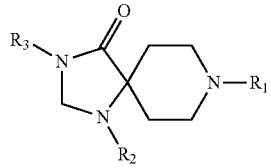

(I)

or pharmaceutically acceptable salts thereof, or isomers thereof, wherein
$R_1$ is chosen from the group consisting of
(2-oxo-2,3-dihydro-1H-benzo[d]imidazol-1-yl)($C_2$-$C_4$alkyl) optionally substituted at the 3 position with cyclopropyl or at the 6 position with chlorine,
(2-oxobenzo[d]oxazol-3(2H)-yl)($C_2$-$C_4$alkyl),
(2-oxobenzo[d]thiazol-3(2H)-yl)($C_2$-$C_4$alkyl),
(2-oxoindolin-1-yl)($C_2$-$C_4$alkyl) optionally substituted at the 3-position with one or two components chosen from methyl or fluoro,
(3-spirocyclopropane-(2-oxoindolin-1-yl))($C_2$-$C_4$alkyl),
(2-oxoindolin-3-yl))($C_2$-$C_4$alkyl),
phenyl($C_1$-$C_6$alkyl),
1-hydroxy-1-phenylmethyl($C_2$-$C_6$ alkyl),
1-acetoxyoxy-1-phenylmethyl($C_2$-$C_6$ alkyl),
bis(4-fluorophenyl)methyl-($C_1$-$C_6$alkyl),
(1H-benzo[d][1,2,3]triazol-1-yl)($C_2$-$C_4$alkyl),
1-phenyl-1-oxo-($C_2$-$C_6$alkyl) optionally substituted at the 4 position of the phenyl with halo,
2,3-dihydrobenzo[b][1,4]dioxine-2-($C_2$-$C_4$alkyl),
1-(thiophen-2-yl)-1-oxo-($C_1$-$C_6$alkyl),
3-oxo-2H-benzo[b][1,4]oxazin-4-yl-($C_2$-$C_4$alkyl),
(2-(cycloalkyl)-1H-benzo[d]imidazol-1-yl)($C_2$-$C_4$ alkyl),
((3-(($C_1$-$C_6$ alkyl)carbonyloxy(methyl))-2-oxo-2,3-dihydro-1H-benzo[d]imidazol-1-yl))($C_2$-$C_4$ alkyl),
((3-(methoxycarbonylethyl)-2-oxo-2,3-dihydro-1H-benzo[d]imidazol-1-yl))($C_2$-$C_4$ alkyl),
((2-(t-butoxycarbonyl)-2,3-dihydro-1H-benzo[d]imidazol-1-yl))($C_2$-$C_4$ alkyl),
1H-indazol-3-yl($C_2$-$C_4$ alkyl),
(1-(indolin-1-yl)-1-oxo)($C_2$-$C_4$alkyl),
((3-($C_1$-$C_6$alkyl)oxycarbonyl($C_1$-$C_6$alkyl))-1H-indol-1-yl) ($C_2$-$C_4$ alkyl), or
(2-($C_1$-$C_6$alkyl)oxycarbonyl-1H-indol-1-yl)($C_2$-$C_4$alkyl);

$R_2$ is phenyl optionally para-substituted with chloro, fluoro or methoxy, linear or branched $C_2$-$C_6$ alkyl, cycloalkyl of three to seven carbon atoms optionally substituted with one to six halogens; and
$R_3$ is

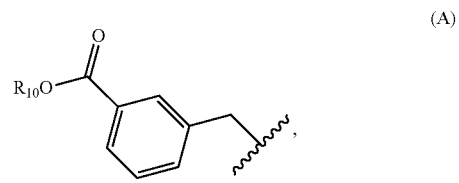

(A)

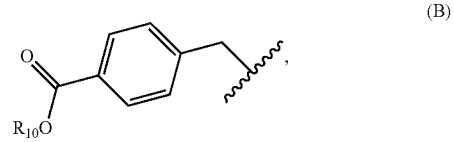

(B)

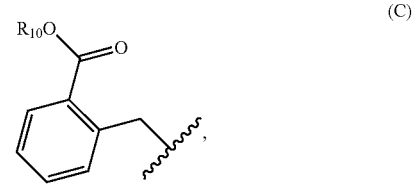

(C)

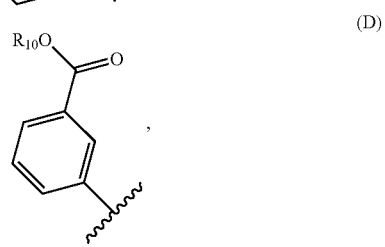

(D)

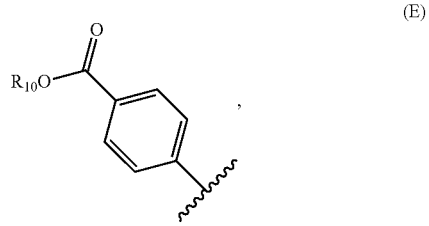

(E)

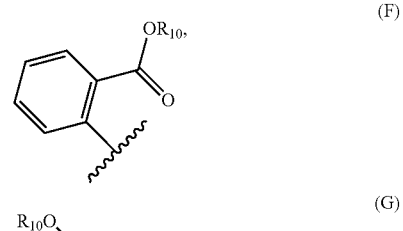

(F)

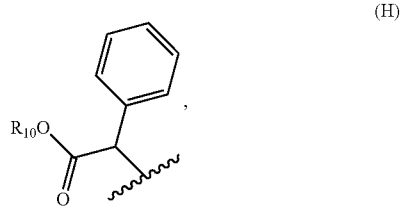

(G)

wherein n is 3-5,

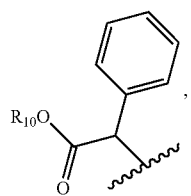

(H)

-continued

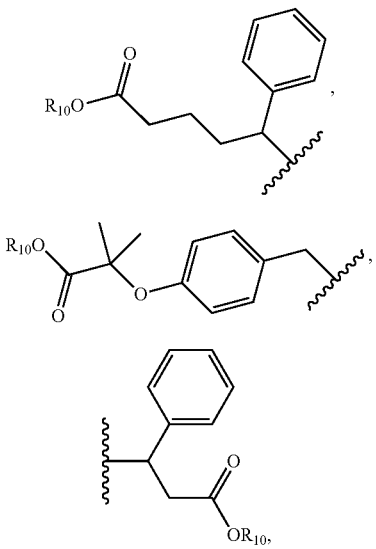

and
$R_{10}$ is H or alkyl of one to six carbons.

In one aspect, $R_1$ is not $C_1$-$C_6$ alkyl.

Another aspect of the invention provides a process for treating a disease that is respondent to dopamine $D_2$ or $D_3$ receptor antagonist therapy by administering a compound of this invention to a patient in need thereof.

Another aspect of this invention comprises a pharmaceutical composition containing a compound of this invention in combination with a pharmaceutically acceptable excipient.

In another aspect, the invention provides methods of preparing the compounds of interest, as well as intermediates useful in preparing the compounds of interest.

DETAILED DESCRIPTION

In one aspect, the invention provides compounds of formula I

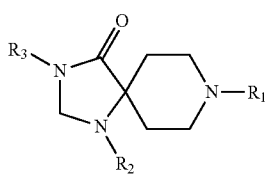
(I)

or pharmaceutically acceptable salts thereof, or isomers thereof, wherein
$R_1$ is chosen from the group consisting of
(2-oxo-2,3-dihydro-1H-benzo[d]imidazol-1-yl)($C_2$-$C_4$alkyl) optionally substituted at the 3 position with cyclopropyl or at the 6 position with chlorine,
(2-oxobenzo[d]oxazol-3(2H)-yl)($C_2$-$C_4$alkyl),
(2-oxobenzo[d]thiazol-3(2H)-yl)($C_2$-$C_4$alkyl),
(2-oxoindolin-1-yl)($C_2$-$C_4$alkyl) optionally substituted at the 3-position with one or two components chosen from methyl or fluoro,
(3-spirocyclopropane-(2-oxoindolin-1-yl))($C_2$-$C_4$alkyl),
(2-oxoindolin-3-yl))($C_2$-$C_4$alkyl),
phenyl($C_1$-$C_6$alkyl),
1-hydroxy-1-phenylmethyl($C_2$-$C_6$ alkyl),
1-acetoxyoxy-1-phenylmethyl($C_2$-$C_6$ alkyl),
bis(4-fluorophenyl)methyl-($C_1$-$C_6$alkyl),
(1H-benzo[d][1,2,3]triazol-1-yl)($C_2$-$C_4$alkyl),
1-phenyl-1-oxo-($C_2$-$C_6$alkyl) optionally substituted at the 4 position of the phenyl with halo,
2,3-dihydrobenzo[b][1,4]dioxine-2-($C_2$-$C_4$alkyl),
1-(thiophen-2-yl)-1-oxo-($C_1$-$C_6$alkyl),
3-oxo-2H-benzo[b][1,4]oxazin-4-yl))($C_2$-$C_4$alkyl),
(2-(cycloalkyl)-1H-benzo[d]imidazol-1-yl)($C_2$-$C_4$alkyl),
((3-(($C_1$-$C_6$alkyl)carbonyloxy(methyl))-2-oxo-2,3-dihydro-1H-benzo[d]imidazol-1-yl))($C_2$-$C_4$ alkyl),
((3-(methoxycarbonylethyl)-2-oxo-2,3-dihydro-1H-benzo[d]imidazol-1-yl))($C_2$-$C_4$ alkyl),
((2-(t-butoxycarbonyl)-2,3-dihydro-1H-benzo[d]imidazol-1-yl))($C_2$-$C_4$ alkyl),
1H-indazol-3-yl($C_2$-$C_4$ alkyl),
(1-(indolin-1-yl)-1-oxo)($C_2$-$C_4$alkyl),
((3-($C_1$-$C_6$alkyl)oxycarbonyl($C_1$-$C_6$alkyl))-1H-indol-1-yl)($C_2$-$C_4$alkyl), or
(2-($C_1$-$C_6$alkyl)oxycarbonyl-1H-indol-1-yl)($C_2$-$C_4$alkyl);
$R_2$ is phenyl optionally para-substituted with chloro, fluoro or methoxy, linear or branched $C_2$-$C_6$ alkyl, cycloalkyl of three to seven carbon atoms optionally substituted with one to six halogens; and
$R_3$ is

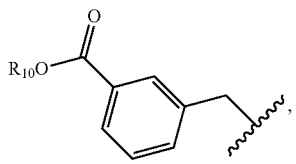
(A)

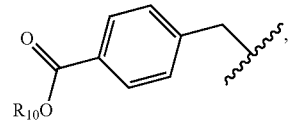
(B)

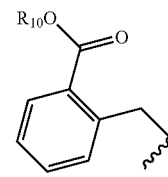
(C)

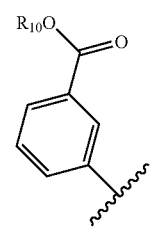
(D)

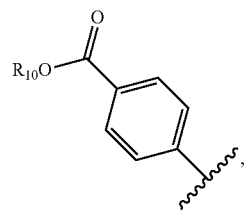
(E)

-continued

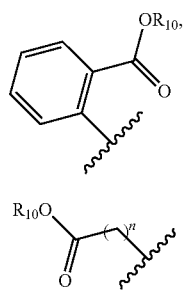
(F)

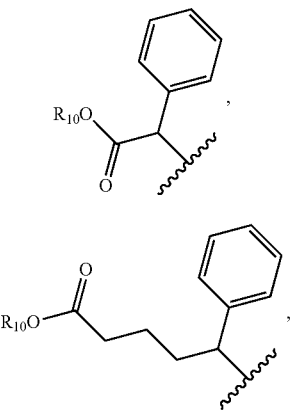
(G)

wherein n is 3-5,

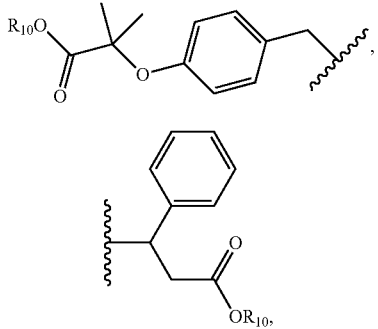
(H)

(I)

(J)

(L)

and
R$_{10}$ is H or alkyl of one to six carbons.

One aspect of the invention is a subgroup of these compounds wherein R$_1$ is (2-oxoindolin-1-yl)(C$_2$-C$_4$alkyl) optionally substituted at the 3-position with one or two components chosen from methyl or fluoro, (3-spirocyclopropane-(2-oxoindolin-1-yl))(C$_2$-C$_4$alkyl), (2-oxoindolin-3-yl))(C$_2$-C$_4$alkyl), or 1-phenyl-1-oxo-(C$_2$-C$_6$alkyl) optionally substituted at the 4 position of the phenyl with halo.

Another aspect of the invention includes those compounds wherein R$_3$ is represented by formula A, C, D, or F and R$_{10}$ is H.

Another aspect of the invention includes the compounds wherein R$_3$ is represented by formula A or D.

Another aspect of the invention includes the compounds wherein R$_2$ is phenyl or cyclohexyl.

Another aspect of the invention includes the compounds wherein R$_2$ is cyclohexyl.

Another aspect of the invention includes the compounds wherein R$_2$ is phenyl.

Another aspect of the invention includes the compounds wherein R$_1$ is not C$_1$-C$_6$ alkyl.

Another aspect of the invention includes the compounds wherein R$_1$ is (2-oxoindolin-1-yl) propyl optionally substituted at the 3-position with one or two components chosen from methyl or fluoro, (3-spirocyclopropane-(2-oxoindolin-1-yl))propyl, (2-oxoindolin-3-yl))propyl, or 1-phenyl-1-oxo-propyl optionally substituted at the 4 position of the phenyl with halo.

Another aspect of the invention includes the compounds wherein
R$_1$ is (2-oxoindolin-1-yl)propyl optionally substituted at the 3-position with one or two components chosen from methyl or fluoro, (3-spirocyclopropane-(2-oxoindolin-1-yl))propyl, (2-oxoindolin-3-yl))propyl, or 1-phenyl-1-oxo-propyl optionally substituted at the 4 position of the phenyl with halo;
R$_2$ is phenyl or cyclohexyl; and
R$_3$ is represented by formula A, C, D, or F and R$_{10}$ is H.

Another aspect of the invention includes the compounds wherein R$_1$ is (2-oxoindolin-1-yl) propyl and R$_2$ is cyclohexyl.

Another aspect of the invention includes the compounds wherein R$_3$ is represented by formula A.

Specific compounds falling within the scope of this invention include, without limitation:

| | |
|---|---|
| Compound 6 (Example 2) | Methyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 7 (Example 3) | Methyl 5-(4-oxo-8-(3-(2-oxo-2,3-dihydro-1H-benzo[d]imidazol-1-yl)propyl)-1-phenyl-1,3,8-triazaspiro[4.5]decan-3-yl)pentanoate |
| Compound 8 (Example 4) | Ethyl 4-(4-oxo-8-(3-(2-oxo-2,3-dihydro-1H-benzo[d]imidazol-1-yl)propyl)-1-phenyl-1,3,8-triazaspiro[4.5]decan-3-yl)butanoate |
| Compound 11 (Example 5) | 3-((4-Oxo-8-(3-(2-oxo-2,3-dihydro-1H-benzo[d]imidazol-1-yl)propyl)-1-phenyl-1,3,8-triazaspiro[4.5]decan-3-yl)methyl)benzoic acid |
| Compound 13 (Example 6) | Methyl 5-(4-oxo-8-(3-(2-oxo-2,3-dihydro-1H-benzo[d]imidazol-1-yl)propyl)-1-phenyl-1,3,8-triazaspiro[4.5]decan-3-yl)-5-phenylpentanoate |
| Compound 14 (Example 7) | Methyl 2-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 15 (Example 8) | Methyl 4-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 16 (Example 9) | 2-(Dimethylamino)ethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 17 (Example 10) | 4-((4-Oxo-8-(3-(2-oxo-2,3-dihydro-1H-benzo[d]imidazol-1-yl)propyl)-1-phenyl-1,3,8-triazaspiro[4.5]decan-3-yl)methyl)benzoic acid |
| Compound 18 (Example 11) | (S)-sec-Butyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 19 (Example 12) | 2-((4-Oxo-8-(3-(2-oxo-2,3-dihydro-1H-benzo[d]imidazol-1-yl)propyl)-1-phenyl-1,3,8-triazaspiro[4.5]decan-3-yl)methyl)benzoic acid |
| Compound 20 (Example 13) | 1-Methylpiperidin-4-yl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 21 (Example 14) | Benzyl 6-(4-oxo-8-(3-(2-oxo-2,3-dihydro-1H-benzo[d]imidazol-1-yl)propyl)-1-phenyl-1,3,8-triazaspiro[4.5]decan-3-yl)hexanoate |
| Compound 22 (Example 15) | 6-(4-Oxo-8-(3-(2-oxo-2,3-dihydro-1H-benzo[d]imidazol-1-yl)propyl)-1-phenyl-1,3,8-triazaspiro[4.5]decan-3-yl)hexanoic acid |
| Compound 24 (Example 16) | 2-(Dimethylamino)-2-oxoethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |

-continued

| | |
|---|---|
| Compound 25 (Example 17) | 2-Morpholinoethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 26 (Example 18) | (R)-Quinuclidin-3-yl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 30 (Example 19) | 2-(Diethylamino)-2-oxoethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 31 (Example 20) | 2-Amino-2-oxoethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 32 (Example 21) | 2-Oxo-2-(piperidin-1-yl)ethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 33 (Example 22) | (S)-methyl 2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetate |
| Compound 34 (Example 23) | (R)-methyl 2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetate |
| Compound 35 (Example 24) | 2-(4-Methylpiperazin-1-yl)-2-oxoethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoat |
| Compound 39 (Example 25) | (R)-2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetic acid |
| Compound 40 (Example 26) | (S)-2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetic acid |
| Compound 42 (Example 27) | Methyl 3-((1-(4-fluorophenyl)-4-oxo-8-(3-(2-oxo-2,3-dihydro-1H-benzo[d]imidazol-1-yl)propyl)-1,3,8-triazaspiro[4.5]decan-3-yl)methyl)benzoate |
| Compound 43 (Example 28) | 3-((1-(4-Fluorophenyl)-4-oxo-8-(3-(2-oxo-2,3-dihydro-1H-benzo[d]imidazol-1-yl)propyl)-1,3,8-triazaspiro[4.5]decan-3-yl)methyl)benzoic acid |
| Compound 45 (Example 29) | (S)-Quinuclidin-3-yl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 46 (Example 30) | Methyl 3-((4-oxo-8-(3-(2-oxobenzo[d]oxazol-3(2H)-yl)propyl)-1-phenyl-1,3,8-triazaspiro[4.5]decan-3-yl)methyl)benzoate |
| Compound 47 (Example 31) | Methyl 3-((4-oxo-8-(3-(2-oxobenzo[d]thiazol-3(2H)-yl)propyl)-1-phenyl-1,3,8-triazaspiro[4.5]decan-3-yl)methyl)benzoate |
| Compound 48 (Example 32) | methyl 3-((8-(4-(4-fluorophenyl)-4-oxobutyl)-4-oxo-1-phenyl-1,3,8-triazaspiro[4.5]decan-3-yl)methyl)benzoate |
| Compound 49 (Example 33) | 3-((8-(4-(4-fluorophenyl)-4-oxobutyl)-4-oxo-1-phenyl-1,3,8-triazpiro[4.5]decan-3-yl)methyl)benzoic acid |
| Compound 50 (Example 34) | methyl 3-((8-(3-(3-methyl-2-oxo-2,3-dihydro-1H-benzo[d]imidazol-1-yl)propyl)-4-oxo-1-phenyl-1,3,8-triazaspiro[4.5]decan-3-yl)methyl)benzoate |
| Compound 52 (Example 35) | 3-((4-Oxo-8-(3-(2-oxobenzo[d]thiazol-3(2H)-yl)propyl)-1-phenyl-1,3,8-triazaspiro[4.5]decan-3-yl)methyl)benzoic acid |
| Compound 55 (Example 36) | Methyl 3-((1-(4-methoxyphenyl)-4-oxo-8-(3-(2-oxo-2,3-dihydro-1H-benzo[d]imidazol-1-yl)propyl)-1,3,8-triazaspiro[4.5]decan-3-yl)methyl)benzoate |
| Compound 56 (Example 37) | 3-((1-(4-Methoxyphenyl)-4-oxo-8-(3-(2-oxo-2,3-dihydro-1H-benzo[d]imidazol-1-yl)propyl)-1,3,8-triazaspiro[4.5]decan-3-yl)methyl)benzoic acid |
| Compound 57 (Example 38) | methyl 3-((8-(3-(1H-indol-3-yl)propyl)-4-oxo-1-phenyl-1,3,8-triazaspiro[4.5]decan-3-yl)methyl)benzoate |
| Compound 58 (Example 39) | 3-((8-(3-(3-methyl-2-oxo-2,3-dihydro-1H-benzo[d]imidazol-1-yl)propyl)-4-oxo-1-phenyl-1,3,8-triazaspiro[4.5]decan-3-yl)methyl)benzoic acid |
| Compound 59 (Example 40) | 3-((8-(3-(1H-indol-3-yl)propyl)-4-oxo-1-phenyl-1,3,8-triazaspiro[4.5]decan-3-yl)methyl)benzoic acid |
| Compound 60 (Example 41) | tert-Butyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 61 (Example 42) | tert-butyl 3-((8-(3-(3-(heptanoyloxymethyl)-2-oxo-2,3-dihydro-1H-benzo[d]imidazol-1-yl)propyl)-4-oxo-1-phenyl-1,3,8-triazaspiro[4.5]decan-3-yl)methyl)benzoate |
| Compound 62 (Example 43) | tert-butyl 3-((1-cyclohexyl-4-oxo-8-(3-(2-oxo-2,3-dihydro-1H-benzo[d]imidazol-1-yl)propyl)-1,3,8-triazaspiro[4.5]decan-3-yl)methyl)benzoate |
| Compound 64 (Example 44) | Benzyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate |
| Compound 69 (Example 45) | 5-(4-Oxo-8-(3-(2-oxo-2,3-dihydro-1H-benzo[d]imidazol-1-yl)propyl)-1-phenyl-1,3,8-triazaspiro[4.5]decan-3-yl)-5-phenylpentanoic acid |
| Compound 70 (Example 46) | 3-(4-Oxo-8-(3-(2-oxo-2,3-dihydro-1H-benzo[d]imidazol-1-yl)propyl)-1-phenyl-1,3,8-triazaspiro[4.5]decan-3-yl)-3-phenylpropanoic acid |
| Compound 71 (Example 47) | 3-((4-Oxo-8-(3-(3-oxo-2H-benzo[b][1,4]oxazin-4(3H)-yl)propyl)-1-phenyl-1,3,8-triazaspiro[4.5]decan-3-yl)methyl)benzoic acid |
| Compound 72 (Example 48) | 3-((1-cyclohexyl-4-oxo-8-(3-(2-oxo-2,3-dihydro-1H-benzo[d]imidazol-1-yl)propyl)-1,3,8-triazaspiro[4.5]decan-3-yl)methyl)benzoic acid, formate |
| Compound 74 (Example 49) | 3-((8-(heptanoyloxymethyl)-4-oxo-1-phenyl-1,3,8-triazaspiro[4.5]decan-3-yl)methyl)benzoic acid, formate |
| Compound 76 (Example 50) | 3-((8-(((2,3-Dihydrobenzo[b][1,4]dioxin-2-yl)methyl)-4-oxo-1-phenyl-1,3,8-triazaspiro[4.5]decan-3-yl)methyl)benzoic acid |
| Compound 77 (Example 51) | 3-((8-(4,4-(4-fluorophenyl)butyl)-4-oxo-1-phenyl-1,3,8-triazaspiro[4.5]decan-3-yl)methyl)benzoic acid |
| Compound 82 (Example 52) | 3-((1-(4-Methoxyphenyl)-4-oxo-8-(3-(2-oxobenzo[d]thiazol-3(2H)-yl)propyl)-1,3,8-triazaspiro[4.5]decan-3-yl)methyl)benzoic acid |
| Compound 82 (Example 53) | 3-((8-(3-(1H-Indazol-1-yl)propyl)-4-oxo-1-phenyl-1,3,8-triazaspiro[4.5]decan-3-yl)methyl)benzoic acid |
| Compound 83 (Example 54) | methyl 3-((1-oxo-8-(3-(2-oxo-2,3-dihydro-1H-benzo[d]imidazol-1-yl)propyl)-4-phenyl-2,8-diazaspiro[4.5]decan-2-yl)methyl)benzoate |
| Compound 85 (Example 55) | 3-((8-(3-(1H-Benzo[d][1,2,3]triazol-1-yl)propyl)-4-oxo-1-phenyl-1,3,8-triazaspiro[4.5]decan-3-yl)methyl)benzoic acid |
| Compound 89 (Example 56) | 3-((4-oxo-8-(3-(2-oxoindolin-1-yl)propyl)-1-phenyl-1,3,8-triazaspiro[4.5]decan-3-yl)methyl)benzoic acid, hydrochloride |
| Compound 91 (Example 57) | 3-((8-(4-(4-methoxyphenyl)-4-oxobutyl)-4-oxo-1-phenyl-1,3,8-triazpiro[4.5]decan-3-yl)methyl)benzoic acid |
| Compound 92 (Example 58) | tert-butyl 3-((8-(3-(3,3-difluoro-2-oxoindolin-1-yl)propyl)-4-oxo-1-phenyl-1,3,8-triazaspiro[4.5]decan-3-yl)methyl)benzoate |
| Compound 93 (Example 59) | tert-butyl 3-((8-(3-(3,3-dimethyl-2-oxoindolin-1-yl)propyl)-4-oxo-1-phenyl-1,3,8-triazaspiro[4.5]decan-3-yl)methyl)benzoate |
| Compound 94 (Example 60) | 3-((8-(3-(3,3-difluoro-2-oxoindolin-1-yl)propyl)-4-oxo-1-phenyl-1,3,8-triazaspiro[4.5]decan-3-yl)methyl)benzoic acid |
| Compound 100 (Example 61) | 3-((8-(3-(6-Chloro-2-oxo-2,3-dihydro-1H-benzo[d]imidazol-1-yl)propyl)-4-oxo-1-phenyl-1,3,8-triazaspiro[4.5]decan-3-yl)methyl)benzoic acid |
| Compound 102 (Example 62) | 2-Methyl-2-(4-((4-oxo-8-(3-(2-oxo-2,3-dihydro-1H-benzo[d]imidazol-1-yl)propyl)-1-phenyl-1,3,8-triazaspiro[4.5]decan-3-yl)methyl)phenoxy)propanoic acid |
| Compound 108 (Example 63) | tert-Butyl 3-((8-(3-(1H-indazol-1-yl)propyl)-4-oxo-1-phenyl-1,3,8-triazaspiro[4.5]decan-3-yl)methyl)benzoate |
| Compound 110 (Example 64) | 3-((8-(3-(2-(tert-Butoxycarbonyl)-1H-indol-1-yl)propyl)-4-oxo-1-phenyl-1,3,8-triazaspiro[4.5]decan-3-yl)methyl)benzoic acid |
| Compound 120 (Example 65) | 3-((8-(3-Cyclopropyl-2-oxo-2,3-dihydro-1H-benzo[d]imidazol-1-yl)propyl)-4-oxo-1-phenyl-1,3,8-triazaspiro[4.5]decan-3-yl)methyl)benzoic acid |
| Compound 123 (Example 66) | 3-((8-(3,3-Dimethyl-2-oxoindolin-1-yl)propyl)-1-(4-fluorophenyl)-4-oxo-1,3,8-triazaspiro[4.5]decan-3-yl)methyl)benzoic acid |
| Compound 126 (Example 67) | 3-((8-(3-(3-methoxy-3-oxopropyl)-1H-indol-1-yl)propyl)-4-oxo-1-phenyl-1,3,8-triazaspiro[4.5]decan-3-yl)methyl)benzoic acid |
| Compound 130 (Example 68) | 3-((4-oxo-8-(3-(2'-oxospiro[cyclopropane-1,3'-indoline]-1'-yl)propyl)-1-phenyl-1,3,8-triazaspiro[4.5]decan-3-yl)methyl)benzoic acid, hydrochloride salt |
| Compound 131 (Example 69) | 3-((4-Oxo-8-(4-oxo-4-phenylbutyl)-1-phenyl-1,3,8-triazaspiro[4.5]decan-3-yl)methyl)benzoic acid |
| Compound 137 (Example 70) | 2-((8-(3-(3,3-Dimethyl-2-oxoindolin-1-yl)propyl)-4-oxo-1-phenyl-1,3,8-triazaspiro[4.5]decan-3-yl)methyl)benzoic acid |
| Compound 138 (Example 71) | 3-((1-(4-Fluorophenyl)-4-oxo-8-(3-(2'-oxospiro[cyclopropane-1,3'-indoline]-1'-yl)propyl)-1,3,8-triazaspiro[4.5]decan-3-yl)methyl)benzoic acid |

| | |
|---|---|
| Compound 142 (Example 72) | 3-((4-oxo-1-phenyl-8-(4-phenylbutyl)-1,3,8-triazaspiro[4.5]decan-3-yl)methyl)benzoic acid, formate |
| Compound 143 (Example 73) | 3-((4-oxo-8-(4-oxo-4-(thiophen-2-yl)butyl)-1-phenyl-1,3,8-triazaspiro[4.5]decan-3-yl)methyl)benzoic acid, hydrochloride |
| Compound 145 (Example 74) | 3-((1-(4-Fluorophenyl)-4-oxo-8-(3-(2-oxoindolin-1-yl)propyl)-1,3,8-triazaspiro[4.5]decan-3-yl)methyl)benzoic acid |
| Compound 146 (Example 75) | 3-((8-(3-(3-methyl-2-oxoindolin-1-yl)propyl)-4-oxo-1-phenyl-1,3,8-triazaspiro[4.5]decan-3-yl)methyl)benzoic acid |
| Compound 148 (Example 76) | 2-((4-Oxo-8-(3-(2-oxoindolin-1-yl)propyl)-1-phenyl-1,3,8-triazaspiro[4.5]decan-3-yl)methyl)benzoic acid |
| Compound 149 (Example 77) | 2-((4-Oxo-8-(3-(2'-oxospiro[cyclopropane-1,3'-indoline]-1'-yl)propyl)-1-phenyl-1,3,8-triazaspiro[4.5]decan-3-yl)methyl)benzoic acid |
| Compound 150 (Example 78) | 3-((1-cyclohexyl-8-(4-(4-fluorophenyl)-4-oxobutyl)-4-oxo-1,3,8-triazaspiro[4.5]decan-3-yl)methyl)benzoic acid, hydrochloride |
| Compound 153 (Example 79) | 2-((1-(4-Fluorophenyl)-4-oxo-8-(3-(2-oxoindolin-1-yl)propyl)-1,3,8-triazaspiro[4.5]decan-3-yl)methyl)benzoic acid |
| Compound 153 (Example 80) | 2-((8-(3-(3,3-Dimethyl-2-oxoindolin-1-yl)propyl)-1-(4-fluorophenyl)-4-oxo-1,3,8-triazaspiro[4.5]decan-3-yl)methyl)benzoic acid |
| Compound 154 (Example 81) | 2-((4-oxo-8-(4-oxo-4-phenylbutyl)-1-phenyl-1,3,8-triazaspiro[4.5]decan-3-yl)methyl)benzoic acid |
| Compound 155 (Example 82) | 2-((8-(3-(3-cyclopropyl-2-oxo-2,3-dihydro-1H-benzo[d]imidazol-1-yl)propyl)-4-oxo-1-phenyl-1,3,8-triazaspiro[4.5]decan-3-yl)methyl)benzoic acid |
| Compound 156 (Example 83) | 3-((8-(3-(3-cyclopropyl-2-oxo-2,3-dihydro-1H-benzo[d]imidazol-1-yl)propyl)-1-(4-fluorophenyl)-4-oxo-1,3,8-triazaspiro[4.5]decan-3-yl)methyl)benzoic acid |
| Compound 157 (Example 84) | 3-((8-(4-(4-fluorophenyl)-4-(methoxyimino)butyl)-4-oxo-1-phenyl-1,3,8-triazaspiro[4.5]decan-3-yl)methyl)benzoic acid, hydrochloride |
| Compound 158 (Example 85) | 3-((1-(4-fluorophenyl)-4-oxo-8-(4-oxo-4-phenylbutyl)-1,3,8-triazaspiro[4.5]decan-3-yl)methyl)benzoic acid |
| Compound 159 (Example 86) | 2-((8-(3-(3-cyclopropyl-2-oxo-2,3-dihydro-1H-benzo[d]imidazol-1-yl)propyl)-1-(4-fluorophenyl)-4-oxo-1,3,8-triazaspiro[4.5]decan-3-yl)methyl)benzoic acid |
| Compound 160 (Example 87) | 3-((4-oxo-8-(3-(2-oxoindolin-3-yl)propyl)-1-phenyl-1,3,8-triazaspiro[4.5]decan-3-yl)methyl)benzoic acid, hydrochloride |
| Compound 161 (Example 88) | 2-((1-(4-Fluorophenyl)-4-oxo-8-(3-(2'-oxospiro[cyclopropane-1,3'-indoline]-1'-yl)propyl)-1,3,8-triazaspiro[4.5]decan-3-yl)methyl)benzoic acid |
| Compound 162 (Example 89) | 2-((8-(3-(3-Fluoro-3-methyl-2-oxoindolin-1-yl)propyl)-4-oxo-1-phenyl-1,3,8-triazaspiro[4.5]decan-3-yl)methyl)benzoic acid |
| Compound 163 (Example 90) | 2-((8-(3-(3-Fluoro-3-methyl-2-oxoindolin-1-yl)propyl)-1-(4-fluorophenyl)-4-oxo-1,3,8-triazaspiro[4.5]decan-3-yl)methyl)benzoic acid |
| Compound 164 (Example 91) | 3-((8-(3-(3-Fluoro-3-methyl-2-oxoindolin-1-yl)propyl)-1-(4-fluorophenyl)-4-oxo-1,3,8-triazaspiro[4.5]decan-3-yl)methyl)benzoic acid |
| Compound 166 (Example 92) | (R)-2-(4-oxo-8-(3-(2-oxoindolin-1-yl)propyl)-1-phenyl-1,3,8-triazaspiro[4.5]decan-3-yl)-2-phenylacetic acid |
| Compound 167 (Example 93) | (R)-2-(4-oxo-8-(4-oxo-4-phenylbutyl)-1-phenyl-1,3,8-triazaspiro[4.5]decan-3-yl)-2-phenylacetic acid |
| Compound 168 (Example 94) | (S)-2-(4-oxo-8-(4-oxo-4-phenylbutyl)-1-phenyl-1,3,8-triazaspiro[4.5]decan-3-yl)-2-phenylacetic acid |
| Compound 170 (Example 95) | (S)-2-(4-oxo-8-(3-(2-Oxoindolin-1-yl)propyl)-1-phenyl-1,3,8-triazaspiro[4.5]decan-3-yl)-2-phenylacetic acid |
| Compound 171 (Example 96) | 4-((8-(3-(3,3-dimethyl-2-oxoindolin-1-yl)propyl)-4-oxo-1-phenyl-1,3,8-triazaspiro[4.5]decan-3-yl)methyl)benzoic acid, hydrochloride |
| Compound 172 (Example 97) | 4-((4-oxo-8-(3-(2-oxoindolin-1-yl)propyl)-1-phenyl-1,3,8-triazaspiro[4.5]decan-3-yl)methyl)benzoic acid, hydrochloride |
| Compound 173 (Example 98) | 3-((8-(4-hydroxy-4-phenylbutyl)-4-oxo-1-phenyl-1,3,8-triazpiro[4.5]decan-3-yl)methyl)benzoic acid |
| Compound 176 (Example 99) | 3-((1-cyclohexyl-4-oxo-8-(4-oxo-4-phenylbutyl)-1,3,8-triazaspiro[4.5]decan-3-yl)methyl)benzoic acid, hydrochloride |
| Compound 177 (Example 100) | 3-(4-Oxo-8-(4-oxo-4-phenylbutyl)-1-phenyl-1,3,8-triazaspiro[4.5]decan-3-yl)benzoic acid |
| Compound 179 (Example 101) | Methyl 3-(4-oxo-8-(4-oxo-4-phenylbutyl)-1,3,8-triazpiro[4.5]decan-3-yl)benzoate |
| Compound 180 (Example 102) | 2-(4-oxo-8-(4-oxo-4-phenylbutyl)-1-phenyl-1,3,8-triazaspiro[4.5]decan-3-yl)benzoic acid |
| Compound 182 (Example 103) | 4-(4-Oxo-8-(4-oxo-4-phenylbutyl)-1-phenyl-1,3,8-triazaspiro[4.5]decan-3-yl)benzoic acid, hydrochloride |
| Compound 186 (Example 104) | N-(4-((4-oxo-8-(4-oxo-4-phenylbutyl)-1-phenyl-1,3,8-triazaspiro[4.5]decan-3-yl)methyl)phenyl)methanesulfonamide |
| Compound 211 (Example 105) | N-(3-(4-(4-fluorophenyl)-4-oxobutyl)-4-oxo-1-phenyl-1,3,8-triazaspiro[4.5]decan-3-yl)methyl)phenyl)methanesulfonamide |
| Compound 212 (Example 106) | N-(3-((4-Oxo-8-(3-(2'-oxospiro[cyclopropane-1,3'-indoline]-1'-yl)propyl)-1-phenyl-1,3,8-triazaspiro[4.5]decan-3-yl)methyl)phenyl)methanesulfonamide |
| Compound 213 (Example 107) | N-(3-((4-Oxo-8-(3-(2-oxoindolin-1-yl)propyl)-1-phenyl-1,3,8-triazaspiro[4.5]decan-3-yl)methyl)phenyl)methanesulfonamide |
| Compound 214 (Example 108) | N-(4-(8-(4-(4-Fluorophenyl)-4-oxobutyl)-4-oxo-1-phenyl-1,3,8-triazpiro[4.5]decan-3-yl)phenyl)methanesulfonamide |
| Compound 215 (Example 109) | N-(4-(4-oxo-8-(3-(2-oxoindolin-1-yl)propyl)-1-phenyl-1,3,8-triazaspiro[4.5]decan-3-yl)phenyl)methanesulfonamide |
| Compound 216 (Example 110) | N-(4-(4-Oxo-8-(3-(2'-oxospiro[cyclopropane-1,3'-indoline]-1'-yl)propyl)-1-phenyl-1,3,8-triazaspiro[4.5]decan-3-yl)phenyl)methanesulfonamide |
| Compound 217 (Example 111) | N-(4-(8-(3-(3,3-Dimethyl-2-oxoindolin-1-yl)propyl)-4-oxo-1-phenyl-1,3,8-triazaspiro[4.5]decan-3-yl)phenyl)methanesulfonamide. |
| Compound 218 (Example 112) | 2-((1-Cyclohexyl-4-oxo-8-(4-oxo-4-phenylbutyl)-1,3,8-triazaspiro[4.5]decan-3-yl)methyl)benzoic acid, hydrochloride |

The preceding compound names, as well as the compound names in the examples below, were generated using either ChemDraw Ultra version 8.03 or ChemBioDraw Ultra version 10, both of which are available from Cambridgesoft Corporation, as well as ACD Namepro software, version 6.0, or the AutoNom plugin for MDL Draw 2.1.

Utility and Administration

Motility functions of the gastrointestinal tract require interactions of inhibitory and stimulatory processes controlled by the vagus nerve and myenteric plexus. An inhibitory mechanism that appears to play a part in delayed gastric emptying is stimulation of the dopamine receptors. Dopamine $D_2$ and/or $D_3$ receptor stimulation increases fundic relaxation, diminishes peristalsis, decreases gastric tone, and a causes a loss of coordination between gastric and duodenal contractile activity. Dopamine itself also stimulates receptors in brain regions that can induce nausea and vomiting.

Gastroparesis is a condition of decreased gastric motility characterized by delayed gastric emptying in the absence of mechanical outlet obstruction. Four to seven million people in the United States suffer from some degree of gastroparesis. The most distressing symptoms of severe gastroparesis are nausea and vomiting following a meal. Other symptoms include heartburn and regurgitation despite treatment, abdominal bloating, early satiety, and abdominal pain. The use of prokinetic agents can restore gastric motility and normalize the absorption of food and may play an important part in facilitating euglycemia. Alleviating the distressing symptoms of nausea and vomiting can improve patients' lives by correcting fluid, electrolyte balance and nutritional deficiencies.

Post-operative nausea and vomiting (PONV) is one of the most common and distressing side effects associated with surgical procedures, with reported rates of 37% of nausea and 20% for vomiting (Quinn A C, Brown J H, Wallace P G, Asbury A J; Anaesthesia 49, 62-65 (1994)). It is a complication dreaded by many patients that can lead to medical complications and impose an economic burden. Gastrointestinal atony is a common phenomenon contributing to vomiting in post-operative patients. The medical complications of PONV include an increased risk of pulmonary aspiration of vomitus or fluid but also possible wound complication, gastric herniation, esophageal tears and muscular fatigue. Dehydration and electrolyte imbalance can occur if PONV is severe, which can be an issue with young children. Finally, another concern may be the delayed ability to take oral therapy and nutrition.

PONV may be caused by the use of analgesics as well as by after-effects of anesthetic gases, which are not completely excreted for many hours following recovery.

Several classes of drugs constitute the backbone of antiemetic therapy, from older drugs like droperidol and metoclopramide to 5-$HT_3$ receptor antagonists, which were the focus of many studies and clinical trials in the 1990s. However, only modest progress has been made in reducing the incidence of PONV despite extensive research and the use of various classes of antiemetic drugs (i.e. butyrophenones, domperidone, benzamides such as metoclopramide, histamine receptor antagonists such as ondansetron, muscarinic receptor antagonists, glucocorticoids, NK1 receptor antagonists), Despite the antiemetic drugs available, PONV still has a high incidence. Similarly, despite the gastric motility drugs available, gastroparesis and gastropathies in general are still significant medical problems. Thus, we have found that there is still a significant medical need for efficacious and safe drugs for PONV, gastroparesis and other maladies mediated via the $D_2$ receptor.

The compounds of this invention exhibit activity as dopamine $D_2$ receptor antagonists and/or $D_3$ receptor antagonists and thus are useful for treating conditions in humans that are regulated by the dopamine $D_2$ and/or $D_3$ receptor. A $D_2$ and/or $D_3$ antagonist is a compound, such as those described herein, that binds to the appropriate receptor but that does not provoke a biological response itself. Instead it blocks or dampens an agonist-mediated response. Thus, the compounds of this invention are useful for the treatment of a disease that is respondent to dopamine $D_2$ and/or $D_3$ receptor antagonist therapy by administering a compound of this invention to a patient in need thereof. Generally such receptor antagonist activity results in increased gastrointestinal activity and normalized gut function. The compounds find particular applicability as an anti-emetic, a drug that is effective in reducing nausea and vomiting that may be induced by motion sickness, gastroenteritis, use of opioid analgesics, and chemotherapy in the treatment of cancer.

Non-limiting examples of conditions that might be treated with a compound of this invention include gastroparesis, gastric stasis, irritable bowel syndrome, functional dyspepsia, improvement of diabetic metabolic control, gastro-esophageal reflux disease, heartburn, constipation, post-operative ileus, opioid-induced ileus, visceral hypersensitivity, postprandial distress syndrome and other gastrointestinal disorders. Other conditions for which the antagonists of this invention can be useful include post-operative nausea and vomiting, chemotherapy-induced nausea and vomiting, cyclic vomiting syndrome, gastritis, gastroenteritis induced nausea and vomiting, hyperemesis gravidarum, symptoms related to migraine, and symptoms related to Parkinson's disease (or Parkinson's disease therapies), idiopathic nausea and vomiting, functional gallbladder disorder, functional biliary sphincter of Oddi disorder, and functional pancreatic sphincter of Oddi disorder, diarrhea, and treatment of drug dependence, among others. $D_2$ dopamine receptor antagonists of this invention can also be used to increase milk production in lactating women.

The compounds of the invention may also be useful in increasing gastroprokinetic activity, improving gastric emptying, reducing gastric dysrhythmias (normalization of gastrointestinal electrical activity), reduction of dyspeptic symptoms, relieving upper abdominal fullness (epigastric fullness), reducing early satiety, bloating, including postprandial bloating, belching, abdominal pain, epigastric pain (syndrome), regurgitation as well as reversal of hyperglycemic inhibitory activity on gastrointestinal motility.

The compounds of the invention may be administered in combination with gastrointestinal prokinetics, nonlimiting examples including prucalopride, naronapride, cisapride, mosapride, velusetrag, and tegaserod. Antinausea and antiemetic activity makes coadministration valuable with analgesics susceptible to nausea and vomiting complications such as fentanyl, tramadol, sufentanil, alfentanil, remifentanil, carfentanil, lofentanil and opiates in general.

Compounds of the invention may be useful for use in diagnostic procedures, for example endoscopy.

Compounds of the invention may be useful for other indications such as schizophrenia and bipolar disorder.

To determine $D_2$ antagonist activity, one of ordinary skill may do so using in vivo or in vitro tests. A standard in vitro test is set forth in Example 1 of this patent application. Results of such tests on representative compounds of this invention are set forth therein. In vivo tests can be performed in the shrew in accordance with the procedure set forth by Darmani, et. al. in J. Neural Transm (1999) 106: 1045-1061. In vivo tests in dogs can be performed in accordance with the procedure set forth Depoortère R, Barret-Grévoz C, Bardin L, Newman-Tancredi A. Apomorphine-induced emesis in dogs: differential sensitivity to established and novel dopamine D2/5-HT(1A) antipsychotic compounds. Eur J Pharmacol. 2008 Nov. 12; 597(1-3):34-8.

To determine $D_3$ antagonist activity, one of ordinary skill may do so using in vivo or in vitro tests. A standard in vitro test is a radioligand binding assay carried out using the cloned human dopamine $D_3$ receptor expressed in Chinese hamster ovary (CHO) cell membranes as described by MacKenzie et al. 1994 (see Eur J Pharmacl. 1994 Jan. 1; 266(1):79-85). In this assay test articles are incubated with $D_3$ receptor membranes in the presence of [$^3$H]methyl-spiperone for 60 minutes at room temperature followed by filtrations and counting of filters by liquid scintillation spectroscopy. $IC_{50}$ values are determined from displacement of [$^3$H]methyl-spiperone and corresponding constants (Ki) are calculated according to the methods of Cheng and Prusoff 1973 (see Biochem Pharmacol 22 (23):3099-3108, 1973). In vivo tests can be performed in accordance with the procedure set forth by Darmani, et al. in J. Neural Transm (1999) 106: 1045-1061. For a discussion of clinical relevance, see Levant, B. The D3 Dopamine Receptor: Neurobiology and Potential Clinical Relevance. Pharmacological Reviews Sep. 1, 1997 vol. 49 no. 3 231-252.

The compounds of this invention are are particularly valuable in that they generally have fewer side effects that may create problems for the patient being treated. For example, it is useful if a compound being administered exhibits reduced mu opioid receptor binding activity. The mu opioid receptor is the primary site of action for most commonly used opioids such as morphine, fentanyl, and the like. Compounds of this invention that show reduced mu opioid binding will not interfere with the action of the opioid to reduce pain. Such binding activity may be determined by one of ordinary skill in the art by using in vivo or in vitro tests. An example of an in vitro test may be found at Zhang S, Tong Y, Tian M, Dehaven R N, Cortesburgos L, Mansson E, Simonin F, Kieffer B, Yu L. Dynorphin A as a potential endogenous ligand for four members of the opioid receptor gene family. J Pharmacol Exp Ther. 1998 July; 286(1):136-41. An example of an in vivo test may be found at D'Amour F E, Smith D L (1941). A method for determining loss of pain sensation. J. Pharmacol. Exp. Ther., 72: 74. An example of a group of compounds of this invention having such reduced opioid activity includes those where the $R_2$ group is cyclohexyl.

Another side effect that is avoided using the compounds of this invention is referred as QTc prolongation. QTc prolongation is characterized by the prolongation of the QT interval on electrocardiograph (ECG) and a propensity to ventricular tachyarrhythmias, which may lead to cardiac arrest and death. It is found that some marketed anti-emetic compounds and compounds to treat gastroparesis, such as domperidome, exhibit such activity and can cause sudden cardiac death, which is thought to result from the repolarization of the ventricle of the heart that leads to atrial fibrillation. Compounds of the invention can be tested for QTc prolongation using in vivo or in vitro testing. Examples in the literature for such testing can be found at Yan G X, Shimizu W, Antzelevitch, C: Characteristics and distribution of M cells in arterially perfused canine left ventricular wedge preparations: Circulation 1998; 98:1921-1927 and also Kirsch G E, Trepakova E S, Brimecombe J C, Sidach S S, Erickson H D, Kochan M C, Shyjka L M, Lacerda A E, Brown A M: Variability in the measurement of hERG potassium channel inhibition: Effects of temperature and stimulus pattern. J Pharmacol Toxicol Methods 2004; 50: 93-101.

Another side effect that is sometimes seen in known compounds that exhibit D2 and/or D3 activity is CNS penetration, which not desirable because it can lead to dyskinesia and dystonia (Parkinson's disease-like symptoms). Benzimidazole/benzamide derivatives such as metoclopramide and domperidone, exhibit such activity, with the former penetrating the CNS more readily than the latter. The compounds of this invention show reduced CNS penetration. Compounds of the invention can be tested for CNS penetration using in vivo or in vitro testing. Examples in the literature for such testing can be found at Yu S, Li S, Yang H, Lee F, Wu J T, Qian M G. A novel liquid chromatography/tandem mass spectrometry based depletion method for measuring red blood cell partitioning of pharmaceutical compounds in drug discovery. Rapid Commun Mass Spectrom. 2005; 19(2):250-4.

The subject invention further provides treatment for the above listed maladies comprising the administration of a therapeutically effective amount of one or more compounds of the invention to an individual in need of treatment. Accordingly, the subject invention provides pharmaceutical compositions of these compounds. In a preferred embodiment the patient is a human; however, non-human animals also can be treated.

The compounds of the invention set forth herein may be administered orally (PO), intravenously (IV), subcutaneously (SC/SQ), intramuscular (IM), rectally (PR), sublingually (SL) and parenteral, more generally, routes of delivery and via immediate release (IR) and controlled release (CR) formulations. Compounds of the invention may be administered in dosage unit formulations containing conventional non-toxic pharmaceutically acceptable excipients such as carriers, adjuvants, vehicles and the like. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of this invention and a pharmaceutically acceptable excipient. One or more compounds of the invention may be present in association with one or more non-toxic pharmaceutically acceptable carriers and/or diluents and/or adjuvants, and if desired other active ingredients. The pharmaceutical compositions containing compounds of the invention may be in a form suitable for oral use, for example, as tablets, troches, lozenges, aqueous or oily suspensions, dispersible powders or granules, emulsion, hard or soft capsules, or syrups or elixirs.

Formulations are described in detail in a number of sources that are well known and readily available to those skilled in the art. For example, *Remington's Pharmaceutical Science* by E. W. Martin describes formulations that can be used in connection with the subject invention. In general, the compositions of the subject invention will be formulated such that an effective amount of the bioactive compound(s) is combined with at least one suitable carrier, solvent, excipient, and/or adjuvant in order to facilitate effective administration of the composition.

In accordance with the invention, pharmaceutical compositions comprising, as an active ingredient, an effective amount of one or more of the compounds of the invention and one or more non-toxic, pharmaceutically acceptable carrier(s) and/or diluent(s). Examples of such carriers for use in the invention include ethanol, dimethylsulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances that may act as diluents, flavoring agents, solubilizers, lubricants, suspending agents, binders, preservatives, tablet disintegrating agents or an encapsulating material.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenge.

The term "individual(s)" is defined as a single mammal to which is administered a compound of the present invention. The mammal may be a rodent, for example a mouse or a rat, or a non-rodent, for example a pig, a horse, a rabbit, a goat, a cow, a cat, a dog, or can be a human. In a preferred embodiment, the individual is a human.

Process for Making the Compounds

Compounds of this invention are prepared by following standard chemical reactions based on the teachings of this invention, once the novel compounds set forth herein are defined.

Compounds of this invention can be prepared in accordance with one or more of the Schemes discussed below. All of the starting materials are either commercially available or can be prepared by procedures that would be well known to one of ordinary skill in organic chemistry. The products may be used as collected or may first be purified using conventional techniques such as preparative TLC or HPLC, chromatography, precipitation, crystallization and the like.

SCHEME I

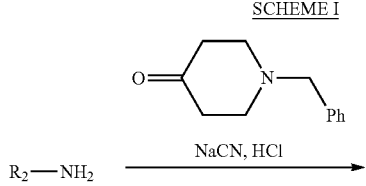

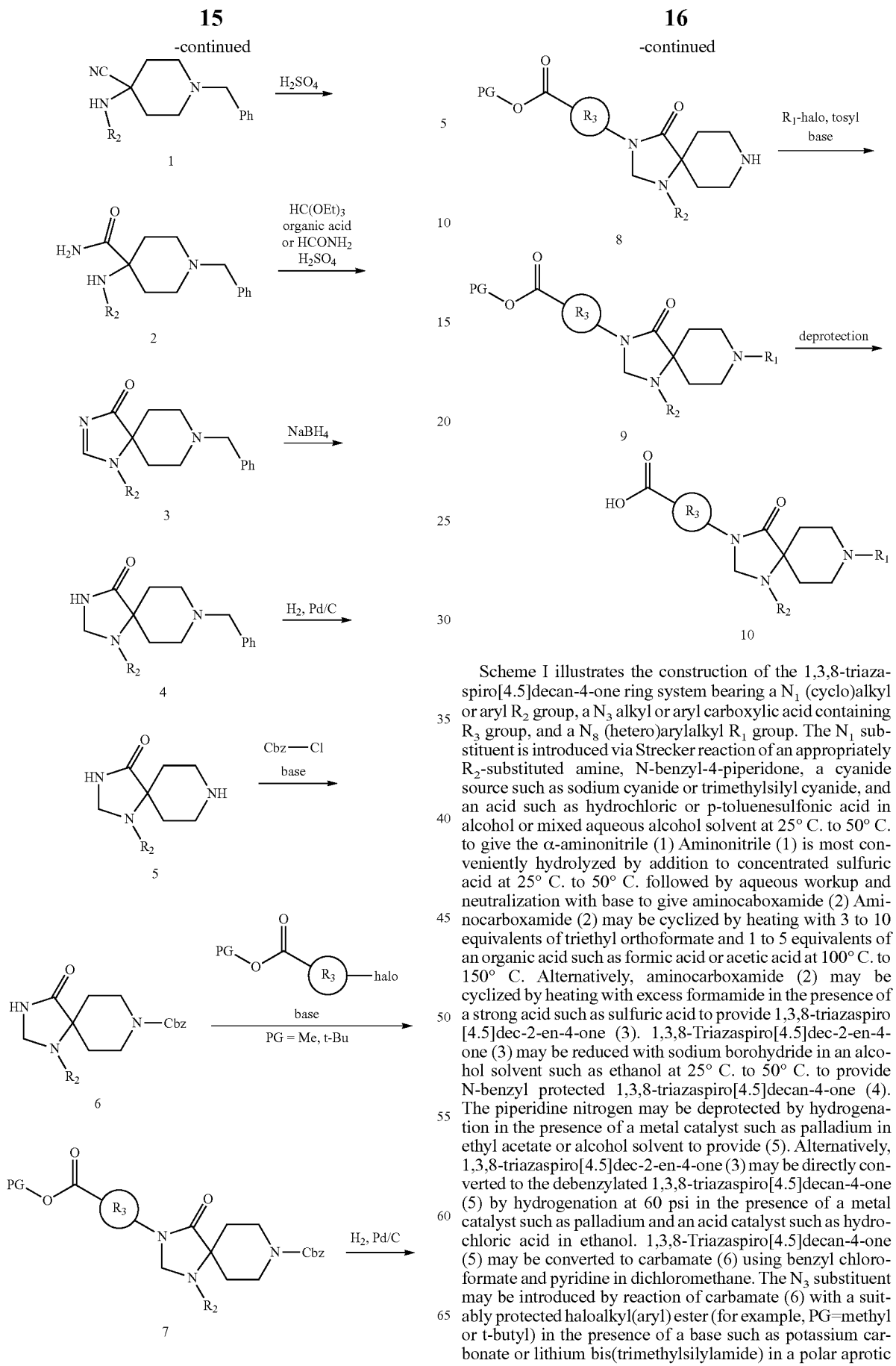

Scheme I illustrates the construction of the 1,3,8-triazaspiro[4.5]decan-4-one ring system bearing a $N_1$ (cyclo)alkyl or aryl $R_2$ group, a $N_3$ alkyl or aryl carboxylic acid containing $R_3$ group, and a $N_8$ (hetero)arylalkyl $R_1$ group. The $N_1$ substituent is introduced via Strecker reaction of an appropriately $R_2$-substituted amine, N-benzyl-4-piperidone, a cyanide source such as sodium cyanide or trimethylsilyl cyanide, and an acid such as hydrochloric or p-toluenesulfonic acid in alcohol or mixed aqueous alcohol solvent at 25° C. to 50° C. to give the α-aminonitrile (1) Aminonitrile (1) is most conveniently hydrolyzed by addition to concentrated sulfuric acid at 25° C. to 50° C. followed by aqueous workup and neutralization with base to give aminocaboxamide (2) Aminocarboxamide (2) may be cyclized by heating with 3 to 10 equivalents of triethyl orthoformate and 1 to 5 equivalents of an organic acid such as formic acid or acetic acid at 100° C. to 150° C. Alternatively, aminocarboxamide (2) may be cyclized by heating with excess formamide in the presence of a strong acid such as sulfuric acid to provide 1,3,8-triazaspiro[4.5]dec-2-en-4-one (3). 1,3,8-Triazaspiro[4.5]dec-2-en-4-one (3) may be reduced with sodium borohydride in an alcohol solvent such as ethanol at 25° C. to 50° C. to provide N-benzyl protected 1,3,8-triazaspiro[4.5]decan-4-one (4). The piperidine nitrogen may be deprotected by hydrogenation in the presence of a metal catalyst such as palladium in ethyl acetate or alcohol solvent to provide (5). Alternatively, 1,3,8-triazaspiro[4.5]dec-2-en-4-one (3) may be directly converted to the debenzylated 1,3,8-triazaspiro[4.5]decan-4-one (5) by hydrogenation at 60 psi in the presence of a metal catalyst such as palladium and an acid catalyst such as hydrochloric acid in ethanol. 1,3,8-Triazaspiro[4.5]decan-4-one (5) may be converted to carbamate (6) using benzyl chloroformate and pyridine in dichloromethane. The $N_3$ substituent may be introduced by reaction of carbamate (6) with a suitably protected haloalkyl(aryl) ester (for example, PG=methyl or t-butyl) in the presence of a base such as potassium carbonate or lithium bis(trimethylsilylamide) in a polar aprotic solvent such as N,N-dimethylformamide at 25° C. to 50° C. to provide (7). Alternatively, in situations where the N₃ substituent is a phenyl or aryl ester group it may be necessary to use Buchwald's protocol. In these cases, carbamate (6) may be reacted with an alkyl iodobenzoate in the presence of copper iodide, dimethylethylenediamine, and potassium carbonate in acetonitrile at 75° C. to provide (7). Carbamate (7) may be deprotected via hydrogenation at atmospheric pressure in the presence of a metal catalyst such as palladium in ethyl acetate or alcohol solvent to provide deprotected 1,3,8-triazaspiro[4.5]decan-4-one (8). The N₈ substituent may be introduced by reaction of (8) with the appropriate (hetero)aryl alkyl halide or tosylate in the presence of a base such as potassium carbonate, and 0.1-1 equivalent of sodium iodide catalyst in a suitable solvent such as acetone or 2-butanone at 50° C. to 80° C. to provide fully substituted 1,3,8-triazaspiro[4.5]decan-4-one (9). If the ester protective group in (9) is a t-butyl group it may be removed by treatment with a strong acid such as hydrochloric acid in dioxane or 20-50% trifluoroacetic acid in dichloroethane to provide carboxylic acid (10) as a trifluoroacetic acid salt. If the ester protective group in (9) is a methyl or ethyl group it may be removed by treatment with lithium hydroxide in aqueous methanol followed by careful neutralization with acetic acid to provide carboxylic acid (10). Specific examples of this generic description are found in this application herein.

Definitions

As described herein, $R_1$, $R_2$ and $R_3$ substituents on the 1,3,8-triazaspiro[4.5]decan-4-one core structure are described by their systematic chemical names. For purposes of this application, the $R_1$ is substituted at the 8 position of the 1,3,8-triazaspiro[4.5]decan-4-one core structure, $R_2$ is substituted at the 1 position, and $R_3$ substituents are at the 3 position. For example, one $R_1$ substitution described herein is 2-oxo-2,3-dihydro-1H-benzo[d]imidazol-1-yl)propyl. The chemical structure defined by that systematic name is as follows:

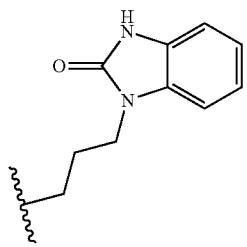 [SMILES: *CCCn1c(=O)[nH]c2ccccc21]

The described moiety connects to the core via the propyl group, thus the core plus 2-oxo-2,3-dihydro-1H-benzo[d]imidazol-1-yl)propyl for $R_1$ yields the following:

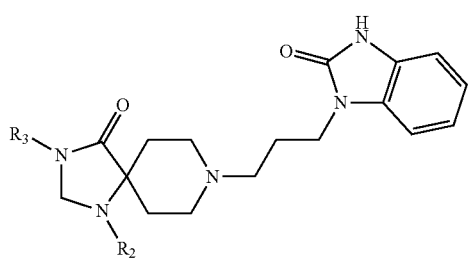

$R_2$ and $R_3$ substitutions are described in the same manner. An $R_2$ substituent described herein is 4-fluorophenyl. According to standard chemical naming conventions, and as one of ordinary skill in the art would readily know, for the fluoro atom to attach at the 4-position of the phenyl ring, by definition the phenyl attaches at $R_2$ para to the fluoro:

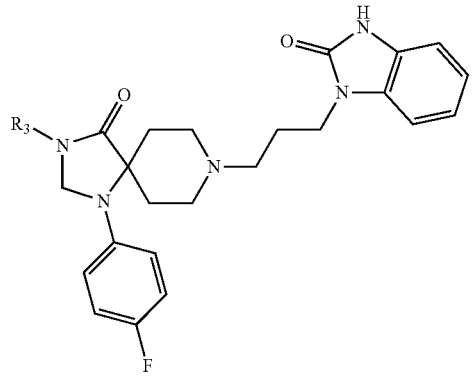

An $R_3$ described herein is:

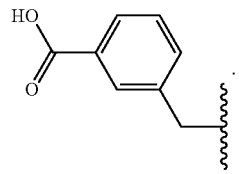 [SMILES: *Cc1cccc(C(=O)O)c1]

Combined with the structure above, the following compound is described:

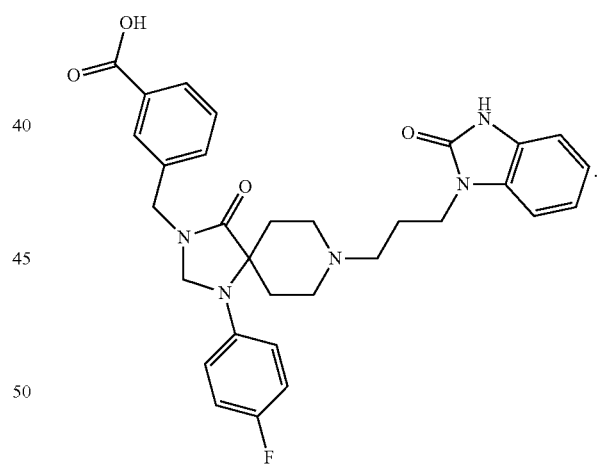

The term "$C_1$-$C_6$alkyl" refers to straight or branched hydrocarbon chains. Examples of alkyl groups include methyl, ethyl, propyl, isopropyl, butyl, isobutyl, sec-butyl, tert-butyl, pentyl, pentan-2-yl, pentan-3-yl, isopentyl, neopentyl, hexyl, hexan-2-yl, hexan-3-yl, 4-methylpentyl, 3,3-dimethylbutyl, 4,4-dimethylpental-2-yl, 2-methylpentan-3-yl, 4-methylpentan-2-yl, 2-methylpentyl, 3-methylpentyl, 2,3-dimethylbutyl, and the like. The term "$C_1$-$C_6$alkyl" is considered herein to be equivalent to term written with a space between the "$C_1$-$C_6$" and the "alkyl" ("$C_1$-$C_6$ alkyl"). In one aspect of the invention the alkyl linking group at the $R_1$ position is $C_2$-$C_4$alkyl, that is, ethyl, propyl or butyl.

The term "cycloalkyl" refers to a non-aromatic carbocyclic ring or ring system, which may be saturated (i.e., a "cycloalkyl"), or unsaturated (i.e., a "cycloalkenyl"), generally the former. Cycloalkyl groups may have a simple single ring system or a more complex multi-ring fused or bridged system. Preferred cycloalkyl groups have from 3 to 7 members. More preferred cycloalkyl groups have 5 or 6 members. Examples of cycloalkyl groups include, for example, cyclohexyl, cyclopentyl, cyclobutyl, cyclopropyl and cycloheptyl. Examples of more complex cycloalkyl groups include the following: Examples of more complex cycloalkyl groups include the following: bicyclo[4.1.0]hept-2-yl-, bicyclo[4.1.0]hept-3-yl-, bicyclo[4.1.0]hept-1-yl-, bicyclo[3.1.0]hex-6-yl-, adamantyl-1-yl-, adamantyl-2-yl-, octahydro-pentalen-2-yl-, endo-bicyclo[2.2.1]hept-2-yl-, exo-bicyclo[2.2.1]hept-2-yl-, endo-bicyclo[2.2.2]oct-2-yl-, and exo-bicyclo[2.2.2]oct-2-yl-.

The term "halo" and "halogen" refer to one or more —F, —Cl, —Br and —I.

The term "optionally substituted" refers to the presence or absence of one or more substitutions, as set forth herein.

As used herein, the term "pharmaceutically acceptable salts" or "a pharmaceutically acceptable salt thereof" refer to organic and inorganic acids that include, but not limited to, acetic, acrolate, ascorbic, benzenesulfonic (besylate), benzoic, bicarbonic, bisulfate, bisulfic, bitartaric, camphorsulfonic, carbonic, citric, edetic, ethane disulfonic, ethenesulfonic, formic, fumaric, glucoheptonic, gluconic, glucuronic, glutamic, glycolic, glycollyarsanilic, hexylresorcinic, dydrabamic, hydrobromic, hydrochloric, hydroiodide, isethionic, lactic, lactobionic, lauryl sulfonic, maleic, malic, mandelic, methanesulfonic, mucic, napsylic, nitric, oxalic, pamoic, pantothenic, phenylacetic, phosphoric, polygalacturonic, phthalic, propionic, pyrosulfate, salicyclic, stearic, subacetic, succinic, sulfamic, sulfanilic, sulfuric, tannic, tartaric, p-toluenesulfonic, and the like. The terms also refer to the group including, but not limited to, alkali metals such as sodium, potassium, and lithium; alkaline earth metals such as calcium and magnesium; other metals, such as aluminum, zinc; ammonia and organic amines, such as mono-, di- or trialkylamines; dicyclohexylamine; tributyl amine; pyridine; N-methyl, N-ethylamine; diethylamine; triethylamine; mono-, bis, or tris-(2-hydroxy-lower alkyl amines, such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethylamine; N-methyl-D-glucamine; amino acids such as arginine, lysine, and the like, and zwitterions, such as glycine and the like.

Furthermore, the term "salt" as used herein also includes coordination complexes between ionic compounds of the invention and one or more counterions.

There are numerous substituents that may be chosen as $R_1$ substituents. Here are generic names and specific formulas that are used to exemplify the names.

(2-oxo-2,3-dihydro-1H-benzo[d]imidazol-1-yl)($C_1$-$C_4$alkyl) optionally substituted at the 3 position with cyclopropyl or at the 6 position with chlorine (the latter shown),

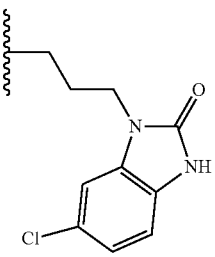 [SMILES: *CCCn1c(=O)[nH]c2ccc(Cl)cc21]

(2-oxobenzo[d]oxazol-3(2H)-yl)($C_1$-$C_4$alkyl)—propyl shown,

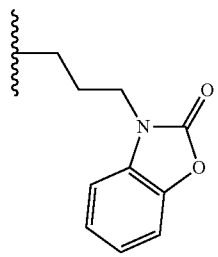 [SMILES: *CCCn1c(=O)oc2ccccc21]

(2-oxobenzo[d]thiazol-3(2H)-yl)($C_1$-$C_6$alkyl)—propyl shown,

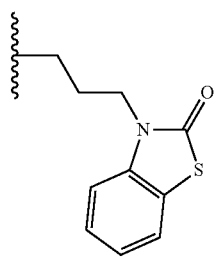 [SMILES: *CCCn1c(=O)sc2ccccc21]

(2-oxoindolin-1-yl)($C_1$-$C_6$alkyl) optionally substituted at the 3-position with one or two components chosen from methyl or fluoro—propyl link with 3-methyl, 3-flours shown,

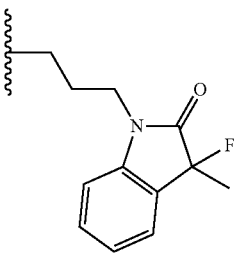 [SMILES: *CCCN1C(=O)C(C)(F)c2ccccc21]

(3-spirocyclopropane-(2-oxoindolin-1-yl))($C_1$-$C_6$alkyl),

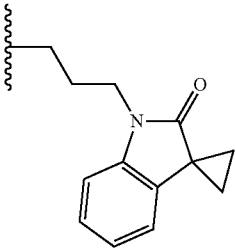 [SMILES: *CCCN1C(=O)C2(CC2)c2ccccc21]

(2-oxoindolin-3-yl))($C_1$-$C_6$alkyl),

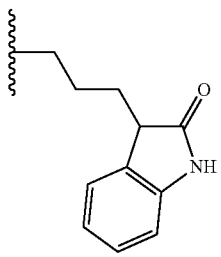 [SMILES: *CCCC1C(=O)Nc2ccccc21]

phenyl($C_1$-$C_6$alkyl),

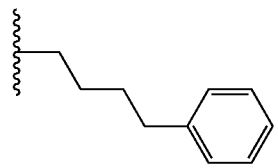 [SMILES: *CCCCc1ccccc1]

1-hydroxy-1-phenylmethyl($C_2$-$C_6$ alkyl),

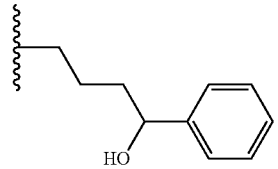

1-acetoxy-1-phenylmethyl($C_2$-$C_6$ alkyl),

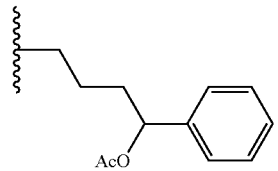 [SMILES: *CCCC(O)c1ccccc1]

bis(4-fluorophenyl)methyl-($C_1$-$C_6$alkyl),

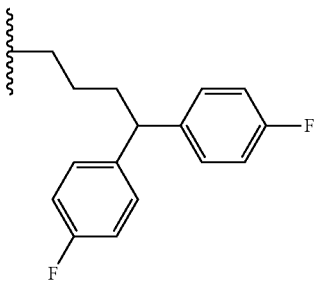 [SMILES: *CCCC(c1ccc(F)cc1)c1ccc(F)cc1]

(1H-benzo[d][1,2,3]triazol-1-yl)($C_2$-$C_6$alkyl),

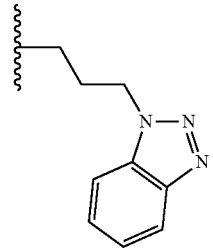 [SMILES: *CCCn1nnc2ccccc21]

1-phenyl-1-oxo-($C_2$-$C_6$alkyl) optionally substituted at the 4 position of the phenyl with halo,

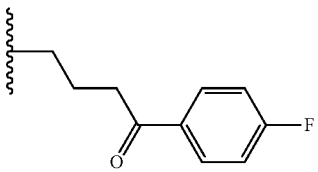 [SMILES: *CCCC(=O)c1ccc(F)cc1]

2,3-dihydrobenzo[b][1,4]dioxine-1-($C_1$-$C_6$alkyl),

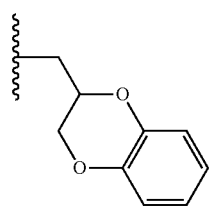 [SMILES: *CC1COc2ccccc2O1]

1-(thiophen-2-yl)-1-oxo-($C_1$-$C_6$ alkyl),

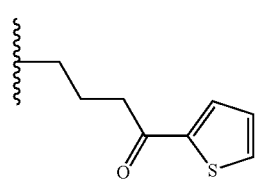 [SMILES: *CCCC(=O)c1cccs1]

3-oxo-2H-benzo[b][1,4]oxazin-4-yl))($C_1$-$C_6$alkyl),

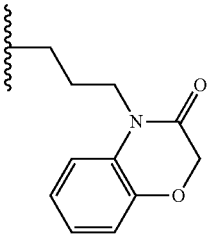 [SMILES: *CCCN1C(=O)COc2ccccc21]

((3-($C_1$-$C_6$alkyl)oxycarbonyl($C_1$-$C_6$alkyl))-1H-indol-1-yl)($C_1$-$C_6$ alkyl)

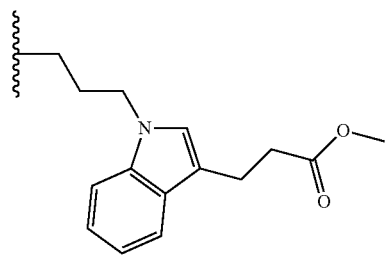 [SMILES: *CCCn1cc(CCC(=O)OC)c2ccccc21]

(2-($C_1$-$C_6$alkyl)oxycarbonyl-1H-indol-1-yl)($C_1$-$C_6$ alkyl)

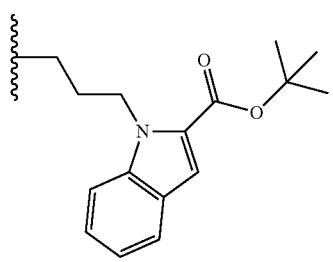 [SMILES: *CCCn1c(C(=O)OC(C)(C)C)cc2ccccc21]

Example 1

Compound Affinity

Affinity for the dopamine D2 receptor was tested in vitro, and the following describes the construction of cell lines expressing human D2 receptor, as well as the binding assays themselves.

Establishment of Stable Cell Lines Expressing Either the Cloned Human $D_{2S}$ Receptor or the Cloned Human $D_{2L}$ Receptor.

The human $D_2$ receptor exists in two isoforms: the short form ($D_{2S}$) and the long form ($D_{2L}$). The two isoforms are generated from the $D_2$ gene by alternative splicing and the $D_{2L}$ isoform differs from the $D_{2S}$ isoform by the addition of 29 amino acids in the third intracellular loop of its protein structure.

To establish HEK-293 cell lines stably expressing either the human $D_{2S}$ or the human $D_{2L}$, the human dopamine $D_{2S}$ receptor (Genebank Accession Number NM_016574) and human dopamine $D_{2L}$ receptor (Genebank Accession Number BC021195) were amplified by PCR from Origene cDNA clones TC308892 and SC123573 (respectively) using the following primers: 5-CACCATGGATCCACTGAATCTGTCCTG-3 (SEQ ID NO: 1) sense and 5-GCAGCAGAGTCAGCAGTGGA-3 (SEQ ID NO: 2) antisense. The resulting PCR products were respectively cloned into pENTR-D-TOPO (Invitrogen), sequenced and then transferred into the pCDNA3.2-DEST (Invitrogen) using the LR-clonasc gateway reaction (Invitrogen) and sequenced again to verify the genes sequence.

HEK293 cells were maintained in Eagles Minimum Essential Medium (MEM) supplemented with 0.292 g/L L-glutamine and 10% (v/v) fetal calf serum at 37° C. in a 5% $CO_2$ humidified atmosphere. Cells were grown to 60-80% confluency in 10 cm dishes before transfection. Transfection of the $D_{2S}$ and $D_{2L}$ containing pcDNA3.2-DEST into HEK-293 cells were performed using Lipofectamine 2000 (Invitrogen). Transfected cells were seeded and diluted 2 days after transfection and maintained in culture medium supplemented with 500 µg/mL G418. The HEK-293 cell line expressing the $huD_{2S}$ (R2$D_{2S}$) and the $huD_{2L}$ (R2$D_{2L}$) were maintained in culture medium supplemented with 500 µg/mL G418.

D2 Receptor Binding Assays

Cell Culture

HEK293 cells were in Eagles Minimum Essential Medium (MEM) supplemented with 10% FBS, 0.292 g/liter L-glutamine, $10^5$ units/liter penicillin, 100 mg/liter streptomycin and 500 mg/ml Geneticin at 37° C. in a 5% $CO_2$ humidified atmosphere. Cells were grown to 80-90% confluence and harvested with cell stripper (Cellgro #25-056-CI). Cells were then washed with PBS (2×). Cells were either pelleted and frozen at −80° C. or membranes were prepared immediately.

Membrane Preparation

Cells from pellet were resuspended in homogenization buffer (15 mM Tris*HCl, 2 mM $MgCl_2$*$6H_2O$, 0.3 mM EDTA, 1 mM EGTA pH 7.4 @ 4° C.). Cells were then homogenized using a Polytron (PT 1200) homogenizer at setting 6 for 10 seconds. Crude membranes were pelleted at 39,412 g for 15 min, at 4° C. (2×) in a Sorval RC6 plus centrifuge. Membranes were finally resuspended in resuspension buffer (50 mM Tris*HCl, 120 mM NaCl, 10 mM $MgCl_2$*$6H_2O$, 1 mM EDTA pH 7.4 @ 4° C.) and sonicated (Fisher Sonic Dismembrator) at setting 5 for 10 seconds.

Assay

The radioligand binding assays were conducted in microtiter plates (Costar #3961) with a final volume of 1.0 mL.

The membranes were thawed at room temperature, briefly homogenized using a sonicator, diluted in assay buffer and kept on wet ice until being added to the assay plate. Membranes were diluted to a final target tissue concentration of 10 µg protein per well. The specific binding should be greater than 80% with less than 10% total radioligand bound to minimize ligand depletion errors.

First compound of the invention (50 µL) or assay buffer (50 mM Tris*HCl, 120 mM NaCl, 5 mM $MgCl_2$*$6H_2O$, 1 mM EDTA, 5 mM KCl pH 7.4 @37° C. plus 0.025% BSA), buffer (700 µL) and then membrane (200 µL) were added to the deep well assay plate, which was then shaken for 10 minutes. Finally, radioligand (50 µL) was added.

The assay plates were incubated at 37° C. for 120 minutes.

The assay plate were filtered over 0.3% PEI pretreated glass fiber filtermats (GF/C) using a Packard Filtermate cell harvester. The plate were then rinsed with ice cold wash buffer (1 mL/well; 50 mM Tris*HCl, 0.9% NaCl pH 7.4 @ 4° C.) three times and then air dried.

For each compound of the invention tested, the concentration producing 50% inhibition of binding ($IC_{50}$) was determined using the OneSite Competition equation, since the F-test did not yield significance when compared with a Sigmoidal Dose-response curve with variable slope. Since the radioligand $K_D$ is known (0.09 nM), the inhibition dissociation constant ($K_i$) of each compound was determined according to the method of Cheng & Prusoff (Cheng, Y-C and Prusoff (1973). Biochem Pharmacol., 22: 3099-3108).

Bound radioligand was determined by liquid scintillation counting. To determine radioligand concentration, three (3) aliquots of the radioligand solution were counted by liquid scintillation (10 uL diluted $^3$H-ligand+40 uL Scin 20 into GF/C filter plate).

In the following tables, compound $IC_{50}$ values for $D_2$ are shown. $IC_{50}$ values are reported on a scale of 1 through 5, wherein the value scale is defined as follows:

| Receptor Affinity Scale | | | | | |
|---|---|---|---|---|---|
| $IC_{50}$ value | <10 nM | 10-50 nM | 51-200 nM | 201-999 nM | >1 uM |
| Scaled number | 1 | 2 | 3 | 4 | 5 |

| Compound | Affinity Score |
|---|---|
| 11 | 1 |
| 17 | 1 |
| 19 | 1 |
| 21 | 1 |
| 22 | 1 |
| 23 | 1 |
| 25 | 1 |
| 26 | 1 |
| 30 | 1 |
| 35 | 1 |
| 38 | 1 |
| 39 | 1 |
| 40 | 1 |
| 43 | 1 |
| 52 | 1 |
| 56 | 1 |
| 69 | 1 |
| 70 | 1 |
| 71 | 1 |
| 72 | 1 |
| 76 | 1 |
| 85 | 1 |
| 89 | 1 |

-continued

| Receptor Affinity Scale | |
|---|---|
| 100 | 1 |
| 102 | 1 |
| 104 | 1 |
| 108 | 1 |
| 120 | 1 |
| 123 | 1 |
| 130 | 1 |
| 137 | 1 |
| 138 | 1 |
| 143 | 1 |
| 145 | 1 |
| 146 | 1 |
| 148 | 1 |
| 149 | 1 |
| 152 | 1 |
| 153 | 1 |
| 154 | 1 |
| 155 | 1 |
| 156 | 1 |
| 159 | 1 |
| 160 | 1 |
| 161 | 1 |
| 162 | 1 |
| 163 | 1 |
| 164 | 1 |
| 166 | 1 |
| 167 | 1 |
| 168 | 1 |
| 170 | 1 |
| 171 | 1 |
| 173 | 1 |
| 174 | 1 |
| 175 | 1 |
| 176 | 1 |
| 177 | 1 |
| 179 | 1 |
| 180 | 1 |
| 182 | 1 |
| 186 | 1 |
| 187 | 1 |
| 188 | 1 |
| 189 | 1 |
| 190 | 1 |
| 191 | 1 |
| 192 | 1 |
| 193 | 1 |
| 194 | 1 |
| 195 | 1 |
| 196 | 1 |
| 197 | 1 |
| 198 | 1 |
| 199 | 1 |
| 210 | 1 |
| 211 | 1 |
| 212 | 1 |
| 213 | 1 |
| 214 | 1 |
| 215 | 1 |
| 216 | 1 |
| 217 | 1 |
| 218 | 1 |

For Examples 2 through 112:

PTLC=preparative thin layer chromatography

Reported HPLC retention times (rt=min) chromatography conditions: Phenomenex 150×4.6 mm, 5µ; Gradient 20 mM ammonium acetate buffer, pH 5.7: acetonitrile=85:15 for 2 min, up to 10:90 in 18 min, stay at 10:90 for 3 min and back to 85:15 in 2 min. 30 min run, monitor at 254 nm, flow rate 1 mL/min, injection 20 µL Example 2

Compound 6

Methyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

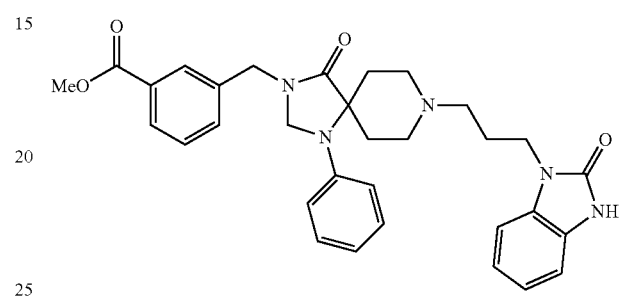

To tert-butyl 3-(3-(methoxycarbonyl)benzyl)-4-oxo-1-phenyl-1,3,8-triazaspiro[4.5]decane-8-carboxylate (0.19 g, 0.4 mmol) was added 4M solution of HCl in dioxane (2 mL). After stirring at room temperature for 3 hours, the reaction mixture was concentrated in vacuo to obtain methyl 3-((4-oxo-1-phenyl-1,3,8-triazaspiro[4.5]decan-3-yl)methyl)benzoate as a hydrochloride salt.

To a solution of the hydrochloride salt and potassium carbonate (0.138 g, 1.0 mmol) in N,N-dimethylformamide (4 mL), was added 1-(3-iodopropyl)-1,3-dihydro-2H-benzimidazol-2-one (0.121 g, 0.4 mmol). After stirring at 55° C. for 18 hours, the reaction mixture was diluted with ethyl acetate (25 mL), washed with water and brine. The organic phase was dried over $MgSO_4$, filtered, concentrated and isolated by pTLC (10% methanol/dichloromethane) to obtain the product (0.09 g, 41%); $^1$H NMR (DMSO-$d_6$): δ 1.61 (br, 2H), 1.83 (br, 2H), 2.32-2.34 (m, 2H), 2.50-2.53 (m, 2H), 2.64-2.66 (m, 6H), 3.85 (s, 3H), 4.58-4.62 (m, 4H) 6.88-6.97 (m, 4H), 7.21-7.23 (m, 4H), 7.51-7.57 (m, 3H), 7.89 (d, 2H, J=7.2 Hz), 10.80 (s, 1H); MS for $C_{32}H_{35}N_5O_4$ m/z 554.12 (M+H)$^+$.

tert-Butyl 3-(3-(methoxycarbonyl)benzyl)-4-oxo-1-phenyl-1,3,8-triazaspiro[4.5]decane-8-carboxylate

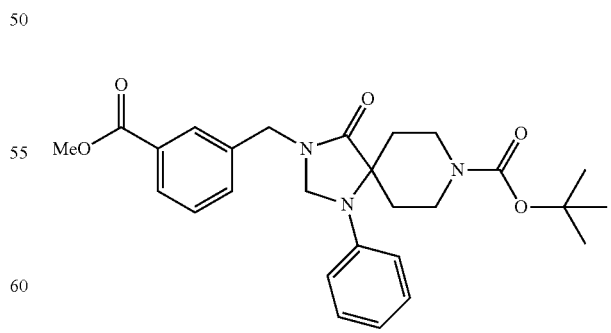

To a solution of tert-butyl 4-oxo-1-phenyl-1,3,8-triazaspiro[4.5]decane-8-carboxylate (0.15 g, 0.45 mmol) and potassium carbonate (0.124 g, 0.9 mmol) in N,N-dimethylformamide (4 mL), was added methyl 3-(bromomethyl)benzoate (0.114 g, 0.5 mmol). After stirring at 60° C. for 60 hours, the reaction mixture was diluted with ethyl acetate (25 mL), washed with dilute citric acid, water and brine. The organic phase was dried over MgSO$_4$, filtered and concentrated to a yellowish brown solid (0.2 g, 93%); $^1$H NMR (DMSO-d$_6$): δ 1.45 (s, 9H), 1.64 (d, 2H, J=13.6 Hz), 2.41-2.49 (m, 2H), 3.48 (br, 2H), 3.85 (s, 3H), 3.86-3.90 (m, 2H), 4.59-4.64 (m, 4H), 6.68 (d, 2H, J=8.4 Hz), 6.77 (t, 1H, J=7.4 Hz), 7.17 (t, 2H, J=8 Hz), 7.54-7.60 (m, 2H), 7.89-7.92 (m, 2H); MS for C$_{27}$H$_{33}$N$_3$O$_5$ m/z 480.08 (M+H)$^+$.

tert-Butyl 4-oxo-1-phenyl-1,3,8-triazaspiro[4.5]decane-8-carboxylate

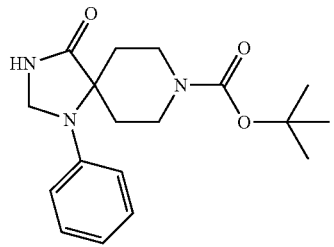 [SMILES: CC(C)(C)OC(=O)N1CCC2(CC1)C(=O)NCN2c1ccccc1]

To a solution of 1-phenyl-1,3,8-triazaspiro[4.5]decan-4-one (0.75 g, 3.24 mmol) in dichloromethane (25 mL) and N,N-diisopropylethylenediamine (1.13 mL, 6.48 mmol, d=0.742), was added di-tert-butyl dicarbonate (0.71 g, 3.27 mmol). After stirring at room temperature for 18 hours, the reaction mixture was diluted with dichloromethane (100 mL), washed with dilute citric acid, water and brine. The organic phase was dried over MgSO$_4$, filtered and concentrated to cream solid (1.1 g, 99%); $^1$H NMR (DMSO-d$_6$): δ 1.45 (s, 9H), 1.58 (d, 2H, J=14 Hz), 2.36-2.39 (m, 2H), 3.39 (br, 2H), 3.84 (br, 2H), 4.59 (s, 2H), 6.68 (d, 2H, J=8 Hz), 6.75 (t, 1H, J=7.2 Hz), 7.18 (t, 2H, J=8.2 Hz), 8.77 (s, 1H); MS for C$_{18}$H$_{25}$N$_3$O$_3$ m/z 332.04 (M+H)$^+$.

Example 3

Compound 7

Methyl 5-(4-oxo-8-(3-(2-oxo-2,3-dihydro-1H-benzo[d]imidazol-1-yl)propyl)-1-phenyl-1,3,8-triazaspiro[4.5]decan-3-yl)pentanoate

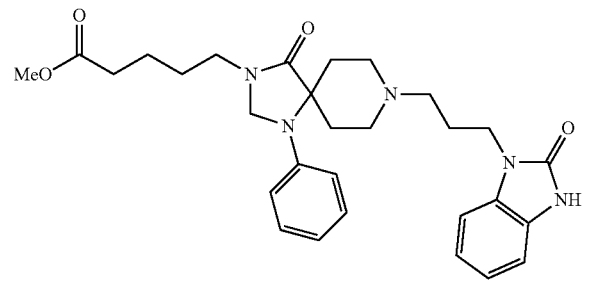 [SMILES: COC(=O)CCCCN1CN(c2ccccc2)C2(CCN(CCCn3c(=O)[nH]c4ccccc43)CC2)C1=O]

To tert-butyl 3-(5-methoxy-5-oxopentyl)-4-oxo-1-phenyl-1,3,8-triazaspiro[4.5]decane-8-carboxylate (0.09 g, 0.2 mmol) was added 4M solution of HCl in dioxane (1 mL). After stirring at room temperature for 2 hours, the reaction mixture was concentrated in vacuo to obtain methyl 5-(4-oxo-1-phenyl-1,3,8-triazaspiro[4.5]decan-3-yl)pentanoate as a hydrochloride salt. To a solution of the hydrochloride salt and potassium carbonate (0.069 g, 0.5 mmol) in N,N-dimethylformamide (2 mL), was added 1-(3-iodopropyl)-1,3-dihydro-2H-benzimidazol-2-one (0.06 g, 0.2 mmol). After stirring at 55° C. for 18 hours, the reaction mixture was diluted with ethyl acetate (25 mL), washed with water and brine. The organic phase was dried over MgSO$_4$, filtered, concentrated and isolated by pTLC (10% methanol/dichloromethane) to obtain the product (0.05 g, 48%); $^1$H NMR (DMSO-d$_6$): δ 1.50-1.57 (m, 6H), 1.81 (br, 2H), 2.32-2.36 (m, 4H), 2.60-2.67 (m, 8H), 3.57 (s, 3H), 3.84 (t, 2H, J=6.8 Hz), 4.64 (s, 2H), 6.77 (t, 1H, J=7.2 Hz), 6.88 (d, 2H, J=8 Hz), 6.96 (d, 3H, J=3.2 Hz), 7.17-7.19 (m, 1H), 7.25 (t, 2H, J=8.4 Hz), 10.8 (s, 1H); MS for C$_{29}$H$_{37}$N$_5$O$_4$ m/z 520.11 (M+H)$^+$.

tert-Butyl 3-(5-methoxy-5-oxopentyl)-4-oxo-1-phenyl-1,3,8-triazaspiro[4.5]decane-8-carboxylate

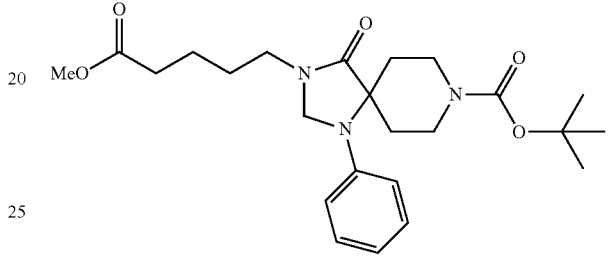

To a solution of tert-butyl 4-oxo-1-phenyl-1,3,8-triazaspiro[4.5]decane-8-carboxylate (0.15 g, 0.45 mmol) and potassium carbonate (0.093 g, 0.68 mmol) in N,N-dimethylformamide (4 mL), was added methyl-5-bromovalerate (0.071 mL, 0.5 mmol, d=1.374). After stirring at 60° C. for 60 hours, the reaction mixture was diluted with ethyl acetate (25 mL), washed with dilute citric acid, water and brine. The organic phase was dried over MgSO$_4$, filtered and isolated by pTLC (50% ethyl acetate/hexanes) to get the title compound (0.1 g, 50%); $^1$H NMR (DMSO-d$_6$): δ 1.43 (s, 9H), 1.46-1.57 (m, 8H), 2.35 (t, 4H, J=7.6 Hz), 3.35 (t, 2H, J=6.8 Hz), 3.57 (s, 3H), 3.85 (br, 2H), 4.67 (s, 2H), 6.71 (d, 2H, J=8 Hz), 6.71 (t, 1H, J=7.2 Hz), 7.20 (t, 2H, J=7.2 Hz); MS for C$_{24}$H$_{35}$N$_3$O$_5$ m/z 446.09 (M+H)$^+$.

Example 4

Compound 8

Ethyl 4-(4-oxo-8-(3-(2-oxo-2,3-dihydro-1H-benzo[d]imidazol-1-yl)propyl)-1-phenyl-1,3,8-triazaspiro[4.5]decan-3-yl)butanoate

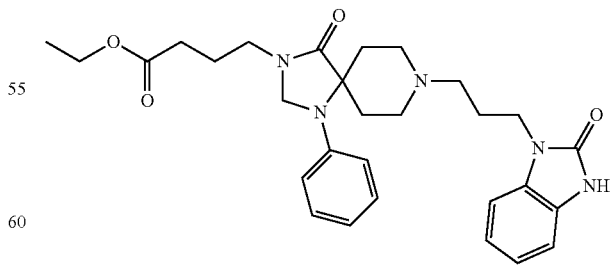

To a solution of tert-butyl 4-oxo-1-phenyl-1,3,8-triazaspiro[4.5]decane-8-carboxylate (0.15 g, 0.45 mmol) and potassium carbonate (0.124 g, 0.9 mmol) in N,N-dimethylformamide (4 mL), was added ethyl-4-bromobutyrate (0.072 mL, 0.5 mmol, d=1.35). After stirring at 60° C. for 60 hours, the reaction mixture was diluted with ethyl acetate (25 mL), washed with dilute citric acid, water and brine. The organic phase was dried over MgSO$_4$, filtered and concentrated in vacuo to obtain tert-butyl 3-(4-ethoxy-4-oxobutyl)-4-oxo-1-phenyl-1,3,8-triazaspiro[4.5]decane-8-carboxylate.

To tert-butyl 3-(4-ethoxy-4-oxobutyl)-4-oxo-1-phenyl-1,3,8-triazaspiro[4.5]decane-8-carboxylate (0.09 g, 0.2 mmol) was added 4M solution of HCl in dioxane (2 mL). After stirring at room temperature for 2 hours, the reaction mixture was concentrated in vacuo to obtain ethyl 4-(4-oxo-1-phenyl-1,3,8-triazaspiro[4.5]decan-3-yl)butanoate as a hydrochloride salt.

To a solution of the hydrochloride salt and potassium carbonate (0.124 g, 0.9 mmol) in N,N-dimethylformamide (3 mL), was added 1-(3-iodopropyl)-1,3-dihydro-2H-benzimidazol-2-one (0.109 g, 0.36 mmol). After stirring at 60° C. for 18 hours, the reaction mixture was diluted with ethyl acetate (25 mL), washed with water and brine. The organic phase was dried over MgSO$_4$, filtered, concentrated and isolated by pTLC (10% methanol/dichloromethane) to obtain the product (0.085 g, 36%); $^1$H NMR (DMSO-d$_6$): δ 1.16 (t, 3H, J=7.2 Hz), 1.52 (d, 2H, J=12.4 Hz), 1.80-1.84 (m, 4H), 2.29-2.32 (m, 4H), 2.61-2.67 (m, 6H), 3.31-3.35 (m, 2H), 3.84 (m, 2H), 4.03 (q, 2H, J=6.8 Hz), 4.65 (br, 2H), 6.76 (t, 1H, J=7.2 Hz), 6.88 (d, 2H, J=8 Hz), 6.96-7.07 (m, 3H), 7.14 (m, 1H), 7.25 (t, 2H, J=8 Hz), 10.8 (s, 1H); MS for C$_{29}$H$_{37}$N$_5$O$_4$ m/z 520.15 (M+H)$^+$.

Example 5

Compound 11

3-((4-Cho-8-(3-(2-oxo-2,3-dihydro-1H-benzo[d]imidazol-1-yl)propyl)-1-phenyl-1,3,8-triazaspiro[4.5]decan-3-yl)methyl)benzoic acid

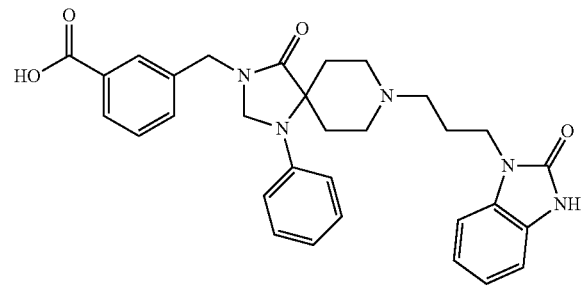 [SMILES: O=C(O)c1cccc(CN2CN(c3ccccc3)C3(CCN(CCCn4c(=O)[nH]c5ccccc54)CC3)C2=O)c1]

To tert-butyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate (0.86 g, 1.44 mmol) was added 4M solution of HCl in dioxane (10 mL). After stirring at room temperature for 4 hours, the reaction mixture was concentrated in vacuo and lyophilized in acetonitrile/water (1:1) to obtain the title compound as a hydrochloride salt (0.8 g); $^1$H NMR (DMSO-d$_6$): δ 1.89 (d, 2H, J=14.4 Hz), 2.15 (t, 2H, J=6.4 Hz), 2.90-2.96 (m, 2H), 3.19-3.22 (m, 2H), 3.50-3.66 (m, 6H), 3.90 (t, 2H, J=7.2 Hz), 4.63-4.66 (m, 4H), 6.76 (t, 1H, J=7.2 Hz), 6.99-7.04 (m, 5H), 7.18-7.24 (m, 3H), 7.50-7.57 (m, 2H), 10.77 (br, 1H), 10.91 (s, 1H), 13.01 (br, 1H); MS for C$_{31}$H$_{33}$N$_5$O$_4$ m/z 540.07 (M+H)$^+$.

tert-Butyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

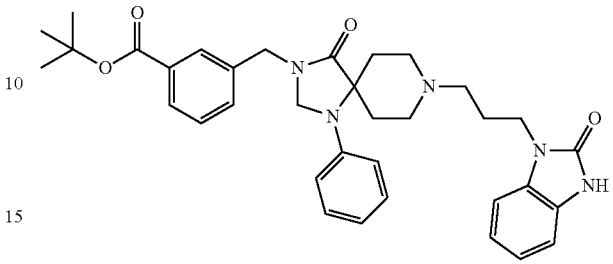

To a solution of benzyl 3-(3-(tert-butoxycarbonyl)benzyl)-4-oxo-1-phenyl-1,3,8-triazaspiro[4.5]decane-8-carboxylate (1.7 g, 3.06 mmol) in methanol (20 mL), was added 10 wt % palladium on carbon (0.5 g). After stirring under hydrogen at room temperature and atmospheric pressure for 2 hours, the reaction mixture was filtered, washed with methanol, concentrated in vacuo to obtain tert-butyl 3-((4-oxo-1-phenyl-1,3,8-triazaspiro[4.5]decan-3-yl)methyl)benzoate (1.2 g, 94%).

To a solution of tert-butyl 3-((4-oxo-1-phenyl-1,3,8-triazaspiro[4.5]decan-3-yl)methyl)benzoate (1.2 g, 2.84 mmol) and potassium carbonate (0.59 g, 4.3 mmol) in N,N-dimethylformamide (20 mL), was added 1-(3-iodopropyl)-1,3-dihydro-2H-benzimidazol-2-one (0.86 g, 2.84 mmol). After stirring at 55° C. for 5 hours, the reaction mixture was diluted with ethyl acetate (100 mL), washed with water and brine. The organic phase was dried over MgSO$_4$, filtered, concentrated and isolated by Biotage flash chromatography (2-10% methanol/dichloromethane) to obtain the title compound (1 g, 59%); $^1$H NMR (DMSO-d$_6$): δ 1.51 (s, 9H), 1.60 (d, 2H, J=13.2 Hz), 1.82 (t, 2H, J=6.4 Hz), 2.35 (t, 2H, J=6.4 Hz), 2.53-2.60 (m, 4H), 2.65-2.71 (m, 4H), 3.85 (t, 2H, J=6.8 Hz), 4.56-4.60 (m, 2H), 6.76 (t, 1H, J=14.4 Hz), 6.85 (d, 2H, J=8 Hz), 6.95-6.97 (m, 3H), 7.17-7.24 (m, 3H), 7.48-7.54 (m, 2H), 7.78 (s, 1H), 7.82 (dt, 1H, J=7.2 and 1.6 Hz) 10.81 (s, 1H); MS for C$_{35}$H$_{41}$N$_5$O$_4$ m/z 596 (M+H)$^+$.

Benzyl 3-(3-tert-butoxycarbonyl)benzyl)-4-oxo-1-phenyl-1,3,8-triazaspiro[4.5]decane-8-carboxylate

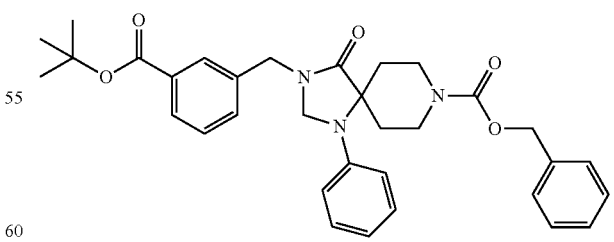

To a solution of benzyl 4-oxo-1-phenyl-1,3,8-triazaspiro[4.5]decane-8-carboxylate (3 g, 8.2 mmol) and potassium carbonate (1.7 g, 12.3 mmol) in N,N-dimethylformamide (50 mL), was added tert-butyl-3-(bromomethyl)benzoate (2.34 g, 8.62 mmol). After stirring at 55° C. for 18 hours, the reaction mixture was diluted with ethyl acetate (200 mL), washed with dilute citric acid, water and brine. The organic phase was dried over MgSO$_4$, filtered, and isolated by Biotage flash chromatography (10-100% ethyl acetate/hexanes) to obtain the title compound (1.7 g, 37%); $^1$H NMR (DMSO-d$_6$): δ 1.52 (s, 9H), 1.71 (d, 2H, J=13.6 Hz), 2.35-2.43 (m, 2H), 3.57 (br, 2H), 3.99-4.05 (m, 2H), 4.61-4.63 (m, 4H), 5.10-5.16 (m, 2H), 6.71 (d, 2H, J=8.4 Hz), 6.78 (t, 1H, J=7.2 Hz), 7.17 (t, 2H, J=7.6 Hz), 7.33-7.38 (m, 5H), 7.49-7.56 (m, 2H), 7.80-7.84 (m, 2H); MS for C$_{33}$H$_{37}$N$_3$O$_5$ m/z 556.07 (M+H)$^+$.

Benzyl 4-oxo-1-phenyl-1,3,8-triazaspiro[4.5]decane-8-carboxylate

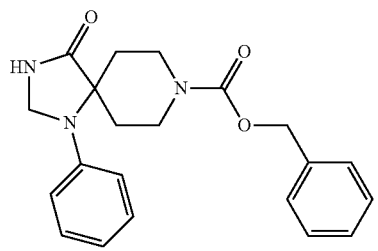 [SMILES: O=C(OCc1ccccc1)N1CCC2(CC1)C(=O)NCN2c1ccccc1]

To a solution of 1-phenyl-1,3,8-triazaspiro[4.5]decan-4-one (5 g, 21.6 mmol) in dichloromethane (50 mL) and pyridine (3.5 mL, 43.2 mmol, d=0.978), was added benzyl chloroformate (3.15 mL, 22.04 mmol, d=1.195). After stirring at room temperature for 16 hours, the reaction mixture was diluted with dichloromethane (100 mL), washed with dilute citric acid, water and brine. The organic phase was dried over MgSO$_4$, filtered and concentrated to cream solid (6 g, 76%); $^1$H NMR (DMSO-d$_6$): δ 1.65 (d, 2H, J=13.6 Hz), 2.32-2.40 (m, 2H), 3.51 (br, 2H), 3.95-3.99 (m, 2H), 4.59 (s, 2H), 5.11-5.15 (m, 2H), 6.68 (d, 2H, J=8 Hz), 6.75 (t, 1H, J=7.2 Hz), 7.18 (t, 2H, J=7.6 Hz), 7.30-7.38 (m, 5H), 8.81 (s, 1H); MS for C$_{21}$H$_{23}$N$_3$O$_3$ m/z 366 (M+H)$^+$.

Example 6

Compound 13

Methyl 5-(4-oxo-8-(3-(2-oxo-2,3-dihydro-1H-benzo[d]imidazol-1-yl)propyl)-1-phenyl-1,3,8-triazaspiro[4.5]decan-3-yl)-5-phenylpentanoate

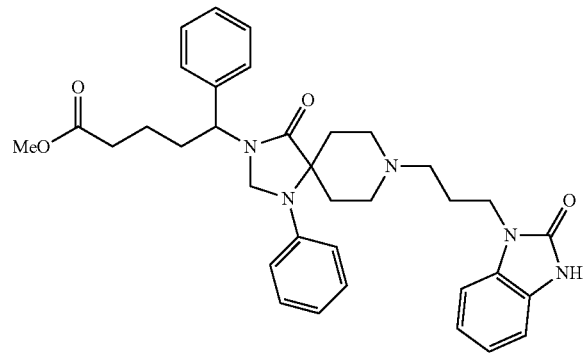 [SMILES: COC(=O)CCCC(c1ccccc1)N1CN(c2ccccc2)C2(CCN(CCCn3c(=O)[nH]c4ccccc43)CC2)C1=O]

To a solution of tert-butyl 4-oxo-1-phenyl-1,3,8-triazaspiro[4.5]decane-8-carboxylate (0.2 g, 0.6 mmol) and potassium carbonate (0.124 g, 0.9 mmol) in N,N-dimethylformamide (3 mL), was added methyl 5-bromo-5-phenylpentanoate (0.163 g, 0.6 mmol). After stirring at 60° C. for 18 hours, the reaction mixture was diluted with ethyl acetate (25 mL), washed with dilute citric acid, water and brine. The organic phase was dried over MgSO$_4$, filtered and concentrated in vacuo to obtain the title compound.

To tert-butyl 3-(5-methoxy-5-oxo-1-phenylpentyl)-4-oxo-1-phenyl-1,3,8-triazaspiro[4.5]decane-8-carboxylate (0.07 g, 0.13 mmol) was added 4M solution of HCl in dioxane (1.5 mL). After stirring at room temperature for 90 minutes, the reaction mixture was concentrated in vacuo to obtain methyl 5-(4-oxo-1-phenyl-1,3,8-triazaspiro[4.5]decan-3-yl)-5-phenylpentanoate as a hydrochloride salt.

To a solution of the hydrochloride salt and potassium carbonate (0.045 g, 0.32 mmol) in N,N-dimethylformamide (2 mL), was added 1-(3-iodopropyl)-1,3-dihydro-2H-benzimidazol-2-one (0.041 g, 0.13 mmol). After stirring at 60° C. for 18 hours, the reaction mixture was diluted with ethyl acetate (20 mL), washed with water and brine. The organic phase was dried over MgSO$_4$, filtered, concentrated and isolated by preparatory TLC (10% methanol/dichloromethane) to obtain the title compound (0.019 g, 25%); $^1$H NMR (DMSO-d$_6$): δ 1.41-1.57 (m, 4H), 1.80 (t, 2H, J=6.4 Hz), 1.98-2.10 (m, 2H), 2.33-2.49 (m, 7H), 2.64-2.70 (m, 4H), 3.56 (s, 3H), 3.84 (t, 2H, J=6.8 Hz), 4.26 (d, 1H, J=5.2 Hz), 4.72 (d, 1H, J=5.2 Hz), 5.15-5.19 (m, 1H), 6.76 (t, 1H, J=7.2 Hz), 6.86 (d, 2H, J=8.4 Hz), 6.96 (d, 3H, J=3.2 Hz), 7.17-7.24 (m, 3H), 7.29-7.32 (m, 1H), 7.35-7.40 (m, 3H), 10.80 (s, 1H); MS for C$_{35}$H$_{41}$N$_5$O$_4$ m/z 596.06 (M+H)$^+$.

Example 7

Compound 14

Methyl 2-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

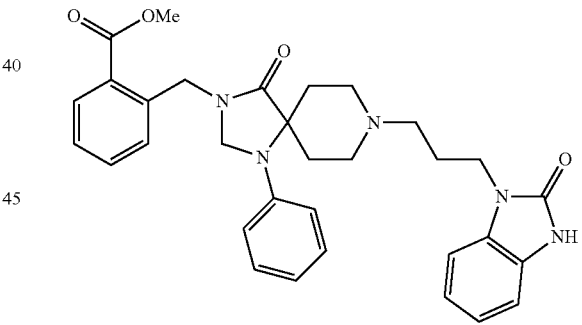

To tert-butyl 3-(2-(methoxycarbonyl)benzyl)-4-oxo-1-phenyl-1,3,8-triazaspiro[4.5]decane-8-carboxylate (0.12 g, 0.25 mmol) was added 4M solution of HCl in dioxane (2.5 mL). After stirring at room temperature for 90 minutes, the reaction mixture was concentrated in vacuo to obtain methyl 2-((4-oxo-1-phenyl-1,3,8-triazaspiro[4.5]decan-3-yl)methyl)benzoate as a hydrochloride salt.

To a solution of the hydrochloride salt and potassium carbonate (0.086 g, 0.625 mmol) in N,N-dimethylformamide (2 mL), was added 1-(3-iodopropyl)-1,3-dihydro-2H-benzimidazol-2-one (0.076 g, 0.25 mmol). After stirring at 60° C. for 18 hours, the reaction mixture was diluted with ethyl acetate (25 mL), washed with water and brine. The organic phase was dried over MgSO$_4$, filtered, concentrated and isolated by preparatory TLC (10% methanol/dichloromethane) to obtain the title compound (0.04 g, 29%); $^1$H NMR (DMSO-d$_6$): δ 1.64 (d, 2H, J=12.8 Hz), 1.82 (t, 2H, J=6.8 Hz), 2.32 (t, 2H, J=6.4

Hz), 2.52-2.72 (m, 6H), 3.83-3.85 (m, 5H), 4.59 (s, 2H), 5.86 (s, 2H), 6.76 (t, 1H, J=7.6 Hz), 6.83 (d, 2H, J=8 Hz), 6.97 (d, 3H, J=2.8 Hz), 7.18-7.25 (m, 3H), 7.31 (d, 1H, J=7.2 Hz), 7.44 (t, 1H, J=7.6 Hz), 7.61 (dt, 1H, J=7.2 and 1.2 Hz), 7.89 (dd, 1H, J=8 and 1.6 Hz), 10.82 (s, 1H); MS for $C_{32}H_{35}N_5O_4$ m/z 554.05 (M+H)$^+$.

tert-Butyl 3-(2-(methoxycarbonyl)benzyl)-4-oxo-1-phenyl-1,3,8-triazaspiro[4.5]decane-8-carboxylate

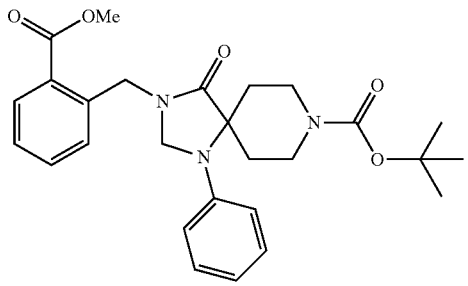 [SMILES: COC(=O)c1ccccc1CN1CN(c2ccccc2)C2(CCN(C(=O)OC(C)(C)C)CC2)C1=O]

To a solution of tert-butyl 4-oxo-1-phenyl-1,3,8-triazaspiro[4.5]decane-8-carboxylate (0.5 g, 1.5 mmol) and potassium carbonate (0.41 g, 3.0 mmol) in N,N-dimethylformamide (3 mL), was added methyl 2-(bromomethyl)benzoate (0.38 g, 1.66 mmol). After stirring at 55° C. for 18 hours, the reaction mixture was diluted with ethyl acetate (25 mL), washed with dilute citric acid, water and brine. The organic phase was dried over MgSO$_4$, filtered and isolated by Biotage flash chromatography (10-60% ethyl acetate/hexanes) to obtain the title compound (0.12 g, 17%); $^1$H NMR (DMSO-d$_6$): δ 1.46 (s, 9H), 1.70 (d, 2H, J=14 Hz), 2.41-2.49 (m, 2H), 3.49-3.53 (m, 2H), 3.83-3.87 (m, 5H), 4.63 (s, 2H), 4.89 (s, 4H), 6.67 (d, 2H, J=8.4 Hz), 6.77 (t, 1H, J=7.4 Hz), 7.18 (t, 2H, J=8.4 Hz), 7.34 (d, 1H, J=8 Hz), 7.46 (d, 1H, J=7.6 Hz), 7.59-7.63 (m, 2H), 7.68 (dt, 1H, J=7.6 and 0.8 Hz), 7.78 (t, 1H, J=6.8 Hz), 7.85 (d, 1H, J=7.6 Hz), 7.91 (dd, 1H, J=7.6 and 1.6 Hz); MS for $C_{27}H_{33}N_3O_5$ m/z 480.04 (M+H)$^+$.

Example 8

Compound 15

Methyl 4-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

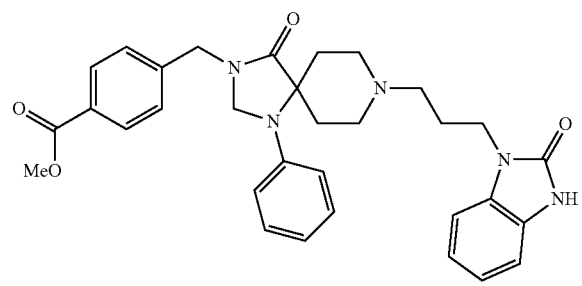 [SMILES: COC(=O)c1ccc(CN2CN(c3ccccc3)C3(CCN(CCCn4c(=O)[nH]c5ccccc54)CC3)C2=O)cc1]

To tert-butyl 3-(4-(methoxycarbonyl)benzyl)-4-oxo-1-phenyl-1,3,8-triazaspiro[4.5]decane-8-carboxylate (0.31 g, 0.65 mmol) was added 4M solution of HCl in dioxane (3 mL). After stirring at room temperature for 90 minutes, the reaction mixture was concentrated in vacuo to obtain methyl 4-((4-oxo-1-phenyl-1,3,8-triazaspiro[4.5]decan-3-yl)methyl)benzoate as a hydrochloride salt.

To a solution of the hydrochloride salt and potassium carbonate (0.225 g, 1.625 mmol) in N,N-dimethylformamide (3 mL), was added 1-(3-iodopropyl)-1,3-dihydro-2H-benzimidazol-2-one (0.196 g, 0.65 mmol). After stirring at 60° C. for 18 hours, the reaction mixture was diluted with ethyl acetate (25 mL), washed with water and brine. The organic phase was dried over MgSO$_4$, filtered, concentrated and isolated by preparatory TLC (10% methanol/dichloromethane) to obtain the title compound (0.11 g, 31%); $^1$H NMR (DMSO-d$_6$): δ 1.61 (d, 2H, J=12.8 Hz), 1.82 (t, 2H, J=6.8 Hz), 2.34 (t, 2H, J=6.4 Hz), 2.50-2.72 (m, 6H), 3.83-3.87 (m, 5H), 4.54-4.61 (m, 4H), 6.76 (t, 1H, J=7.2 Hz), 6.84 (d, 2H, J=8 Hz), 6.96 (d, 3H, J=3.2 Hz), 7.17-7.24 (m, 3H), 7.42 (d, 2H, J=8 Hz), 7.96 (d, 2H, J=8.4 Hz), 10.82 (s, 1H); MS for $C_{32}H_{35}N_5O_4$ m/z 554.05 (M+H)$^+$.

tert-Butyl 3-(4-(methoxycarbonyl)benzyl)-4-oxo-1-phenyl-1,3,8-triazaspiro[4.5]decane-8-carboxylate

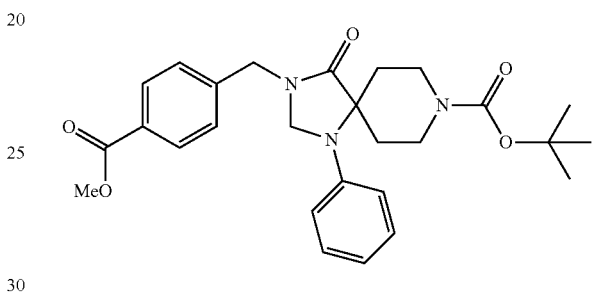

To a solution of tert-butyl 4-oxo-1-phenyl-1,3,8-triazaspiro[4.5]decane-8-carboxylate (0.75 g, 2.26 mmol) and potassium carbonate (0.62 g, 4.52 mmol) in N,N-dimethylformamide (10 mL), was added methyl 4-(bromomethyl)benzoate (0.52 g, 2.26 mmol). After stirring at 60° C. for 18 hours, the reaction mixture was diluted with ethyl acetate (25 mL), washed with dilute citric acid, water and brine. The organic phase was dried over MgSO$_4$, filtered and isolated by Biotage flash chromatography (10-60% ethyl acetate/hexanes) to obtain the title compound (0.31 g, 29%); $^1$H NMR (DMSO-d$_6$): δ 1.46 (s, 9H), 1.66 (d, 2H, J=14.4 Hz), 2.41-2.49 (m, 2H), 3.83-3.85 (m, 7H), 4.56-4.64 (m, 4H), 6.68 (d, 2H, J=8 Hz), 6.77 (t, 1H, J=7.6 Hz), 7.17 (t, 2H, J=8.4 Hz), 7.44 (dd, 2H, J=8.8 and 2 Hz), 7.96 (dd, 2H, J=8 and 3.2 Hz); MS for $C_{27}H_{33}N_3O_5$ m/z 480.04 (M+H)$^+$.

Example 9

Compound 16

2-(Dimethylamino)ethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

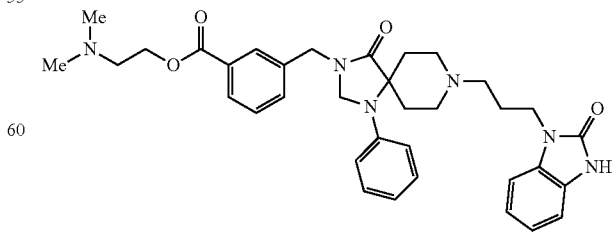

To tert-butyl 3-(3-((2-(dimethylamino)ethoxy)carbonyl)benzyl)-4-oxo-1-phenyl-1,3,8-triazaspiro[4.5]decane-8-carboxylate (0.17 g, 0.32 mmol) was added 4M solution of HCl in dioxane (3 mL). After stirring at room temperature for 90 minutes, the reaction mixture was concentrated in vacuo to obtain 2-(dimethylamino)ethyl 3-((4-oxo-1-phenyl-1,3,8-triazaspiro[4.5]decan-3-yl)methyl)benzoate as a hydrochloride salt.

To a solution of the hydrochloride salt and potassium carbonate (0.111 g, 0.8 mmol) in N,N-dimethylformamide (2 mL), was added 1-(3-iodopropyl)-1,3-dihydro-2H-benzimidazol-2-one (0.097 g, 0.32 mmol). After stirring at 55° C. for 18 hours, the reaction mixture was diluted with ethyl acetate (25 mL), washed with water and brine. The organic phase was dried over MgSO$_4$, filtered, concentrated and isolated by preparatory TLC (15% methanol/dichloromethane followed by 10% methanol/dichloromethane) to obtain the product (0.033 g, 17%); $^1$H NMR (DMSO-d$_6$): δ 1.60 (d, 2H, J=12.4 Hz), 1.83 (t, 2H, J=6.4 Hz), 2.17 (s, 6H), 2.32-2.34 (m, 2H), 2.59 (t, 2H, J=5.6 Hz), 2.67-2.72 (m, 6H), 3.85 (t, 2H, J=6.4 Hz), 4.33 (t, 2H, J=5.6 Hz) 4.58-4.62 (m, 4H), 6.76 (t, 1H, J=7.6 Hz), 6.84 (d, 2H, J=8 Hz), 6.96 (d, 3H, J=3.6 Hz), 7.18-7.24 (m, 3H), 7.52-7.58 (m, 2H), 7.85-7.89 (m, 2H), 10.82 (s, 1H); MS for C$_{35}$H$_{42}$N$_6$O$_4$ m/z 611.10 (M+H)$^+$.

tert-Butyl 3-(3-(((2-(dimethylamino)ethoxy)carbonyl)benzyl)-4-oxo-1-phenyl-1,3,8-triazaspiro[4.5]decane-8-carboxylate

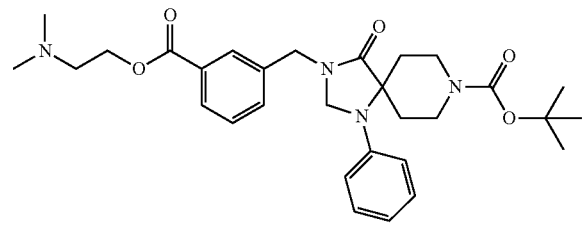 [SMILES: CN(C)CCOC(=O)c1cccc(CN2CN(c3ccccc3)C3(CCN(C(=O)OC(C)(C)C)CC3)C2=O)c1]

To a solution of tert-Butyl 3-(3-(methoxycarbonyl)benzyl)-4-oxo-1-phenyl-1,3,8-triazaspiro[4.5]decane-8-carboxylate (2 g, 4.17 mmol) in methanol (28 mL) was added lithium hydroxide monohydrate (0.35 g, 8.34 mmol) in water (14 mL). After stirring at room temperature for 18 h, the reaction mixture was concentrated in vacuo, acidified with dilute citric acid, extracted with dichloromethane. The organic extracts were washed with brine, dried over MgSO$_4$, filtered and concentrated to obtain 3-((8-(tert-butoxycarbonyl)-4-oxo-1-phenyl-1,3,8-triazaspiro[4.5]decan-3-yl)methyl)benzoic acid (1.88 g, 97%).

To a solution of 3-((8-(tert-butoxycarbonyl)-4-oxo-1-phenyl-1,3,8-triazaspiro[4.5]decan-3-yl)methyl)benzoic acid (0.34 g, 0.73 mmol), dicyclohexylcarbodiimide (0.18 g, 0.88 mmol) and 4-(dimethylamino)pyridine (0.011 g, 0.088 mmol) in dichloromethane (10 mL), was added N,N-dimethylethanolamine (0.065 mg, 0.73 mmol). After stirring at room temperature for 60 hours, the reaction mixture was filtered, concentrated in vacuo and isolated by preparatory TLC (10% methanol/dichloromethane) to obtain tert-butyl 3-(3-((2-(dimethylamino)ethoxy)carbonyl)benzyl)-4-oxo-1-phenyl-1,3,8-triazaspiro[4.5]decane-8-carboxylate (0.17 g, 43%); MS for C$_{30}$H$_{40}$N$_4$O$_5$ m/z 537 (M+H)$^+$.

Example 10

Compound 17

4-((4-Oxo-8-(3-(2-oxo-2,3-dihydro-1H-benzo[d]imidazol-1-yl)propyl)-1-phenyl-1,3,8-triazaspiro[4.5]decan-3-yl)methyl)benzoic acid

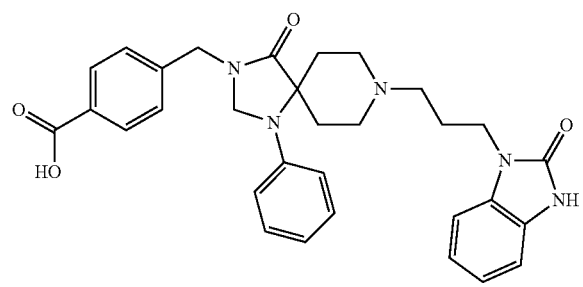 [SMILES: O=C(O)c1ccc(CN2CN(c3ccccc3)C3(CCN(CCCn4c(=O)[nH]c5ccccc54)CC3)C2=O)cc1]

To a solution of methyl 4-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate (0.4 g, 0.72 mmol) in methanol (6 mL) was added lithium hydroxide monohydrate (0.061 g, 1.44 mmol) in water (2 mL). After stirring at room temperature for 18 h, the reaction mixture was concentrated in vacuo and isolated by reverse phase HPLC to obtain the title compound as an acetate salt (0.05 g, 13%); $^1$H NMR (DMSO-d$_6$): δ 1.60 (d, 2H, J=6.8 Hz), 1.82 (t, 2H, J=6.8 Hz), 2.35 (t, 2H, J=6.8 Hz), 2.50-2.71 (m, 7H), 3.85 (t, 2H, J=6.8 Hz), 4.55-4.56 (m, 4H), 6.75 (t, 1H, J=7.2 Hz), 6.84 (d, 2H, J=8.4 Hz), 6.96 (d, 3H, J=2.4 Hz), 7.17-7.26 (m, 5H), 7.85 (d, 2H, J=8 Hz); MS for C$_{31}$H$_{33}$N$_5$O$_4$ m/z 540.05 (M+H)$^+$.

Example 11

Compound 18

(S)-sec-Butyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

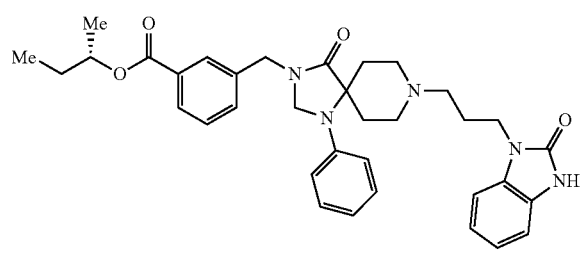 [SMILES: CC[C@H](C)OC(=O)c1cccc(CN2CN(c3ccccc3)C3(CCN(CCCn4c(=O)[nH]c5ccccc54)CC3)C2=O)c1]

To (S)-tert-butyl 3-(3-(sec-butoxycarbonyl)benzyl)-4-oxo-1-phenyl-1,3,8-triazaspiro[4.5]decane-8-carboxylate (0.072 g, 0.14 mmol) was added 4M solution of HCl in dioxane (1.5 mL). After stirring at room temperature for an hour, the reaction mixture was concentrated in vacuo to obtain (S)-sec-butyl 3-((4-oxo-1-phenyl-1,3,8-triazaspiro[4.5]decan-3-yl)methyl)benzoate as a hydrochloride salt.

To a solution of the hydrochloride salt and potassium carbonate (0.048 g, 0.35 mmol) in N,N-dimethylformamide (2 mL), was added 1-(3-iodopropyl)-1,3-dihydro-2H-benzimidazol-2-one (0.042 g, 0.14 mmol). After stirring at 55° C. for 18 hours, the reaction mixture was diluted with ethyl acetate (25 mL), washed with water and brine. The organic phase was dried over MgSO$_4$, filtered, concentrated and isolated by preparatory TLC (10% methanol/dichloromethane) to obtain the product (0.028 g, 34%); $^1$H NMR (DMSO-d$_6$): δ 0.87 (t, 3H, J=7.2 Hz), 1.25 (d, 3H, J=6.4 Hz), 1.59-1.64 (m, 4H), 1.83 (br, 2H), 2.35 (br, 2H), 2.50-2.72 (m, 6H), 3.86 (br, 2H), 4.59-4.62 (m, 4H), 4.94-4.99 (m, 1H), 6.67 (d, 2H, J=8.4 Hz), 6.86 (t, 1H, J=7.2 Hz), 6.97 (s, 3H), 7.19-7.25 (m, 3H), 7.51-7.56 (m, 2H), 7.85-7.89 (m, 2H), 10.82 (s, 1H); MS for C$_{35}$H$_{41}$N$_5$O$_4$ m/z 596.13 (M+H)$^+$.

(S)-tert-Butyl 3-(3-(sec-butoxycarbonyl)benzyl)-4-oxo-1-phenyl-1,3,8-triazaspiro[4.5]decane-8-carboxylate

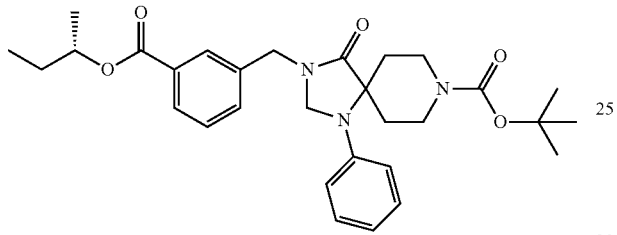

To a solution of 3-((8-(tert-butoxycarbonyl)-4-oxo-1-phenyl-1,3,8-triazaspiro[4.5]decan-3-yl)methyl)benzoic acid (0.1 g, 0.22 mmol), dicyclohexylcarbodiimide (0.055 g, 0.22 mmol) and 4-(dimethylamino)pyridine (0.003 g, 0.026 mmol) in dichloromethane (5 mL), was added (S)-2-butanol (0.020 mL, 0.22 mmol, d=0.803). After stirring at room temperature for 60 hours, the reaction mixture was filtered, concentrated in vacuo and isolated by preparatory TLC (50% ethyl acetate/hexanes) to obtain the title compound (0.076 g, 66%); $^1$H NMR (DMSO-d$_6$): δ 0.89 (t, 3H, J=7.2 Hz), 1.26 (d, 3H, J=6.4 Hz), 1.45 (s, 9H), 1.60-1.66 (m, 4H), 2.32-2.45 (m, 2H), 3.45 (br, 2H), 3.89 (br, 2H), 4.62-4.64 (m, 4H), 4.95-5.00 (m, 1H), 6.68 (d, 2H, J=8.4 Hz), 6.77 (t, 1H, J=7.2 Hz), 7.17 (t, 2H, J=7.2 Hz), 7.51-7.59 (m, 2H), 7.86-7.92 (m, 2H); MS for C$_{30}$H$_{39}$N$_3$O$_5$ m/z 544.05 (M+Na)$^+$.

Example 12

Compound 19

2-((4-Oxo-8-(3-(2-oxo-2,3-dihydro-1H-benzo[d]imidazol-1-yl)propyl)-1-phenyl-1,3,8-triazaspiro[4.5]decan-3-yl)methyl)benzoic acid

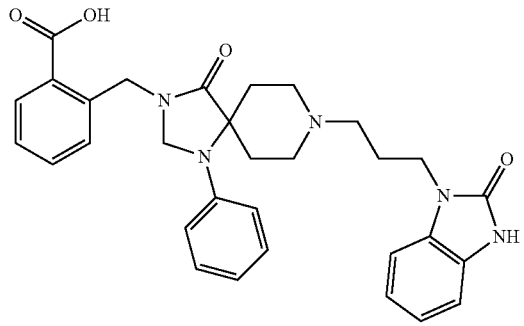 [SMILES: O=C(O)c1ccccc1CN1CN(c2ccccc2)C2(CCN(CCCn3c(=O)[nH]c4ccccc43)CC2)C1=O]

To a solution of methyl 2-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate (0.27 g, 0.49 mmol) in methanol (3 mL) was added lithium hydroxide monohydrate (0.041 g, 0.98 mmol) in water (1 mL). After stirring at room temperature for 18 h, the reaction mixture was concentrated in vacuo and isolated by reverse phase HPLC to obtain the title compound as an acetate salt (0.124 g, 47%); $^1$H NMR (DMSO-d$_6$): δ 1.68 (d, 2H, J=13.2 Hz), 1.85 (t, 2H, J=6.8 Hz), 2.42 (t, 2H, J=6.8 Hz), 2.59-2.65 (m, 2H), 2.71-2.75 (m, 4H), 3.85 (t, 2H, J=6.8 Hz), 4.61 (s, 2H), 4.90 (s, 2H), 6.74 (t, 1H, J=7.2 Hz), 6.83 (d, 2H, J=8.8 Hz), 6.96 (d, 3H, J=3.6 Hz), 7.18-7.26 (m, 4H), 7.39 (t, 1H, J=8 Hz), 7.55 (t, 1H, J=6.8 Hz), 7.89 (dd, 1H, J=8 and 1.2 Hz), 10.83 (s, 1H), 12.60 (br, 1H); MS for C$_{31}$H$_{33}$N$_5$O$_4$ m/z 540.01 (M+H)$^+$.

Example 13

Compound 20

1-Methylpiperidin-4-yl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

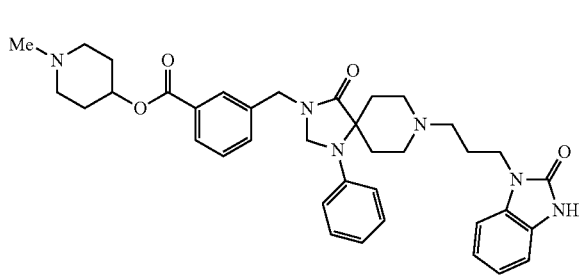 [SMILES: CN1CCC(OC(=O)c2cccc(CN3CN(c4ccccc4)C4(CCN(CCCn5c(=O)[nH]c6ccccc65)CC4)C3=O)c2)CC1]

To tert-butyl 3-(3-((1-methylpiperidin-4-yloxy)carbonyl)benzyl)-4-oxo-1-phenyl-1,3,8-triazaspiro[4.5]decane-8-carboxylate (0.01 g, 0.18 mmol) was added 4M solution of HCl in dioxane (2 mL). After stirring at room temperature for 2 hours, the reaction mixture was concentrated in vacuo to obtain 1-methylpiperidin-4-yl 3-((4-oxo-1-phenyl-1,3,8-triazaspiro[4.5]decan-3-yl)methyl)benzoate as a hydrochloride salt.

To a solution of the hydrochloride salt and potassium carbonate (0.062 g, 0.45 mmol) in N,N-dimethylformamide (1 mL), was added 1-(3-iodopropyl)-1,3-dihydro-2H-benzimidazol-2-one (0.054 g, 0.18 mmol). After stirring at 55° C. for 18 hours, the reaction mixture was diluted with ethyl acetate (25 mL), washed with water and brine. The organic phase was dried over MgSO$_4$, filtered, concentrated and isolated by preparatory TLC (10% methanol/dichloromethane) to obtain the product (0.03 g, 26%); $^1$H NMR (DMSO-d$_6$): δ1.59-1.70 (m, 4H), 1.83-1.87 (m, 4H), 2.15-2.35 (m, 7H), 2.50-2.72 (m, 8H), 3.85 (t, 2H, J=6.4 Hz), 4.59-4.62 (m, 4H), 4.90-4.94 (m, 1H), 6.76 (t, 1H, J=7.6 Hz), 6.84 (d, 2H, J=8.4 Hz), 6.96 (d, 3H, J=3.6 Hz), 7.18-7.24 (m, 3H), 7.51-7.58 (m, 2H), 7.85 (s, 1H), 7.89 (d, 1H, J=7.2 Hz), 10.82 (s, 1H); MS for C$_{37}$H$_{44}$N$_6$O$_4$ m/z 637.22 (M+H)$^+$.

tert-Butyl 3-(3-((1-methylpiperidin-4-yloxy)carbonyl)benzyl)-4-oxo-1-phenyl-1,3,8-triazaspiro[4.5]decane-8-carboxylate

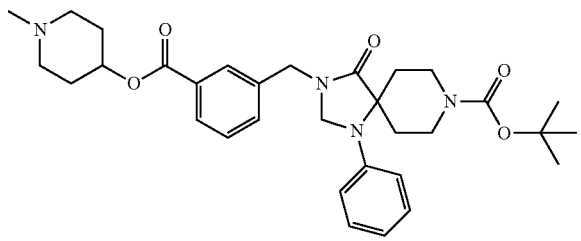 [SMILES: CN1CCC(OC(=O)c2cccc(CN3CN(c4ccccc4)C4(CCN(C(=O)OC(C)(C)C)CC4)C3=O)c2)CC1]

To a solution of 3-((8-(tert-butoxycarbonyl)-4-oxo-1-phenyl-1,3,8-triazaspiro[4.5]decan-3-yl)methyl)benzoic acid (0.15 g, 0.32 mmol), dicyclohexylcarbodiimide (0.079 g, 0.38 mmol) and 4-(dimethylamino)pyridine (0.005 g, 0.038 mmol) in dichloromethane (5 mL), was added (S)-2-butanol (0.037 g, 0.32 mmol). After stirring at room temperature for 60 hours, the reaction mixture was filtered, concentrated in vacuo and isolated by preparatory TLC (10% methanol/dichloromethane) to obtain the title compound (0.1 g, 56%); $^1$H NMR (DMSO-$d_6$): δ 1.45 (s, 9H), 1.63-1.66 (m, 4H), 1.89 (br, 2H), 2.15-2.23 (m, 5H), 2.43-2.48 (m, 4H), 3.43 (br, 2H), 3.89 (br, 2H), 4.60-4.65 (m, 4H), 4.95-5.00 (m, 1H), 6.67 (d, 2H, J=8.4 Hz), 6.76 (t, 1H, J=7.6 Hz), 7.17 (t, 2H, J=8.4 Hz), 7.52-7.60 (m, 2H), 7.86-7.91 (m, 2H); MS for $C_{32}H_{42}N_4O_5$ m/z 563.06 (M+H)$^+$.

Example 14

Compound 21

Benzyl 6-(4-oxo-8-(3-(2-oxo-2,3-dihydro-1H-benzo[d]imidazol-1-yl)propyl)-1-phenyl-1,3,8-triazaspiro[4.5]decan-3-yl)hexanoate To tert-butyl 3-(6-(benzyloxy)-6-oxohexyl)-4-oxo-1-phenyl-1,3,8-triazaspiro[4.5]decane-8-carboxylate (0.08 g, 0.15 mmol) was added 4M solution of HCl in dioxane (1.5 mL). After stirring at room temperature for 2 hours, the reaction mixture was concentrated in vacuo to obtain benzyl 6-(4-oxo-1-phenyl-1,3,8-triazaspiro[4.5]decan-3-yl)hexanoate as a hydrochloride salt.

To a solution of the hydrochloride salt and potassium carbonate (0.052 g, 0.38 mmol) in N,N-dimethylformamide (1.5 mL), was added 1-(3-iodopropyl)-1,3-dihydro-2H-benzimidazol-2-one (0.045 g, 0.15 mmol). After stirring at 55° C. for 24 hours, the reaction mixture was diluted with ethyl acetate (25 mL), washed with water and brine. The organic phase was dried over MgSO$_4$, filtered, concentrated and isolated by preparatory TLC (10% methanol/dichloromethane) to obtain the title compound (0.026 g, 28%); $^1$H NMR (DMSO-$d_6$): δ 1.23-1.29 (m, 2H), 1.49-1.60 (m, 7H), 1.80 (t, 2H, J=6.4 Hz), 2.31-2.37 (m, 4H), 2.54-2.66 (m, 6H), 3.30 (t, 2H, J=7.2 Hz), 3.84 (t, 2H, J=6.4 Hz), 4.63 (s, 2H), 5.05 (s, 2H), 6.76 (t, 1H, J=7.2 Hz), 6.87 (d, 2H, J=8.4 Hz), 6.96 (d, 3H, J=3.2 Hz), 7.12-7.18 (m, 1H), 7.25 (t, 2H, J=8.4 Hz), 7.29-7.34 (m, 5H), 10.82 (s, 1H); MS for $C_{36}H_{43}N_5O_4$ m/z 610.12 (M+H)$^+$.

tert-Butyl 3-(6-(benzyloxy)-6-oxohexyl)-4-oxo-1-phenyl-1,3,8-triazaspiro[4.5]decane-8-carboxylate

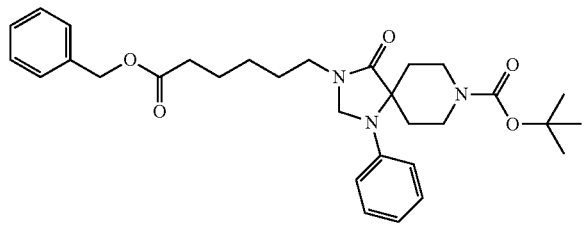

To a solution of tert-butyl 4-oxo-1-phenyl-1,3,8-triazaspiro[4.5]decane-8-carboxylate (0.4 g, 1.2 mmol) and potassium carbonate (0.25 g, 1.8 mmol) in N,N-dimethylformamide (5 mL), was added benzyl 6-bromohexanoate (0.34 g, 1.2 mmol). After stirring at 55° C. for 18 hours, the reaction mixture was diluted with ethyl acetate (25 mL), washed with dilute citric acid, water and brine. The organic phase was dried over MgSO$_4$, filtered and concentrated in vacuo to obtain the title compound (0.08 g, 12%); MS for $C_{31}H_{41}N_3O_5$ m/z 536.16 (M+H)$^+$.

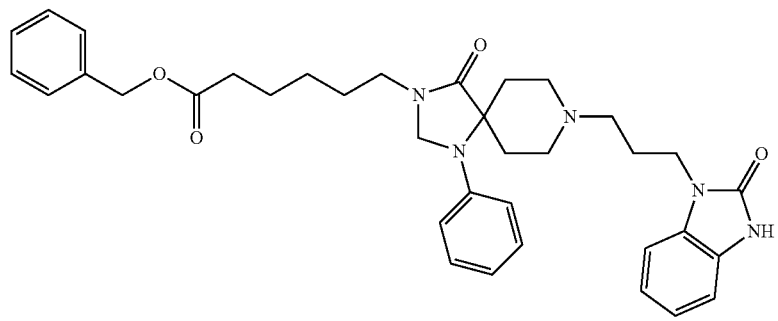 [SMILES: O=C(CCCCCN1CN(c2ccccc2)C2(CCN(CCCn3c(=O)[nH]c4ccccc43)CC2)C1=O)OCc1ccccc1]

Example 15

Compound 22

6-(4-Oxo-8-(3-(2-oxo-2,3-dihydro-1H-benzo[d]imidazol-1-yl)propyl)-1-phenyl-1,3,8-triazaspiro[4.5]decan-3-yl)hexanoic acid

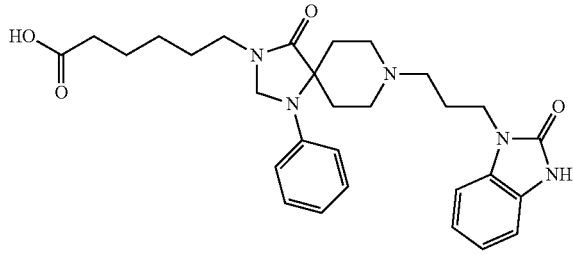 [SMILES: O=C(O)CCCCCN1CN(c2ccccc2)C2(CCN(CCCn3c(=O)[nH]c4ccccc43)CC2)C1=O]

To a solution of benzyl 6-(4-oxo-8-(3-(2-oxo-2,3-dihydro-1H-benzo[d]imidazol-1-yl)propyl)-1-phenyl-1,3,8-triazaspiro[4.5]decan-3-yl)hexanoate (0.25 g, 0.41 mmol) in 4:1 ratio of ethyl acetate/methanol (4 mL), was added 10 wt % palladium on carbon (0.1 g). After stirring under hydrogen at room temperature and atmospheric pressure for 2 hours, the reaction mixture was filtered, washed with 1% acetic acid in methanol, concentrated in vacuo and isolated by reverse phase HPLC to obtain the title compound (0.09 g, 42%); $^1$H NMR (DMSO-$d_6$): δ 1.21-1.26 (m, 2H), 1.47-1.57 (m, 6H), 1.77-1.82 (m, 2H), 2.18 (t, 2H, J=7.2 Hz), 2.32 (t, 2H, J=6.4 Hz), 2.59-2.67 (m, 6H), 2.91 (d, 2H, J=11.2 Hz), 3.84 (t, 2H, J=6.4 Hz), 4.64 (s, 2H), 6.76 (t, 1H, J=7.2 Hz), 6.88 (d, 2H, J=8.4 Hz), 6.96 (d, 3H, J=3.6 Hz), 7.18-7.20 (m, 1H), 7.24 (t, 2H, J=8.8 Hz), 10.82 (s, 1H); MS for $C_{29}H_{37}N_5O_4$ m/z 520.08 (M+H)$^+$.

Example 16

Compound 24

2-(Dimethylamino)-2-oxoethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

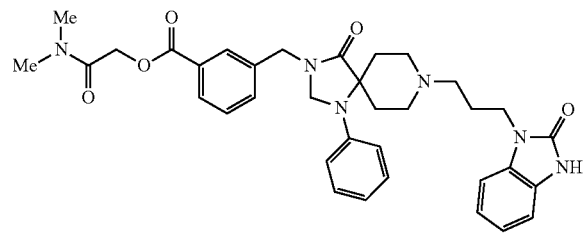 [SMILES: CN(C)C(=O)COC(=O)c1cccc(CN2CN(c3ccccc3)C3(CCN(CCCn4c(=O)[nH]c5ccccc54)CC3)C2=O)c1]

To tert-butyl 3-(3-((2-(dimethylamino)-2-oxoethoxy)carbonyl)benzyl)-4-oxo-1-phenyl-1,3,8-triazaspiro[4.5]decane-8-carboxylate (0.26 g, 0.47 mmol) was added 4M solution of HCl in dioxane (5 mL). After stirring at room temperature for 2 hours, the reaction mixture was concentrated in vacuo to obtain 2-(dimethylamino)-2-oxoethyl 3-((4-oxo-1-phenyl-1,3,8-triazaspiro[4.5]decan-3-yl)methyl)benzoate as a hydrochloride salt.

To a solution of the hydrochloride salt and potassium carbonate (0.162 g, 1.18 mmol) in N,N-dimethylformamide (5 mL), was added 1-(3-iodopropyl)-1,3-dihydro-2H-benzimidazol-2-one (0.142 g, 0.47 mmol). After stirring at 55° C. for 24 hours, the reaction mixture was diluted with ethyl acetate (40 mL), washed with water and brine. The organic phase was dried over MgSO$_4$, filtered, concentrated and isolated by pTLC (10% methanol/dichloromethane) to obtain the title compound (0.140 g, 48%); $^1$H NMR (DMSO-$d_6$): δ 1.60 (d, 2H, J=14 Hz), 1.82 (t, 2H, J=7.2 Hz), 2.31-2.34 (m, 2H), 2.50-2.71 (m, 6H), 2.82 (s, 3H), 2.96 (s, 3H), 3.85 (t, 2H, J=7.2 Hz), 4.61 (d, 4H, J=14.8 Hz), 5.02 (s, 2H), 6.76 (t, 1H, J=7.2 Hz), 6.85 (d, 2H, J=7.6 Hz), 6.96 (d, 3H, J=3.2 Hz), 7.19-7.24 (m, 3H), 7.80-7.83 (m, 2H), 7.89-7.92 (m, 2H), 10.81 (s, 1H); MS for $C_{35}H_{40}N_6O_5$ m/z 625.05 (M+H)$^+$.

tert-Butyl 3-(3-((2-(dimethylamino)-2-oxoethoxy)carbonyl)benzyl)-4-oxo-1-phenyl-1,3,8-triazaspiro[4.5]decane-8-carboxylate

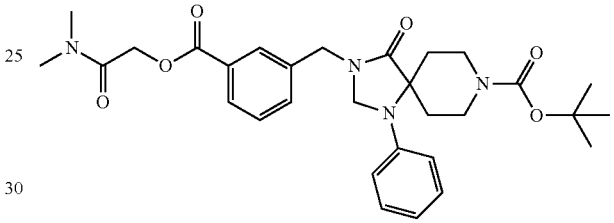

To a solution of tert-butyl 4-oxo-1-phenyl-1,3,8-triazaspiro[4.5]decane-8-carboxylate (0.25 g, 0.54 mmol) and potassium carbonate (0.11 g, 0.81 mmol) in N,N-dimethylformamide (5 mL), was added 2-chloro-N,N-dimethylacetamide (0.055 mL, 0.54 mmol, d=1.182). After stirring at 65° C. for 18 hours, the reaction mixture was diluted with ethyl acetate (25 mL), washed with dilute citric acid, water and brine. The organic phase was dried over MgSO$_4$, filtered and purified by Biotage flash chromatography (1-15% methanol/dichloromethane) to obtain the title compound (0.27 g, 91%); $^1$H NMR (DMSO-$d_6$): δ 1.45 (s, 9H), 1.65 (d, 2H, J=13.6 Hz), 2.41-2.48 (m, 2H), 2.82 (s, 3H), 2.96 (s, 3H), 3.45 (br, 2H), 3.90 (br, 2H), 4.63-4.66 (m, 4H), 5.03 (s, 2H), 6.68 (d, 2H, J=8 Hz), 6.76 (t, 1H, J=7.6 Hz), 7.17 (t, 2H, J=8.8 Hz), 7.54-7.63 (m, 2H), 7.91-7.93 (m, 2H); MS for $C_{30}H_{38}N_4O_6$ m/z 551.04 (M+H)$^+$.

Example 17

Compound 25

2-Morpholinoethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

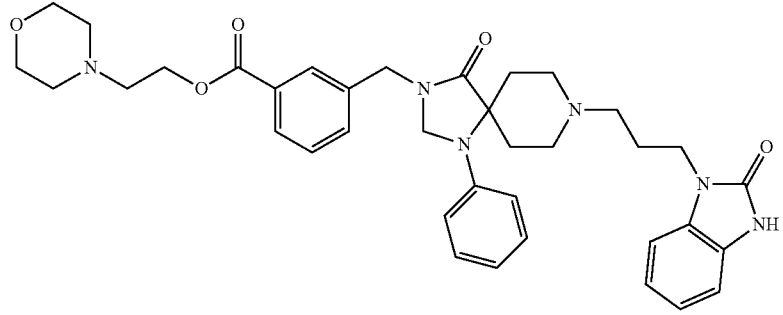 [SMILES: O=C(OCCN1CCOCC1)c1cccc(CN2CN(c3ccccc3)C3(CCN(CCCn4c(=O)[nH]c5ccccc54)CC3)C2=O)c1]

To tert-butyl 3-(3-((2-morpholinoethoxy)carbonyl)benzyl)-4-oxo-1-phenyl-1,3,8-triazaspiro[4.5]decane-8-carboxylate (0.22 g, 0.38 mmol) was added 4M solution of HCl in dioxane (4 mL). After stirring at room temperature for 2 hours, the reaction mixture was concentrated in vacuo to obtain 2-morpholino-2-oxoethyl 3-((4-oxo-1-phenyl-1,3,8-triazaspiro[4.5]decan-3-yl)methyl)benzoate as a hydrochloride salt.

To a solution of the hydrochloride salt and potassium carbonate (0.1312 g, 0.95 mmol) in N,N-dimethylformamide (4 mL), was added 1-(3-iodopropyl)-1,3-dihydro-2H-benzimidazol-2-one (0.115 g, 0.38 mmol). After stirring at 55° C. for 60 hours, the reaction mixture was diluted with ethyl acetate (40 mL), washed with water and brine. The organic phase was dried over MgSO$_4$, filtered, concentrated and isolated by preparatory TLC (12% methanol/dichloromethane) to obtain the title compound (0.13 g, 52%); $^1$H NMR (DMSO-d$_6$): δ 1.60 (d, 2H, J=12.4 Hz), 1.82 (t, 2H, J=7.2 Hz), 2.32-2.42 (m, 6H), 2.57-2.72 (m, 8H), 3.51 (t, 4H, J=4.4 Hz), 3.86 (br, 2H), 4.36 (t, 2H, J=5.6 Hz), 4.59-4.62 (m, 4H), 6.76 (t, 1H, J=7.2 Hz), 6.85 (d, 2H, J=7.6 Hz), 6.97 (s, 3H), 7.18-7.25 (m, 3H), 7.52-7.59 (m, 2H), 7.85-7.89 (m, 2H), 10.82 (s, 1H); MS for C$_{37}$H$_{44}$N$_6$O$_5$ m/z 653.09 (M+H)$^+$.

tert-Butyl 3-(3-((2-morpholinoethoxy)carbonyl)benzyl)-4-oxo-1-phenyl-1,3,8-triazaspiro[4.5]decane-8-carboxylate

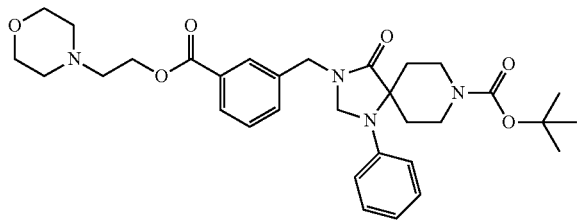 [SMILES: CC(C)(C)OC(=O)N1CCC2(CC1)C(=O)N(Cc1cccc(C(=O)OCCN3CCOCC3)c1)CN2c1ccccc1]

To a solution of 3-((8-(tert-butoxycarbonyl)-4-oxo-1-phenyl-1,3,8-triazaspiro[4.5]decan-3-yl)methyl)benzoic acid (0.3 g, 0.65 mmol), dicyclohexylcarbodiimide (0.16 g, 0.78 mmol) and 4-(dimethylamino)pyridine (0.01 g, 0.078 mmol) in dichloromethane (10 mL), was added hydroxyethyl morpholine (0.037 g, 0.32 mmol, d=1.072). After stirring at room temperature for 18 hours, the reaction mixture was filtered, concentrated in vacuo and isolated by preparatory TLC (5% methanol/dichloromethane) to obtain the title compound (0.22 g, 59%); $^1$H NMR (DMSO-d$_6$): δ 1.45 (s, 9H), 1.59-1.66 (m, 4H), 2.43-2.48 (m, 4H), 2.66 (t, 2H, J=5.6 Hz), 3.32-3.51 (m, 4H), 3.89 (br, 2H), 3.90 (br, 2H), 4.37 (t, 2H, J=5.6 Hz), 4.62-4.65 (m, 4H), 6.68 (d, 2H, J=8.4 Hz), 6.77 (t, 1H, J=7.2 Hz), 7.17 (t, 2H, J=8.8 Hz), 7.53-7.61 (m, 2H), 7.86-7.90 (m, 2H); MS for C$_{32}$H$_{42}$N$_4$O$_6$ m/z 579.09 (M+H)$^+$.

Example 18

Compound 26

(R)-Quinuclidin-3-yl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

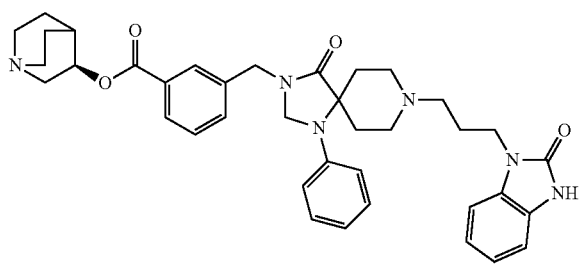 [SMILES: O=C(O[C@H]1CN2CCC1CC2)c1cccc(CN2CN(c3ccccc3)C3(CCN(CCCn4c(=O)[nH]c5ccccc54)CC3)C2=O)c1]

To a refluxing solution of methyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate (0.33 g, 0.59 mmol) and (R)-3-quinuclidinol (0.3 g, 2.4 mmol) in toluene (5 mL), was added titanium(IV)-i-propoxide (0.173 mL, 0.59 mmol, d=0.97). After refluxing for 18 h, the reaction mixture was concentrated in vacuo and isolated by reverse phase HPLC to obtain the title compound (0.13 g, 34%); $^1$H NMR (DMSO-d$_6$): δ 1.31-1.34 (m, 1H), 1.51-1.55 (m, 4H), 1.78-1.88 (m, 3H), 1.98-2.01 (m, 1H), 2.33 (t, 2H, J=7.2 Hz), 2.52-2.72 (m, 11H), 3.15-3.21 (m, 1H), 3.85 (t, 2H, J=6.8 Hz), 4.59-4.62 (m, 4H), 4.90-4.92 (m, 1H), 6.76 (t, 1H, J=7.2 Hz), 6.84 (d, 2H, J=8.4 Hz), 6.96 (d, 3H, J=2.4 Hz), 7.17-7.24 (m, 3H), 7.52-7.59 (m, 2H), 7.87-7.92 (m, 2H), 10.80 (br, 1H); MS for C$_{38}$H$_{44}$N$_6$O$_4$ m/z 649.11 (M+H)$^+$.

Example 19

Compound 30

2-(Diethylamino)-2-oxoethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

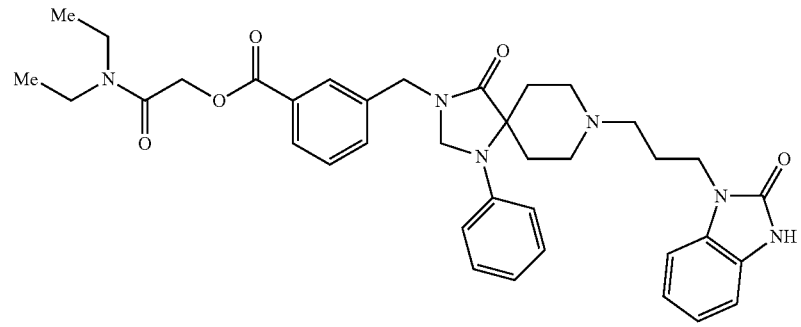 [SMILES: CCN(CC)C(=O)COC(=O)c1cccc(CN2CN(c3ccccc3)C3(CCN(CCCn4c(=O)[nH]c5ccccc54)CC3)C2=O)c1]

To tert-butyl 3-(3-((2-(diethylamino)-2-oxoethoxy)carbonyl)benzyl)-4-oxo-1-phenyl-1,3,8-triazaspiro[4.5]decane-8-carboxylate (0.22 g, 0.38 mmol) was added 4M solution of HCl in dioxane (3 mL). After stirring at room temperature for 2 hours, the reaction mixture was concentrated in vacuo to obtain 2-(diethylamino)-2-oxoethyl 3-((4-oxo-1-phenyl-1,3,8-triazaspiro[4.5]decan-3-yl)methyl)benzoate as a hydrochloride salt.

To a solution of the hydrochloride salt and potassium carbonate (0.131 g, 0.95 mmol) in N,N-dimethylformamide (3 mL), was added 1-(3-iodopropyl)-1,3-dihydro-2H-benzimidazol-2-one (0.115 g, 0.38 mmol). After stirring at 55° C. for 18 hours, the reaction mixture was diluted with ethyl acetate (25 mL), washed with water and brine. The organic phase was dried over MgSO$_4$, filtered, concentrated and isolated by preparatory TLC (10% methanol/dichloromethane) to obtain the title compound (0.070 g, 28%); $^1$H NMR (DMSO-d$_6$): δ 1.00 (t, 3H, J=7.2 Hz), 1.14 (t, 3H, J=7.6 Hz), 1.61 (d, 2H, J=12 Hz), 1.82 (t, 2H, J=6 Hz), 2.34 (t, 2H, J=6.8 Hz), 2.54-2.71 (m, 6H), 3.22-3.31 (m, 4H), 3.85 (t, 2H, J=6.8 Hz), 4.61 (d, 4H, J=15.2 Hz), 5.01 (s, 2H), 6.76 (t, 1H, J=7.6 Hz), 6.85 (d, 2H, J=8 Hz), 6.96 (d, 3H, J=2.8 Hz), 7.12-7.24 (m, 3H), 7.54-7.60 (m, 2H), 7.90-7.93 (m, 2H), 10.82 (s, 1H); MS for C$_{37}$H$_{44}$N$_6$O$_5$ m/z 653.08 (M+H)$^+$.

tert-Butyl 3-(3-((2-(diethylamino)-2-oxoethoxy)carbonyl)benzyl)-4-oxo-1-phenyl-1,3,8-triazaspiro[4.5]decane-8-carboxylate

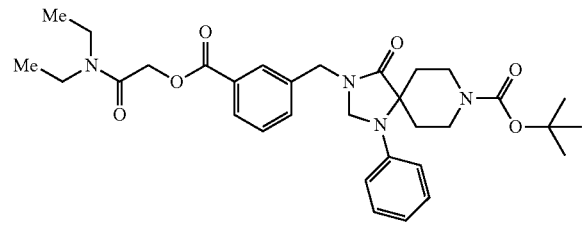 [SMILES: CCN(CC)C(=O)COC(=O)c1cccc(CN2CN(c3ccccc3)C3(CCN(C(=O)OC(C)(C)C)CC3)C2=O)c1]

To a solution of tert-butyl 4-oxo-1-phenyl-1,3,8-triazaspiro[4.5]decane-8-carboxylate (0.2 g, 0.43 mmol) and potassium carbonate (0.089 g, 0.65 mmol) in N,N-dimethylformamide (4 mL), was added 2-chloro-N,N-diethylacetamide (0.059 g, 0.43 mmol, d=1.089). After stirring at 55° C. for 18 hours, the reaction mixture was diluted with ethyl acetate (25 mL), washed with dilute citric acid, water and brine. The organic phase was dried over MgSO$_4$, filtered and isolated by Biotage flash chromatography to obtain the title compound (0.22 g, 88%); MS for C$_{32}$H$_{42}$N$_4$O$_6$ m/z 579.10 (M+H)$^+$.

Example 20

Compound 31

2-Amino-2-oxoethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

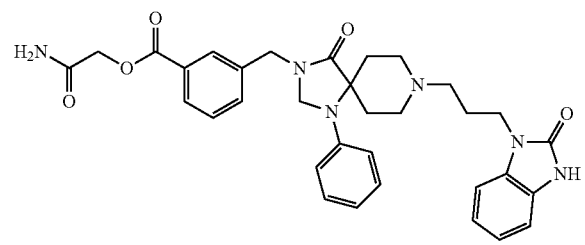 [SMILES: NC(=O)COC(=O)c1cccc(CN2CN(c3ccccc3)C3(CCN(CCCn4c(=O)[nH]c5ccccc54)CC3)C2=O)c1]

To tert-butyl 3-(3-((2-amino-2-oxoethoxy)carbonyl)benzyl)-4-oxo-1-phenyl-1,3,8-triazaspiro[4.5]decane-8-carboxylate (0.22 g, 0.42 mmol) was added 4M solution of HCl in dioxane (4 mL). After stirring at room temperature for 2 hours, the reaction mixture was concentrated in vacuo to obtain 2-amino-2-oxoethyl 3-((4-oxo-1-phenyl-1,3,8-triazaspiro[4.5]decan-3-yl)methyl)benzoate as a hydrochloride salt.

To a solution of the hydrochloride salt and potassium carbonate (0.145 g, 1.05 mmol) in N,N-dimethylformamide (4 mL), was added 1-(3-iodopropyl)-1,3-dihydro-2H-benzimidazol-2-one (0.127 g, 0.42 mmol). After stirring at 55° C. for 18 hours, the reaction mixture was diluted with ethyl acetate (25 mL), washed with water and brine. The organic phase was dried over MgSO$_4$, filtered, concentrated and isolated by preparatory TLC (10% methanol/dichloromethane) to obtain the title compound (0.12 g, 48%); $^1$H NMR (DMSO-d$_6$): δ 1.60 (d, 2H, J=12.8 Hz), 1.82 (t, 2H, J=6.4 Hz), 2.34 (t, 2H, J=6.4 Hz), 2.54-2.72 (m, 6H), 3.85 (t, 2H, J=6.8 Hz), 4.59-4.67 (m, 6H), 6.76 (t, 1H, J=7.2 Hz), 6.85 (d, 2H, J=8 Hz), 6.96 (d, 3H, J=2.8 Hz), 7.18-7.24 (m, 3H), 7.30 (s, 1H), 7.53-7.60 (m, 3H), 7.93-7.97 (m, 2H), 10.82 (s, 1H); MS for C$_{33}$H$_{36}$N$_6$O$_5$ m/z 597.01 (M+H)$^+$.

tert-Butyl 3-(3-((2-amino-2-oxoethoxy)carbonyl)benzyl)-4-oxo-1-phenyl-1,3,8-triazaspiro[4.5]decane-8-carboxylate

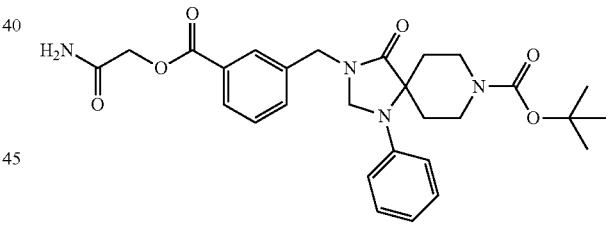

To a solution of tert-butyl 4-oxo-1-phenyl-1,3,8-triazaspiro[4.5]decane-8-carboxylate (0.2 g, 0.43 mmol) and potassium carbonate (0.089 g, 0.65 mmol) in N,N-dimethylformamide (3 mL), was added chloroacetamide (0.04 g, 0.43 mmol). After stirring at 65° C. for 18 hours, the reaction mixture was diluted with ethyl acetate (25 mL), washed with dilute citric acid, water and brine. The organic phase was dried over MgSO$_4$, filtered and isolated by Biotage flash chromatography (2-10% methanol/dichloromethane) to obtain the title compound (0.22 g, 98%); $^1$H NMR (DMSO-d$_6$): δ 1.45 (s, 9H), 1.65 (d, 2H, J=13.2 Hz), 2.32-2.45 (m, 2H), 3.50 (br, 2H), 3.88 (br, 2H), 4.62-4.66 (m, 6H), 6.68 (d, 2H, J=8 Hz), 6.77 (t, 1H, J=7.6 Hz), 7.17 (t, 2H, J=8.4 Hz), 7.30 (s, 1H), 7.54-7.62 (m, 3H), 7.95-7.98 (m, 2H); MS for C$_{28}$H$_{34}$N$_4$O$_6$ m/z 523.04 (M+H)$^+$.

Example 21

Compound 32

2-Oxo-2-(piperidin-1-yl)ethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

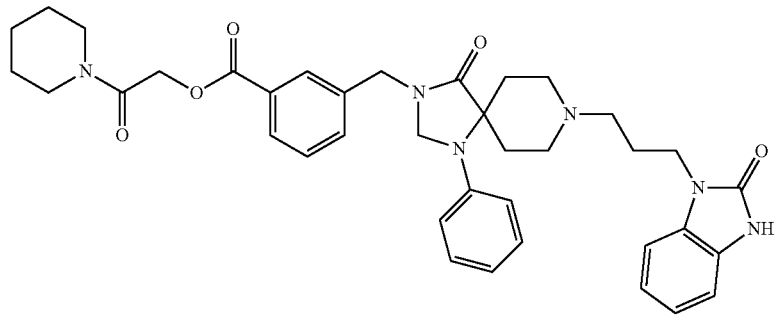 [SMILES: O=C(OCC(=O)N1CCCCC1)c1cccc(CN2CN(c3ccccc3)C3(CCN(CCCn4c(=O)[nH]c5ccccc54)CC3)C2=O)c1]

To tert-Butyl 4-oxo-3-(3-((2-oxo-2-(piperidin-1-yl)ethoxy)carbonyl)benzyl)-1-phenyl-1,3,8-triazaspiro[4.5]decane-8-carboxylate (0.17 g, 0.29 mmol) was added 4M solution of HCl in dioxane (3 mL). After stirring at room temperature for 2 hours, the reaction mixture was concentrated in vacuo to obtain 2-oxo-2-(piperidin-1-yl)ethyl 3-((4-oxo-1-phenyl-1,3,8-triazaspiro[4.5]decan-3-yl)methyl)benzoate as a hydrochloride salt.

To a solution of the hydrochloride salt and potassium carbonate (0.1 g, 0.73 mmol) in N,N-dimethylformamide (2 mL), was added 1-(3-iodopropyl)-1,3-dihydro-2H-benzimidazol-2-one (0.088 g, 0.29 mmol). After stirring at 55° C. for 18 hours, the reaction mixture was diluted with ethyl acetate (25 mL), washed with water and brine. The organic phase was dried over MgSO$_4$, filtered, concentrated and isolated by preparatory TLC (10% methanol/dichloromethane) to obtain the title compound (0.092 g, 48%); $^1$H NMR (DMSO-d$_6$): δ 1.41 (br, 2H), 1.52-1.62 (m, 6H), 1.82 (t, 2H, J=6.4 Hz), 2.34 (t, 2H, J=6.8 Hz), 2.56-2.72 (m, 6H), 3.34-3.38 (m, 4H), 3.85 (t, 2H, J=6.4 Hz), 4.59-4.63 (m, 4H), 5.02 (s, 2H), 6.76 (t, 1H, J=7.2 Hz), 6.85 (d, 2H, J=8.4 Hz), 6.96 (d, 3H, J=3.6 Hz), 7.18-7.24 (m, 3H), 7.53-7.60 (m, 2H), 7.90-7.92 (m, 2H), 10.81 (s, 1H); MS for C$_{38}$H$_{44}$N$_6$O$_5$ m/z 665.17 (M+H)$^+$.

tert-Butyl 4-oxo-3-(3-((2-oxo-2-(piperidin-1-yl)ethoxy)carbonyl)benzyl)-1-phenyl-1,3,8-triazaspiro[4.5]decane-8-carboxylate

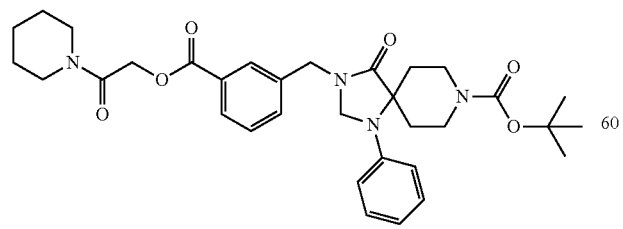

To a solution of piperidine (0.084 mL, 0.86 mmol, d=0.862) stirring in dichloromethane (4 mL) at 0° C., was added chloro acetylchloride (0.034 mL, 0.43 mmol, d=1.419). After stirring at 0° C. for a hour, the reaction mixture was diluted with dichloromethane (25 mL), washed with dilute citric acid, water and brine. The organic phase was dried over MgSO$_4$, filtered and concentrated in vacuo to obtain 2-chloro-1-(piperidin-1-yl)ethanone.

To a solution of 2-chloro-1-(piperidin-1-yl)ethanone in N,N-dimethylformamide (3 mL), was added tert-butyl 4-oxo-1-phenyl-1,3,8-triazaspiro[4.5]decane-8-carboxylate (0.2 g, 0.43 mmol) and potassium carbonate (0.119 g, 0.86 mmol). After stirring at 65° C. for 18 hours, the reaction mixture was diluted with ethyl acetate (25 mL), washed with dilute citric acid, water and brine. The organic phase was dried over MgSO$_4$, filtered and isolated by preparatory TLC (10% methanol/dichloromethane) to obtain the title compound (0.17 g, 67%); $^1$H NMR (DMSO-d$_6$): δ 1.45 (s, 9H), 1.52-1.58 (m, 8H), 2.32-2.45 (m, 2H), 3.35-3.40 (m, 6H), 3.88 (br, 2H), 4.63-4.66 (m, 4H), 5.03 (s, 2H), 6.68 (d, 2H, J=8 Hz), 6.70 (t, 1H, J=7.6 Hz), 7.17 (t, 2H, J=8 Hz), 7.56-7.60 (m, 2H), 7.91-7.93 (m, 2H); MS for C$_{33}$H$_{42}$N$_4$O$_6$ m/z 591.08 (M+H)$^+$.

Example 22

Compound 33

(S)-methyl 2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetate

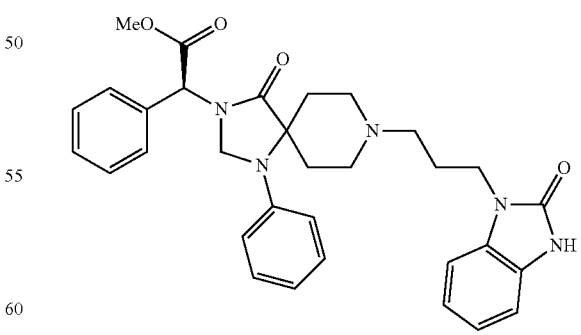

A mixture of (S)-methyl 2-(4-oxo-1-phenyl-1,3,8-triazaspiro[4.5]decan-3-yl)-2-phenylacetate (159 mg, 0.383 mmol, 1 equiv), 1-(3-iodopropyl)-1,3-dihydro-2H-benzimidazol-2-one (115.6 mg, 0.38 mmol, 1 equiv) and potassium carbonate (158.6 mg, 1.148 mmol, 3 equiv) in N,N-dimethylformamide was heated at 65° C. for 16 h. The reaction was cooled to ambient temperature and worked up using 5% methanol in dichloromethane and water. The organic layer was dried over MgSO$_4$, and concentrated in vacuo under a high vacuum. The crude mixture was purified by preparatory thin layer chromatography using 7% methanol in dichloromethane. The purified extract was lyophilized to afford the title compound as a white solid (25 mg, <10%); $^1$H NMR (400 MHz, DMSO-d$_6$): δ 1.61 (bs, 2H), 1.84 (bs, 2H), 2.46 (bs, 4H); 2.50-2.51 (m, 4H); 3.74 (s, 3H); 3.85 (t, 2H, J=7.2 and 6.4 Hz); 4.15 (d, 1H, J=4.8 Hz); 4.80 (d, 1H, J=4.8 Hz); 5.89 (s, 1H)); 6.79-6.85 (m, 3H); 6.97 (d, 3H, J=2.8 Hz); 7.16-7.18 (m, 1H); 7.23 (t, 2H, J=7.2 and 8.8 Hz); 7.39-7.46 (m, 5H); 10.82 (s, 1H); MS for C$_{32}$H$_{35}$N$_5$O$_4$ m/z 554.11 (M+H)$^+$.

Preparation of (S)-methyl 2-(4-oxo-1-phenyl-1,3,8-triazaspiro[4.5]decan-3-yl)-2-phenylacetate

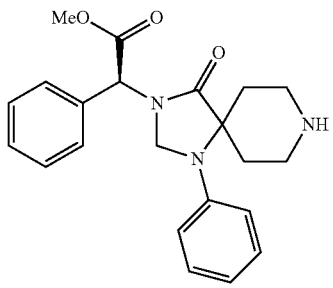 [SMILES: COC(=O)[C@H](c1ccccc1)N1CN(c2ccccc2)C2(CCNCC2)C1=O]

(R)-methyl 2-amino-2-phenylacetate (5 g, 24.8 mmol, 1 equiv) was dissolved in a mixture of 48% Hydrogen bromide (13 ml, 198 mmol, 8 equiv) and water (19 ml). An aqueous solution of sodium nitrite (5.48 g, 79.36 mmol, 3.2 equiv) was added slowly and the mixture stirred at 0° C. for 1.5 h. The reaction was degassed in vaccuo and extracted with ether. The organic layer was further washed with water and brine, dried over MgSO$_4$, and concentrated in vacuo. The resulting residue was purified using the Biotage flash chromatography system (SNAP 100 g cartridge, R$_f$=0.5, 10% ethyl acetate/hexanes) to afford the (S)-methyl 2-bromo-2-phenylacetate as a light yellow oil (2.3 g, 40% yield). $^1$H NMR (400 MHz, DMSO-d$_6$): δ 3.72 (s, 3H); 5.95 (s, 1H); 7.36-7.42 (m, 3H); 7.532 (d, 2H, J=1.2 Hz); 7.56 (d, 1H, J=2 Hz). MS for C$_9$H$_9$BrO$_2$ m/z 229.98 (M+H)$^+$.

A mixture of tert-butyl 4-oxo-1-phenyl-1,3,8-triazaspiro[4.5]decane-8-carboxylate (300 mg, 0.905 mmol, 1 equiv), (S)-methyl 2-bromo-2-phenylacetate (207.4 mg, 0.905 mmol, 1 equiv) and potassium carbonate (312.7 mg, 2.26 mmol, 2.5 equiv) in N,N-dimethylformamide was stirred at 65° C. for 2 hours. The reaction mixture was cooled to ambient temperature and the mixture was partitioned between ethyl acetate and water. The organic layer was further washed with brine, dried over MgSO$_4$, and concentrated in vacuo. The resulting residue was purified using the Biotage flash chromatography system (SNAP 50 g cartridge, R$_f$=0.4, 20% ethyl acetate/hexanes) to afford (S)-tert-butyl 3-(2-methoxy-2-oxo-1-phenylethyl)-4-oxo-1-phenyl-1,3,8-triazaspiro[4.5]decane-8-carboxylate as an oil (183 mg, 42.3%). MS for C$_{27}$H$_{33}$N$_3$O$_5$ m/z 479.57 (M+H)$^+$.

Deprotection of (S)-tert-butyl 3-(2-methoxy-2-oxo-1-phenylethyl)-4-oxo-1-phenyl-1,3,8-triazaspiro[4.5]decane-8-carboxylate (183 mg, 0.382 mmol, 1 equiv) was accomplwashed in 3 hours in the presence of 4M hydrochloric acid in dioxane at ambient temperature. The resulting mixture was concentrated and dried in vacuo to afford the hydrogen chloride salt of the title compound as a white solid (158 mg, quant); $^1$H NMR (400 MHz, DMSO-d$_6$): δ 1.82 (d, 2H, J=14.4 Hz), 2.67-2.77 (m, 2H); 2.93 (bs, 1H); 3.35-3.39 (m, 2H); 3.75 (s, 3H); 4.21 (d, 1H, J=4.8 Hz); 4.84 (d, 1H, J=4.4 Hz); 5.93 (s, 1H); 6.84 (t, 1H, J=7.2 Hz); 6.96 (d, 2H, J=8 Hz); 7.21-7.25 (m, 2H); 7.41-7.47 (m, 4H); 7.53 (s, 1H); 9.06 (bs, 1H); 9.14 (bs, 1H); MS for C$_{22}$H$_{25}$N$_3$O$_3$ m/z 380.01 (M+H)$^+$.

Example 23

Compound 34

(R)-methyl 2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetate

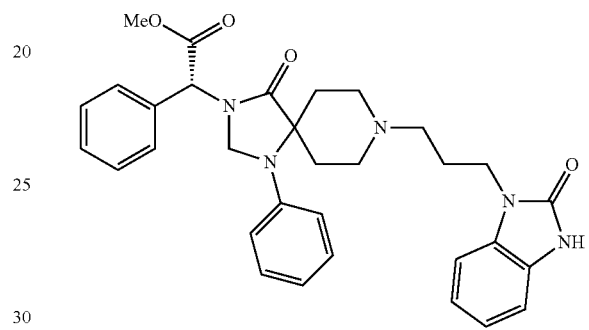

A mixture of (R)-methyl 2-(4-oxo-1-phenyl-1,3,8-triazaspiro[4.5]decan-3-yl)-2-phenylacetate (355 mg, 0.854 mmol, 1 equiv), 1-(3-iodopropyl)-1,3-dihydro-2H-benzimidazol-2-one (258.06 mg, 0.854 mmol, 1 equiv) and potassium carbonate (354.1 mg, 2.562 mmol, 3 equiv) in N,N-dimethylformamide was heated at 65° C. for 16 h. The reaction was cooled to ambient temperature and worked up using 5% methanol in dichloromethane and water. The organic layer was dried over MgSO$_4$, and concentrated in vacuo. The crude mixture was purified by preparatory thin layer chromatography using 7% methanol in dichloromethane. The purified extract was lyophilized to afford the title compound as a white solid (140 mg, ~30%); $^1$H NMR (400 MHz, DMSO-d$_6$): δ 1.59 (t, 2H, J=15.2 Hz, J=14.8 Hz), 1.81 (bs, 2H), 2.33 (bs, 4H); 2.54-2.64 (m, 2H); 2.69-2.73 (m, 2H); 3.74 (s, 3H); 3.84 (t, 2H, J=6.8 Hz); 4.14 (d, 1H, J=4.4 Hz); 4.79 (d, 1H, J=4.8 Hz); 5.89 (s, 1H)); 6.78-6.84 (m, 3H); 6.97 (d, 3H, J=2.4 Hz); 7.16-7.18 (m, 1H); 7.23 (t, 2H, J=7.2 and 8.8 Hz); 7.39-7.46 (m, 5H); 10.82 (s, 1H; MS for C$_{32}$H$_{35}$N$_5$O$_4$ m/z 554.07 (M+H)$^+$.

Preparation of (R)-methyl 2-(4-oxo-1-phenyl-1,3,8-triazaspiro[4.5]decan-3-yl)-2-phenylacetate

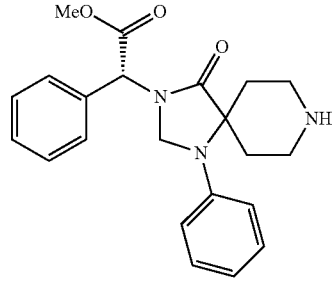 [SMILES: COC(=O)[C@@H](c1ccccc1)N1CN(c2ccccc2)C2(CCNCC2)C1=O]

(S)-methyl 2-amino-2-phenylacetate (5 g, 24.8 mmol, 1 equiv) was dissolved in a mixture of 48% hydrogen bromide (13 ml, 198 mmol, 8 equiv) and water (19 ml). An aqueous solution of sodium nitrite (5.48 g, 79.36 mmol, 3.2 equiv) was added slowly and the mixture stirred at 0° C. for 1.5 h. The reaction was degassed in vacuo and extracted with ether. The organic layer was further washed with water and brine, dried over MgSO$_4$, and concentrated in vacuo. The resulting residue was purified using the Biotage flash chromatography system (SNAP 100 g cartridge, R$_f$=0.5, gradient—1%-10% ethyl acetate/hexanes) to afford the (R)-methyl 2-bromo-2-phenylacetate as a light yellow oil (2.3 g, 40% yield).). $^1$H NMR (400 MHz, DMSO-d$_6$): δ 3.72 (s, 3H); 5.95 (s, 1H); 7.36-7.42 (m, 3H); 7.54 (d, 2H, J=1.6 Hz); 7.56 (d, 1H, J=2 Hz). MS for $C_9H_9BrO_2$ m/z 229.98 (M+H)$^+$.

A mixture of tert-butyl 4-oxo-1-phenyl-1,3,8-triazaspiro [4.5]decane-8-carboxylate (400 mg, 1.21 mmol, 1 equiv), (R)-methyl 2-bromo-2-phenylacetate (276.6 mg, 1.21 mmol, 1 equiv) and potassium carbonate (418.1 mg, 3.025 mmol, 2.5 equiv) in N,N-dimethylformamide was stirred at 65° C. for 3.5 hours. The reaction mixture was cooled to ambient temperature and the mixture was partitioned between ethyl acetate and water. The organic layer was further washed with brine, dried over MgSO$_4$, and concentrated in vacuo. The resulting residue was purified using the Biotage flash chromatography system (SNAP 50 g cartridge, R$_f$=0.4, gradient—5%-20% ethyl acetate/hexanes) to afford (R)-tert-butyl 3-(2-methoxy-2-oxo-1-phenylethyl)-4-oxo-1-phenyl-1,3,8-triazaspiro[4.5]decane-8-carboxylate as an oil (410 mg, 71.1%). MS for $C_{27}H_{33}N_3O_5$ m/z 479.57 (M+H)$^+$.

Deprotection of (R)-tert-butyl 3-(2-methoxy-2-oxo-1-phenylethyl)-4-oxo-1-phenyl-1,3,8-triazaspiro[4.5]decane-8-carboxylate (410 mg, 0.86 mmol, 1 equiv) was accomplished in 3 hours in the presence of 4M hydrogen chloride solution in dioxane at ambient temperature. The resulting mixture was concentrated and dried in vacuo to afford the hydrogen chloride salt of the title compound as a white solid (355 mg, quant); $^1$H NMR (400 MHz, DMSO-d$_6$): δ 1.83 (d, 2H, J=14.0 Hz), 2.66-2.74 (m, 2H); 3.44-3.51 (m, 4H); 3.75 (s, 3H); 4.21 (d, 1H, J=4.4 Hz); 4.84 (d, 1H, J=4.8 Hz); 5.93 (s, 1H); 6.85 (t, 1H, J=7.2 and 7.6 Hz); 6.95 (d, 2H, J=8 Hz); 7.21-7.25 (m, 2H); 7.39-7.45 (m, 4H); 7.53 (s, 1H); 8.97-9.04 (m, 2H); MS for $C_{22}H_{25}N_3O_3$ m/z 380.03 (M+H)$^+$.

Example 24

Compound 35

2-(4-Methylpiperazin-1-yl)-2-oxoethyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

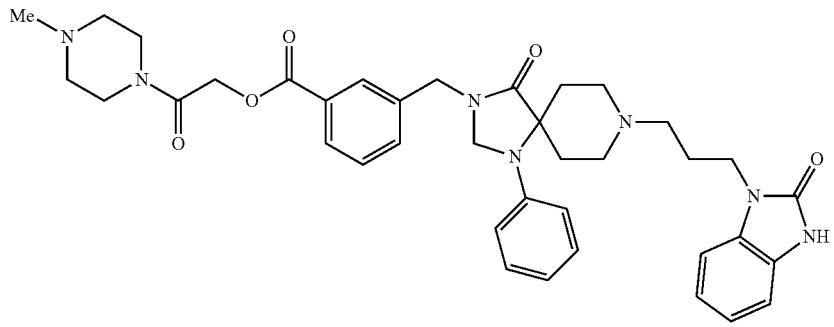 [SMILES: CN1CCN(C(=O)COC(=O)c2cccc(CN3CN(c4ccccc4)C4(CCN(CCCn5c(=O)[nH]c6ccccc65)CC4)C3=O)c2)CC1]

To tert-butyl 3-(3-((2-(4-methylpiperazin-1-yl)-2-oxoethoxy)carbonyl)benzyl)-4-oxo-1-phenyl-1,3,8-triazaspiro[4.5]decane-8-carboxylate (0.16 g, 0.26 mmol) was added 4M solution of HCl in dioxane (3 mL). After stirring at room temperature for 2 hours, the reaction mixture was concentrated in vacuo to obtain 2-(4-methylpiperazin-1-yl)-2-oxoethyl 3-((4-oxo-1-phenyl-1,3,8-triazaspiro[4.5]decan-3-yl)methyl)benzoate as a hydrochloride salt.

To a solution of the hydrochloride salt and potassium carbonate (0.09 g, 0.65 mmol) in N,N-dimethylformamide (2 mL), was added 1-(3-iodopropyl)-1,3-dihydro-2H-benzimidazol-2-one (0.079 g, 0.26 mmol). After stirring at 55° C. for 18 hours, the reaction mixture was diluted with ethyl acetate (25 mL), washed with water and brine. The organic phase was dried over MgSO$_4$, filtered, concentrated and isolated by reverse phase HPLC to obtain the title compound (0.052 g, 29%); $^1$H NMR (DMSO-d$_6$): δ 1.61 (d, 2H, J=13.6 Hz), 1.83 (t, 2H, J=6.4 Hz), 2.17 (s, 3H), 2.24-2.36 (m, 6H), 2.52-2.72 (m, 6H), 3.32-3.40 (m, 4H), 3.85 (t, 2H, J=6.8 Hz), 4.61 (d, 4H, J=14.4 Hz), 5.04 (s, 2H), 6.76 (t, 1H, J=7.2 Hz), 6.85 (d, 2H, J=8 Hz), 6.96 (d, 3H, J=2 Hz), 7.17-7.24 (m, 3H), 7.53-7.60 (m, 2H), 7.90-7.92 (m, 2H), 10.82 (s, 1H); MS for $C_{38}H_{45}N_7O_5$ m/z 680.17 (M+H)$^+$.

tert-Butyl 3-(3-((2-(4-methylpiperazin-1-yl)-2-oxoethoxy)carbonyl)benzyl)-4-oxo-1-phenyl-1,3,8-triazaspiro[4.5]decane-8-carboxylate

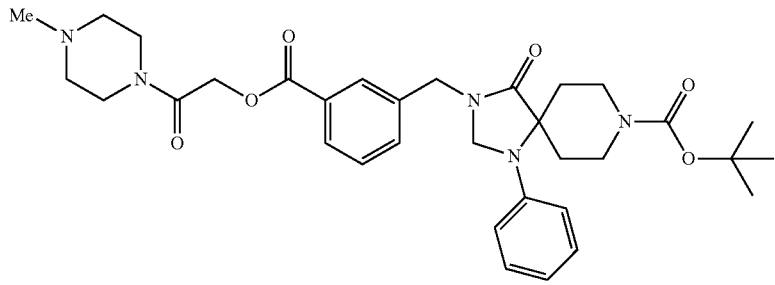 [SMILES: CN1CCN(C(=O)COC(=O)c2cccc(CN3CN(c4ccccc4)C4(CCN(C(=O)OC(C)(C)C)CC4)C3=O)c2)CC1]

To a solution of N-methylpiperazine (0.096 mL, 0.86 mmol, d=0.902) stirring in dichloromethane (5 mL) at 0° C., was added chloro acetylchloride (0.034 mL, 0.43 mmol, d=1.419). After stirring at 0° C. for an hour, the reaction mixture was diluted with dichloromethane (25 mL), washed with dilute citric acid, water and brine. The organic phase was dried over MgSO$_4$, filtered and concentrated in vacuo to obtain 2-chloro-1-(4-methylpiperazin-1-yl)ethanone.

To a solution of 2-chloro-1-(4-methylpiperazin-1-yl)ethanone in N,N-dimethylformamide (3 mL), was added tert-butyl 4-oxo-1-phenyl-1,3,8-triazaspiro[4.5]decane-8-carboxylate (0.2 g, 0.43 mmol) and potassium carbonate (0.119 g, 0.86 mmol). After stirring at 65° C. for 18 hours, the reaction mixture was diluted with ethyl acetate (25 mL), washed with dilute citric acid, water and brine. The organic phase was dried over MgSO$_4$, filtered and isolated by Biotage flash chromatography (2-20% methanol/dichloromethane) to obtain the title compound (0.16 g, 62%); $^1$H NMR (DMSO-d$_6$): δ 1.45 (s, 9H), 1.64 (t, 2H, J=12.8 Hz), 2.18 (s, 3H), 2.25-2.45 (m, 6H), 3.41-3.50 (m, 6H), 3.85 (br, 2H), 4.60-4.65 (m, 4H), 5.05 (s, 2H), 6.64-6.69 (m, 2H), 6.76-6.79 (m, 1H), 7.13-7.19 (m, 2H), 7.54-7.60 (m, 2H), 7.91-7.93 (m, 2H); MS for C$_{33}$H$_{43}$N$_5$O$_6$ m/z 606.08 (M+H)$^+$.

Example 25

Compound 39

(R)-2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetic acid

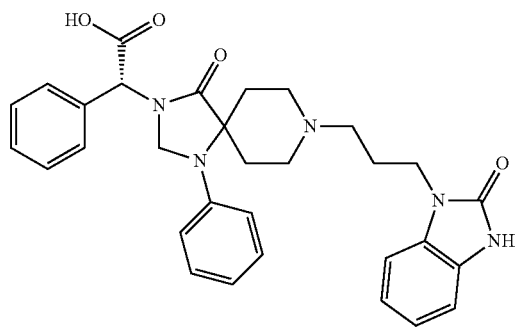 [SMILES: O=C(O)[C@@H](c1ccccc1)N1CN(c2ccccc2)C2(CCN(CCCn3c(=O)[nH]c4ccccc43)CC2)C1=O]

A solution of (R)-methyl 2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetate (105 mg, 0.189 mmol, 1 equiv) and lithium hydroxide (15.9 mg, 0.38 mmol, 2.0 equiv) in a 3:1 mixture of methanol and water (5 ml t/v) was stirred at ambient temperature for 24 hrs. The reaction was concentrated in vacuo and purified using preparatory high performance liquid chromatography. The combined pure fractions were lyophilized to afford the acetate salt of the title compound as a white solid (21 mg, 20%); $^1$H NMR (400 MHz, DMSO-d$_6$): δ 1.57-1.66 (m, 2H), 1.87-1.91 (m, 2H); 2.79-2.85 (m, 4H); 3.27-3.42 (bs, 4H); 3.85 (t, 2H, J=6.8 Hz); 4.11 (d, 1H, J=4.8 Hz); 4.91 (d, 1H, J=4.8 Hz); 5.71 (s, 1H); 6.76-6.82 (m, 3H); 6.97-6.98 (m, 3H); 7.17-7.23 (m, 3H); 7.35-7.43 (m, 5H); 10.83 (s, 1H); 12.5 (bs, 1H); MS for C$_{31}$H$_{33}$ClN$_5$O$_4$ 540.01 (M+H)$^+$.

Preparation of (R)-methyl 2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetate

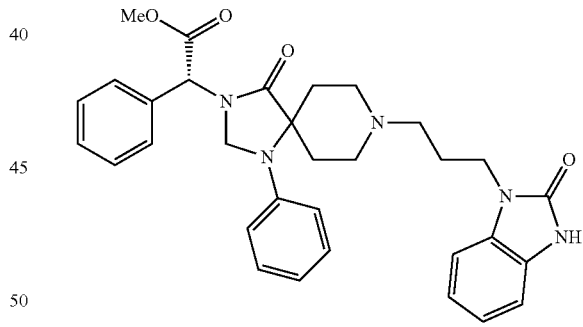

A mixture of (R)-methyl 2-(4-oxo-1-phenyl-1,3,8-triazaspiro[4.5]decan-3-yl)-2-phenylacetate (355 mg, 0.854 mmol, 1 equiv), 1-(3-iodopropyl)-1,3-dihydro-2H-benzimidazol-2-one (258.06 mg, 0.854 mmol, 1 equiv) and potassium carbonate (354.1 mg, 2.562 mmol, 3 equiv) in N,N-dimethylformamide was heated at 65° C. for 16 h. The reaction was cooled to ambient temperature and worked up using 5% methanol in dichloromethane and water. The organic layer was dried over MgSO$_4$, and concentrated in vacuo. The crude mixture was purified by preparatory thin layer chromatography using 7% methanol in dichloromethane. The purified extract was lyophilized to afford the title compound as a white solid (140 mg, ~30%); $^1$H NMR (400 MHz, DMSO-d$_6$): δ 1.59 (t, 2H, J=15.2 and 14.8 Hz), 1.81 (bs, 2H), 2.33 (bs, 4H); 2.54-2.64 (m, 2H); 2.69-2.73 (m, 2H); 3.74 (s, 3H); 3.84 (t, 2H, J=6.8

Hz); 4.14 (d, 1H, J=4.4 Hz); 4.79 (d, 1H, J=4.8 Hz); 5.89 (s, 1H)); 6.78-6.84 (m, 3H); 6.97 (d, 3H, J=2.4 Hz); 7.16-7.18 (m, 1H); 7.23 (t, 2H, J=7.2 and 8.8 Hz); 7.39-7.46 (m, 5H); 10.82 (s, 1H); MS for $C_{32}H_{35}N_5O_4$ m/z 554.07 (M+H)$^+$.

Preparation of (R)-methyl 2-(4-oxo-1-phenyl-1,3,8-triazaspiro[4.5]decan-3-O-2-phenylacetate

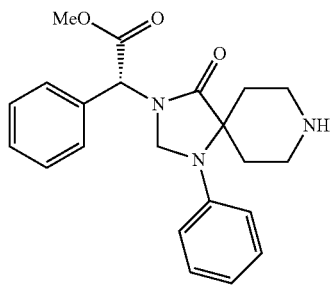 [SMILES: COC(=O)[C@@H](c1ccccc1)N1CN(c2ccccc2)C2(CCNCC2)C1=O]

(S)-methyl 2-amino-2-phenylacetate (5 g, 24.8 mmol, 1 equiv) was dwassolved in a mixture of 48% hydrogen bromide (13 ml, 198 mmol, 8 equiv) and water (19 ml). An aqueous solution of sodium nitrite (5.48 g, 79.36 mmol, 3.2 equiv) was added slowly and the mixture stirred at 0° C. for 1.5 h. The reaction was degassed in vacuo and extracted with ether. The organic layer was further washed with water and brine, dried over MgSO$_4$, and concentrated in vacuo. The resulting residue was purified using the Biotage flash chromatography system (SNAP 100 g cartridge, R$_f$=0.5, gradient—1%-10% ethyl acetate in hexanes) to afford the (R)-methyl 2-bromo-2-phenylacetate as a light yellow oil (2.3 g, 40% yield); $^1$H NMR (400 MHz, DMSO-d$_6$): δ 3.72 (s, 3H); 5.95 (s, 1H); 7.36-7.42 (m, 3H); 7.54 (d, 2H, J=1.6 Hz); 7.56 (d, 1H, J=2 Hz); MS for $C_9H_9BrO_2$ m/z 229.98 (M+H)$^+$.

A mixture of tert-butyl 4-oxo-1-phenyl-1,3,8-triazaspiro [4.5]decane-8-carboxylate (400 mg, 1.21 mmol, 1 equiv), (R)-methyl 2-bromo-2-phenylacetate (276.6 mg, 1.21 mmol, 1 equiv) and potassium carbonate (418.1 mg, 3.025 mmol, 2.5 equiv) in N,N-dimethylformamide was stirred at 65° C. for 3.5 hours. The reaction mixture was cooled to ambient temperature and the mixture was partitioned between ethyl acetate and water. The organic layer was further washed with brine, dried over MgSO$_4$, and concentrated in vacuo. The resulting residue was purified using the Biotage flash chromatography system (SNAP 50 g cartridge, R$_f$=0.4, gradient—2%-20% ethyl acetate/hexanes,) to afford (R)-tert-butyl 3-(2-methoxy-2-oxo-1-phenylethyl)-4-oxo-1-phenyl-1,3,8-triazaspiro[4.5]decane-8-carboxylate as an oil (410 mg, 71.1%); MS for $C_{27}H_{33}N_3O_5$ m/z 479.57 (M+H)$^+$.

Deprotection of (R)-tert-butyl 3-(2-methoxy-2-oxo-1-phenylethyl)-4-oxo-1-phenyl-1,3,8-triazaspiro[4.5]decane-8-carboxylate (410 mg, 0.86 mmol, 1 equiv) was accomplished in 3 hours in the presence of 4M hydrogen chloride solution in dioxane at ambient temperature. The resulting mixture was concentrated and dried in vacuo to afford the hydrogen chloride salt of the title compound as a white solid (355 mg, quant); $^1$H NMR (400 MHz, DMSO-d$_6$): δ 1.81-1.85 (d, 2H, J=14.0 Hz), 2.66-2.74 (m, 2H); 3.44-3.51 (m, 4H); 3.75 (s, 3H); 4.21 (d, 1H, J=4.4 Hz); 4.84 (d, 1H, J=4.8 Hz); 5.93 (s, 1H); 6.85 (t, 1H, J=7.2 and 7.6 Hz); 6.95 (d, 2H, J=8 Hz); 7.21-7.25 (m, 2H); 7.39-7.45 (m, 4H); 7.53 (s, 1H); 8.97-9.04 (m, 2H); MS for $C_{22}H_{25}N_3O_3$ m/z 380.03 (M+H)$^+$.

Example 26

Compound 40

(S)-2-(4-oxo-8-(3-(2-oxo-2,3-dihydro-1H-benzo[d] imidazol-1-yl)propyl)-1-phenyl-1,3,8-triazaspiro [4.5]decan-3-yl)-2-phenylacetic acid

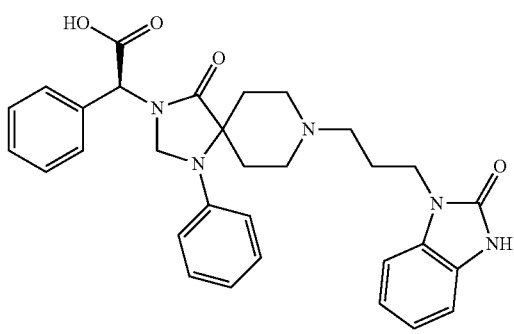 [SMILES: O=C(O)[C@H](c1ccccc1)N1CN(c2ccccc2)C2(CCN(CCCn3c(=O)[nH]c4ccccc43)CC2)C1=O]

A solution of (S)-methyl 2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetate (295 mg, 0.533 mmol, 1 equiv) and lithium hydroxide (44.77 mg, 1.07 mmol, 2.0 equiv) in a 3:1 mixture of methanol and water (5 ml t/v) was stirred at ambient temperature for 24 hrs. The reaction was concentrated in vacuo and purified using preparatory high performance liquid chromatography. The combined pure fractions were lyophilized to afford the acetate salt of the title compound as a white solid (61 mg, 21%); $^1$H NMR (400 MHz, DMSO-d$_6$): δ 1.57-1.66 (m, 2H), 1.87-1.91 (m, 2H); 2.79-2.86 (m, 4H); 3.27-3.42 (bs, 4H); 3.85 (t, 2H, J=6.8 and 6.4 Hz); 4.11 (d, 1H, J=4.8 Hz); 4.94 (d, 1H, J=3.2 Hz); 5.68 (s, 1H); 6.74-6.80 (m, 3H); 6.95-6.98 (m, 3H); 7.17-7.21 (m, 3H); 7.33-7.42 (m, 5H); 10.85 (s, 1H); 12.5 (bs, 1H); MS for $C_{31}H_{33}ClN_5O_4$ m/z 540.07 (M+H)$^+$.

Preparation of (S)-methyl 2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetate

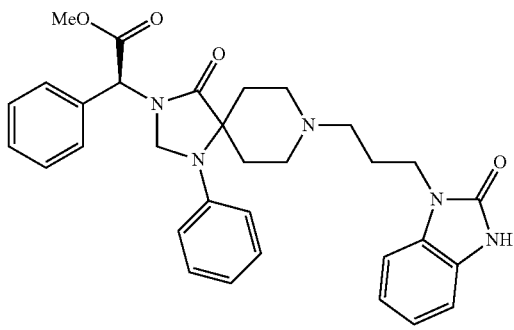 [SMILES: COC(=O)[C@H](c1ccccc1)N1CN(c2ccccc2)C2(CCN(CCCn3c(=O)[nH]c4ccccc43)CC2)C1=O]

A mixture of (S)-methyl 2-(4-oxo-1-phenyl-1,3,8-triazaspiro[4.5]decan-3-yl)-2-phenylacetate (159 mg, 0.383 mmol, 1 equiv), 1-(3-iodopropyl)-1,3-dihydro-2H-benzimidazol-2-one (115.6 mg, 0.38 mmol, 1 equiv) and potassium carbonate (158.6 mg, 1.148 mmol, 3 equiv) in N,N-dimethylformamide was heated at 65° C. for 16 h. The reaction was cooled to ambient temperature and worked up using 5% methanol in dichloromethane and water. The organic layer was dried over MgSO$_4$, and concentrated in vacuo. The crude mixture was purified using preparatory thin layer chromatography in 7% methanol in dichloromethane. The purified extract was lyophilized to afford the title compound as a white solid (25 mg, <10%); $^1$H NMR (400 MHz, DMSO-d$_6$): δ 1.61 (bs, 2H), 1.84 (bs, 2H), 2.46 (bs, 4H); 2.50-2.51 (m, 4H); 3.74 (s, 3H); 3.85 (t, 2H, J=7.2 and 6.4 Hz); 4.15 (d, 1H, J=4.8 Hz); 4.80 (d, 1H, J=4.8 Hz); 5.89 (s, 1H)); 6.79-6.85 (m, 3H); 6.97 (d, 3H, J=2.8 Hz); 7.16-7.18 (m, 1H); 7.23 (t, 2H, J=7.2 and 8.8 Hz); 7.39-7.46 (m, 5H); 10.82 (s, 1H); MS for C$_{32}$H$_{35}$N$_5$O$_4$ m/z 554.11 (M+H)$^+$.

Preparation of (S)-methyl 2-(4-oxo-1-phenyl-1,3,8-triazaspiro[4.5]decan-3-yl)-2-phenylacetate

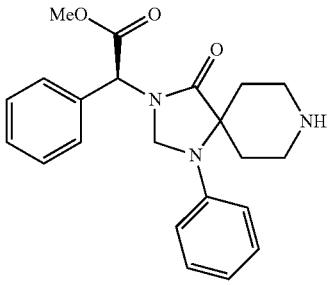 [SMILES: COC(=O)[C@H](c1ccccc1)N1CN(c2ccccc2)C2(CCNCC2)C1=O]

(R)-methyl 2-amino-2-phenylacetate (5 g, 24.8 mmol, 1 equiv) was dissolved in a mixture of 48% hydrogen bromide (13 ml, 198 mmol, 8 equiv) and water (19 ml). An aqueous solution of sodium nitrite (5.48 g, 79.36 mmol, 3.2 equiv) was added slowly and the mixture stirred at 0° C. for 1.5 h. The reaction was degassed in vacuo and extracted with ether. The organic layer was further washed with water and brine, dried over MgSO$_4$, and concentrated in vacuo. The resulting residue was purified using the Biotage flash chromatography system (SNAP 100 g cartridge, R$_f$=0.5, gradient—1%-10% ethyl acetate/hexanes) to afford the (S)-methyl 2-bromo-2-phenylacetate as a light yellow oil (2.3 g, 40% yield); $^1$H NMR (400 MHz, DMSO-d$_6$): δ 3.72 (s, 3H); 5.95 (s, 1H); 7.36-7.42 (m, 3H); 7.53 (d, 2H, J=1.2 Hz); 7.56 (d, 1H, J=2 Hz); MS for C$_9$H$_9$BrO$_2$ m/z 229.98 (M+H)$^+$.

A mixture of tert-butyl 4-oxo-1-phenyl-1,3,8-triazaspiro[4.5]decane-8-carboxylate (300 mg, 0.905 mmol, 1 equiv), (S)-methyl 2-bromo-2-phenylacetate (207.4 mg, 0.905 mmol, 1 equiv) and potassium carbonate (312.7 mg, 2.26 mmol, 2.5 equiv) in N,N-dimethylformamide was stirred at 65° C. for 2 hours. The reaction mixture was cooled to ambient temperature and the mixture was partitioned between ethyl acetate and water. The organic layer was further washed with brine, dried over MgSO$_4$, and concentrated in vacuo. The resulting residue was purified using a Biotage flash chromatography system (SNAP 50 g cartridge, R$_f$=0.4, gradient-2%-20% ethyl acetate/hexanes) to afford (S)-tert-butyl 3-(2-methoxy-2-oxo-1-phenylethyl)-4-oxo-1-phenyl-1,3,8-triazaspiro[4.5]decane-8-carboxylate as an oil (183 mg, 42.3%); MS for C$_{27}$H$_{33}$N$_3$O$_5$ m/z 479.57 (M+H)$^+$.

Deprotection of (S)-tert-butyl 3-(2-methoxy-2-oxo-1-phenylethyl)-4-oxo-1-phenyl-1,3,8-triazaspiro[4.5]decane-8-carboxylate (183 mg, 0.382 mmol, 1 equiv) was accomplished in 3 hours in the presence of 4M hydrogen chloride solution in dioxane at ambient temperature. The resulting mixture was concentrated and dried in vacuo to afford the hydrogen chloride salt of the title compound as a white solid (158 mg, quant); $^1$H NMR (400 MHz, DMSO-d$_6$): δ 1.82 (d, 2H, J=14.4 Hz), 2.67-2.77 (m, 2H); 2.93 (bs, 1H); 3.35-3.39 (m, 2H); 3.75 (s, 3H); 4.21 (d, 1H, J=4.8 Hz); 4.84 (d, 1H, J=4.4 Hz); 5.93 (s, 1H); 6.84 (t, 1H, J=7.2 Hz); 6.96 (d, 2H, J=8 Hz); 7.21-7.25 (m, 2H); 7.41-7.47 (m, 4H); 7.53 (s, 1H); 9.06 (bs, 1H); 9.14 (bs, 1H); MS for C$_{22}$H$_{25}$N$_3$O$_3$ m/z 399.93 (M+H)$^+$.

Example 27

Compound 42

Methyl 3-((1-(4-fluorophenyl)-4-oxo-8-(3-(2-oxo-2,3-dihydro-1H-benzo[d]imidazol-1-yl)propyl)-1,3,8-triazaspiro[4.5]decan-3-yl)methyl)benzoate

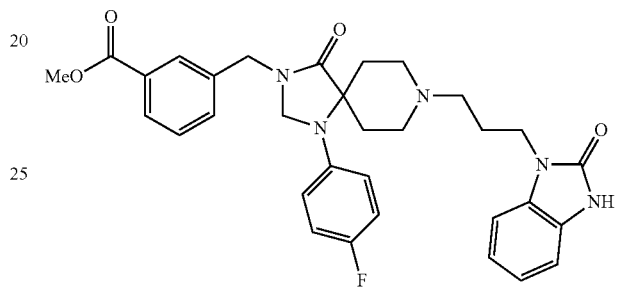

To tert-butyl 1-(4-fluorophenyl)-3-(3-(methoxycarbonyl)benzyl)-4-oxo-1,3,8-triazaspiro[4.5]decane-8-carboxylate (0.42 g, 0.84 mmol) was added 4M solution of HCl in dioxane (5 mL). After stirring at room temperature for 2 hours, the reaction mixture was concentrated in vacuo to obtain methyl 3-((1-(4-fluorophenyl)-4-oxo-1,3,8-triazaspiro[4.5]decan-3-yl)methyl)benzoate as a hydrochloride salt.

To a solution of the hydrochloride salt and potassium carbonate (0.290 g, 2.1 mmol) in N,N-dimethylformamide (5 mL), was added 1-(3-iodopropyl)-1,3-dihydro-2H-benzimidazol-2-one (0.254 g, 0.84 mmol). After stirring at 55° C. for 60 hours, the reaction mixture was diluted with ethyl acetate (50 mL), washed with water and brine. The organic phase was dried over MgSO$_4$, filtered, concentrated and isolated by preparatory TLC (10% methanol/dichloromethane) to obtain the product (0.085 g, 18%); $^1$H NMR (DMSO-d$_6$): δ 1.61 (d, 2H, J=13.6 Hz), 1.83 (m, 2H), 2.31-2.39 (m, 4H), 2.62-2.73 (m, 4H), 3.81-3.84 (s, 5H), 4.55-4.59 (m, 4H) 6.90-6.91 (m, 2H), 6.96 (d, 2H, J=2.4 Hz), 7.07-7.15 (m, 4H), 7.51-7.57 (m, 2H), 7.87-7.89 (m, 2H), 10.80 (s, 1H); MS for C$_{32}$H$_{34}$FN$_5$O$_4$ m/z 572.07 (M+H)$^+$.

tert-Butyl 1-(4-fluorophenyl)-3-(3-(methoxycarbonyl)benzyl)-4-oxo-1,3,8-triazaspiro[4.5]decane-8-carboxylate

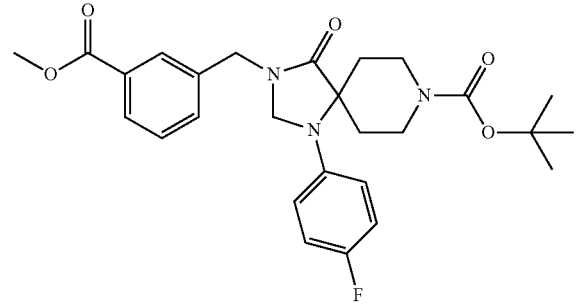 [SMILES: COC(=O)c1cccc(CN2CN(c3ccc(F)cc3)C3(CCN(C(=O)OC(C)(C)C)CC3)C2=O)c1]

To a solution of 1-(4-fluorophenyl)-1,3,8-triazaspiro[4.5]decan-4-one (prepared according to methods described in U.S. Pat. No. 3,155,670 and U.S. Pat. No. 3,238,216) (2 g, 8.02 mmol) in dichloromethane (20 mL) and N,N-diisopropylethylenediamine (2.8 mL, 16.04 mmol, d=0.742), was added di-tert-butyl dicarbonate (1.77 g, 8.10 mmol). After stirring at room temperature for 18 hours, the reaction mixture was diluted with dichloromethane (100 mL), washed with dilute citric acid, water and brine. The organic phase was dried over MgSO$_4$, filtered and concentrated to obtain of tert-butyl 1-(4-fluorophenyl)-4-oxo-1,3,8-triazaspiro[4.5]decane-8-carboxylate (2.8 g, 99%).

To a solution of tert-butyl 1-(4-fluorophenyl)-4-oxo-1,3,8-triazaspiro[4.5]decane-8-carboxylate (0.4 g, 1.14 mmol) and potassium carbonate (0.124 g, 0.9 mmol) in N,N-dimethylformamide (4 mL), was added methyl 3-(bromomethyl)benzoate (0.315 g, 2.28 mmol). After stirring at 55° C. for 18 hours, the reaction mixture was diluted with ethyl acetate (50 mL), washed with dilute citric acid, water and brine. The organic phase was dried over MgSO$_4$, filtered and isolated by Biotage flash chromatography (10-100% ethyl acetate/hexanes) (0.43 g, 75%); $^1$H NMR (DMSO-d$_6$): δ 1.45 (s, 9H), 1.67 (d, 2H, J=14 Hz), 2.09-2.16 (m, 2H), 3.45 (br, 2H), 3.85-3.86 (m, 5H), 4.52-4.62 (m, 4H), 6.71-6.81 (m, 2H), 7.05 (t, 2H, J=9.2 Hz), 7.52-7.59 (m, 2H), 7.89-7.91 (m, 2H).

Example 28

Compound 43

3-((1-(4-Fluorophenyl)-4-oxo-8-(3-(2-oxo-2,3-dihydro-1H-benzo[d]imidazol-1-yl)propyl)-1,3,8-triazaspiro[4.5]decan-3-yl)methyl)benzoic acid

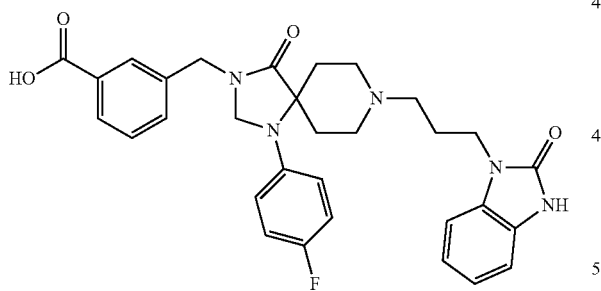

To a solution of methyl 3-((1-(4-fluorophenyl)-4-oxo-8-(3-(2-oxo-2,3-dihydro-1H-benzo[d]imidazol-1-yl)propyl)-1,3,8-triazaspiro[4.5]decan-3-yl)methyl)benzoate (0.25 g, 0.44 mmol) in methanol (3 mL) was added lithium hydroxide monohydrate (0.037 g, 0.88 mmol) in water (1 mL). After stirring at room temperature for 18 h, the reaction mixture was concentrated in vacuo and isolated by reverse phase HPLC to obtain the title compound as an acetate salt (0.05 g, 13%); $^1$H NMR (DMSO-d$_6$): δ 1.62 (d, 2H, J=13.2 Hz), 1.81 (t, 2H, J=6.4 Hz), 2.27-2.37 (m, 4H), 2.50-2.69 (m, 4H), 3.83 (t, 2H, J=6.8 Hz), 4.56 (d, 4H, J=15.2 Hz), 6.88-6.91 (m, 2H), 6.95-6.98 (m, 3H), 7.08 (d, 2H, J=5.2 Hz), 7.13-7.16 (m, 1H), 7.47-7.52 (m, 2H), 7.85-7.87 (m, 2H), 10.81 (s, 1H), 13.10 (br, 1H); MS for C$_{31}$H$_{32}$FN$_5$O$_4$ m/z 558.02 (M+H)$^+$.

Example 29

Compound 45

(S)-Quinuclidin-3-yl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

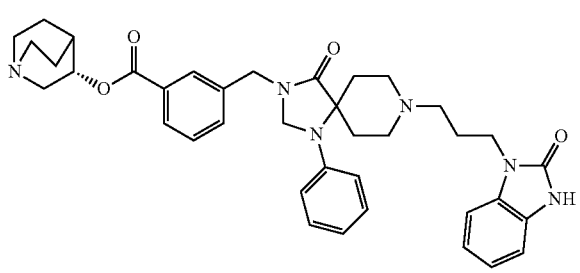 [SMILES: O=C(O[C@@H]1CN2CCC1CC2)c1cccc(CN2CN(c3ccccc3)C3(CCN(CCCn4c(=O)[nH]c5ccccc54)CC3)C2=O)c1]

To a refluxing solution of methyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate (0.2 g, 0.36 mmol) and (S)-3-quinuclidinol (0.184 g, 1.44 mmol) in toluene (2 mL), was added titanium(IV)-i-propoxide (0.105 mL, 0.36 mmol, d=0.97). After refluxing for 18 h, the reaction mixture was diluted with 5% methanol/dichloromethane, washed with water and brine. The organic phase was dried over MgSO$_4$, filtered, concentrated and isolated by reverse phase HPLC to obtain the title compound as an acetate salt (0.08 g, 34%); $^1$H NMR (DMSO-d$_6$): δ 1.32-1.36 (m, 1H), 1.51-1.54 (m, 4H), 1.79-1.84 (m, 3H), 1.99-2.01 (m, 1H), 2.35 (t, 2H, J=6.8 Hz), 2.52-2.72 (m, 11H), 3.15-3.21 (m, 1H), 3.85 (t, 2H, J=6.8 Hz), 4.61 (d, 4H, J=13.2 Hz), 4.90-4.92 (m, 1H), 6.76 (t, 1H, J=6.8 Hz), 6.84 (d, 2H, J=8 Hz), 6.96 (d, 3H, J=2.4 Hz), 7.17-7.24 (m, 3H), 7.52-7.59 (m, 2H), 7.87-7.92 (m, 2H), 10.80 (br, 1H); MS for C$_{38}$H$_{44}$N$_6$O$_4$ m/z 649.11 (M+H)$^+$.

Example 30

Compound 46

Methyl 3-((4-oxo-8-(3-(2-oxobenzo[d]oxazol-3(2H)-yl)propyl)-1-phenyl-1,3,8-triazaspiro[4.5]decan-3-yl)methyl)benzoate

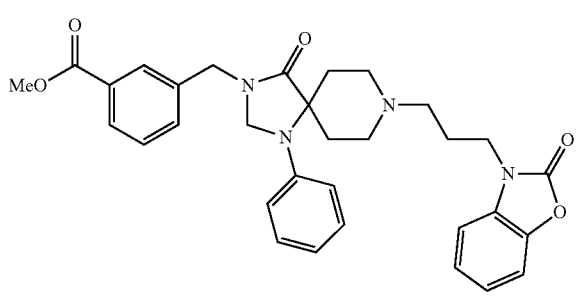 [SMILES: COC(=O)c1cccc(CN2CN(c3ccccc3)C3(CCN(CCCn4c(=O)oc5ccccc54)CC3)C2=O)c1]

To tert-butyl 3-(3-(methoxycarbonyl)benzyl)-4-oxo-1-phenyl-1,3,8-triazaspiro[4.5]decane-8-carboxylate (0.23 g, 0.48 mmol) was added 4M solution of HCl in dioxane (5 mL). After stirring at room temperature for an hour, the reaction mixture was concentrated in vacuo to obtain methyl 3-((4-oxo-1-phenyl-1,3,8-triazaspiro[4.5]decan-3-yl)methyl)benzoate as a hydrochloride salt.

To a solution of the hydrochloride salt and potassium carbonate (0.166 g, 1.2 mmol) in N,N-dimethylformamide (4 mL), was added 3-(3-iodopropyl)benzo[d]oxazol-2(3H)-one (0.145 g, 0.48 mmol). After stirring at 55° C. for 18 hours, the reaction mixture was diluted with ethyl acetate (50 mL), washed with water and brine. The organic phase was dried over MgSO$_4$, filtered, concentrated and isolated by preparatory TLC (10% methanol/dichloromethane) to obtain the product (0.21 g, 86%); $^1$H NMR (DMSO-d$_6$): δ 1.55 (d, 2H, J=14 Hz), 1.88 (t, 2H, J=6.8 Hz), 2.38 (t, 2H, J=6.4 Hz), 2.43-2.46 (m, 2H), 2.63-2.65 (m, 4H), 3.85 (s, 3H), 3.92 (t, 2H, J=6.4 Hz), 4.58 (d, 4H, J=14.8 Hz), 6.79 (t, 1H, J=7.6 Hz), 6.84 (d, 2H, J=8 Hz), 7.10 (t, 1H, J=8 Hz), 7.19 (t, 1H, J=7.6 Hz), 7.23-7.29 (m, 3H), 7.36 (d, 1H, J=7.2 Hz), 7.51-7.57 (m, 2H), 7.87-7.89 (m, 2H); MS for C$_{32}$H$_{34}$N$_4$O$_5$ m/z 555.05 (M+H)$^+$.

3-(3-Iodopropyl)benzo[d]oxazol-2 (3H)-one

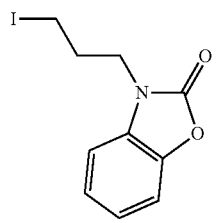 [SMILES: O=c1oc2ccccc2n1CCCI]

To a solution of 2-benzoxazolinone (2.0 g, 14.8 mmol) and potassium carbonate (3.07 g, 22.2 mmol) in N,N-dimethylformamide (20 mL), was added 1-bromo-3-chloropropane (4.4 mL, 44.4 mmol, d=1.6). After stirring at 55° C. for 18 hours, the reaction mixture was diluted with ethyl acetate (100 mL), washed with dilute citric acid, water and brine. The organic phase was dried over MgSO$_4$ and concentrated to obtain 3-(3-chloropropyl)benzo[d]oxazol-2(3H)-one (3.1 g, 99%).

To a solution of 3-(3-chloropropyl)benzo[d]oxazol-2(3H)-one (3.04 g, 14.36 mmol) in acetone (60 mL), was added sodium iodide (4.3 g, 28.73 mmol). After refluxing for 60 hours, the reaction mixture was filtered. The filtrate was washed with water and dried to obtain the title compound (3.6 g, 83%); $^1$H NMR (DMSO-d$_6$): δ 2.19-2.24 (m, 2H), 3.28 (t, 2H, J=6.8 Hz), 3.87 (t, 2H, J=6.8 Hz), 7.11 (t, 1H, J=8 Hz), 7.22 (t, 1H, J=8 Hz), 7.32 (t, 2H, J=8.4 Hz). MS for C$_{10}$H$_{10}$INO$_2$ m/z 304.33 (M+H)$^+$.

Example 31

Compound 47

Methyl 3-((4-oxo-8-(3-(2-oxobenzo[d]thiazol-3(2H)-yl)propyl)-1-phenyl-1,3,8-triazaspiro[4.5]decan-3-yl)methyl)benzoate

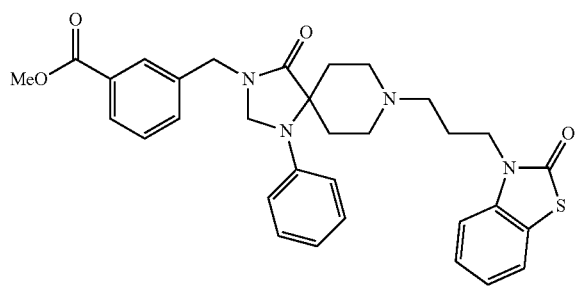 [SMILES: COC(=O)c1cccc(CN2CN(c3ccccc3)C3(CCN(CCCn4c(=O)sc5ccccc54)CC3)C2=O)c1]

To tert-butyl 3-(3-(methoxycarbonyl)benzyl)-4-oxo-1-phenyl-1,3,8-triazaspiro[4.5]decane-8-carboxylate (0.24 g, 0.5 mmol) was added 4M solution of HCl in dioxane (5 mL). After stirring at room temperature for an hour, the reaction mixture was concentrated in vacuo to obtain methyl 3-((4-oxo-1-phenyl-1,3,8-triazaspiro[4.5]decan-3-yl)methyl)benzoate as a hydrochloride salt.

To a solution of the hydrochloride salt and potassium carbonate (0.173 g, 1.25 mmol) in N,N-dimethylformamide (4 mL), was added 3-(3-iodopropyl)benzo[d]thiazol-2(3H)-one (0.16 g, 0.5 mmol). After stirring at 55° C. for 18 hours, the reaction mixture was diluted with ethyl acetate (50 mL), washed with water and brine. The organic phase was dried over MgSO$_4$, filtered, concentrated and isolated by preparatory TLC (10% methanol/dichloromethane) to obtain the product (0.25 g, 88%); $^1$H NMR (DMSO-d$_6$): δ 1.59 (d, 2H, J=12.8 Hz), 1.84 (t, 2H, J=6.8 Hz), 2.38 (t, 2H, J=6.4 Hz), 2.45-2.49 (m, 2H), 2.64-2.69 (m, 4H), 3.85 (s, 3H), 4.04 (t, 2H, J=6.8 Hz), 4.59 (d, 4H, J=13.2 Hz), 6.78 (t, 1H, J=7.2 Hz), 6.85 (d, 2H, J=7.6 Hz), 7.16-7.25 (m, 3H), 7.33 (t, 1H, J=7.6 Hz), 7.46 (d, 1H, J=7.2 Hz), 7.51-7.58 (m, 2H), 7.64 (d, 1H, J=7.6 Hz), 7.87-7.90 (m, 2H); MS for C$_{32}$H$_{34}$N$_4$O$_4$S m/z 571.05 (M+H)$^+$.

3-(3-Iodopropyl)benzo[d]thiazol-2(3H)-one

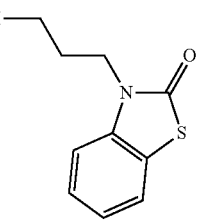

To a solution of 2-hydroxybenzothiazole (2.0 g, 13.2 mmol) and potassium carbonate (2.74 g, 19.8 mmol) in N,N-dimethylformamide (20 mL), was added 1-bromo-3-chloropropane (3.92 mL, 39.7 mmol, d=1.6). After stirring at 55° C. for 18 hours, the reaction mixture was diluted with ethyl acetate (100 mL), washed with dilute citric acid, water and brine. The organic phase was dried over MgSO$_4$ and concentrated to obtain 3-(3-chloropropyl)benzo[d]thiazol-2(3H)-one (2.86 g, 95%).

To a solution of 3-(3-chloropropyl)benzo[d]thiazol-2(3H)-one (2.86 g, 12.56 mmol) in acetone (50 mL), was added sodium iodide (3.77 g, 25.12 mmol). After refluxing for 60 hours, the reaction mixture was filtered. The filtrate was washed with water and dried to obtain the title compound (3.85 g, 83%); $^1$H NMR (DMSO-d$_6$): δ 2.13-2.16 (m, 2H), 3.28 (t, 2H, J=6.8 Hz), 4.05 (t, 2H, J=6.8 Hz), 7.18-7.22 (m, 1H), 7.38-7.39 (m, 2H), 7.66 (dt, 1H, J=7.6 and 0.8 Hz).

Example 32

Compound 48 methyl 3-((8-(4-(4-fluorophenyl)-4-oxobutyl)-4-oxo-1-phenyl-1,3,8-triazaspiro[4.5]decan-3-yl)methyl)benzoate

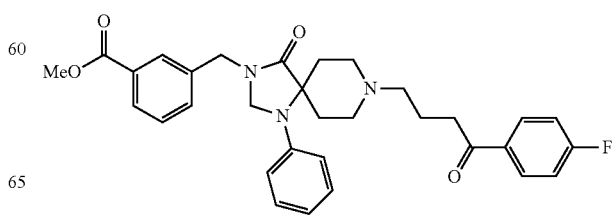

A mixture of methyl 3-((4-oxo-1-phenyl-1,3,8-triazaspiro[4.5]decan-3-yl)methyl)benzoate (500 mg, 1.2 mmol, 1 equiv), 1-(4-fluorophenyl)-4-iodobutan-1-one (351.1 mg, 1.2 mmol, 1 equiv), and potassium carbonate (497.6 mg, 3.6 mmol, 3 equiv) in N,N-dimethylformamide was heated at 65° C. for 16 h. The reaction was cooled to ambient temperature and partitioned between ethyl acetate and water. The organic layer was dried over MgSO$_4$, and concentrated in vacuo. The crude was purified using preparatory thin layer chromatography in 10% methanol in dichloromethane followed by a purification using preparatory high performance liquid chromatography to afford the acetate salt of the title compound as a yellow powder (65 mg, ~10%); $^1$H NMR (400 MHz, DMSO-d$_6$): δ 1.58 (d, 2H, J=14 Hz), 1.81-1.88 (m, 2H); 2.39-2.47 (m, 4H); 2.67-2.75 (m, 4H); 3.04 (t, 2H, J=6.4 and 7.2 Hz); 3.84 (s, 3H); 4.57 (s, 2H); 4.61 (s, 2H); 6.74-6.77 (m, 3H); 7.14-7.18 (m, 2H); 7.32-7.37 (m, 2H); 7.52-7.58 (m, 2H); 7.88-7.90 (m, 2H); 8.05-8.08 (m, 2H); 10.82 (s, 1H); MS for C$_{32}$H$_{34}$FN$_3$O$_4$ m/z 544.02 (M+H)$^+$.

Preparation of methyl 3-((4-oxo-1-phenyl-1,3,8-triazaspiro[4.5]decan-3-yl)methyl)benzoate

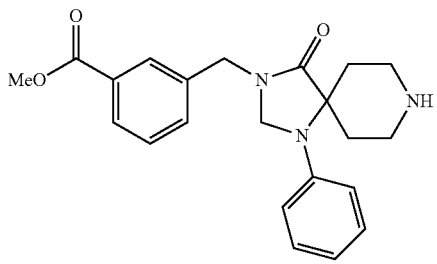

A mixture of tert-butyl 4-oxo-1-phenyl-1,3,8-triazaspiro[4.5]decane-8-carboxylate (2 g, 6.02 mmol, 1 equiv), methyl 3-(bromomethyl)benzoate (1.38 g, 6.02 mmol, 1 equiv) and potassium carbonate (1.25 g, 9.03 mmol, 1.5 equiv) in N,N-dimethylformamide was heated at 65° C. for 16 h. Upon cooling the mixture was partitioned between ethyl acetate and water. The organic layer was further washed with brine, dried over MgSO$_4$, filtered and concentrated in vacuo. The residue was purified using the Biotage flash chromatography system (SNAP 50 g cartridge, R$_f$=0.5, gradient—10%-50% ethyl acetate in hexanes) to afford tert-butyl 3-(3-(methoxycarbonyl)benzyl)-4-oxo-1-phenyl-1,3,8-triazaspiro[4.5]decane-8-carboxylate as a white solid (1.67 g, 58%); MS for C$_{27}$H$_{33}$N$_3$O$_5$ m/z 479.24 (M+H)$^+$.

A solution of tert-butyl 3-(3-(methoxycarbonyl)benzyl)-4-oxo-1-phenyl-1,3,8-triazaspiro[4.5]decane-8-carboxylate (1.2 g, 2.5 mmol, 1 equiv) in 4M hydrogen chloride solution in dioxane was stirred at ambient temperature for 3 h. The reaction mixture was concentrated and dried in vacuo to afford the hydrogen chloride salt of the title compound as a white powder (0.95 g, quant.); MS for C$_{22}$H$_{25}$N$_3$O$_3$ m/z 379.19 (M+H)$^+$.

Preparation of 1-(4-fluorophenyl)-4-iodobutan-1-one

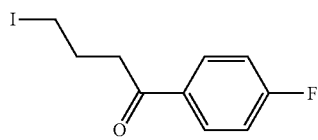 [SMILES: O=C(CCCI)c1ccc(F)cc1]

Sodium iodide (7.47 g, 49.84 mmol, 2 equiv) was added to a solution of 4-chloro-1-(4-fluorophenyl)butan-1-one (5 g, 24.92 mmol, 1 equiv) in acetone. The reaction mixture was refluxed for 16 h. After cooling to ambient temperature, it was evaporated under reduced pressure. The residue was partitioned between ethyl acetate and sodium bisulfite, followed by a wash with brine. The organic layer was dried over MgSO$_4$, filtered and concentrated in vacuo. The crude residue was purified using the Biotage flash chromatography system (SNAP 100 g cartridge, R$_f$=0.5, gradient—1%-10% ethyl acetate in hexanes) to afford the title compound as a clear oil (5.62 g, 77%). The bottle containing the compound was wrapped in aluminium foil and stored in the freezer to avoid further darkening of the mixture; MS for C$_{10}$H$_{10}$FIO m/z 291.98 (M+H)$^+$.

Example 33

Compound 49

3-((8-(4-(4-fluorophenyl)-4-oxobutyl)-4-oxo-1-phenyl-1,3,8-triazaspiro[4.5]decan-3-yl)methyl)benzoic acid

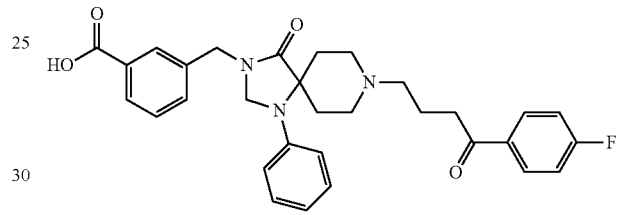

A solution of methyl 3-((8-(4-(4-fluorophenyl)-4-oxobutyl)-4-oxo-1-phenyl-1,3,8-triazaspiro[4.5]decan-3-yl)methyl)benzoate (450 mg, 0.828 mmol, 1 equiv) and lithium hydroxide (34.7 mg, 1.656 mmol, 2.0 equiv) in a 3:1 mixture of methanol and water (5 ml t/v) was stirred at 35° C. for 24 hrs. The reaction was concentrated in vacuo and purified using preparatory high performance liquid chromatography. The combined pure fractions were lyophilized to afford the acetate salt of the title compound as a white solid (100 mg, 25%); $^1$H NMR (400 MHz, DMSO-d$_6$): δ 1.59 (d, 2H, J=13.6 Hz), 1.84 (t, 2H, J=7.2 and 6.8 Hz); 2.45-2.46 (m, 4H); 2.72-2.78 (m, 4H); 3.05 (t, 2H, J=6.8 and 7.2 Hz); 4.57 (s, 2H); 4.60 (s, 2H); 6.72-6.78 (m, 3H); 7.12-7.16 (m, 2H); 7.32-7.36 (m, 2H); 7.47-7.53 (m, 2H); 7.86-7.88 (m, 2H); 8.04-8.08 (m, 2H); 10.82 (s, 1H); 12.9 (bs, 1H); MS for C$_{31}$H$_{32}$FN$_3$O$_4$ m/z 529.99 (M+H)$^+$.

Example 34

Compound 50 methyl 3-((8-(3-(3-methyl-2-oxo-2,3-dihydro-1H-benzo[d]imidazol-1-yl)propyl)-4-oxo-1-phenyl-1,3,8-triazaspiro[4.5]decan-3-yl)methyl)benzoate

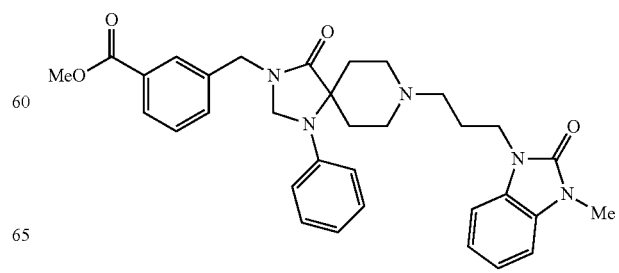

A mixture of methyl 3-((4-oxo-1-phenyl-1,3,8-triazaspiro[4.5]decan-3-yl)methyl)benzoate (400 mg, 0.962 mmol, 1 equiv), 1-(3-iodopropyl)-3-methyl-1H-benzo[d]imidazol-2(3H)-one (304.8 mg, 0.962 mmol, 1 equiv), and potassium carbonate (399 mg, 2.88 mmol, 3 equiv) was heated at 65° C. for 16 h. The reaction was cooled to ambient temperature and worked up using ethyl acetate and water. The organic layer was dried over MgSO₄, filtered and concentrated in vacuo. The crude residue was purified using preparatory thin layer chromatography in 5% methanol in dichloromethane to afford the title compound as an oil (427 mg, 78%); ¹H NMR (400 MHz, DMSO-d₆): δ 1.61 (d, 2H, J=13.2 Hz), 1.85 (t, 2H, J=7.2 and 6.8 Hz); 2.34 (d, 2H, J=6.4 Hz); 2.64-2.66 (m, 2H); 2.89 (s, 3H); 3.843 (s, 3H); 3.91 (t, 2H, J=6.4 and 6.8 Hz); 4.58 (s, 2H); 4.62 (s, 2H); 6.78 (t, 1H, J=7.2 Hz); 6.86 (d, 2H, J=8.8 Hz); 7.01-7.07 (m, 2H); 7.13-7.14 (m, 1H); 7.21-7.26 (m, 3H); 7.52-7.58 (m, 2H); 7.88 (s, 1H); 7.90 (s, 1H); MS for C₃₃H₃₇N₅O₄ m/z 568.13 (M+H)⁺.

Preparation of 1-(3-iodopropyl)-3-methyl-1H-benzo[d]imidazol-2(3H)-one

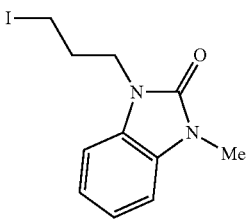 [SMILES: Cn1c(=O)n(CCCI)c2ccccc21]

A mixture of 1-methyl-1H-benzo[d]imidazol-2(3H)-one (2 g, 13.5 mmol, 1 equiv), 1-bromo-3-chloropropane (3.98 ml, 40.5 mmol, 3 equiv), and potassium carbonate (2.79 g, 20.25 mmol, 1.5 equiv) in N,N-dimethylformamide was heated at 65° C. for 16 h. The reaction was cooled to ambient temperature and diluted with ethyl acetate. After being washed with water and brine, the organic layer was dried over MgSO₄, filtered, and concentrated in vacuo. The resulting residue was purified using the Biotage chromatography system (SNAP 100 g cartridge, R_f=0.6, gradient—10%-50% ethyl acetate/hexanes) to afford 1-(3-chloropropyl)-3-methyl-1H-benzo[d]imidazol-2(3H)-one as a clear oil (2.57 g, 85%); ¹H NMR (400 MHz, DMSO-d₆): δ 2.05-2.12 (m, 1H); 2.14-2.21 (m, 1H); 3.32 (s, 3H); 3.53 (t, 1H, J=6.8 and 6.4 Hz); 3.66 (t, 1H, J=6.4 Hz); 3.92-3.97 (m, 2H); 7.05-7.09 (m, 2H); 7.12-7.16 (m, 1H); 7.17-7.21 (m, 1H); MS for C₁₁H₁₃ClN₂O m/z 226.07 (M+H)⁺.

Sodium iodide (3.43 g, 22.89 mmol, 2 equiv) was added to a solution of 1-(3-chloropropyl)-3-methyl-1H-benzo[d]imidazol-2(3H)-one (2.57 g, 11.44 mmol, 1 equiv) in acetone. The reaction mixture was refluxed for 16 h. After cooling to ambient temperature, it was evaporated under reduced pressure to remove all the acetone. The residue was worked up using ethyl acetate and water, followed by a wash with brine. The organic layer was dried over MgSO₄, filtered and concentrated in vacuo to afford the title compound as a red oil (3.62 g, quant); ¹H NMR (400 MHz, DMSO-d₆): δ 2.12-2.19 (m, 2H); 3.24 (t, 2H, J=7.2 and 6.8 u Hz); 3.28 (s, 3H); 3.89 (t, 2H, J=6.8 Hz); 7.04-7.09 (m, 2H); 7.13-7.16 (m, 1H); 7.18-7.22 (m, 1H); MS for C₁₁H₁₃IN₂O m/z 316.89 (M+H)⁺.

Example 35

Compound 52

3-((4-Oxo-8-(3-(2-oxobenzo[d]thiazol-3(2H)-yl)propyl)-1-phenyl-1,3,8-triazaspiro[4.5]decan-3-yl)methyl)benzoic acid

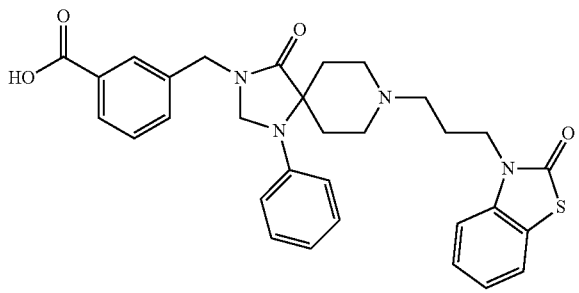 [SMILES: O=C(O)c1cccc(CN2CN(c3ccccc3)C3(CCN(CCCn4c(=O)sc5ccccc54)CC3)C2=O)c1]

To a solution of methyl 3-((4-oxo-8-(3-(2-oxobenzo[d]thiazol-3(2H)-yl)propyl)-1-phenyl-1,3,8-triazaspiro[4.5]decan-3-yl)methyl)benzoate (0.17 g, 0.3 mmol) in methanol (3 mL) was added lithium hydroxide monohydrate (0.025 g, 0.6 mmol) in water (1 mL). After stirring at room temperature for 18 h, the reaction mixture was concentrated in vacuo and isolated by preparatory TLC (10% methanol/dichloromethane) to obtain the title compound (0.06 g, 36%); ¹H NMR (DMSO-d₆): δ 1.60 (d, 2H, J=14 Hz), 1.85 (t, 2H, J=5.6 Hz), 2.48-2.53 (m, 7H), 2.66-2.75 (m, 4H), 4.04 (t, 2H, J=8.4 Hz), 4.59 (d, 2H, J=8.4 Hz), 6.77 (t, 1H, J=7.6 Hz), 6.85 (d, 2H, J=8.4 Hz), 7.18-7.24 (m, 3H), 7.33 (t, 1H, J=7.2 Hz), 7.45-7.51 (m, 3H), 7.64 (d, 1H, J=7.2 Hz), 7.85 (d, 2H, J=8 Hz); MS for C₃₁H₃₂N₄O₄S m/z 556.95 (M+H)⁺.

Example 36

Compound 55

Methyl 3-((1-(4-methoxyphenyl)-4-oxo-8-(3-(2-oxo-2,3-dihydro-1H-benzo[d]imidazol-1-yl)propyl)-1,3,8-triazaspiro[4.5]decan-3-yl)methyl)benzoate

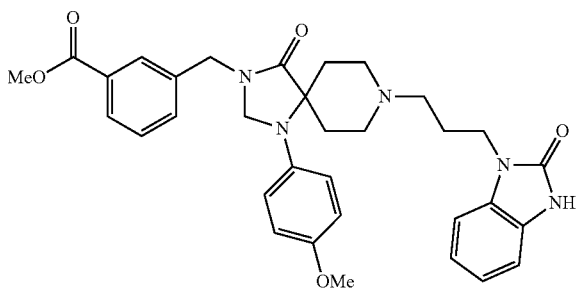 [SMILES: COC(=O)c1cccc(CN2CN(c3ccc(OC)cc3)C3(CCN(CCCn4c(=O)[nH]c5ccccc54)CC3)C2=O)c1]

To tert-butyl 3-(3-(methoxycarbonyl)benzyl)-1-(4-methoxyphenyl)-4-oxo-1,3,8-triazaspiro[4.5]decane-8-carboxylate (0.47 g, 0.92 mmol) was added 4M solution of HCl in dioxane (10 mL). After stirring at room temperature for 2 hours, the reaction mixture was concentrated in vacuo to obtain methyl 3-((1-(4-methoxyphenyl)-4-oxo-1,3,8-triazaspiro[4.5]decan-3-yl)methyl)benzoate as a hydrochloride salt.

To a solution of the hydrochloride salt and potassium carbonate (0.318 g, 2.3 mmol) in N,N-dimethylformamide (5 mL), was added 1-(3-iodopropyl)-1,3-dihydro-2H-benzimidazol-2-one (0.278 g, 0.92 mmol). After stirring at 55° C. for 18 hours, the reaction mixture was diluted with ethyl acetate (25 mL), washed with water and brine. The organic phase was dried over MgSO$_4$, filtered, concentrated and isolated by pTLC (10% methanol/dichloromethane) to obtain the product (0.43 g, 80%); $^1$H NMR (DMSO-d$_6$): δ 1.65 (d, 2H, J=8.8 Hz), 1.76 (t, 2H, J=6.4 Hz), 1.95-2.01 (m, 2H), 2.29 (t, 2H, J=7.6 Hz), 2.53-2.59 (m, 4H), 3.68 (s, 3H), 3.79 (t, 2H, J=6.4 Hz), 3.84 (s, 3H), 4.54 (d, 4H, J=31.2 Hz), 6.85 (d, 2H, J=8.8 Hz), 6.93-6.97 (m, 5H), 7.10 (m, 1H), 7.51-7.57 (m, 2H), 7.88-7.89 (m, 2H), 10.78 (s, 1H); MS for C$_{33}$H$_{37}$N$_5$O$_5$ m/z 584.04 (M+H)$^+$.

tert-Butyl 3-(3-(methoxycarbonyl)benzyl)-1-(4-methoxyphenyl)-4-oxo-1,3,8-triazaspiro[4.5]decane-8-carboxylate

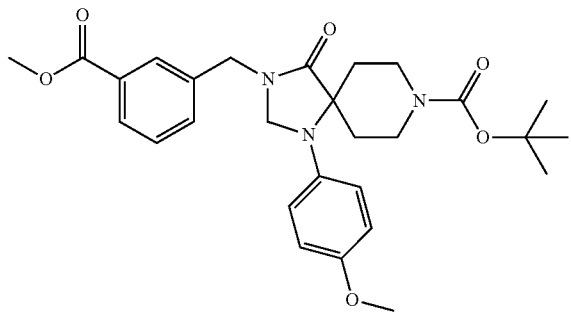 [SMILES: COC(=O)c1cccc(CN2CN(c3ccc(OC)cc3)C3(CCN(C(=O)OC(C)(C)C)CC3)C2=O)c1]

To a solution of 1-(4-methoxyphenyl)-1,3,8-triazaspiro[4.5]decan-4-one (3.0 g, 11.5 mmol) in dichloromethane (50 mL) and N,N-diisopropylethylenediamine (4.0 mL, 23 mmol, d=0.742), was added di-tert-butyl dicarbonate (2.53 g, 11.6 mmol). After stirring at room temperature for 18 hours, the reaction mixture was diluted with dichloromethane (100 mL), washed with dilute citric acid, water and brine. The organic phase was dried over MgSO$_4$, filtered and concentrated to obtain tert-butyl 1-(4-methoxyphenyl)-4-oxo-1,3,8-triazaspiro[4.5]decane-8-carboxylate (4.1 g, 99%).

To a solution of tert-butyl 1-(4-methoxyphenyl)-4-oxo-1,3,8-triazaspiro[4.5]decane-8-carboxylate (prepared according to methods described in U.S. Pat. No. 3,155,670 and U.S. Pat. No. 3,238,216) (1.3 g, 3.6 mmol) and potassium carbonate (1.0 g, 7.2 mmol) in N,N-dimethylformamide (20 mL), was added methyl 3-(bromomethyl)benzoate (0.90 g, 3.96 mmol). After stirring at 55° C. for 4 hours, the reaction mixture was diluted with ethyl acetate (100 mL), washed with dilute citric acid, water and brine. The organic phase was dried over MgSO$_4$, filtered and isolated by Biotage flash chromatography (10-100% ethyl acetate/hexanes) to obtain the title compound (1.2 g, 65%); $^1$H NMR (DMSO-d$_6$): δ 1.39 (s, 9H), 1.68 (d, 2H, J=9.6 Hz), 1.80-1.88 (m, 2H), 3.43 (br, 2H), 3.68 (s, 3H), 3.76 (br, 2H), 3.85 (s, 3H), 4.55 (s, 2H), 4.60 (s, 2H), 6.80-6.88 (m, 4H), 7.49-7.59 (m, 2H), 7.89-7.90 (m, 2H); MS for C$_{28}$H$_{35}$N$_3$O$_6$ m/z 510.01 (M+H)$^+$.

Example 37

Compound 56

3-((1-(4-Methoxyphenyl)-4-oxo-8-(3-(2-oxo-2,3-dihydro-1H-benzo[d]imidazol-1-yl)propyl)-1,3,8-triazaspiro[4.5]decan-3-yl)methyl)benzoic acid

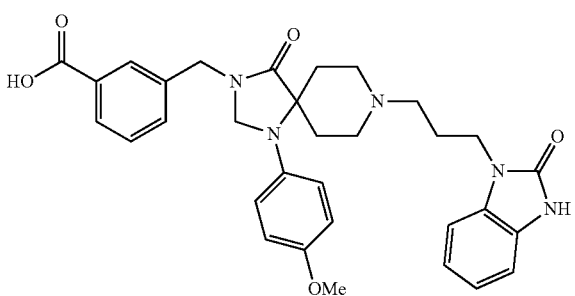 [SMILES: COc1ccc(N2CN(Cc3cccc(C(=O)O)c3)C(=O)C23CCN(CCCn2c(=O)[nH]c4ccccc42)CC3)cc1]

To a solution of methyl 3-((1-(4-methoxyphenyl)-4-oxo-8-(3-(2-oxo-2,3-dihydro-1H-benzo[d]imidazol-1-yl)propyl)-1,3,8-triazaspiro[4.5]decan-3-yl)methyl)benzoate (0.32 g, 0.55 mmol) in methanol (3 mL) was added lithium hydroxide monohydrate (0.046 g, 1.1 mmol) in water (1 mL). After stirring at room temperature for 18 h, the reaction mixture was concentrated in vacuo and isolated by reverse phase HPLC to obtain the title compound as an acetate salt (0.15 g, 48%); $^1$H NMR (DMSO-d$_6$): δ 1.64 (d, 2H, J=13.6 Hz), 1.77 (t, 2H, J=6.4 Hz), 1.95-2.02 (m, 2H), 2.31 (t, 2H, J=6 Hz), 2.57-2.67 (m, 4H), 3.68 (s, 3H), 3.79 (t, 2H, J=6.8 Hz), 4.34 (d, 4H, J=26.8 Hz), 6.84 (dd, 2H, J=4.8 and 2 Hz), 6.92-6.96 (m, 5H), 7.09-7.12 (m, 1H), 7.49-7.52 (m, 2H), 7.86-7.87 (m, 2H), 10.77 (s, 1H), 12.95 (br, 1H); MS for C$_{32}$H$_{35}$N$_5$O$_5$ m/z 570.04 (M+H)$^+$.

Example 38

Compound 57 methyl 3-((8-(3-(1H-indol-3-yl)propyl)-4-oxo-1-phenyl-1,3,8-triazaspiro[4.5]decan-3-yl)methyl)benzoate

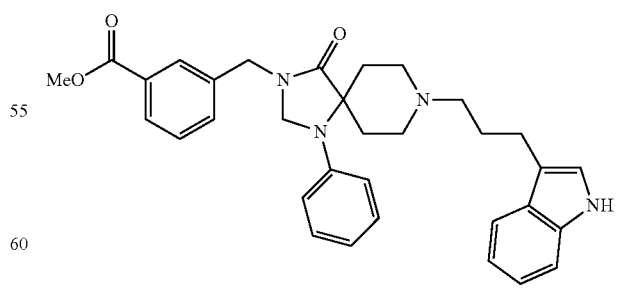

A mixture of methyl 3-((4-oxo-1-phenyl-1,3,8-triazaspiro[4.5]decan-3-yl)methyl)benzoate (871 mg, 2.11 mmol, 1.05 equiv), 3-(3-iodopropyl)-1H-indole (574 mg, 2.01 mmol, 1 equiv), and potassium carbonate (833 mg, 6.03 mmol, 3 equiv) in N—N-dimethylformamide was heated at 65° C. for 16 h. The reaction was cooled to ambient temperature and worked up using ethyl acetate and water. The organic layer was dried over MgSO$_4$, filtered and concentrated in vacuo. The crude residue was purified using preparatory thin layer chromatography in 7% methanol in dichloromethane to afford the title compound as cream crystals (252 mg, 46%); $^1$H NMR (400 MHz, DMSO-d$_6$): δ 1.62 (d, 2H, J=12 Hz), 1.84 (bs, 2H); 2.41 (bs, 2H); 2.57 (bs, 2H); 2.67 (bs, 2H); 2.71-2.75 (m, 4H); 3.85 (s, 3H); 4.59 (s, 2H); 4.63 (s, 2H); 6.77 (d, 1H, J=7.6 Hz); 6.85 (d, 2H, J=8 Hz); 6.96 (t, 1H, J=6.8 and 7.6 Hz); 7.03-7.07 (m, 1H); 7.13 (bs, 1H); 7.22 (t, 2H, J=8 Hz); 7.33 (d, 1H, J=8 Hz); 7.52-7.59 (m, 3H); 7.89-7.91 (m, 2H); 10.75 (s, 1H); MS for C$_{33}$H$_{36}$N$_4$O$_3$ m/z 537.06 (M+H)$^+$.

Preparation of 3 (3-iodopropyl)-1H-indole

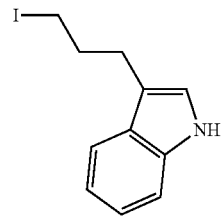 [SMILES: ICCCc1c[nH]c2ccccc12]

Sodium iodide (827 mg, 5.52 mmol, 2 equiv) was added to a solution of 3-(1H-indol-3-yl)propyl 4-methylbenzenesulfonate (909 mg, 2.76 mmol, 1 equiv) in acetone, and the mixture was refluxed for 16 h. Upon cooling the reaction, it was evaporated under reduced pressure and the residue was taken into dichloromethane. The organic layer was washed with water, dried over MgSO$_4$, filtered and concentrated in vacuo. The crude mixture was purified using the Biotage flash chromatography system (SNAP 50 g cartridge, R$_f$=0.7, gradient—5%-30% ethyl acetate in hexanes) to afford the title compound as an oil (789 mg, quant); $^1$H NMR (400 MHz, DMSO-d$_6$): δ 2.07-2.14 (m, 2H); 2.78 (t, 2H, J=7.6 and 6.8 Hz); 3.29 (t, 2H, J=6.8 Hz); 6.95-6.99 (m, 1H); 7.04-7.08 (m, 1H); 7.14 (d, 1H, J=2 Hz); 7.32-7.34 (m, 1H); 7.52 (d, 1H, J=8 Hz); 10.81 (s, 1H); MS for C$_{11}$H$_{12}$IN m/z 285.12 (M+H)$^+$.

Example 39

Compound 58

3-((8-(3-(3-methyl-2-oxo-2,3-dihydro-1H-benzo[d]imidazol-1-yl)propyl)-4-oxo-1-phenyl-1,3,8-triazaspiro[4.5]decan-3-yl)methyl)benzoic acid

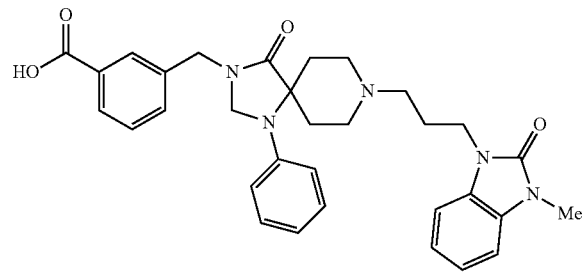

A solution of methyl 3-((8-(3-(3-methyl-2-oxo-2,3-dihydro-1H-benzo[d]imidazol-1-yl)propyl)-4-oxo-1-phenyl-1,3,8-triazaspiro[4.5]decan-3-yl)methyl)benzoate (326 mg, 0.575 mmol, 1 equiv) and lithium hydroxide (48.3 mg, 1.15 mmol, 2.0 equiv) in a 4:1 mixture of methanol and water (5 ml t/v) was stirred at 35° C. for 24 hrs. The reaction was concentrated in vacuo and purified using preparatory high performance liquid chromatography. The combined pure fractions were lyophilized to afford the acetate salt of the title compound as a white solid (56 mg, 17%); $^1$H NMR (400 MHz, DMSO-d$_6$): δ 1.61 (d, 2H, J=13.6 Hz), 1.84 (t, 2H, J=6.8 Hz); 2.37 (t, 2H, J=7.2 Hz, J=6.4 Hz); 2.54-2.59 (m, 2H); 2.66-2.73 (m, 4H); 3.32 (s, 3H); 3.91 (t, 2H, J=6.8 Hz); 4.58 (s, 2H); 4.60 (s, 2H); 6.76 (t, 1H, J=7.2 Hz); 6.85 (d, 2H, J=8 Hz); 7-7.07 (m, 2H); 7.12-7.15 (m, 1H); 7.2-7.26 (m, 3H); 7.47-7.53 (m, 2H); 7.86-7.88 (m, 2H); 12.9 (bs, 1H); MS for C$_{32}$H$_{35}$N$_5$O$_4$ m/z 554.05 (M+H)$^+$.

Example 40

Compound 59

3-((8-(3-(1H-indol-3-yl)propyl)-4-oxo-1-phenyl-1,3,8-triazaspiro[4.5]decan-3-yl)methyl)benzoic acid

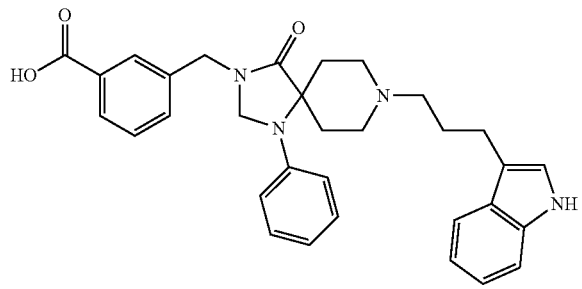 [SMILES: O=C(O)c1cccc(CN2CN(c3ccccc3)C3(CCN(CCCc4c[nH]c5ccccc45)CC3)C2=O)c1]

A solution of methyl methyl 3-((8-(3-(1H-indol-3-yl)propyl)-4-oxo-1-phenyl-1,3,8-triazaspiro[4.5]decan-3-yl)methyl)benzoate (350 mg, 0.651 mmol, 1 equiv) and lithium hydroxide (54.65 mg, 1.302 mmol, 2.0 equiv) in a 4:1 mixture of methanol and water (5 ml t/v) was stirred at 35° C. for 24 hrs. The reaction was concentrated in vacuo and purified using preparatory high performance liquid chromatography. The combined pure fractions were lyophilized to afford the acetate salt of the title compound as a white solid (170 mg, 50%); $^1$H NMR (400 MHz, DMSO-d$_6$): δ 1.63 (d, 2H, J=13.6 Hz), 1.86 (t, 2H, J=7.6 Hz, J=7.2 Hz); 2.46 (bs, 2H); 2.59-2.62 (m, 2H); 2.71-2.85 (m, 4H); 4.59 (s, 2H); 4.61 (s, 2H); 6.74 (t, 1H, J=7.2 Hz); 6.84 (d, 2H, J=8 Hz); 6.93-6.97 (m, 1H); 7.03-7.07 (m, 1H); 7.13 (d, 1H, J=2.4 Hz); 7.18 (t, 2H, J=7.6 and 8.4 Hz); 7.32 (d, 1H, J=8.4 Hz); 7.47-7.54 (m, 3H); 7.86-7.88 (m, 2H); 10.74 (s, 1H); 12.6 (bs, 1H); MS for C$_{32}$H$_{34}$N$_4$O$_3$ m/z 523.07 (M+H)$^+$.

Example 41

Compound 60 tert-Butyl 3-((4-oxo-8-(3-(2-oxo-2,3-dihydro-1H-benzo[d]imidazol-1-yl)propyl)-1-phenyl-1,3,8-triazaspiro[4.5]decan-3-yl)methyl)benzoate

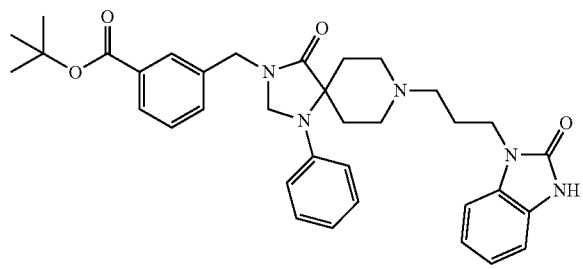

A mixture of tert-butyl 3-((4-oxo-1-phenyl-1,3,8-triazaspiro[4.5]decan-3-yl)methyl)benzoate (500 mg, 1.19 mmol, 1 equiv), 1-(3-iodopropyl)-1,3-dihydro-2H-benzimidazol-2-one-one (358.8 mg, 1.19 mmol, 1 equiv), and potassium carbonate (493.4 mg, 3.57 mmol, 3 equiv) in N,N-dimethylformamide was heated at 65° C. for 16 h. After cooling to ambient temperature, the crude mixture was partitioned between ethyl acetate and water. The organic layer was dried over $MgSO_4$, filtered, concentrated, and the crude residue was purified using preparatory thin layer chromatography in 10% methanol in dichloromethane to afford the title compound (548 mg, 77.4%); $^1$H NMR (400 MHz, DMSO-$d_6$): δ 1.52 (s, 9H); 1.61 (d, 2H, J=12.8 Hz); 1.83 (t, 2H, J=6.8 Hz); 2.36 (t, 2H, J=6.8 Hz); 2.54-2.73 (m, 6H); 3.86 (t, 2H, J=6.8 and 6.4 Hz); 4.58 (s, 2H); 4.61 (s, 2H); 6.77 (t, 1H, J=7.6 and 7.2 Hz); 6.85 (d, 2H, J=8 Hz); 6.97 (d, 1H, J=2.8 Hz); 7.18-7.25 (m, 3H); 7.48-7.55 (m, 2H); 7.79-7.84 (m, 2H); 10.81 (s, 1H); MS for $C_{35}H_{41}N_5O_4$ m/z 596.16 (M+H)$^+$.

Example 42

Compound 61 tert-butyl 3-((8-(3-(3-(heptanoyloxymethyl)-2-oxo-2,3-dihydro-1H-benzo[d]imidazol-1-yl)propyl)-4-oxo-1-phenyl-1,3,8-triazaspiro[4.5]decan-3-yl)methyl)benzoate

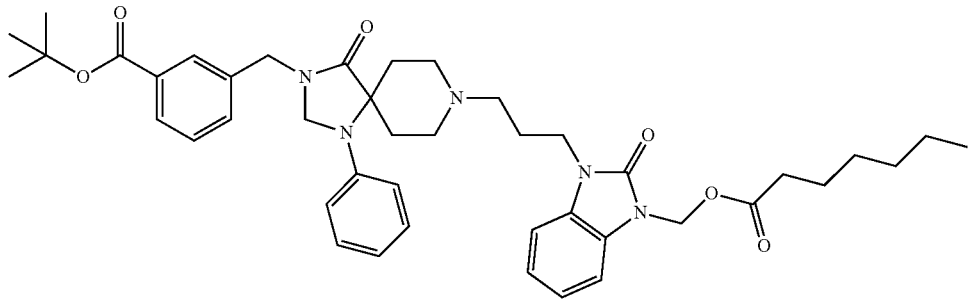 [SMILES: CCCCCCC(=O)OCn1c(=O)n(CCCN2CCC3(CC2)C(=O)N(Cc2cccc(C(=O)OC(C)(C)C)c2)CN3c2ccccc2)c2ccccc21]

tert-Butyl 3-((4-oxo-1-phenyl-1,3,8-triazaspiro[4.5]decan-3-yl)methyl)benzoate (0.200 g, 0.474 mmol), (3-(3-chloropropyl)-2-oxo-2,3-dihydro-1H-benzo[d]imidazol-1-yl) methyl heptanoate (0.17 g, 0.474 mmol), sodium iodide (0.021 g, 0.142 mmol), and potassium carbonate (0.0983 g, 0.711 mmol) in 2-butanone (5 mL) were heated at 78° C. for 4 hours. The reaction was diluted with 10% methanol/dichloromethane, filtered, and evaporated. The residue was purified by PTLC (50% ethyl acetate/hexanes) to give product as foam (0.30 g, 86%); NMR (DMSO-$d_6$); δ0.78 (t, J=6.4 Hz, 3H); 1.16 (m, 6H); 1.44-1.48 (m, 2H); 1.51 (s, 9H); 1.60 (m, 2H); 1.84-1.87 (m, 2H); 2.28 (t, J=6.8 Hz, 2H); 2.35 (m, 2H); 2.51-2.59 (m, 2H); 2.65-2.71 (m, 4H); 3.93 (t, J=6.8 Hz, 2H); 4.58 (s, 2H); 4.61 (s, 2H); 5.88 (s, 2H); 6.77 (t, J=7.2 Hz, 1H); 6.85 (d, J=8 Hz, 2H); 7.06-7.10 (m, 2H); 7.22 (t, J=8.4 Hz, 2H); 7.26-7.32 (m, 2H); 7.48-7.54 (m, 2H); 7.79 (s, 1H); 7.82-7.84 (m, 1H); MS for $C_{43}H_{55}N_5O_6$ m/z 738 (M+H)$^+$.

Preparation of tert-butyl 3-((4-oxo-1-phenyl-1,3,8-triazaspiro[4.5]decan-3-yl)methyl)benzoate

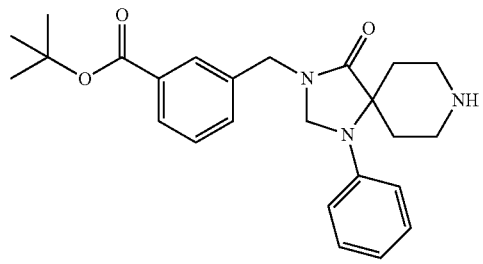 [SMILES: CC(C)(C)OC(=O)c1cccc(CN2CN(c3ccccc3)C3(CCNCC3)C2=O)c1]

A solution of 1-phenyl-1,3,8-triazaspiro[4.5]decan-4-one (10 g, 43.23 mmol, 1 equiv) in dichloromethane was treated with pyridine (6.99 ml, 86.46 mmol, 2 equiv) at 0° C. This was followed by the slow addition of benzyl chloroformate (6.39 ml, 45.4 mmol, 1.05 equiv). The reaction was stirred at ambient temperature for 16 h. The mixture was partitioned between dichloromethane and 10% citric acid followed by washes with water and brine. The combined organic layers were dried over $MgSO_4$, filtered and concentrated in vacuo to afford benzyl 4-oxo-1-phenyl-1,3,8-triazaspiro[4.5]decane-8-carboxylate as an off-white powder (12.5 g, 79%); MS for $C_{21}H_{23}N_3O_3$ m/z 366.18 (M+H)$^+$.

A mixture of benzyl 4-oxo-1-phenyl-1,3,8-triazaspiro[4.5]decane-8-carboxylate (12.5 g, 34.21 mmol, 1 equiv), sodium bis(trimethylsilyl)amide, 1M in tetrahydrofuran (37.63 ml, 37.63 mmol, 1.1 equiv), and tert-butyl 3-(bromomethyl)benzoate (9.27 g, 34.21 mmol, 1 equiv) in N,N-dimethylformamide was stirred for 16 h at ambient temperature. Reaction was diluted with ethyl acetate and the organic layer was washed with water and brine. The combined organic layers were dried over MgSO₄ and concentrated in vacuo. The crude residue was purified using the Biotage flash chromatography system (SNAP 100 g cartridge, $R_f$=0.6, 10%-50% ethyl acetate in hexanes) to afford benzyl 3-(3-(tert-butoxycarbonyl)benzyl)-4-oxo-1-phenyl-1,3,8-triazaspiro[4.5]decane-8-carboxylate (19 g, quant) as a cream solid; ¹H NMR (400 MHz, DMSO-d₆): δ 1.53 (s, 9H); 1.71 (d, 2H, J=13.6 Hz); 2.37-2.42 (m, 2H); 3.6 (bs, 2H); 4.01-4.03 (m, 2H); 4.61 (s, 2H); 4.64 (s, 2H); 5.14 (d, 2H, J=7.2 Hz); 6.69 (d, 2H, J=8 Hz); 6.79 (t, 2H, J=7.2 Hz); 7.16-7.2 (m, 2H); 7.32-7.39 (m, 5H); 7.49-7.56 (m, 2H); 7.81-7.85 (m, 2H); MS for C₃₃H₃₇N₃O₅ m/z 556.28 (M+H)⁺.

A solution of benzyl 3-(3-(tert-butoxycarbonyl)benzyl)-4-oxo-1-phenyl-1,3,8-triazaspiro[4.5]decane-8-carboxylate (5 g, 9.0 mmol, 1 equiv) in a mixture of ethyl acetate and ethanol was charged with 10% palladium on carbon (1 g, 20%/wt) and the resulting mixture was stabilized to a hydrogen atmosphere. The reaction was stirred as such for 2 h, filtered through Celite and the filtrate was concentrated in vacuo to afford the title compound as a grey foam (3.69 g, 97%); ¹H NMR (400 MHz, DMSO-d₆): δ 1.52 (s, 9H); 1.54-1.56 (m, 2H); 2.43-2.49 (m, 2H); 2.88-2.93 (m, 2H); 3.18-3.24 (m, 2H); 4.58 (s, 2H); 4.62 (s, 2H); 6.74 (t, 2H, J=6.8 and 7.6 Hz); 6.88 (d, 2H, J=8 Hz); 7.18-7.22 (m, 2H); 7.49-7.55 (m, 2H); 7.79-7.85 (m, 2H); MS for C₂₅H₃₁N₃O₃ m/z 422.24 (M+H)⁺.

Preparation of (3-(3-chloropropyl)-2-oxo-2,3-dihydro-1H-benzo[d]imidazol-1-yl)methyl heptanoate

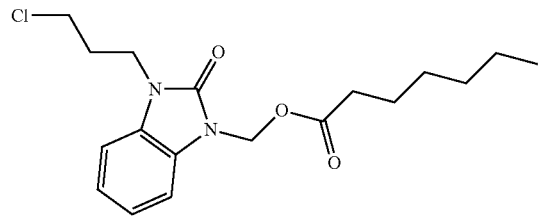 [SMILES: CCCCCCC(=O)OCn1c(=O)n(CCCCl)c2ccccc21]

Heptanoyl chloride (0.64 mL, 4.15 mmol) was added dropwise at 0° C. to 1-(3-chloropropyl)-3-(hydroxymethyl)-1H-benzo[d]imidazol-2(3H)-one (1.00 g, 4.15 mmol) and pyridine (0.50 mL, 6.23 mmol) in dichloromethane (20 mL) and then allowed to warm to room temperature. The mixture was washed with water and brine, dried (MgSO₄), and evaporated. The residue was purified by PTLC (30% ethyl acetate/hexanes) to give product as an oil (1.35 g, 92%); NMR (DMSO-d₆); δ0.80 (t, J=6.8 Hz, 3H); 1.15-1.19 (m, 6H); 1.46-1.49 (m, 2H); 2.08-2.12 (m, 2H); 2.30 (t, J=7.2 Hz, 2H); 3.67 (t, J=6.4 Hz, 2H); 3.97 (t, J=6.8 Hz, 2H); 5.88 (s, 2H); 7.10-7.16 (m, 2H); 7.24-7.29 (m, 2H); MS for C₁₈H₂₅ClN₂O₃ m/z 353 (M+H)⁺.

Preparation of 1-(3-chloropropyl)-3-(hydroxymethyl)-1H-benzo[d]imidazol-2(3H)-one

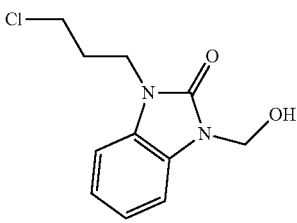 [SMILES: O=c1n(CO)c2ccccc2n1CCCCl]

1-(3-Chloropropyl)-1,3-dihydro-2H-benzimidazol-2-one (0.30 g, 1.42 mmol), paraformaldehyde (0.0853 g, 2.84 mmol), and sodium acetate (0.117 g, 1.42 mmol) in acetic acid (3 mL) were heated at 65° C. for 20 hours. The mixture was evaporated to dryness, dissolved in ethyl acetate, washed with saturated aqueous sodium bicarbonate and brine, dried (MgSO₄), and evaporated. The residue was purified by PTLC (50% ethyl acetate/hexanes) to give product as a white solid (0.31 g, 90%); NMR (DMSO-d₆); δ2.06-2.13 (m, 2H); 3.66 (t, J=6.4 Hz, 2H); 3.96 (t, J=6.8 Hz, 2H); 5.22 (d, J=7.2 Hz, 2H); 6.38 (t, J=7.2 Hz, 1H); 7.07 (m, 2H); 7.20-7.22 (m, 1H); 7.23-7.25 (m, 1H); MS for C₁₁H₁₃ClN₂O₂ m/z 241 (M+H)⁺.

Example 43

Compound 62 tert-butyl 3-((1-cyclohexyl-4-oxo-8-(3-(2-oxo-2,3-dihydro-1H-benzo[d]imidazol-1-yl)propyl)-1,3,8-triazaspiro[4.5]decan-3-yl)methyl)benzoate

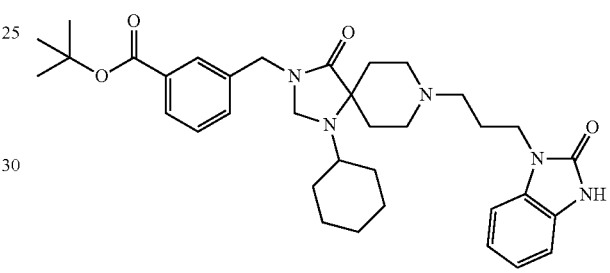

tert-Butyl 3-((1-cyclohexyl-4-oxo-1,3,8-triazaspiro[4.5]decan-3-yl)methyl)benzoate (0.823 g, 1.92 mmol), 1-(3-iodopropyl)-1,3-dihydro-2H-benzimidazol-2-one (0.58 g, 1.92 mmol), and potassium carbonate (0.39 g, 2.88 mmol) in N,N-dimethylformamide (8 mL) were heated at 65° C. for 2 hours. The reaction was diluted with ethyl acetate, washed with water and brine, dried (MgSO₄), and evaporated. The residue was purified by PTLC (5% methanol/dichloromethane) to give product as a white solid (0.84 g, 73%); ¹H NMR (DMSO-d₆); δ 0.93-0.96 (m, 1H); 1.14-1.25 (m, 4H); 1.52 (s, 9H); 1.57-1.62 (m, 9H); 1.79 (m, 2H); 2.29-2.36 (m, 4H); 2.63 (m, 3H); 3.82 (t, J=6.8 Hz, 2H); 4.08 (s, 2H); 4.43 (s, 2H); 6.97-7.01 (m, 3H); 7.14 (d, J=6.4 Hz, 1H); 7.44-7.49 (m, 2H); 7.72 (s, 1H); 7.81 (dt, J=2.4 Hz and 6.4 Hz, 1H); 10.8 (s, 1H); MS for C₃₅H₄₇N₅O₄ m/z 602 (M+H)⁺.

Preparation of tert-butyl 3-((1-cyclohexyl-4-oxo-1,3,8-triazaspiro[4.5]decan-3-yl)methyl)benzoate

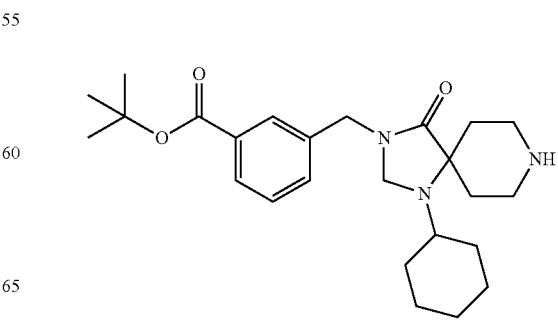

Benzyl 3-(3-(tert-butoxycarbonyl)benzyl)-1-cyclohexyl-4-oxo-1,3,8-triazaspiro[4.5]decane-8-carboxylate (1.37 g, 2.44 mmol) and palladium on carbon (10 wt. %, wet, Degussa type E101 NE/W,) (0.27 g) in ethyl acetate (20 mL) was stirred at room temperature under hydrogen (balloon) for 3 hours. The catalyst was removed by filtration and the filtrate evaporated and dried under vacuum to give product as a foam (1.04 g, quant.); MS for $C_{25}H_{37}N_3O_3$ m/z 428 (M+H)$^+$.

Preparation of benzyl 3-(3-(tert-butoxycarbonyl) benzyl)-1-cyclohexyl-4-oxo-1,3,8-triazaspiro[4.5] decane-8-carboxylate

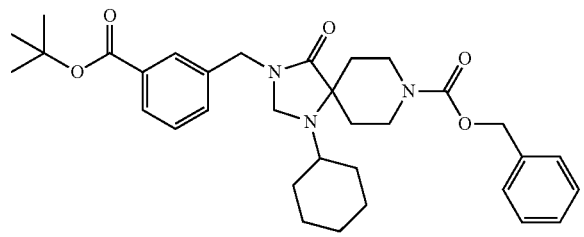 [SMILES: CC(C)(C)OC(=O)c1cccc(CN2CN(C3CCCCC3)C3(CCN(C(=O)OCc4ccccc4)CC3)C2=O)c1]

Sodium hydride (0.0699 g, 2.91 mol) was added portion-wise at 0° C. to benzyl 1-cyclohexyl-4-oxo-1,3,8-triazaspiro [4.5]decane-8-carboxylate (1.03 g, 2.77 mmol) in N,N-dimethylformamide (5 mL) and stirred at 0° C. for 10 minutes. tert-Butyl 3-(bromomethyl)benzoate (0.75 g, 2.77 mmol) was added dropwise at 0° C., the mixture allowed to warm to room temperature, and stirred overnight. The reaction was diluted with water and extracted with ethyl acetate. The extracts were washed with water and brine, dried (MgSO$_4$) and evaporated. The residue was purified by PTLC (50% ethyl acetate/hexanes) to give product as an oil (1.37 g, 88%); $^1$H NMR (DMSO-d$_6$); δ0.97 (m, 1H); 1.20 (m, 4H); 1.53 (s, 9H); 1.53-1.69 (m, 9H); 2.60 (m, 1H); 3.59 (m, 2H); 3.73 (m, 2H); 4.47 (s, 2H); 5.09 (s, 2H); 7.30-7.39 (m, 5H); 7.45-7.50 (m, 2H); 7.73 (m, 1H); 7.81 (m, 1H); MS for $C_{33}H_{43}N_3O_5$ m/z 562 (M+H)$^+$.

Preparation of benzyl 1-cyclohexyl-4-oxo-1,3,8-triazaspiro[4.5]decane-8-carboxylate

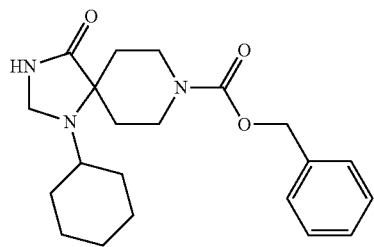 [SMILES: O=C(OCc1ccccc1)N1CCC2(CC1)C(=O)NCN2C1CCCCC1]

Benzyl chloroformate (1.74 mL, 0.0116 mmol) was added dropwise at 0° C. to 1-cyclohexyl-1,3,8-triazaspiro[4.5]decan-4-one, hydrochloride (prepared as described in *J. Med. Chem.* 1998, 41, 5084-5093); $^1$H NMR (DMSO-d$_6$); δ1.11 (m, 2H); 1.24 (m, 4H); 1.58 (m, 4H); 1.77 (m, 4H); 2.38 (m, 2H); 3.32 (m, 3H); 4.21 (s, 2H); 9.35 (br s, 1H); 12.7 (br s, 1H); (3.59 g, 0.0116 mol) in pyridine (35 mL). The mixture was allowed to warm to room temperature and then evaporated. The residue was diluted with ethyl acetate, washed with water and brine, dried (MgSO$_4$) and evaporated. The residue was purified by Biotage flash chromatography (5% methanol/dichloromethane) to give product as a white solid (2.15 g, 50%); $^1$H NMR (DMSO-d$_6$); δ1.04 (m, 1H); 1.23-1.31 (m, 4H); 1.55-1.58 (m, 6H); 1.67 (d, J=10.4 Hz, 2H); 2.52 (m, 2H); 3.51 (m, 2H); 3.74-3.77 (m, 2H); 4.10 (s, 2H); 5.08 (s, 2H); 7.31-7.39 (m, 5H); 8.20 (br s, 1H).

Example 44

Compound 64

Benzyl 3-((4-oxo-8-(3-(2-oxo-2,3-dihydro-1H-benzo [d]imidazol-1-yl)propyl)-1-phenyl-1,3,8-triazaspiro [4.5]decan-3-yl)methyl)benzoate

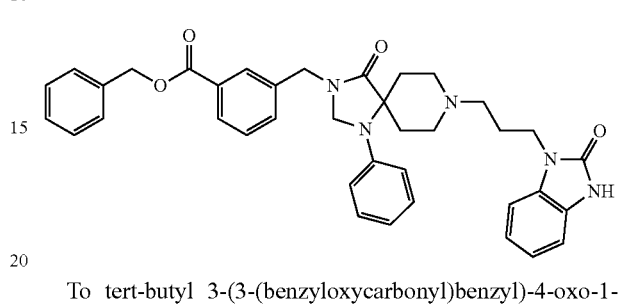

To tert-butyl 3-(3-(benzyloxycarbonyl)benzyl)-4-oxo-1-phenyl-1,3,8-triazaspiro[4.5]decane-8-carboxylate (2.7 g, 4.86 mmol) was added 4M solution of HCl in dioxane (7 mL). After stirring at room temperature for an hour, the reaction mixture was concentrated in vacuo to obtain benzyl 3-((4-oxo-1-phenyl-1,3,8-triazaspiro[4.5]decan-3-yl)methyl)benzoate as a hydrochloride salt.

To a solution of the hydrochloride salt and potassium carbonate (1.68 g, 12.15 mmol) in N,N-dimethylformamide (20 mL), was added 1-(3-iodopropyl)-1,3-dihydro-2H-benzimidazol-2-one (1.47 g, 4.86 mmol). After stirring at 55° C. for 18 hours, the reaction mixture was diluted with ethyl acetate (100 mL), washed with water and brine. The organic phase was dried over MgSO$_4$, filtered, concentrated and isolated by Biotage flash chromatography (2-20% methanol/dichloromethane) to obtain the product (2.6 g, 88%); $^1$H NMR (DMSO-d$_6$): δ 1.55 (d, 2H, J=13.2 Hz), 1.82 (t, 2H, J=6.4 Hz), 2.33 (t, 2H, J=6.8 Hz), 2.50-2.59 (m, 6H), 3.85 (t, 2H, J=6.8 Hz), 4.59 (d, 4H, J=16.8 Hz), 5.32 (s, 2H), 6.76 (t, 1H, J=7.2 Hz), 6.83 (d, 2H, J=8 Hz), 6.96 (d, 3H, J=1.2 Hz), 7.18-7.24 (m, 3H), 7.31-7.36 (m, 3H), 7.42 (dd, 2H, J=7.6 and 1.6 Hz), 7.52-7.59 (m, 2H), 7.86 (s, 1H), 7.91-7.94 (m, 1H), 10.83 (s, 1H); MS for $C_{38}H_{39}N_5O_4$ m/z 630.14 (M+H)$^+$.

Example 45

Compound 69

5-(4-Oxo-8-(3-(2-oxo-2,3-dihydro-1H-benzo[d]imidazol-1-yl)propyl)-1-phenyl-1,3,8-triazaspiro[4.5] decan-3-yl)-5-phenylpentanoic acid

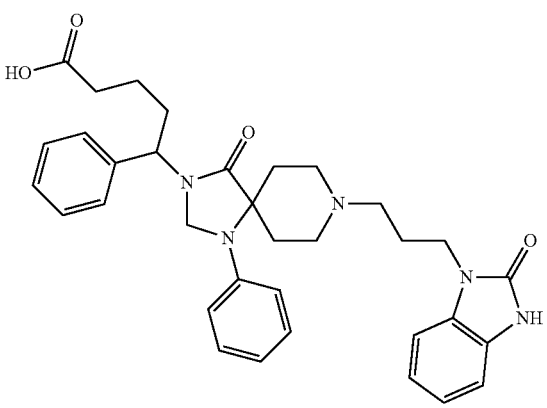 [SMILES: O=C(O)CCCC(c1ccccc1)N1CN(c2ccccc2)C2(CCN(CCCn3c(=O)[nH]c4ccccc43)CC2)C1=O]

To a solution of methyl 5-(4-oxo-8-(3-(2-oxo-2,3-dihydro-1H-benzo[d]imidazol-1-yl)propyl)-1-phenyl-1,3,8-triazaspiro[4.5]decan-3-yl)-5-phenylpentanoate (0.13 g, 0.22 mmol) in methanol (3 mL) was added lithium hydroxide monohydrate (0.018 g, 0.44 mmol) in water (1 mL). After stirring at room temperature for 24 h, the reaction mixture was concentrated in vacuo and isolated by reverse phase HPLC to obtain the title compound as an acetate salt (0.075 g, 56%); $^1$H NMR (DMSO-$d_6$): δ 1.41-1.58 (m, 4H), 1.81 (t, 2H, J=6.8 Hz), 1.97-2.11 (m, 2H), 2.26-2.35 (m, 4H), 2.49-2.53 (m, 2H), 2.61-2.67 (m, 5H), 3.84 (t, 2H, J=6.8 Hz), 4.26 (d, 1H, J=5.6 Hz), 4.74 (d, 1H, J=5.6 Hz), 5.15-5.19 (m, 1H), 6.76 (t, 1H, J=6.8 Hz), 6.86 (d, 2H, J=8 Hz), 6.96 (d, 3H, J=3.6 Hz), 7.17-7.24 (m, 3H), 7.29-7.32 (m, 1H), 7.35-7.38 (m, 3H), 10.80 (s, 1H), 12.07 (br, 1H); MS for $C_{34}H_{39}N_5O_4$ m/z 582.12 (M+H)$^+$.

Example 46

Compound 70

3-(4-Oxo-8-(3-(2-oxo-2,3-dihydro-1H-benzo[d]imidazol-1-yl)propyl)-1-phenyl-1,3,8-triazaspiro[4.5]decan-3-yl)-3-phenylpropanoic acid

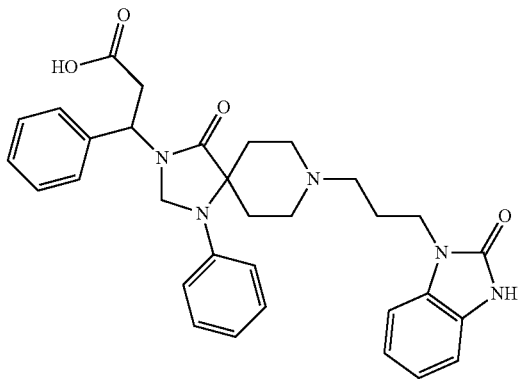 [SMILES: O=C(O)CC(c1ccccc1)N1CN(c2ccccc2)C2(CCN(CCCn3c(=O)[nH]c4ccccc43)CC2)C1=O]

To a solution of methyl 3-(4-oxo-8-(3-(2-oxo-2,3-dihydro-1H-benzo[d]imidazol-1-yl)propyl)-1-phenyl-1,3,8-triazaspiro[4.5]decan-3-yl)-3-phenylpropanoate (0.22 g, 0.39 mmol) in methanol (3 mL) was added lithium hydroxide monohydrate (0.033 g, 0.78 mmol) in water (1 mL). After stirring at room temperature for 24 h, the reaction mixture was concentrated in vacuo and isolated by reverse phase HPLC to obtain the title compound as an acetate salt (0.080 g, 37%); $^1$H NMR (DMSO-$d_6$): δ 1.45 (d, 1H, J=13.2 Hz), 1.55 (d, 1H, J=13.2 Hz), 1.81 (t, 2H, J=6.8 Hz), 2.33 (t, 2H, J=6.8 Hz), 2.48-2.50 (m, 2H), 2.57-2.68 (m, 4H), 3.07-3.10 (m, 2H), 3.84 (t, 2H, J=6.8 Hz), 4.37 (d, 1H, J=5.2 Hz), 4.70 (d, 1H, J=5.2 Hz), 5.52 (t, 1H, J=7.2 Hz), 6.75 (t, 1H, J=7.2 Hz), 6.86 (d, 2H, J=8.4 Hz), 6.96 (d, 3H, J=3.2 Hz), 7.16-7.24 (m, 3H), 7.29-7.32 (m, 1H), 7.37 (d, 4H, J=4 Hz), 10.80 (s, 1H), 11.50 (br, 1H); MS for $C_{32}H_{35}N_5O_4$ m/z 554.05 (M+H)$^+$.

Example 47

Compound 71

3-((4-Oxo-8-(3-(3-oxo-2H-benzo[b][1,4]oxazin-4(3H)-yl)propyl)-1-phenyl-1,3,8-triazaspiro[4.5]decan-3-yl)methyl)benzoic acid

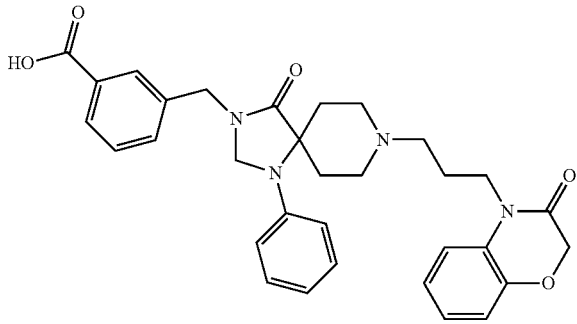 [SMILES: O=C(O)c1cccc(CN2CN(c3ccccc3)C3(CCN(CCCN4C(=O)COc5ccccc54)CC3)C2=O)c1]

To tert-butyl 3-((4-oxo-8-(3-(3-oxo-2H-benzo[b][1,4]oxazin-4(3H)-yl)propyl)-1-phenyl-1,3,8-triazaspiro[4.5]decan-3-yl)methyl)benzoate (0.1 g, 0.16 mmol) was added 4M solution of HCl in dioxane (2 mL). After stirring at room temperature for 3 hours, the reaction mixture was concentrated in vacuo and lyophilized in acetonitrile/water (1:1) to obtain the title compound as a hydrochloride salt (0.095 g, 99%); $^1$H NMR (DMSO-$d_6$): δ 1.92 (d, 2H, J=14 Hz), 2.03-2.07 (m, 2H), 2.85 (t, 2H, J=10 Hz), 3.25 (br, 2H), 3.62-3.72 (m, 4H), 3.99 (t, 2H, J=6.8 Hz), 4.61-4.67 (m, 6H), 6.81 (t, 1H, J=7.6 Hz), 6.96-7.10 (m, 5H), 7.23 (t, 2H, J=7.2 Hz), 7.31 (d, 1H, J=7.6 Hz), 7.48-7.57 (m, 2H), 7.87-7.89 (m, 2H), 9.96 (br, 1H), 13.03 (s, 1H); MS for $C_{32}H_{34}N_4O_5$ m/z 555.06 (M+H)$^+$.

Preparation of tert-butyl 3-((4-oxo-8-(3-(3-oxo-2H-benzo[b][1,4]oxazin-4(3H)-yl)propyl)-1-phenyl-1,3,8-triazaspiro[4.5]decan-3-yl)methyl)benzoate

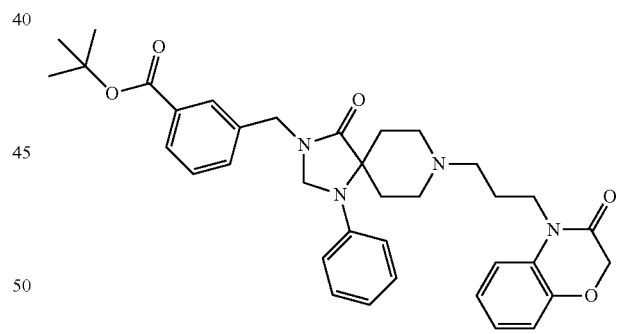

To a solution of tert-butyl 3-((4-oxo-1-phenyl-1,3,8-triazaspiro[4.5]decan-3-yl)methyl)benzoate (0.2 g, 0.47 mmol), potassium carbonate (0.097 g, 0.7 mmol) and sodium iodide (0.021 g, 0.14 mmol) in 2-butanone (5 mL), was added 4-(3-chloropropyl)-2H-benzo[b][1,4]oxazin-3(4H)-one (0.107 g, 0.47 mmol). After stirring at 78° C. for 18 hours, the reaction mixture was filtered, concentrated and isolated by preparatory TLC (10% methanol/dichloromethane) to obtain the title compound (0.1 g, 35%); $^1$H NMR (DMSO-$d_6$): δ 1.52 (s, 9H), 1.62 (d, 2H, J=12.8 Hz), 1.75 (t, 2H, J=6.8 Hz), 2.40 (t, 2H, J=7.2 Hz), 2.45-2.62 (m, 2H), 2.66-2.73 (m, 4H), 3.99 (t, 2H, J=7.2 Hz), 4.58-4.63 (m, 6H), 6.76 (t, 1H, J=7.2 Hz), 6.85 (d, 2H, J=8.4 Hz), 7.00 (m, 3H), 7.21 (t, 2H, J=7.2 Hz), 7.33-7.34 (m, 1H), 7.48-7.55 (m, 2H), 7.79 (s, 1H), 7.83 (d, 1H, J=7.2 Hz); MS for $C_{36}H_{42}N_4O_5$ m/z 611.12 (M+H)$^+$.

Preparation of 4-(3-chloropropyl)-2H-benzo[b][1,4]oxazin-3(4H)-one

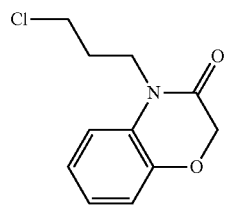 [SMILES: O=C1COc2ccccc2N1CCCCl]

To a solution of 2H-1,4-benzoxazin-3(4H)-one (1.0 g, 6.7 mmol) and potassium carbonate (1.4 g, 10.05 mmol) in N,N-dimethylformamide (20 mL), was added 1-bromo-3-chloropropane (1.99 mL, 20.1 mmol, d=1.6). After stirring at 60° C. for 60 hours, the reaction mixture was diluted with ethyl acetate (100 mL), washed with dilute citric acid, water and brine. The organic phase was dried over MgSO$_4$ and concentrated to the title compound (1.46 g, 97%); $^1$H NMR (DMSO-d$_6$): δ 1.99-2.03 (m, 2H), 3.71 (t, 2H, J=6.4 Hz), 4.00-4.04 (m, 2H), 4.63 (s, 2H), 7.00-7.01 (m, 2H), 7.03-7.09 (m, 1H), 7.22 (d, 1H, J=7.6 Hz); MS for C$_{11}$H$_{12}$ClNO$_2$ m/z 225.96 (M+H)$^+$.

Example 48

Compound 72

3-((1-cyclohexyl-4-oxo-8-(3-(2-oxo-2,3-dihydro-1H-benzo[d]imidazol-1-yl)propyl)-1,3,8-triazaspiro[4.5]decan-3-yl)methyl)benzoic acid, formate

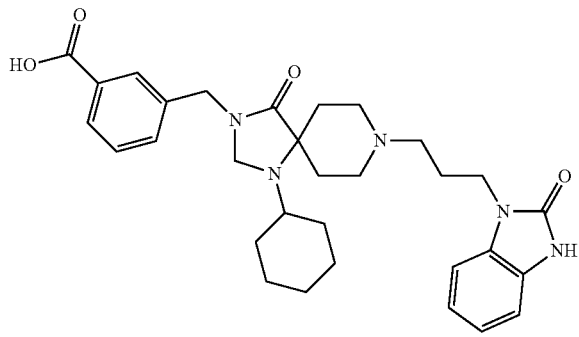 [SMILES: O=C(O)c1cccc(CN2CN(C3CCCCC3)C3(CCN(CCCn4c(=O)[nH]c5ccccc54)CC3)C2=O)c1]

tert-Butyl 3-((1-cyclohexyl-4-oxo-8-(3-(2-oxo-2,3-dihydro-1H-benzo[d]imidazol-1-yl)propyl)-1,3,8-triazaspiro[4.5]decan-3-yl)methyl)benzoate (0.3 g, 0.534 mmol), and formic acid (8 mL) were stirred at room temperature for 20 hours. The reaction was evaporated to dryness and the residue purified by PTLC (10% methanol/dichloromethane). The product was dissolved in formic acid (5 mL) and then evaporated under vacuum. The residue was dissolved in acetonitrile (5 mL) and water (5 mL) and lyophilized to give product as a white solid (0.24 g, 75%); HPLC rt 9.24 min; $^1$H NMR (DMSO-d$_6$); δ0.85-1.00 (m, 1H); 1.12-1.22 (m, 4H); 1.49-1.52 (m, 2H); 1.61-1.72 (m, 6H); 1.84 (t, J=6.4 Hz, 2H); 2.46 (t, J=6.8 Hz, 2H); 2.52-2.56 (m, 4H); 2.79 (t, J=8.4 Hz, 2H); 3.82 (t, J=6.4 Hz, 2H); 4.08 (s, 2H); 4.43 (s, 2H); 6.96-7.00 (m, 3H); 7.14-7.15 (m, 1H); 7.41-7.46 (m, 2H); 7.81-7.83 (m, 2H); 8.17 (br s, 1H); 10.8 (s, 1H); MS for C$_{31}$H$_{39}$N$_5$O$_4$ m/z 546 (M+H)$^+$.

Example 49

Compound 74

3-((8-(heptanoyloxymethyl)-4-oxo-1-phenyl-1,3,8-triazaspiro[4.5]decan-3-yl)methyl)benzoic acid, formate

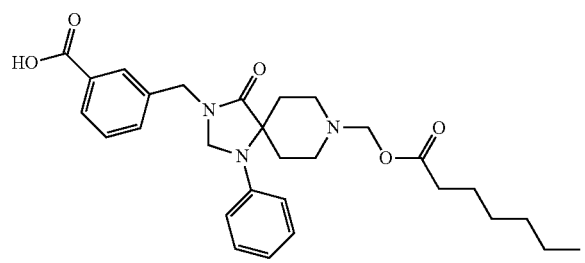 [SMILES: CCCCCCC(=O)OCN1CCC2(CC1)C(=O)N(Cc1cccc(C(=O)O)c1)CN2c1ccccc1]

tert-Butyl 3-((8-(3-(3-(heptanoyloxymethyl)-2-oxo-2,3-dihydro-1H-benzo[d]imidazol-1-yl)propyl)-4-oxo-1-phenyl-1,3,8-triazaspiro[4.5]decan-3-yl)methyl)benzoate (0.30 g, 0.407 mmol) and formic acid (8 mL) were stirred at room temperature for 20 hours. The reaction was evaporated to dryness and the residue purified by PTLC (10% methanol/dichloromethane). The product was dissolved in formic acid (5 mL) and then evaporated under vacuum. The residue was dissolved in acetonitrile (5 mL) and water (5 mL) and lyophilized to give product as a white solid (0.14 g, 60%); NMR (DMSO-d$_6$); δ0.78 (t, J=6.8 Hz, 3H); 1.16-1.18 (m, 6H); 1.43-1.48 (m, 2H); 1.65 (d, J=13.6 Hz, 2H); 1.90 (m, 2H); 2.29 (t, J=7.6 Hz, 2H); 2.49-2.63 (m, 4H); 2.86 (m, 4H); 3.93 (t, J=6.8 Hz, 2H); 4.59 (s, 2H); 4.61 (s, 2H); 5.88 (s, 2H); 5.88 (s, 2H); 6.76 (t, J=7.6 Hz, 1H); 7.86 (d, J=8.4 Hz, 2H); 7.06-7.12 (m, 2H); 7.20 (m, 2H); 7.26-7.32 (m, 2H); 7.48-7.54 (m, 2H); 7.87 (m, 2H); 8.15 (s, 1H); MS for C$_{29}$H$_{37}$N$_3$O$_5$ m/z 508 (M+H)$^+$.

Example 50

Compound 76

3-((8-((2,3-Dihydrobenzo[b][1,4]dioxin-2-yl)methyl)-4-oxo-1-phenyl-1,3,8-triazaspiro[4.5]decan-3-yl)methyl)benzoic acid

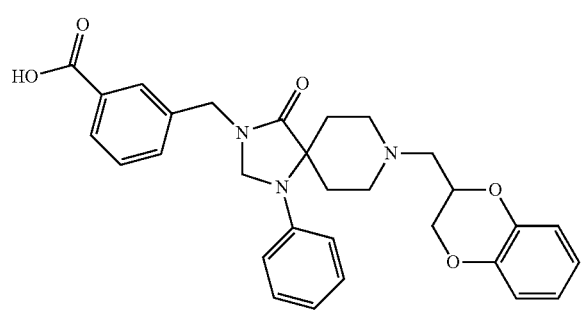

To tert-butyl 3-((8-((2,3-dihydrobenzo[b][1,4]dioxin-2-yl)methyl)-4-oxo-1-phenyl-1,3,8-triazaspiro[4.5]decan-3-yl)methyl)benzoate (0.17 g, 0.3 mmol) was added 4M solution of HCl in dioxane (3 mL). After stirring at room temperature for 4 hours, the reaction mixture was concentrated in vacuo and lyophilized in acetonitrile/water (1:1) to obtain the title compound as a hydrochloride salt (0.16 g, 99%); $^1$H NMR (DMSO-d$_6$): δ 1.96 (d, 2H, J=14 Hz), 2.91-3.02 (m, 2H), 3.45-3.71 (m, 6H), 4.03-4.08 (m, 1H), 4.36 (d, 1H, J=9.2 Hz), 4.61-4.66 (m, 4H), 4.92 (br, 1H), 6.81-6.97 (m, 5H), 7.04 (d, 2H, J=8 Hz), 7.24 (t, 2H, J=8.4 Hz), 7.49-7.59 (m, 2H), 8.89 (d, 2H, J=8.8 Hz), 10.83 (br, 1H), 13.04 (br, 1H); MS for $C_{30}H_{31}N_3O_5$ m/z 513.99 (M+H)$^+$.

Preparation of tert-butyl 3-((8-((2,3-dihydrobenzo[b][1,4]dioxin-2-yl)methyl)-4-oxo-1-phenyl-1,3,8-triazaspiro[4.5]decan-3-yl)methyl)benzoate

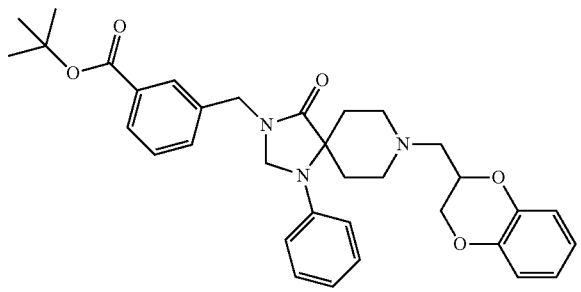

To a solution of tert-butyl 3-((4-oxo-1-phenyl-1,3,8-triazaspiro[4.5]decan-3-yl)methyl)benzoate (0.23 g, 0.55 mmol) and potassium carbonate (0.114 g, 0.83 mmol) in N,N-dimethylformamide (5 mL), was added 2-(bromomethyl)-2,3-dihydrobenzo[b][1,4]dioxine (0.082 mL, 0.55 mmol, d=1.533). After stirring at 55° C. for 18 hours, the reaction mixture was filtered, concentrated and isolated by preparatory TLC (7% methanol/dichloromethane) to obtain the title compound (0.17 g, 54%); $^1$H NMR (DMSO-d$_6$): δ 1.52 (s, 9H), 1.63 (d, 2H, J=12 Hz), 2.54-2.60 (m, 2H), 2.65 (d, 2H, J=6 Hz), 2.81-2.93 (m, 6H), 3.99-4.04 (m, 1H), 4.37 (dt, 2H, J=10.4 and 2.4 Hz), 4.60 (d, 2H, J=11.2 Hz), 6.76-6.88 (m, 7H), 7.23 (t, 2H, J=8.8 Hz), 7.48-7.55 (m, 2H), 7.79 (m, 1H), 7.83 (dt, 1H, J=7.2 and 2 Hz); MS for $C_{34}H_{39}N_3O_5$ m/z 570.12 (M+H)$^+$.

Example 51

Compound 77

3-((8-(4,4-(4-fluorophenyl)butyl)-4-oxo-1-phenyl-1,3,8-triazaspiro[4.5]decan-3-yl)methyl)benzoic acid

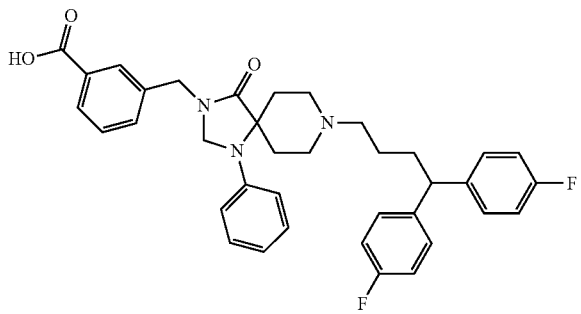 [SMILES: O=C(O)c1cccc(CN2CN(c3ccccc3)C3(CCN(CCCC(c4ccc(F)cc4)c4ccc(F)cc4)CC3)C2=O)c1]

A solution of tert-butyl 3-((8-(4,4-bis(4-fluorophenyl)butyl)-4-oxo-1-phenyl-1,3,8-triazaspiro[4.5]decan-3-yl)methyl)benzoate (400 mg, 0.601 mmol, 1 equiv) in 4M solution hydrogen chloride in dioxane was stirred at ambient temperature for 3 h. The mixture was concentrated in vacuo and the crude residue was purified using preparatory high performance liquid chromatography to afford the acetate salt of the title compound as a white solid (203 mg, 56%); $^1$H NMR (400 MHz, DMSO-d$_6$): δ 1.45 (bs, 2H); 1.71 (d, 2H, J=12.8 Hz); 2.01-2.07 (m, 2H); 2.67 (bs, 4H); 3.32 (bs, 4H); 4.03 (t, 1H, J=8 Hz); 4.59 (s, 2H); 4.61 (s, 2H); 6.76 (t, 1H, J=6.4 and 7.2 Hz); 6.86 (d, 2H, J=8 Hz); 7.11 (t, 4H, J=9.2 and 8.4 Hz); 7.18 (t, 2H, J=7.2 and 8.4 Hz); 7.33-7.36 (m, 4H); 7.48-7.55 (m, 2H); 7.87-7.89 (m, 2H); MS for $C_{37}H_{37}F_2N_3O_3$ m/z 610.18 (M+H)$^+$.

Preparation of tert-butyl 3-((8-(4,4-bis(4-fluorophenyl)butyl)-4-oxo-1-phenyl-1,3,8-triazaspiro[4.5]decan-3-yl)methylbenzoate

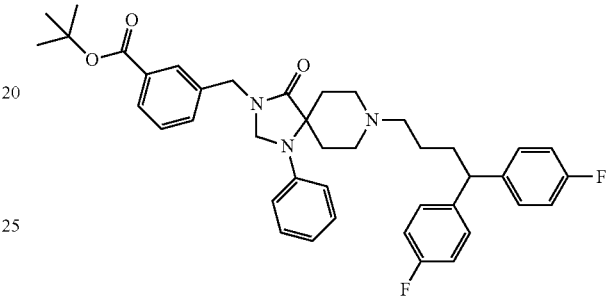

A mixture of tert-butyl 3-((4-oxo-1-phenyl-1,3,8-triazaspiro[4.5]decan-3-yl)methyl)benzoate (400 mg, 0.949 mmol, 1 equiv), 4,4'-(4-chlorobutane-1,1-diyl)bis(fluorobenzene) (222.06 μl, 0.949 mmol, 1 equiv), potassium carbonate (393.5 mg, 2.847 mmol, 3 equiv), and sodium iodide (42.7 mg, 0.285 mmol, 0.3 equiv) in 2-butanone was stirred at 81° C. for 16 h. After cooling, the reaction mixture was filtered, filtrate concentrated, and the crude residue was purified using the Biotage flash chromatography system (SNAP 50 g cartridge, $R_f$=0.5, gradient—1%-10% methanol in dichloromethane) to afford the title compound as a white crystalline solid (500 mg, 80.8%); $^1$H NMR (400 MHz, DMSO-d$_6$): δ 1.35 (bs, 2H); 1.51 (s, 9H); 1.59 (d, 2H, J=13.2 Hz); 2.02-2.04 (m, 2H); 2.36 (bs, 2H); 2.52-2.53 (m, 2H); 2.64-2.67 (m, 4H); 4.11 (s, 1H); 4.57 (s, 2H); 4.60 (s, 2H); 6.75 (bs, 1H); 6.81 (d, 2H, J=8.4 Hz); 7.08-7.12 (m, 4H); 7.16-7.20 (m, 2H); 7.32-7.36 (m, 4H); 7.49-7.53 (m, 2H); 7.78 (bs, 1H); 7.82-7.84 (m, 1H); MS for $C_{41}H_{45}F_2N_3O_3$ m/z 666.18 (M+H)$^+$.

Example 52

Compound 82

3-((1-(4-Methoxyphenyl)-4-oxo-8-(3-(2-oxobenzo[d]thiazol-3(2H)-yl)propyl)-1,3,8-triazaspiro[4.5]decan-3-yl)methyl)benzoic acid

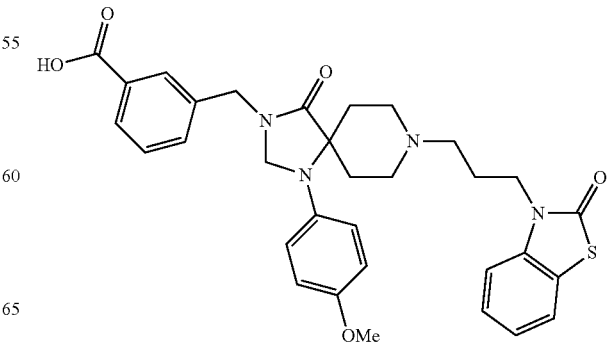

To a solution of methyl 3-((1-(4-methoxyphenyl)-4-oxo-8-(3-(2-oxobenzo[d]thiazol-3(2H)-yl)propyl)-1,3,8-triazaspiro[4.5]decan-3-yl)methyl)benzoate (0.19 g, 0.32 mmol) in methanol (3 mL) was added lithium hydroxide monohydrate (0.027 g, 0.63 mmol) in water (1 mL). After stirring at room temperature for 18 h, the reaction mixture was concentrated in vacuo and isolated by preparatory TLC (10% methanol/dichloromethane) to obtain the title compound (0.11 g, 59%); $^1$H NMR (DMSO-$d_6$): δ 1.64 (d, 2H, J=13.6 Hz), 1.79 (t, 2H, J=6.4 Hz), 1.88-1.95 (m, 2H), 2.38 (t, 2H, J=6 Hz), 2.50-2.66 (m, 4H), 3.69 (s, 3H), 3.97 (t, 2H, J=6.4 Hz), 4.53 (d, 4H, J=26.8 Hz), 6.86 (d, 2H, J=7.2 Hz), 6.94 (d, 2H, J=7.6 Hz), 7.16 (t, 1H, J=7.2 Hz), 7.30 (t, 1H, J=7.6 Hz), 7.38 (d, 1H, J=7.6 Hz), 7.47-7.53 (m, 2H), 7.58 (dd, 1H, J=8 and 1.2 Hz), 7.85-8.87 (m, 2H), 12.95 (br, 1H); MS for $C_{32}H_{34}N_4O_5S$ m/z 587.02 (M+H)$^+$.

Preparation of methyl 3-((1-(4-methoxyphenyl)-4-oxo-8-(3-(2-oxobenzo[d]thiazol-3(2H)-yl)propyl)-1,3,8-triazaspiro[4.5]decan-3-yl)methyl)benzoate

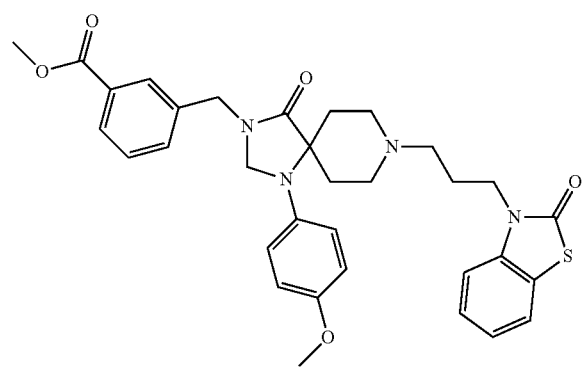 [SMILES: COC(=O)c1cccc(CN2CN(c3ccc(OC)cc3)C3(CCN(CCCn4c(=O)sc5ccccc54)CC3)C2=O)c1]

To tert-butyl 3-(3-(methoxycarbonyl)benzyl)-1-(4-methoxyphenyl)-4-oxo-1,3,8-triazaspiro[4.5]decane-8-carboxylate (0.26 g, 0.51 mmol) was added 4M solution of HCl in dioxane (5 mL). After stirring at room temperature for 3 hours, the reaction mixture was concentrated in vacuo to obtain methyl 3-((1-(4-methoxyphenyl)-4-oxo-1,3,8-triazaspiro[4.5]decan-3-yl)methyl)benzoate as a hydrochloride salt.

To a solution of the hydrochloride salt and potassium carbonate (0.176 g, 1.28 mmol) in N,N-dimethylformamide (5 mL), was added 3-(3-iodopropyl)benzo[d]thiazol-2(3H)-one (0.163 g, 0.51 mmol). After stirring at 55° C. for 18 hours, the reaction mixture was diluted with ethyl acetate (25 mL), washed with water and brine. The organic phase was dried over MgSO$_4$, filtered, concentrated and isolated by pTLC (10% methanol/dichloromethane) to obtain the product (0.2 g, 65%); $^1$H NMR (DMSO-$d_6$): δ 1.62 (d, 2H, J=12.8 Hz), 1.77 (t, 2H, J=6.4 Hz), 1.89-1.92 (m, 2H), 2.33 (t, 2H, J=6.4 Hz), 2.52-2.66 (m, 4H), 3.69 (s, 3H), 3.85 (s, 3H), 3.97 (t, 2H, J=6.8 Hz), 4.49 (s, 2H), 4.57 (m, 2H), 6.87 (d, 2H, J=8 Hz), 6.94 (d, 2H, J=7.6 Hz), 7.16 (t, 1H, J=8 Hz), 7.29 (t, 1H, J=7.6 Hz), 7.37 (d, 1H, J=7.6 Hz), 7.50-7.58 (m, 3H), 7.87-7.90 (m, 2H); MS for $C_{33}H_{36}N_4O_5S$ m/z 601.04 (M+H)$^+$.

Example 53

Compound 82

3-((8-(3-(1H-Indazol-1-yl)propyl)-4-oxo-1-phenyl-1,3,8-triazaspiro[4.5]decan-3-yl)methyl)benzoic acid

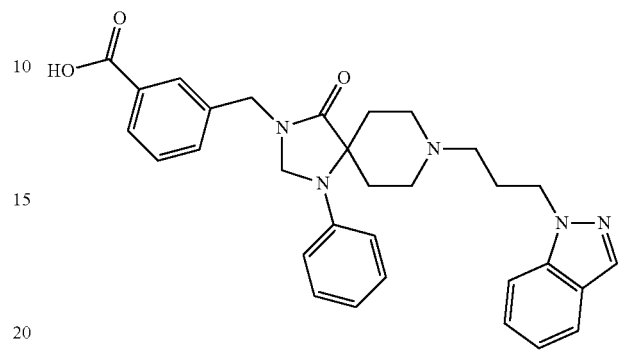

To tert-butyl 3-((8-(3-(1H-indazol-1-yl)propyl)-4-oxo-1-phenyl-1,3,8-triazaspiro[4.5]decan-3-yl)methyl)benzoate (0.16 g, 0.27 mmol) was added 4M solution of HCl in dioxane (2.5 mL). After stirring at room temperature for 3 hours, the reaction mixture was concentrated in vacuo and lyophilized in acetonitrile/water (1:1) to obtain the title compound as a hydrochloride salt (0.12 g, 79%); $^1$H NMR (DMSO-$d_6$): δ 1.97 (d, 2H, J=14.4 Hz), 2.32-2.36 (m, 2H), 2.92-2.98 (m, 2H), 3.19 (br, 2H), 3.45-3.70 (m, 4H), 4.54 (t, 2H, J=6.8 Hz), 4.63 (s, 4H), 6.79 (t, 1H, J=7.6 Hz), 7.02 (d, 2H, J=8.4 Hz), 7.14-7.22 (m, 3H), 7.42 (t, 1H, J=6.8 Hz), 7.48-7.57 (m, 2H), 7.73-7.79 (m, 2H), 7.87-7.88 (m, 2H), 8.11 (s, 1H), 10.65 (br, 1H), 13.03 (br, 1H); MS for $C_{31}H_{33}N_5O_3$ m/z 524.06 (M+H)$^+$.

Preparation of tert-butyl 3-((8-(3-(1H-indazol-1-yl)propyl)-4-oxo-1-phenyl-1,3,8-triazaspiro[4.5]decan-3-yl)methylbenzoate

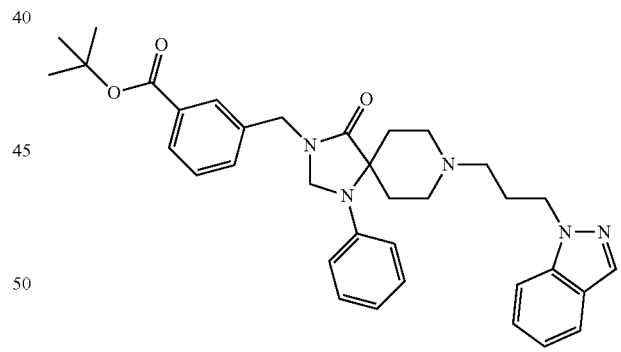

To a solution of tert-butyl 3-((4-oxo-1-phenyl-1,3,8-triazaspiro[4.5]decan-3-yl)methyl)benzoate (0.14 g, 0.33 mmol), potassium carbonate (0.068 g, 0.5 mmol) and sodium iodide (0.015 g, 0.01 mmol) in 2-butanone (3 mL), was added 1-(3-chloropropyl)-1H-indazole (0.065 g, 0.33 mmol). After stirring at 78° C. for 18 hours, the reaction mixture was filtered, concentrated and isolated by preparatory TLC (10% methanol/dichloromethane) to obtain the title compound (0.16 g, 84%); $^1$H NMR (DMSO-$d_6$): δ 1.51 (s, 9H), 1.59 (d, 2H, J=12.8 Hz), 2.03 (t, 2H, J=6.4 Hz), 2.24 (t, 2H, J=7.2 Hz), 2.57-2.67 (m, 4H), 3.56 (t, 2H, J=6.4 Hz), 4.47-4.63 (m, 6H), 6.78 (t, 1H, J=7.2 Hz), 6.85-6.87 (m, 2H), 7.11 (t, 1H, J=8 Hz), 7.24 (t, 2H, J=8 Hz), 7.34 (t, 1H, J=7.6 Hz), 7.48-7.51 (m, 2H), 7.70-7.83 (m, 4H), 8.08 (s, 1H); MS for $C_{35}H_{41}N_5O_3$ m/z 580.14 (M+H)$^+$.

Preparation of 1-(3-chloropropyl)-1H-indazole

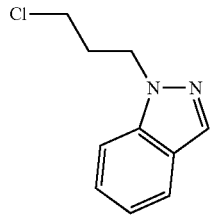 [SMILES: ClCCCn1ncc2ccccc21]

To a cooled (0° C.) solution of indazole (1.0 g, 8.46 mmol) in N,N-dimethylformamide (9 mL), was added 1M solution of lithium bis(trimethylsilyl)amide in tetrahydrofuran (9.3 mL, 9.3 mmol), followed by addition of 1-bromo-3-chloropropane (2.5 mL, 25.4 mmol, d=1.6). After stirring at room temperature for 18 hours, the reaction mixture was diluted with ethyl acetate (100 mL), washed with saturated NH$_4$Cl, water and brine. The organic phase was dried over MgSO$_4$, filtered and isolated by Biotage flash chromatography (10-60% ethyl acetate/hexanes) the fractions with Rf=0.83 (1:1 ethyl acetate/hexanes) to obtain the title compound (1.03 g, 63%); $^1$H NMR (DMSO-d$_6$): δ 2.23-2.30 (m, 2H), 3.58 (t, 2H, J=6.4 Hz), 4.52 (t, 2H, J=6.4 Hz), 7.14 (t, 1H, J=7.2 Hz), 7.39 (t, 1H, J=7.6 Hz), 7.66 (dd, 1H, J=8 and 0.8 Hz), 7.76 (dt, 1H, J=8 and 0.8 Hz), 8.08 (s, 1H); MS for C$_{10}$H$_{11}$ClN$_2$ m/z 195.00 (M+H)$^+$.

Example 54

Compound 83 methyl 3-((1-oxo-8-(3-(2-oxo-2,3-dihydro-1H-benzo[d]imidazol-1-yl)propyl)-4-phenyl-2,8-diazaspiro[4.5]decan-2-yl)methyl)benzoate

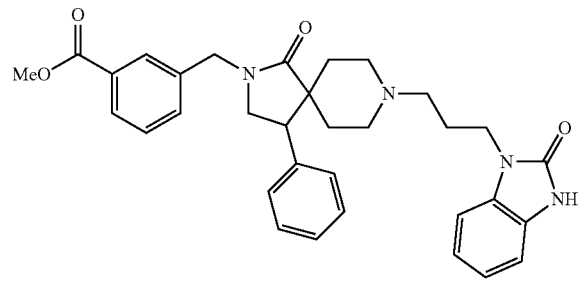 [SMILES: COC(=O)c1cccc(CN2CC(c3ccccc3)C3(CCN(CCCn4c(=O)[nH]c5ccccc54)CC3)C2=O)c1]

A mixture of methyl 3-((1-oxo-4-phenyl-2,8-diazaspiro[4.5]decan-2-yl)methyl)benzoate (500 mg, 1.206 mmol, 1 equiv), 1-(3-iodopropyl)-1,3-dihydro-2H-benzimidazol-2-one-one (364.4 mg, 1.206 mmol, 1 equiv), and potassium carbonate (500 mg, 3.62 mmol, 3 equiv) in N,N-dimethylformamide was stirred at 65° C. for 16 h. After cooling the reaction mixture, the crude mixture was partitioned between ethyl acetate and water. The organic layer was dried over MgSO$_4$, filtered and concentrated in vacuo. The residue was purified using the Biotage flash chromatography system (SNAP 50 g cartridge, R$_f$=0.4, gradient—10% methanol in dichloromethane) to afford the title compound as a white solid (416 mg, 62%); $^1$H NMR (400 MHz, DMSO-d$_6$): δ 0.99 (bs, 1H); 1.57-1.59 (m, 2H); 1.67-1.74 (m, 3H); 1.86 (bs, 1H); 2.22-2.39 (m, 4H); 2.73-2.76 (m, 2H); 3.25-3.27 (m, 1H); 3.59-3.62 (m, 1H); 3.76 (t, 2H, J=6.8 Hz); 3.86 (s, 3H); 4.55 (s, 2H); 6.94-6.95 (m, 3H); 7.09-7.11 (m, 3H); 7.20-7.24 (m, 3H); 7.51-7.58 (m, 2H); 7.88-7.90 (m, 2H); 10.77 (s, 1H); MS for C$_{33}$H$_{36}$N$_4$O$_4$ m/z 553.11 (M+H)$^+$.

Preparation of methyl 3-((1-oxo-4-phenyl-2,8-diazaspiro[4.5]decan-2-yl)methyl)benzoate

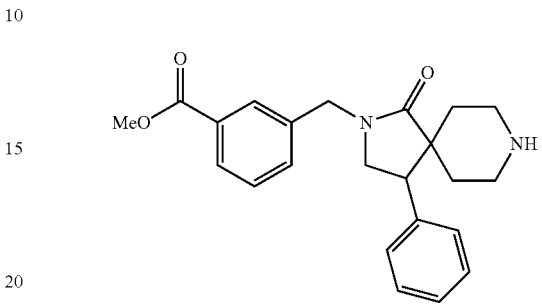

A solution of benzyl 2-(3-(methoxycarbonyl)benzyl)-1-oxo-4-phenyl-2,8-diazaspiro[4.5]decane-8-carboxylate (1.335 g, 2.79 mmol, 1 equiv) in 4M hydrogen chloride solution in dioxane was stirred at ambient temperature for 3 h. The mixture was concentrated in vacuo to afford the hydrogen chloride salt of the title compound as a cream powder (1.116 g, 97%); $^1$H NMR (400 MHz, DMSO-d$_6$): δ 1.11-1.18 (m, 1H); 1.71-1.83 (m, 2H); 1.93-1.97 (m, 1H); 3.38-3.42 (m, 1H); 3.45-3.49 (m, 3H); 3.55-3.59 (m, 2H); 3.65-3.72 (m, 1H); 3.69-3.71 (m, 1H); 3.86 (s, 3H); 4.57 (d, 2H, J=4 Hz); 7.19-7.21 (m, 2H); 7.25-7.33 (m, 3H); 7.53-7.60 (m, 2H); 7.89-7.92 (m, 2H); 8.61 (bs, 1H); 9.07 (bs, 1H); MS for C$_{23}$H$_{26}$N$_2$O$_3$ m/z 379.2 (M+H)$^+$.

Preparation of benzyl 2-(3-(methoxycarbonyl)benzyl)-1-oxo-4-phenyl-2,8-diazaspiro[4.5]decane-8-carboxylate

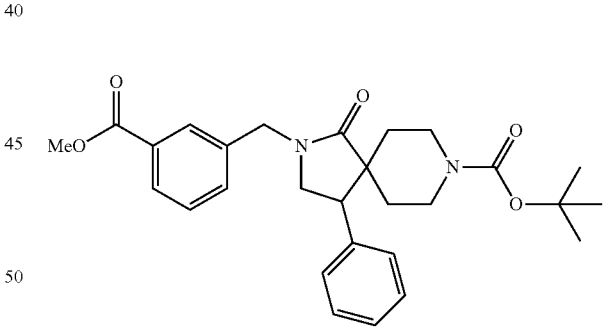

A mixture of benzyl 1-oxo-4-phenyl-2,8-diazaspiro[4.5]decane-8-carboxylate (1 g, 3.03 mmol, 1 equiv), lithium bis(trimethylsilyl)amide, 1M in tetrahydrofuran (3.33 ml, 3.33 mmol, 1.1 equiv), and methyl 3-(bromomethyl)benzoate (694.08 g, 3.03 mmol, 1 equiv) in N,N-dimethylformamide was stirred for 16 h at ambient temperature. Reaction was diluted with ethyl acetate and the organic layer was washed with water and brine. The combined organic layers were dried over MgSO$_4$ and concentrated in vacuo. The crude residue was purified using the Biotage flash chromatography system (SNAP 100 g cartridge, R$_f$=0.6, gradient—10%-50% ethyl acetate in hexanes) to afford the title compound as a cream solid (1.34 g, 92%); $^1$H NMR (400 MHz, DMSO-d$_6$): δ 0.87-0.92 (m, 1H); 1.33 (s, 9H); 1.46-1.51 (m, 2H); 1.54-1.65

(m, 1H); 3.03-3.07 (m, ¹H); 3.34-3.40 (m, 3H); 3.46-3.48 (m, 1H); 3.57-3.61 (m, 1H); 3.69-3.71 (m, 1H); 3.86 (s, 3H); 4.56 (s, 2H); 7.14-7.16 (m, 2H); 7.20-7.28 (m, 3H); 7.52-7.59 (m, 2H); 7.89-7.91 (m, 2H); MS for $C_{31}H_{32}N_2O_5$ m/z 513.23 (M+H)⁺.

Example 55

Compound 85

3-((8-(3-(1H-Benzo[d][1,2,3]triazol-1-yl)propyl)-4-oxo-1-phenyl-1,3,8-triazaspiro[4.5]decan-3-yl)methyl)benzoic acid

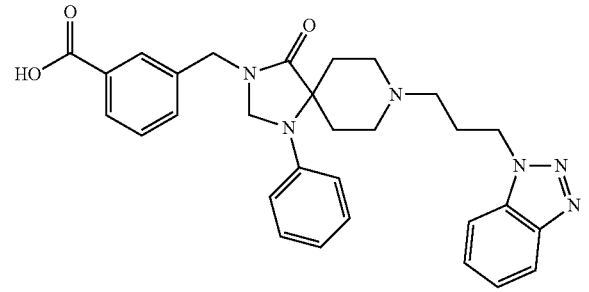 [SMILES: O=C(O)c1cccc(CN2CN(c3ccccc3)C3(CCN(CCCn4nnc5ccccc54)CC3)C2=O)c1]

To tert-butyl 3-((8-(3-(1H-benzo[d][1,2,3]triazol-1-yl)propyl)-4-oxo-1-phenyl-1,3,8-triazaspiro[4.5]decan-3-yl)methyl)benzoate (0.21 g, 0.34 mmol) was added 4M solution of HCl in dioxane (3 mL). After stirring at room temperature for 3 hours, the reaction mixture was concentrated in vacuo and lyophilized in acetonitrile/water (1:1) to obtain the title compound as a hydrochloride salt (0.2 g, 99%); ¹H NMR (DMSO-d₆): δ 1.89 (d, 2H, J=14.8 Hz), 2.49-2.51 (m, 2H), 2.95-3.03 (m, 2H), 3.22-3.27 (m, 2H), 3.53-3.69 (m, 4H), 4.64 (d, 4H, J=4 Hz), 4.86 (t, 2H, J=7.2 Hz), 6.78 (t, 1H, J=7.2 Hz), 7.04 (d, 2H, J=8 Hz), 7.20 (t, 2H, J=7.2 Hz), 7.41-7.61 (m, 4H), 7.86-7.89 (m, 2H), 7.97 (d, 1H, J=8.4 Hz), 8.07 (d, 1H, J=8.8 Hz), 10.94 (br, 1H), 13.03 (br, 1H); MS for $C_{30}H_{32}N_6O_3$ m/z 525.08 (M+H)⁺.

Preparation of tert-butyl 3-((8-(3-(1H-benzo[d][1,2,3]triazol-1-yl)propyl)-4-oxo-1-phenyl-1,3,8-triazaspiro[4.5]decan-3-yl)methyl)benzoate

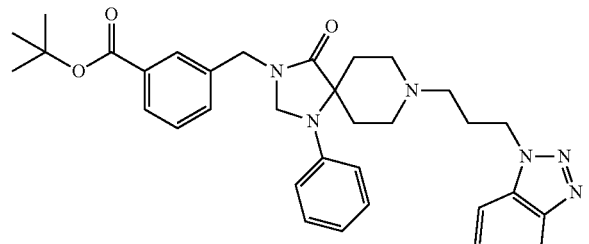

To a solution of tert-butyl 3-((4-oxo-1-phenyl-1,3,8-triazaspiro[4.5]decan-3-yl)methyl)benzoate (0.2 g, 0.47 mmol), potassium carbonate (0.097 g, 0.7 mmol) and sodium iodide (0.021 g, 0.14 mmol) in 2-butanone (5 mL), was added 1-(3-chloropropyl)-1H-benzo[d][1,2,3]triazole (0.093 g, 0.47 mmol). After stirring at 78° C. for 18 hours, the reaction mixture was filtered, concentrated and isolated by preparatory TLC (10% methanol/dichloromethane) to obtain the title compound (0.21 g, 77%); ¹H NMR (DMSO-d₆): δ 1.51 (s, 9H), 1.58 (d, 2H, J=13.2 Hz), 2.13 (t, 2H, J=6.4 Hz), 2.30 (t, 2H, J=6.4 Hz), 2.49-2.53 (m, 2H), 2.66 (d, 4H, J=7.6 Hz), 4.58 (d, 4H, J=9.6 Hz), 4.80 (t, 2H, J=6.4 Hz), 6.78 (t, 1H, J=6.8 Hz), 6.84 (d, 2H, J=8 Hz), 7.25 (t, 2H, J=8 Hz), 7.39 (t, 1H, J=7.2 Hz), 7.47-7.54 (m, 3H), 7.78 (s, 1H), 7.82 (dt, 1H, J=6.8 and 2 Hz), 7.93 (d, 1H, J=8.4 Hz), 8.03 (d, 1H, J=8.4 Hz); MS for $C_{34}H_{40}N_6O_3$ m/z 581.20 (M+H)⁺.

Preparation of 1-(3-chloropropyl)-1H-benzo[d][1,2,3]triazole

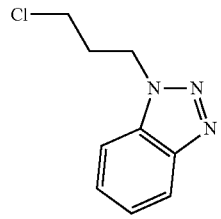

To a cooled (0° C.) solution of benzotriazole (1.0 g, 8.4 mmol) in N,N-dimethylformamide (10 mL), was added 1M solution of lithium bis(trimethylsilyl)amide in tetrahydrofuran (12.6 mL, 12.6 mmol), followed by addition of 1-bromo-3-chloropropane (2.48 mL, 25.2 mmol, d=1.6). After stirring at room temperature for 18 hours, the reaction mixture was diluted with ethyl acetate (100 mL), washed with saturated NH₄Cl, water and brine. The organic phase was dried over MgSO₄, filtered and isolated by Biotage flash chromatography (10-75% ethyl acetate/hexanes) the fractions with Rf=0.66 (1:1 ethyl acetate/hexanes) to obtain the title compound (0.55 g, 33%); ¹H NMR (DMSO-d₆): δ 2.34-2.41 (m, 2H), 3.64 (t, 2H, J=6.4 Hz), 4.84 (t, 2H, J=6.4 Hz), 7.41 (t, 1H, J=7.2 Hz), 7.57 (t, 1H, J=7.2 Hz), 7.88 (dd, 1H, J=8.4 and 1.2 Hz), 8.05 (dd, 1H, J=8.4 and 1.2 Hz); MS for $C_9H_{10}ClN_3$ m/z 196.01 (M+H)⁺.

Example 56

Compound 89

3-((4-oxo-8-(3-(2-oxoindolin-1-yl)propyl)-1-phenyl-1,3,8-triazaspiro[4.5]decan-3-yl)methyl)benzoic acid, hydrochloride

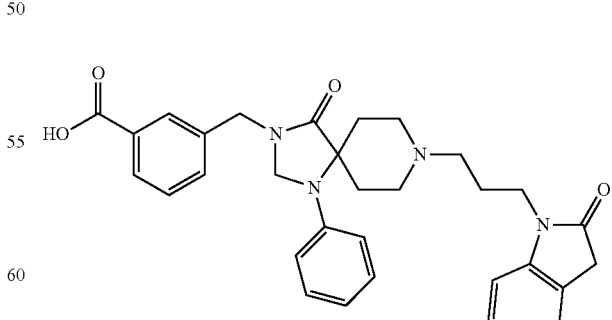

tert-Butyl 3-((4-oxo-8-(3-(2-oxoindolin-1-yl)propyl)-1-phenyl-1,3,8-triazaspiro[4.5]decan-3-yl)methyl)benzoate (0.15 g, 0.252 mmol) and 4M hydrochloric acid in 1,4-dioxane/1% triethylsilane (8 mL) were stirred at room temperature for 4 hours. The reaction was evaporated and the residue purified by PTLC (10% methanol/dichloromethane) to give product as the formate salt; NMR (DMSO-$d_6$); δ1.67 (d, J=13.6 Hz, 2H); 1.82 (t, J=7.2 Hz, 2H); 2.57 (m, 4H); 2.91 (m, 4H); 3.55 (s, 2H); 3.74 (t, J=6.8 Hz, 2H); 4.60 (s, 2H); 4.61 (s, 2H); 6.77 (t, J=7.6 Hz, 1H); 6.86 (d, J=8 Hz, 2H); 6.99 (t, J=8 Hz, 1H); 7.08 (d, J=7.6 Hz, 1H); 7.19-7.27 (m, 4H); 7.48-7.55 (m, 2H); 7.87-7.88 (m, 2H); 8.14 (s, 1H). The formate salt was redissolved in 4M hydrochloric acid in dioxane and evaporated. The residue was dissolved in acetonitrile (5 mL) and water (5 mL) and lyophilized to give product as a white solid (0.10 g, 70%); HPLC rt 9.83 min; NMR (DMSO-$d_6$); δ1.90 (d, J=14 Hz, 2H); 2.08 (m, 2H); 2.94 (m, 2H); 3.20 (m, 2H); 3.43 (m, 2H); 3.50-3.64 (s, 2H); 3.57 (s, 3H); 3.77 (t, J=7.2 Hz, 2H); 4.64 (s, 2H); 4.65 (s, 2H); 6.80 (t, J=7.2 Hz, 1H); 7.01-7.04 (m, 3H); 7.13 (d, J=8 Hz, 1H); 7.21 (t, J=8.8 Hz, 2H); 7.28 (m, 2H); 7.51 (t, J=8 Hz, 1H); 7.56-7.57 (m, 1H); 7.87-7.89 (m, 2H); 10.7 (br s, 1H); 13.0 (br s, 1H); MS for $C_{32}H_{34}N_4O_4$ m/z 539 (M+H)$^+$.

Preparation of tert-butyl 3-((4-oxo-8-(3-(2-oxoindolin-1-yl)propyl)-1-phenyl-1,3,8-triazaspiro[4.5]decan-3-yl)methylbenzoate

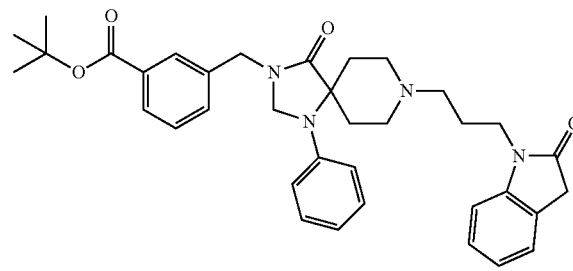 [SMILES: CC(C)(C)OC(=O)c1cccc(CN2CN(c3ccccc3)C3(CCN(CCCn4nnc5ccccc54)CC3)C2=O)c1]

tert-Butyl 3-((4-oxo-1-phenyl-1,3,8-triazaspiro[4.5]decan-3-yl)methyl)benzoate (0.30 g, 0.712 mmol), 1-(3-chloropropyl)indolin-2-one (0.15 g, 0.712 mmol), sodium iodide (0.032 g, 0.214 mmol), and potassium carbonate (0.15 g, 1.07 mmol) in 2-butanone (8 mL) were heated at 78° C. for 4 hours. The reaction was diluted with 10% methanol/dichloromethane, filtered, and evaporated. The residue was purified by PTLC (5% methanol/dichloromethane) to give product as an oil (0.15 g, 35%); NMR (DMSO-$d_6$); δ1.52 (s, 9H); 1.55-1.70 (m, 2H); 1.70-1.83 (m, 2H); 2.33-2.45 (m, 2H); 2.51-2.63 (m, 2H); 2.63-2.80 (m, 4H); 3.55 (s, 2H); 3.74 (t, J=6.8 Hz, 2H); 4.59 (s, 2H); 4.61 (s, 2H); 6.78 (t, J=7.2 Hz, 1H); 6.86 (d, J=8 Hz, 2H); 6.99 (t, J=7.6 Hz, 1H); 7.09 (d, J=8 Hz, 1H); 7.21-7.27 (m, 4H); 7.48-7.55 (m, 2H); 7.79 (s, 1H); 7.82-7.85 (m, 1H); MS for $C_{36}H_{42}N_4O_4$ m/z 595 (M+H)$^+$.

Preparation of 1-(3-chloropropyl)indolin-2-one

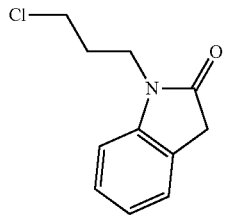 [SMILES: O=C1Cc2ccccc2N1CCCCl]

Oxindole (2.00 g, 0.0150 mol), 1-bromo-3-chloropropane (2.97 mL, 0.03 mol), and potassium carbonate (4.15 g, 0.03 mol) in acetonitrile (40 mL) were heated at reflux for 20 hours. The mixture was evaporated, diluted with ethyl acetate, washed with 2M aqueous hydrochloric acid and brine, dried (MgSO$_4$), and evaporated. The residue was purified by Biotage flash column chromatography (30% ethyl acetate/hexanes) to give product as an oil which solidified on standing (1.57 g, 50%); MS for $C_{11}H_{12}ClNO$ m/z 210 (M+H)$^+$.

Example 57

Compound 91

3-((8-(4-(4-methoxyphenyl)-4-oxobutyl)-4-oxo-1-phenyl-1,3,8-triazaspiro[4.5]decan-3-yl)methyl)benzoic acid

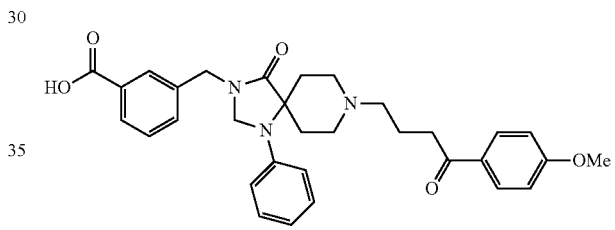

A solution of tert-butyl 3-((8-(4-(4-methoxyphenyl)-4-oxobutyl)-4-oxo-1-phenyl-1,3,8-triazaspiro[4.5]decan-3-yl)methyl)benzoate (100 mg, 0.496 mmol, 1 equiv) in 4M hydrogen chloride solution in dioxane was stirred at ambient temperature for 4 h. The mixture was concentrated in vacuo and the crude residue was purified using preparatory high performance liquid chromatography to afford the acetate salt of the title compound as a white solid (67 mg, 74%); $^1$H NMR (400 MHz, DMSO-$d_6$): δ 1.78 (bs, 2H); 1.95 (bs, 2H); 2.52-2.54 (m, 3H); 2.76 (bs, 4H); 3.08 (bs, 3H); 3.84 (s, 3H); 4.62 (s, 2H); 4.63 (s, 2H); 6.78 (d, 1H, J=7.2 Hz); 6.93 (bs, 2H); 7.05 (d, 2H, J=9.2 Hz); 7.20 (t, 2H, J=7.6 and 7.2 Hz); 7.49-7.57 (m, 2H); 7.87-7.89 (m, 2H); 7.96-7.98 (m, 2H); 12.45 (s, 1H); MS for $C_{32}H_{35}N_3O_5$ m/z 542.02 (M+H)$^+$.

Preparation of tert-butyl 3-((8-(4-(4-methoxyphenyl)-4-oxobutyl)-4-oxo-1-phenyl-1,3,8-triazaspiro[4.5]decan-3-yl)methyl)benzoate

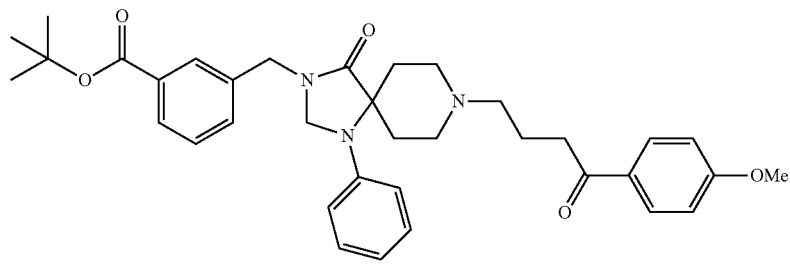 [SMILES: COc1ccc(C(=O)CCCN2CCC3(CC2)C(=O)N(Cc2cccc(C(=O)OC(C)(C)C)c2)CN3c2ccccc2)cc1]

A mixture of tert-butyl 3-((4-oxo-1-phenyl-1,3,8-triazaspiro[4.5]decan-3-yl)methyl)benzoate (300 mg, 0.71 mmol, 1 equiv), 4-iodo-1-(4-methoxyphenyl)butan-1-one (216.5 mg, 0.71 mmol, 1 equiv), and potassium carbonate (285.2 mg, 2.136 mmol, 3 equiv) in N,N-dimethylformamide was stirred at 68° C. for 16 h. After cooling the reaction mixture, the crude mixture was partitioned between ethyl acetate and water. The organic layer was dried over MgSO$_4$, filtered, concentrated, and the crude residue was purified using the Biotage flash chromatography system (SNAP 10 g cartridge, R$_f$=0.4, gradient—1%-8% methanol in dichloromethane) to afford the title compound as an oil (100 mg, 25%); MS for C$_{36}$H$_{43}$N$_3$O$_5$ m/z 598.3 (M+H)$^+$.

Preparation of
4-chloro-1-(4-methoxyphenyl)butan-1-one

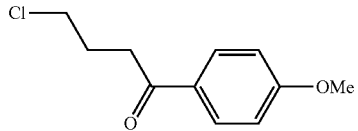 [SMILES: COc1ccc(C(=O)CCCCl)cc1]

Sodium iodide was added to a solution of 4-chloro-1-(4-methoxyphenyl)butan-1-one (1 g, 4.7 mmol, 1 equiv) in acetone, an the reaction mixture was refluxed for 16 h. Upon cooling, the reaction was concentrated in vacuo and the crude mixture was partitioned between dichloromethane and water. The organic layer was dried over MgSO$_4$, filtered and concentrated in vacuo. The residue was purified using the Biotage flash chromatography system (SNAP 50 g cartridge, R$_f$=0.7, gradient—5%-25% ethyl acetate in hexanes) to afford the title compound as a brownish green solid (1.13 g, 79%); MS for C$_{11}$H$_{13}$ClO$_2$ m/z 214.1 (M+H)$^+$.

Example 58

Compound 92 tert-butyl 3-((8-(3-(3,3-difluoro-2-oxoindolin-1-yl)propyl)-4-oxo-1-phenyl-1,3,8-triazaspiro[4.5]decan-3-yl)methyl)benzoate

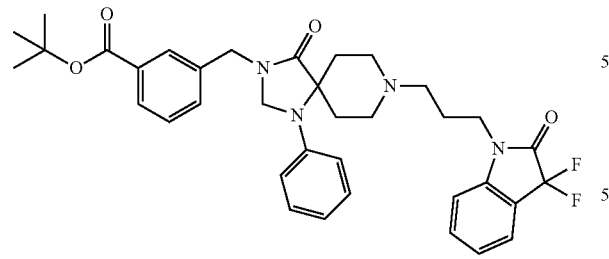

A mixture of tert-butyl 3-((4-oxo-1-phenyl-1,3,8-triazaspiro[4.5]decan-3-yl)methyl)benzoate (300 mg, 0.71 mmol, 1 equiv), 1-(3-chloropropyl)-3,3-difluoroindolin-2-one (206.5 mg, 0.71 mmol, 1 equiv), sodium iodide (42.7 mg, 0.285 mmol, 0.4 equiv), and potassium carbonate (295.2 mg, 2.136 mmol, 3 equiv) in 2-butanone was stirred at 81° C. for 16 h. After cooling the reaction mixture, the crude mixture was partitioned between ethyl acetate and water. The organic layer was dried over MgSO$_4$, filtered, concentrated, and the crude residue was purified using preparatory thin layer chromatography in 5% methanol in dichloromethane to afford the title compound as cream crystals (210 mg, 46.8%); $^1$H NMR (400 MHz, DMSO-d$_6$): δ 1.52 (s, 9H); 1.60 (d, 2H, J=13.2 Hz); 1.84 (t, 2H, J=6.8 and 6.4 Hz); 2.38 (t, 2H, J=6.4 Hz); 2.51 (bs, 2H); 2.71 (bs, 4H); 3.80 (t, 2H, J=6.8 Hz); 4.58 (s, 2H); 4.60 (s, 2H); 6.78 (t, 1H, J=7.2 Hz); 6.83 (d, 2H, J=8.4 Hz); 7.21-7.25 (m, 3H); 7.36 (d, 1H, J=8 Hz); 7.48-7.59 (m, 3H); 7.70 (d, 1H, J=6.8 Hz); 7.79 (s, 1H); 7.82-7.84 (m, 2H); MS for C$_{36}$H$_{40}$F$_2$N$_4$O$_4$ m/z 631.11 (M+H)$^+$.

Preparation of
1-(3-chloropropyl)-3,3-difluoroindolin-2-one

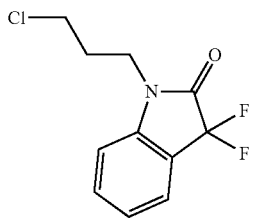 [SMILES: O=C1N(CCCCl)c2ccccc2C1(F)F]

A solution of 3,3-difluoroindolin-2-one (836.6 mg, 4.95 mmol, 1 equiv) in N,N-dimethylformamide was cooled to 0° C. Sodium hydride (60% dispersion) (217.6 mg, 5.44 mmol, 1.1 equiv) was slowly added and the reaction was stirred as such until all bubbling had stopped. 1-bromo-3-chloropropane (1.46 ml, 14.85 mmol, 3 equiv) was added to the reaction mixture in one portion. The reaction was allowed to warm to ambient temperature and stirred as such for 16 h. The crude mixture was partitioned between ethyl acetate and water. The organic layer was dried over MgSO$_4$, filtered, concentrated, and the residue was purified using the Biotage flash chromatography system (SNAP 50 g cartridge, R$_f$=0.5, gradient—5%-30% ethyl acetate in hexanes) to afford the title compound as a yellow oil (1.22 g, quant); MS for C$_{11}$H$_{10}$ClF$_2$NO m/z 247.01 (M+H)$^+$.

Example 59

Compound 93 tert-butyl 3-((8-(3-(3,3-dimethyl-2-oxoindolin-1-yl)propyl)-4-oxo-1-phenyl-1,3,8-triazaspiro[4.5]decan-3-yl)methyl)benzoate

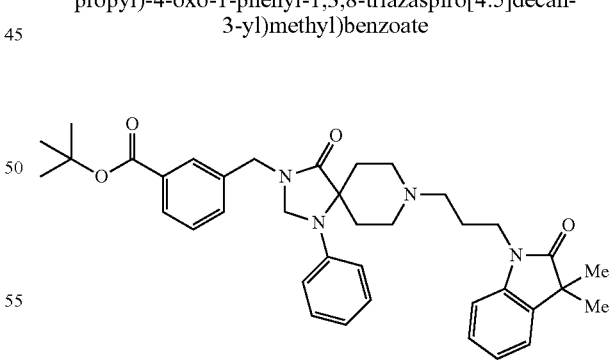

A mixture of tert-butyl 3-((4-oxo-1-phenyl-1,3,8-triazaspiro[4.5]decan-3-yl)methyl)benzoate (300 mg, 0.71 mmol, 1 equiv), 1-(3-chloropropyl)-3,3-dimethylindolin-2-one (200.8 mg, 0.71 mmol, 1 equiv), sodium iodide (42.7 mg, 0.285 mmol, 0.4 equiv), and potassium carbonate (295.2 mg, 2.136 mmol, 3 equiv) in 2-butanone was stirred at 81° C. for 16 h. After cooling the reaction mixture, the crude mixture was partitioned between ethyl acetate and water. The organic layer was dried over MgSO$_4$, filtered, concentrated, and the crude residue was purified using preparatory thin layer chromatography in 5% methanol in dichloromethane to afford the title compound as cream crystals (210 mg, 47.4%); $^1$H NMR (400 MHz, DMSO-d$_6$): δ 1.27 (s, 6H); 1.52 (s, 9H); 1.63 (d, 2H, J=12.4 Hz); 1.79 (bs, 2H); 2.36 (bs, 2H); 2.52-2.59 (m, 2H); 2.66-2.73 (m, 4H); 3.75 (t, 2H, J=6.8 Hz); 4.59 (s, 2H); 4.61 (s, 2H); 6.77 (t, 1H, J=6.8 and 7.2 Hz); 6.85 (d, 2H, J=8.4 Hz); 7.03 (t, 1H, J=7.6 and 6.8 Hz); 7.13 (d, 1H, J=7.6 Hz); 7.23 (t, 3H, J=8 and 7.6 Hz); 7.35 (d, 1H, J=7.2 Hz); 7.48-7.55 (m, 2H); 7.79 (s, 1H); 7.82-7.84 (m, 1H); MS for $C_{38}H_{46}N_4O_4$ m/z 623.18 (M+H)$^+$.

Preparation of
1-(3-chloropropyl)-3,3-dimethylindolin-2-one

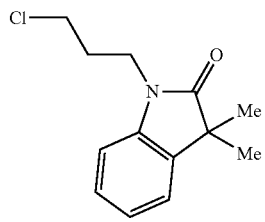 [SMILES: CC1(C)C(=O)N(CCCCl)c2ccccc21]

A solution of 3,3-dimethylindolin-2-one (1.843 g, 11.43 mmol, 1 equiv) in N,N-dimethylformamide was cooled to 0° C. Sodium hydride (60% dispersion) (503 mg, 12.58 mmol, 1.1 equiv) was slowly added and the reaction was stirred as such until all bubbling had stopped. 1-bromo-3-chloropropane (3.37 ml, 34.3 mmol, 3 equiv) was added to the reaction mixture in one portion. The reaction was allowed to warm to ambient temperature and stirred as such for 16 h. The crude mixture was partitioned between ethyl acetate and water. The organic layer was dried over MgSO$_4$, filtered, concentrated, and the residue was purified using the Biotage flash chromatography system (SNAP 50 g cartridge, R$_f$=0.5, gradient— 5%-30% ethyl acetate in hexanes) to afford the title compound as a light orange oil (2.38 g, 87%); $^1$H NMR (400 MHz, DMSO-d$_6$): δ 1.26 (s, 6H); 1.98-2.14 (m, 2H); 3.65 (t, 2H, J=6 and 6.8 Hz); 3.77-3.81 (m, 2H); 7.02-7.07 (m, 2H); 7.24-7.28 (m, 1H); 7.33-7.35 (m, 1H); MS for $C_{13}H_{16}ClNO$ m/z 237.99 (M+H)$^+$.

Example 60

Compound 94

3-((8-(3-(3,3-difluoro-2-oxoindolin-1-yl)propyl)-4-oxo-1-phenyl-1,3,8-triazaspiro[4.5]decan-3-yl)methyl)benzoic acid

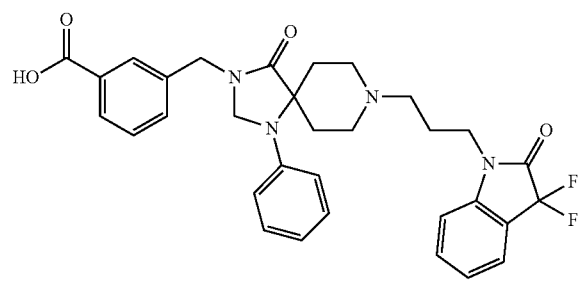 [SMILES: O=C(O)c1cccc(CN2CN(c3ccccc3)C3(CCN(CCCN4C(=O)C(F)(F)c5ccccc54)CC3)C2=O)c1]

A solution of tert-butyl 3-((8-(3-(3,3-difluoro-2-oxoindolin-1-yl)propyl)-4-oxo-1-phenyl-1,3,8-triazaspiro[4.5]decan-3-yl)methyl)benzoate (210 mg, 0.333 mmol, 1 equiv) in 4M hydrogen chloride solution in dioxane was stirred at ambient temperature for 4 h. The mixture was concentrated in vacuo and the crude residue was purified using preparatory high performance liquid chromatography to afford the acetate salt of the title compound as a white solid (80 mg, 42%); $^1$H NMR (400 MHz, DMSO-d$_6$): δ 1.64 (d, 2H, J=12.8 Hz); 1.87 (d, 2H, J=6 Hz); 2.40 (t, 2H, J=6.4 Hz); 2.51 (bs, 2H); 2.81 (bs, 4H); 3.80 (t, 2H, J=6.8 Hz); 4.59 (s, 2H); 4.61 (s, 2H); 6.78 (t, 1H, J=7.2 and 7.6 Hz); 6.85 (d, 2H, J=8 Hz); 7.20-7.24 (m, 3H); 7.36 (d, 1H, J=8 Hz); 7.48-7.53 (m, 2H); 7.59 (t, 1H, J=8 and 7.6 Hz); 7.71 (d, 1H, J=7.6 Hz); 7.87 (d, 1H, J=2 Hz); 7.88 (d, 2H, J=2 Hz); 12.45 (bs, 1H); MS for $C_{32}H_{32}F_2N_4O_4$ m/z 575.03 (M+H)$^+$.

Example 61

Compound 100

3-((8-(3-(6-Chloro-2-oxo-2,3-dihydro-1H-benzo[d]imidazol-1-yl)propyl)-4-oxo-1-phenyl-1,3,8-triazaspiro[4.5]decan-3-yl)methyl)benzoic acid

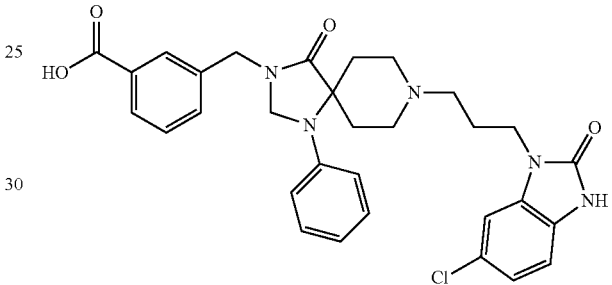

A solution of tert-butyl 3-((8-(3-(6-chloro-2-oxo-2,3-dihydro-1H-benzo[d]imidazol-1-yl)propyl)-4-oxo-1-phenyl-1,3,8-triazaspiro[4.5]decan-3-yl)methyl)benzoate (100 mg, 0.16 mmol, 1 equiv) in 4M hydrogen chloride solution in dioxane was stirred at ambient temperature for 4 h. The mixture was concentrated in vacuo and the crude residue was purified using preparatory high performance liquid chromatography to afford the acetate salt of the title compound as a white solid (22 mg, 24%); $^1$H NMR (400 MHz, DMSO-d$_6$): 1.61 (d, 2H, J=13.2 Hz); 1.83 (t, 2H, J=6.8 Hz); 2.37 (t, 2H, J=7.2 and 6.8 Hz); 2.54-2.58 (m, 2H); 2.67-2.72 (m, 4H); 3.85 (t, 2H, J=6.8 Hz); 4.58 (s, 2H); 4.61 (s, 2H); 6.77 (t, 1H, J=7.6 and 7.2 Hz); 6.85 (d, 2H, J=7.2 Hz); 6.98-7.01 (m, 2H); 7.20-7.24 (m, 3H); 7.47-7.53 (m, 2H); 7.86-7.88 (m, 2H); 11.01 (bs, 1H); MS for $C_{31}H_{32}ClN_5O_4$ m/z 574 (M+H)$^+$.

Preparation of tert-butyl 3-((8-(3-(6-chloro-2-oxo-2,3-dihydro-1H-benzo[d]imidazol-1-yl)propyl)-4-oxo-1-phenyl-1,3,8-triazaspiro[4.5]decan-3-yl)methyl)benzoate

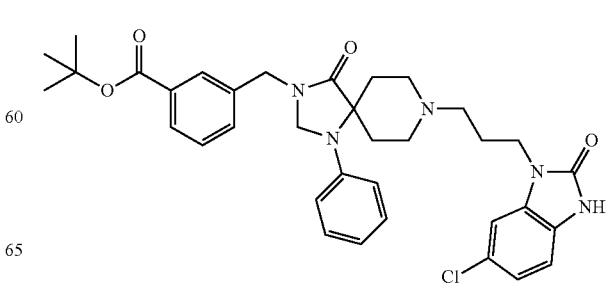

A mixture of tert-butyl 3-((4-oxo-1-phenyl-1,3,8-triazaspiro[4.5]decan-3-yl)methyl)benzoate (329 mg, 0.7807 mmol, 1 equiv), 6-chloro-1-(3-chloropropyl)-1H-benzo[d]imidazol-2(3H)-one (219 mg, 0.7807 mmol, 1 equiv), sodium iodide (46.81 mg, 0.312 mmol, 0.4 equiv), and potassium carbonate (323.7 mg, 2.34 mmol, 3 equiv) in 2-butanone was stirred at 81° C. for 16 h. After cooling the reaction mixture, the crude mixture was partitioned between ethyl acetate and water. The organic layer was dried over MgSO$_4$, filtered, concentrated, and the crude residue was purified using preparatory thin layer chromatography in 10% methanol in dichloromethane to afford the title compound as a white powder (100 mg, ~20%); MS for $C_{35}H_{40}ClN_5O_4$ m/z 630.15 (M+H)$^+$.

Preparation of 6-chloro-1-(3-chloropropyl)-1H-benzo[d]imidazol-2(3H)-one

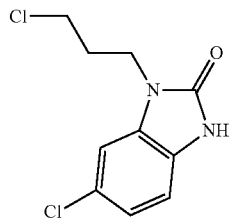 [SMILES: O=c1[nH]c2ccc(Cl)cc2n1CCCCl]

Sodium hydride (60% dispersion) (521.8 mg, 13.04 mmol, 1.1 equiv) was added to a solution of 5-chloro-1H-benzo[d]imidazol-2(3H)-one (2 g, 11.86 mmol, 1 equiv) in N,N-dimethylformamide (50 ml), stirred at ambient temperature under an atmosphere of nitrogen. After 75 minutes a solution of di-tert-butyl dicarbonate (2.59 g, 11.86 mmol, 1 equiv) in N,N-dimethylformamide (10 ml) was added drop-wise and the mixture stirred for 16 h. The solvent was removed in vacuo and the residue was diluted with sat. ammonium chloride solution. The mixture was extracted with ethyl acetate, the organic layer dried over MgSO$_4$, filtered and concentrated in vacuo. The resulting residue was chromatographed using the Biotage flash chromatography system (SNAP 50 g cartridge, R$_f$=0.3, gradient—5%-30% ethyl acetate in hexanes) to afford the tert-butyl 5-chloro-2-oxo-2,3-dihydro-1H-benzo[d]imidazole-1-carboxylate as a cream powder (1.41 g, 45%); $^1$H NMR (400 MHz, DMSO-d$_6$): δ 1.57 (s, 9H); 7.01 (d, 1H, J=2 Hz); 7.09 (dd, 1H, J=2 Hz); 7.61 (d, 1H, J=9.2 Hz); 11.40 (s, 1H); MS for $C_{12}H_{13}ClN_2O_3$ m/z 268.94 (M+H)$^+$.

Sodium hydride (60% dispersion) (169.4 mg, 4.24 mmol, 1.2 equiv) was added to a solution of tert-butyl 6-chloro-2-oxo-2,3-dihydro-1H-benzo[d]imidazole-1-carboxylate (948 mg, 3.53 mmol, 1 equiv) in N,N-dimethylformamide. 1-bromo-3-chloropropane (1.04 ml, 10.59 mmol, 3 equiv) was added and the mixture was stirred at ambient temperature for 16 h. The mixture was partitioned between ethyl acetate and water, the organic layer was dried over MgSO$_4$, filtered, concentrated in vacuo and the residue was chromatographed using the Biotage flash chromatography system (SNAP 50 g cartridge, R$_f$=0.45, 5%-25% ethyl acetate in hexanes) to afford the tert-butyl 5-chloro-3-(3-chloropropyl)-2-oxo-2,3-dihydro-1H-benzo[d]imidazole-1-carboxylate as a syrup (528 mg, 43.5%); $^1$H NMR (400 MHz, DMSO-d$_6$): δ 1.59 (s, 9H); 2.09 (d, 2H, J=6.4 Hz); 3.68 (t, 2H, J=6.4 Hz, J=6.8 Hz); 3.92 (t, 2H, J=7.2 Hz, J=6.8 Hz); 7.29 (m, 2H); 7.71 (d, 1H, J=1.2 Hz); MS for $C_{15}H_{18}Cl_2N_2O_3$ m/z 346.1 (M+H)$^+$.

A solution of tert-butyl 5-chloro-3-(3-chloropropyl)-2-oxo-2,3-dihydro-1H-benzo[d]imidazole-1-carboxylate (528 mg, 1.53 mmol, 1 equiv) in 4M hydrogen chloride solution in dioxane was stirred at ambient temperature for 2 hours. The reaction mixture was concentrated and dried in vacuo to afford the hydrogen chloride salt of the title compound as a cream powder (507 mg, quant); $^1$H NMR (400 MHz, DMSO-d$_6$): δ 2.03-2.12 (m, 2H); 3.63-3.72 (m, 2H); 3.90 (t, 2H, J=7.2 and 6.8 Hz); 7.00 (d, 1H, J=2 Hz); 7.02 (dd, 1H, J=2 Hz); 7.15 (d, 1H, J=8 Hz); MS for $C_{10}H_{10}Cl_2N_2O$ m/z 244.93 (M+H)$^+$.

Example 62

Compound 102

2-Methyl-2-(4-((4-oxo-8-(3-(2-oxo-2,3-dihydro-1H-benzo[d]imidazol-1-yl)propyl)-1-phenyl-1,3,8-triazaspiro[4.5]decan-3-yl)methyl)phenoxy)propanoic acid

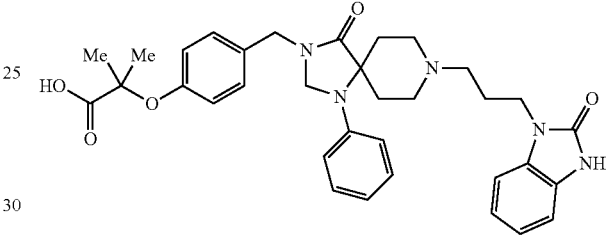

To tert-butyl 2-methyl-2-(4-((4-oxo-8-(3-(2-oxo-2,3-dihydro-1H-benzo[d]imidazol-1-yl)propyl)-1-phenyl-1,3,8-triazaspiro[4.5]decan-3-yl)methyl)phenoxy)propanoate (0.2 g, 0.3 mmol) was added 4M solution of HCl in dioxane (3 mL). After stirring at room temperature for 4 hours, the reaction mixture was concentrated in vacuo and lyophilized in acetonitrile/water (1:1) to obtain the title compound as a hydrochloride salt (0.19 g, 99%); $^1$H NMR (DMSO-d$_6$): δ 1.49 (s, 6H), 1.90 (d, 2H, J=14.4 Hz), 2.12-2.15 (m, 2H), 2.87-2.93 (m, 2H), 3.19-3.22 (m, 2H), 3.44-3.72 (m, 4H), 3.90 (t, 2H, J=6.4 Hz), 4.48 (s, 2H), 4.60 (s, 2H), 6.77-6.81 (m, 3H), 6.97-7.05 (m, 5H), 7.19-7.23 (m, 5H), 10.39 (br, 1H), 10.90 (s, 1H), 13.01 (br, 1H); MS for $C_{34}H_{39}N_5O_5$ m/z 598.21 (M+H)$^+$.

Preparation of tert-butyl 2-methyl-2-(4-((4-oxo-8-(3-(2-oxo-2,3-dihydro-1H-benzo[d]imidazol-1-yl)propyl)-1-phenyl-1,3,8-triazaspiro[4.5]decan-3-yl)methyl)phenoxy)propanoate

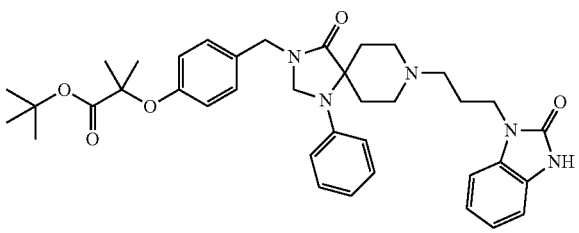 [SMILES: CC(C)(C)OC(=O)C(C)(C)Oc1ccc(CN2CN(c3ccccc3)C3(CCN(CCCn4c(=O)[nH]c5ccccc54)CC3)C2=O)cc1]

To a solution of benzyl 3-(4-(1-tert-butoxy-2-methyl-1-oxopropan-2-yloxy)benzyl)-4-oxo-1-phenyl-1,3,8-triazaspiro[4.5]decane-8-carboxylate (0.69 g, 1.12 mmol) in 1:1 solution of ethyl acetate/methanol (20 mL), was added 10 wt % palladium on carbon (0.2 g). After stirring under hydrogen at room temperature and atmospheric pressure for 2 hours, the reaction mixture was filtered, washed with methanol, concentrated in vacuo to obtain tert-butyl 2-methyl-2-(4-((4-oxo-1-phenyl-1,3,8-triazaspiro[4.5]decan-3-yl)methyl)phenoxy) propanoate (0.5 g, 93%).

To a solution of tert-butyl 2-methyl-2-(4-((4-oxo-1-phenyl-1,3,8-triazaspiro[4.5]decan-3-yl)methyl)phenoxy)propanoate (0.22 g, 0.46 mmol) and potassium carbonate (0.095 g, 0.69 mmol) in N,N-dimethylformamide (4 mL), was added 1-(3-iodopropyl)-1,3-dihydro-2H-benzimidazol-2-one (0.139 g, 0.46 mmol). After stirring at 55° C. for 16 hours, the reaction mixture was diluted with ethyl acetate (100 mL), washed with water and brine. The organic phase was dried over MgSO$_4$, filtered, concentrated and isolated by preparatory TLC (10% methanol/dichloromethane) to obtain the title compound (0.26 g, 86%); $^1$H NMR (DMSO-d$_6$): δ 1.35 (s, 9H), 1.49 (s, 6H), 1.56 (d, 2H, J=13.6 Hz), 1.82 (t, 2H, J=6.4 Hz), 2.32-2.34 (m, 2H), 2.45-2.50 (m, 2H), 2.66-2.72 (m, 4H), 3.85 (t, 2H, J=6.8 Hz), 4.45 (s, 2H), 4.53 (s, 2H), 6.77-6.84 (m, 5H), 6.96 (d, 3H, J=3.2 Hz), 7.17-7.24 (m, 5H), 10.79 (s, 1H); MS for C$_{38}$H$_{47}$N$_5$O$_5$ m/z 654.18 (M+H)$^+$.

Preparation of benzyl 3-(4-(1-tert-butoxy-2-methyl-1-oxopropan-2-yloxy)benzyl)-4-oxo-1-phenyl-1,3,8-triazaspiro[4.5]decane-8-carboxylate

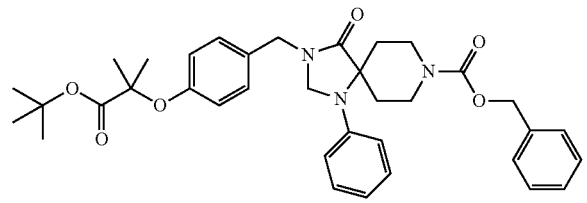 [SMILES: CC(C)(C)OC(=O)C(C)(C)Oc1ccc(CN2CN(c3ccccc3)C3(CCN(C(=O)OCc4ccccc4)CC3)C2=O)cc1]

To a cooled (0° C.) solution of tert-butyl 2-(4-(hydroxymethyl)phenoxy)-2-methylpropanoate (0.5 g, 2.58 mmol) and triethylamine (0.72 mL, 5.16 mmol, d=0.726) in dichloromethane (10 mL), was added methanesulfonyl chloride (0.22 mL, 2.84 mmol, d=1.474). After stirring at 0° C. for an hour, the reaction mixture was washed with dilute citric acid, water and brine. The organic phase was dried over MgSO$_4$, filtered, concentrated in vacuo to obtain tert-butyl 2-methyl-2-(4-((methylsulfonyloxy)methyl)phenoxy) propanoate.

To a solution of benzyl 4-oxo-1-phenyl-1,3,8-triazaspiro[4.5]decane-8-carboxylate (0.5 g, 1.37 mmol) and potassium carbonate (0.28 g, 2.06 mmol) in N,N-dimethylformamide (10 mL), was added tert-butyl 2-methyl-2-(4-((methylsulfonyloxy)methyl)phenoxy)propanoate (0.48 g, 1.37 mmol). After stirring at 55° C. for 18 hours, the reaction mixture was diluted with ethyl acetate (50 mL), washed with dilute citric acid, water and brine. The organic phase was dried over MgSO$_4$, filtered, and isolated by Biotage flash chromatography (10-75% ethyl acetate/hexanes) to obtain the title compound (0.7 g, 83%); $^1$H NMR (DMSO-d$_6$): δ 1.35 (s, 9H), 1.48 (s, 6H), 1.67 (d, 2H, J=13.6 Hz), 2.32-2.38 (m, 2H), 3.56 (br, 2H), 3.98-4.01 (m, 2H), 4.48 (s, 2H), 4.56 (s, 2H), 5.15 (br, 2H), 6.67 (d, 2H, J=8 Hz), 6.75-6.80 (m, 3H), 7.15-7.22 (m, 4H), 7.32-7.38 (m, 5H); MS for C$_{36}$H$_{43}$N$_3$O$_6$ m/z 614.15 (M+H)$^+$.

Example 63

Compound 108 tert-Butyl 3-((8-(3-(1H-indazol-3-yl)propyl)-4-oxo-1-phenyl-1,3,8-triazaspiro[4.5]decan-3-yl)methyl) benzoate

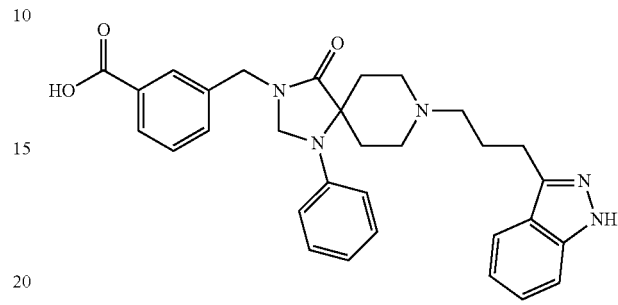

To tert-3-((8-(3-(1H-indazol-3-yl)propyl)-4-oxo-1-phenyl-1,3,8-triazaspiro[4.5]decan-3-yl)methyl)benzoate (0.047 g, 0.08 mmol) was added 4M solution of HCl in dioxane (1 mL). After stirring at room temperature for 3 hours, the reaction mixture was concentrated in vacuo and lyophilized in acetonitrile/water (1:1) to obtain the title compound as a hydrochloride salt (0.045 g, 99%); $^1$H NMR (DMSO-d$_6$): δ 1.90 (d, 2H, J=14 Hz), 2.26 (br, 2H), 3.01 (t, 2H, J=7.6 Hz), 3.24 (br, 2H), 3.45-3.70 (m, 6H), 4.64 (d, 4H, J=4 Hz), 6.79 (t, 1H, J=6.8 Hz), 7.03-7.11 (m, 3H), 7.20 (t, 2H, J=7.2 Hz), 7.33 (t, 1H, J=7.6 Hz), 7.47-7.58 (m, 3H), 7.79 (d, 1H, J=8 Hz), 7.88 (d, 2H, J=9.2 Hz), 10.73 (br, 1H), 12.77 (br, 1H); MS for C$_{31}$H$_{33}$N$_5$O$_3$ m/z 524.07 (M+H)$^+$.

Preparation of tert-butyl 3-((8-(3-(1H-indazol-3-yl) propyl)-4-oxo-1-phenyl-1,3,8-triazaspiro[4.5]decan-3-yl)methyl)benzoate

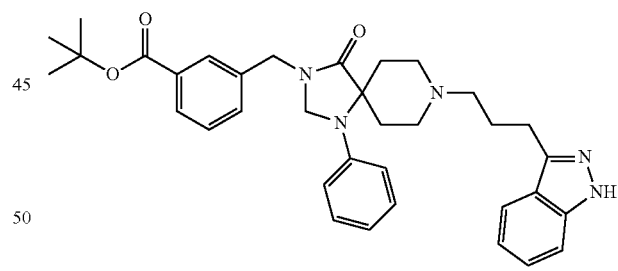

To a solution of tert-butyl 3-((4-oxo-1-phenyl-1,3,8-triazaspiro[4.5]decan-3-yl)methyl)benzoate (0.2 g, 0.47 mmol), potassium carbonate (0.097 g, 0.7 mmol) and sodium iodide (0.021 g, 0.14 mmol) in 2-butanone (5 mL), was added 3-(3-chloropropyl)-1H-indazole (0.092 g, 0.47 mmol). After stirring at 78° C. for 18 hours, the reaction mixture was filtered, concentrated and isolated by preparatory TLC (10% methanol/dichloromethane) to obtain the title compound (0.06 g, 22%); $^1$H NMR (DMSO-d$_6$): δ 1.52 (s, 9H), 1.64 (d, 2H, J=14 Hz), 1.95 (t, 2H, J=6.4 Hz), 2.59-2.85 (m, 8H), 2.96 (t, 2H, J=7.6 Hz), 4.60 (d, 4H, J=9.6 Hz), 6.76 (t, 1H, J=7.2 Hz), 6.85 (d, 2H, J=8 Hz), 7.06 (t, 1H, J=6.8 Hz), 7.21 (t, 2H, J=7.6 Hz), 7.31 (t, 1H, J=7.2 Hz), 7.44-7.53 (m, 3H), 7.74-7.84 (m, 3H), 12.63 (s, 1H); MS for C$_{35}$H$_{41}$N$_5$O$_3$ m/z 580.13 (M+H)$^+$.

Example 64

Compound 110

3-((8-(3-(2-(tert-Butoxycarbonyl)-1H-indol-1-yl)propyl)-4-oxo-1-phenyl-1,3,8-triazaspiro[4.5]decan-3-yl)methyl)benzoic acid

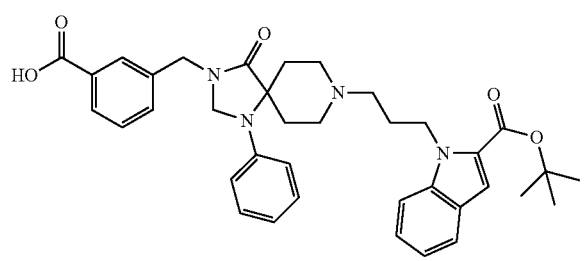 [SMILES: CC(C)(C)OC(=O)c1cc2ccccc2n1CCCN1CCC2(CC1)C(=O)N(Cc1cccc(C(=O)O)c1)CN2c1ccccc1]

To a solution of tert-butyl 1-(3-(3-(3-(benzyloxycarbonyl)benzyl)-4-oxo-1-phenyl-1,3,8-triazaspiro[4.5]decan-8-yl)propyl)-1H-indole-2-carboxylate (0.27 g, 0.32 mmol) in MeOH (5 mL), was added 10%/wt palladium on carbon (0.080 g). The reaction mixture was hydrogenated at 50 psi for 48 hours. It was filtered over Celite, and isolated by preparatory thin layer chromatography in 10% methanol in dichloromethane to obtain the title compound (0.060 g, 30%); $^1$H NMR (DMSO-d$_6$): δ 1.56 (s, 9H), 1.66 (d, 2H, J=14 Hz), 1.95 (t, 2H, J=6.4 Hz), 2.50-2.66 (m, 4H), 2.88 (bs, 4H), 4.59-4.64 (m, 6H), 6.78 (t, 1H, J=7.2 Hz), 6.88 (d, 2H, J=8.4 Hz), 7.10 (t, 1H, J=7.2 Hz), 7.19-7.31 (m, 3H), 7.48-7.54 (m, 2H), 7.67 (t, 2H, J=8.4 Hz), 7.87 (d, 2H, J=6.4 Hz), 8.13 (s, 1H), 12.75 (bs, 1H); MS for C$_{37}$H$_{42}$N$_4$O$_5$ m/z 623.16 (M+H)$^+$.

Preparation of tert-butyl 1-(3-(3-(3-(benzyloxycarbonyl)benzyl)-4-oxo-1-phenyl-1,3,8-triazaspiro[4.5]decan-8-yl)propyl)-1H-indole-2-carboxylate

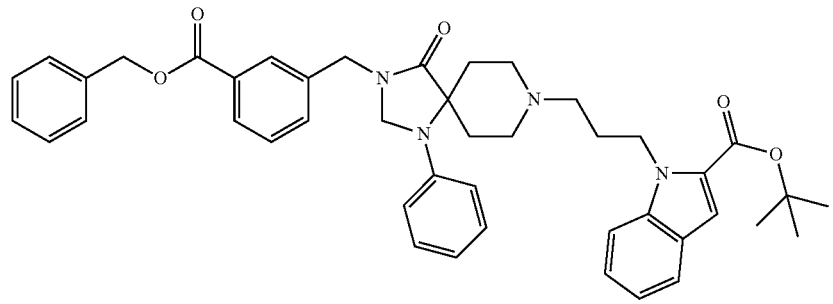 [SMILES: CC(C)(C)OC(=O)c1cc2ccccc2n1CCCN1CCC2(CC1)C(=O)N(Cc1cccc(C(=O)OCc3ccccc3)c1)CN2c1ccccc1]

A mixture of benzyl 3-((4-oxo-1-phenyl-1,3,8-triazaspiro[4.5]decan-3-yl)methyl)benzoate (807 mg, 1.65 mmol, 1 equiv), tert-butyl 1-(3-chloropropyl)-1H-indole-2-carboxylate (507 mg, 1.65 mmol, 1 equiv), sodium iodide (123.3 mg, 0.823 mmol, 0.5 equiv) and potassium carbonate (684.1 mg, 4.95 mmol, 3 equiv) in 2-butanone was stirred at 81° C. for 16 h. After cooling the reaction mixture, the crude mixture was partitioned between ethyl acetate and water. The organic layer was dried over MgSO$_4$, filtered, concentrated, and the crude residue was purified using the Biotage flash chromatography system (SNAP 50 g cartridge, R$_f$=0.2, gradient—10%-50% ethyl acetate in hexanes) to afford the title compound as an oil (230 mg, 19%); MS for C$_{44}$H$_{48}$N$_4$O$_5$ m/z 713.37 (M+H)$^+$.

Preparation of benzyl 3-((4-oxo-1-phenyl-1,3,8-triazaspiro[4.5]decan-3-yl)methyl)benzoate

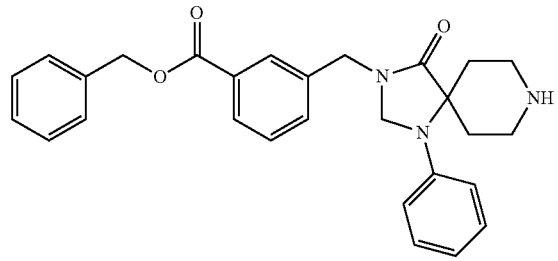 [SMILES: O=C(OCc1ccccc1)c1cccc(CN2CN(c3ccccc3)C3(CCNCC3)C2=O)c1]

A mixture of tert-butyl 4-(5-chloro-2-oxo-2,3-dihydro-1H-benzo[d]imidazol-1-yl)piperidine-1-carboxylate (637 mg, 1.923 mmol, 1 equiv), benzyl 3-(chloromethyl)benzoate (500 mg, 1.923 mmol, 1 equiv) and potassium carbonate (797.3 mg, 5.769 mmol, 3 equiv) in N,N-dimethylformamide was heated at 65° C. for 16 h. The reaction was partitioned between ethyl acetate and water. The organic layer was further washed with brine, dried over MgSO$_4$, filtered and concentrated in vacuo. The resulting residue was purified using the Biotage flash chromatography system (SNAP, 50 g cartridge, R$_f$=0.4, gradient—5%-30% ethyl acetate in hexanes) to afford the tert-butyl 3-(3-(benzyloxycarbonyl)benzyl)-4-oxo-1-phenyl-1,3,8-triazaspiro[4.5]decane-8-carboxylate as an oil (913 mg, 85.6%). MS for C$_{33}$H$_{37}$N$_3$O$_5$ m/z 556.27 (M+H)$^+$.

A solution of tert-butyl 3-(3-(benzyloxycarbonyl)benzyl)-4-oxo-1-phenyl-1,3,8-triazaspiro[4.5]decane-8-carboxylate (913 mg, 1.646 mmol, 1 equiv) in 4M hydrogen chloride solution in dioxane was stirred at ambient temperature for 4-5 h. The mixture was concentrated in vacuo and the residue was lyophilized to afford the hydrogen chloride salt of the title compound as a cream solid (747 mg, quant); MS for C$_{28}$H$_{29}$N$_3$O$_3$ m/z 456.04 (M+H)$^+$.

Preparation of tert-butyl 1-(3-chloropropyl)-1H-indole-2-carboxylate

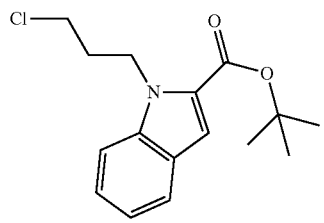 [SMILES: CC(C)(C)OC(=O)c1cc2ccccc2n1CCCCl]

Indole-2-carboxylic acid (1 g, 3.71 mmol, 1 equiv) was suspended in toluene and the mixture was heated to refluxing temperatures. N,N-dimethylformamide di-tert-butyl acetal (5.476 ml, 22.84 mmol, 4 equiv) was added dropwise to the refluxing mixture within 30 minutes. Refluxing was continued for an additional 30-45 minutes after which it was cooled and stirred at ambient temperature for 16 h. The reaction was diluted with ether and the organic layer was washed with sodium bicarbonate (sat), water and brine. The ether layer was dried over MgSO$_4$, filtered, concentrated in vacuo and purified using the Biotage flash chromatography system (SNAP 50 g cartridge, R$_f$=0.4, gradient—1%-10% ethyl acetate in hexanes) to afford the tert-butyl 1H-indole-2-carboxylate as a white powder (1.15 g, 86.8%); MS for C$_{13}$H$_{15}$NO$_2$ m/z 217.99 (M+H)$^+$.

To a cold solution of tert-butyl 1H-indole-2-carboxylate (1.15 g, 4.94 mmol, 1 equiv) in dimthylformamide sodium hydride (60% dispersion) (237 mg, 5.92 mmol, 1.2 equiv) was added and the reaction stirred until all the sodium hydride has been consumed. 1-bromo-3-chloropropane (1.46 ml, 14.88 mmol, 3 equiv) was added and the reaction stirred at 60° C. for 16 h. The reaction was partitioned between ethyl acetate and water. The organic layer was further washed with brine, dried over MgSO$_4$, filtered and concentrated in vacuo. The resulting residue was purified using the Biotage flash chromatography system (SNAP, 50 g cartridge, R$_f$=0.5, gradient—5%-25% ethyl acetate in hexanes) to afford the title compound as an oil (1.52 g, quant); MS for C$_{16}$H$_{20}$ClNO$_2$ m/z 293.12 (M+H)$^+$.

Example 65

Compound 120

3-((8-(3-(3-Cyclopropyl-2-oxo-2,3-dihydro-1H-benzo[d]imidazol-1-yl)propyl)-4-oxo-1-phenyl-1,3,8-triazaspiro[4.5]decan-3-yl)methyl)benzoic acid

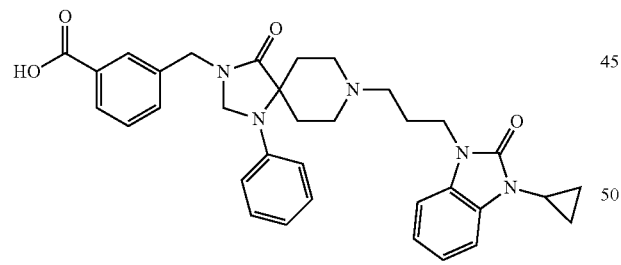

To tert-butyl 3-((8-(3-(3-cyclopropyl-2-oxo-2,3-dihydro-1H-benzo[d]imidazol-1-yl)propyl)-4-oxo-1-phenyl-1,3,8-triazaspiro[4.5]decan-3-yl)methyl)benzoate (0.27 g, 0.42 mmol) was added 4M solution of HCl in dioxane (4 mL) and triethylsilane (0.1 mL). After stirring at room temperature for 3 hours, the reaction mixture was concentrated in vacuo and lyophilized in acetonitrile/water (1:1) to obtain the title compound as a hydrochloride salt (0.215 g, 83%); $^1$H NMR (DMSO-d$_6$): δ 0.88-0.90 (m, 2H), 1.01-1.06 (m, 2H), 1.90 (d, 2H, J=14.4 Hz), 2.12 (br, 2H), 2.87-2.91 (m, 3H), 3.21 (br, 2H), 3.45-3.69 (m, 4H), 3.90 (t, 2H, J=7.2 Hz), 4.64 (d, 4H, J=4.4 Hz), 6.80 (t, 1H, J=7.2 Hz), 7.00 (d, 2H, J=8.4 Hz), 7.07-7.09 (m, 2H), 7.19-7.28 (m, 4H), 7.48-7.57 (m, 2H), 7.88 (d, 2H, J=7.2 Hz), 10.33 (br, 1H), 13.02 (br, 1H); MS for C$_{34}$H$_{37}$N$_5$O$_4$ m/z 580.13 (M+H)$^+$.

Preparation of tert-butyl 3-((8-(3-(3-cyclopropyl-2-oxo-2,3-dihydro-1H-benzo[d]imidazol-1-yl)propyl)-4-oxo-1-phenyl-1,3,8-triazaspiro[4.5]decan-3-yl)methyl)benzoate

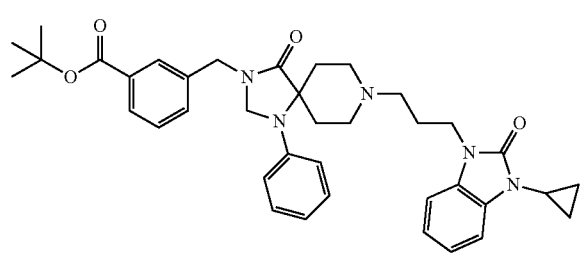 [SMILES: CC(C)(C)OC(=O)c1cccc(CN2CN(c3ccccc3)C3(CCN(CCCn4c(=O)n(C5CC5)c5ccccc54)CC3)C2=O)c1]

To a solution of tert-butyl 3-((4-oxo-1-phenyl-1,3,8-triazaspiro[4.5]decan-3-yl)methyl)benzoate (0.2 g, 0.47 mmol), potassium carbonate (0.097 g, 0.7 mmol) and sodium iodide (0.021 g, 0.14 mmol) in 2-butanone (5 mL), was added 1-(3-chloropropyl)-3-cyclopropyl-1H-benzo[d]imidazol-2(3H)-one (0.119 g, 0.47 mmol). After stirring at 78° C. for 18 hours, the reaction mixture was filtered, concentrated and isolated by preparatory TLC (10% methanol/dichloromethane) to obtain the title compound (0.27 g, 90%); $^1$H NMR (DMSO-d$_6$): δ 0.84-0.88 (m, 2H), 1.01 (d, 2H, J=5.6 Hz), 1.51 (s, 9H), 1.61 (d, 2H, J=14.4 Hz), 1.81 (br, 2H), 2.34 (t, 2H, J=6.8 Hz), 2.48-2.55 (m, 2H), 2.67-2.71 (m, 4H), 2.85-2.88 (m, 1H), 3.86 (t, 2H, J=6.4 Hz), 4.59 (d, 4H, J=10 Hz), 6.77 (t, 1H, J=7.2 Hz), 6.85 (d, 2H, J=8 Hz), 7.03-7.05 (m, 2H), 7.18-7.24 (m, 4H), 7.48-7.54 (m, 2H), 7.79 (s, 1H), 7.83 (d, 1H, J=7.2 Hz); MS for C$_{38}$H$_{45}$N$_5$O$_4$ m/z 636.26 (M+H)$^+$.

Preparation of 1-(3-chloropropyl)-3-cyclopropyl-1H-benzo[d]imidazol-2(3H)-one

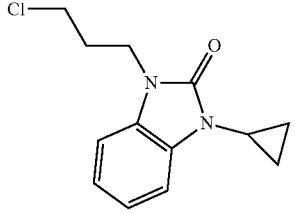 [SMILES: O=c1n(CCCCl)c2ccccc2n1C1CC1]

To a solution of 1-cyclopropyl-1H-benzo[d]imidazol-2(3H)-one (J. Med. Chem. 1997, 40(4), 586-593) (1.0 g, 5.75 mmol) and potassium carbonate (2.4 g, 17.2 mmol) in N,N-dimethylformamide (20 mL), was added 1-bromo-3-chloropropane (1.7 mL, 17.2 mmol, d=1.6). After stirring at 60° C. for 18 hours, the reaction mixture was diluted with ethyl acetate (100 mL), washed with dilute citric acid, water and brine. The organic phase was dried over MgSO$_4$, filtered and isolated by Biotage flash chromatography (10-100% ethyl acetate/hexanes) to obtain the title compound (0.93 g, 65%); $^1$H NMR (DMSO-d$_6$): δ 0.84-0.88 (m, 2H), 0.99-1.03 (m, 2H), 2.03-2.10 (m, 2H), 2.85-2.90 (m, 1H), 3.65 (t, 2H, J=6.4

Hz), 3.88-3.92 (m, 2H), 7.04-7.09 (m, 2H), 7.14-7.22 (m, 2H); MS for $C_{13}H_{15}ClN_2O$ m/z 251.02 $(M+H)^+$.

Example 66

Compound 123

3-((8-(3-(3,3-Dimethyl-2-oxoindolin-1-yl)propyl)-1-(4-fluorophenyl)-4-oxo-1,3,8-triazaspiro[4.5]decan-3-yl)methyl)benzoic acid

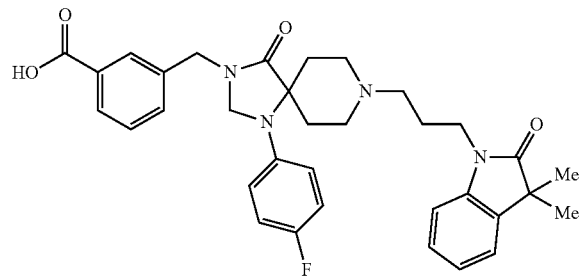 [SMILES: CC1(C)C(=O)N(CCCN2CCC3(CC2)C(=O)N(Cc2cccc(C(=O)O)c2)CN3c2ccc(F)cc2)c2ccccc21]

To tert-butyl 3-((8-(3-(3,3-dimethyl-2-oxoindolin-1-yl)propyl)-1-(4-fluorophenyl)-4-oxo-1,3,8-triazaspiro[4.5]decan-3-yl)methyl)benzoate (0.16 g, 0.25 mmol) was added 4M solution of HCl in dioxane (2.5 mL) and triethylsilane (0.05 mL). After stirring at room temperature for 4 hours, the reaction mixture was concentrated in vacuo and lyophilized in acetonitrile/water (1:1) to obtain the title compound as a hydrochloride salt (0.14 g, 90%); $^1$H NMR (DMSO-$d_6$): δ 1.28 (s, 6H), 1.91 (d, 2H, J=14 Hz), 2.07 (br, 2H), 2.71 (t, 2H, J=10 Hz), 3.17 (br, 2H), 3.45-3.71 (m, 4H), 3.76 (t, 2H, J=7.2 Hz), 4.62 (s, 4H), 7.04-7.07 (m, 5H), 7.15 (d, 1H, J=7.6 Hz), 7.27 (t, 1H, J=8 Hz), 7.36 (d, 1H, J=7.6 Hz), 7.50 (t, 1H, J=8 Hz), 7.55 (d, 1H, J=7.6 Hz), 7.87 (dd, 2H, J=6.8 and 1.6 Hz), 10.39 (br, 1H), 13.03 (br, 1H); MS for $C_{34}H_{37}FN_4O_4$ m/z 585.23 $(M+H)^+$.

Preparation of tert-butyl 3-((8-(3-(3,3-dimethyl-2-oxoindolin-1-yl)propyl)-1-(4-fluorophenyl)-4-oxo-1,3,8-triazaspiro[4.5]decan-3-yl)methylbenzoate

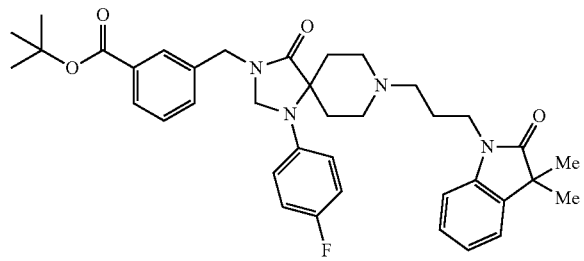

To a solution of benzyl 3-(3-(tert-butoxycarbonyl)benzyl)-1-(4-fluorophenyl)-4-oxo-1,3,8-triazaspiro[4.5]decane-8-carboxylate (0.82 g, 1.43 mmol) in methanol (10 mL), was added 10 wt % palladium on carbon (0.2 g). After stirring under hydrogen at room temperature and atmospheric pressure for 4 hours, the reaction mixture was filtered, washed with methanol, concentrated in vacuo to obtain tert-butyl 3-((1-(4-fluorophenyl)-4-oxo-1,3,8-triazaspiro[4.5]decan-3-yl)methyl)benzoate (0.62 g, 99%).

To a solution of tert-butyl 3-((1-(4-fluorophenyl)-4-oxo-1,3,8-triazaspiro[4.5]decan-3-yl)methyl)benzoate (1.2 g, 2.84 mmol), sodium iodide (0.015 g, 0.1 mmol) and potassium carbonate (0.07 g, 0.51 mmol) in 2-butanone (3 mL), was added 1-(3-chloropropyl)-3,3-dimethylindolin-2-one (0.081 g, 0.34 mmol). After stirring at 78° C. for 18 hours, the reaction mixture was filtered and isolated by preparatory TLC (10% methanol/dichloromethane) to obtain the title compound (0.17 g, 78%); $^1$H NMR (DMSO-$d_6$): δ 1.26 (s, 6H), 1.51 (s, 9H), 1.63 (d, 2H, J=12.4 Hz), 1.75-1.76 (m, 2H), 2.29-2.32 (m, 4H), 2.66-2.67 (m, 4H), 3.72 (t, 2H, J=6.8 Hz), 4.57 (d, 2H, J=14.8 Hz), 6.91 (s, 2H), 7.02 (t, 1H, J=7.2 Hz), 7.07-7.09 (m, 3H), 7.22 (t, 1H, J=7.2 Hz), 7.34 (d, 1H, J=7.2 Hz), 7.47-7.54 (m, 2H), 7.78 (s, 1H), 7.82 (d, 1H, J=6.8 Hz).

Preparation of benzyl 3-(3-(tert-butoxycarbonyl)benzyl)-1-(4-fluorophenyl)-4-oxo-1,3,8-triazaspiro[4.5]decane-8-carboxylate

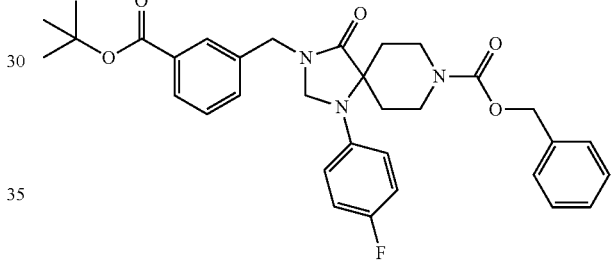

To a solution of 1-(4-fluorophenyl)-1,3,8-triazaspiro[4.5]decan-4-one (2 g, 8.02 mmol) in dichloromethane (30 mL) and pyridine (1.3 mL, 16.04 mmol, d=0.978), was added benzyl chloroformate (1.17 mL, 8.18 mmol, d=1.195). After stirring at room temperature for 24 hours, the reaction mixture was diluted with dichloromethane (100 mL), washed with dilute citric acid, water and brine. The organic phase was dried over MgSO$_4$, filtered and concentrated to obtain benzyl 1-(4-fluorophenyl)-4-oxo-1,3,8-triazaspiro[4.5]decane-8-carboxylate (2.12 g).

To a solution of benzyl 4-oxo-1-phenyl-1,3,8-triazaspiro[4.5]decane-8-carboxylate (1 g, 2.61 mmol) and potassium carbonate (0.54 g, 3.91 mmol) in N,N-dimethylformamide (20 mL), was added tert-butyl-3-(bromomethyl)benzoate (0.74 g, 2.74 mmol). After stirring at 55° C. for 60 hours, the reaction mixture was diluted with ethyl acetate (100 mL), washed with dilute citric acid, water and brine. The organic phase was dried over MgSO$_4$, filtered, and isolated by Biotage flash chromatography (10-75% ethyl acetate/hexanes) to obtain the title compound (0.82 g, 55%); $^1$H NMR (DMSO-$d_6$): δ 1.54 (s, 9H), 1.74 (d, 2H, J=14 Hz), 2.08-2.13 (m, 2H), 3.56 (br, 2H), 3.95 (d, 2H, J=8.8 Hz), 4.60 (d, 2H, J=13.2 Hz), 5.10 (s, 2H), 6.80-6.83 (m, 2H), 7.05 (t, 2H, J=8.8 Hz), 7.32-7.37 (m, 5H), 7.48-7.55 (m, 2H), 7.80 (s, 1H), 7.83 (d, 1H, J=7.6 Hz); MS for $C_{33}H_{36}FN_3O_5$ m/z 574.11 $(M+H)^+$.

Example 67

Compound 126

3-((8-(3-(3-(3-methoxy-3-oxopropyl)-1H-indol-1-yl)propyl)-4-oxo-1-phenyl-1,3,8-triazaspiro[4.5]decan-3-yl)methyl)benzoic acid

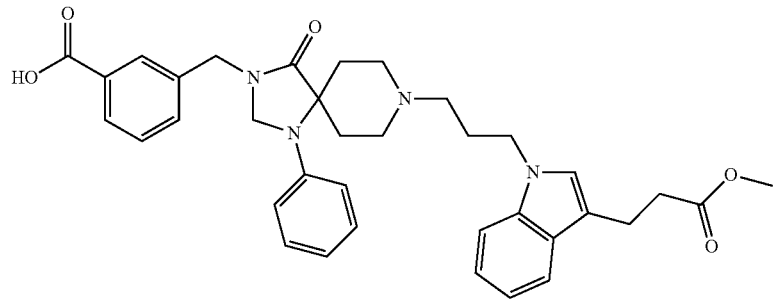 [SMILES: COC(=O)CCc1cn(CCCN2CCC3(CC2)C(=O)N(Cc2cccc(C(=O)O)c2)CN3c2ccccc2)c2ccccc12]

A solution of tert-butyl 3-((8-(3-(3-(3-methoxy-3-oxopropyl)-1H-indol-1-yl)propyl)-4-oxo-1-phenyl-1,3,8-triazaspiro[4.5]decan-3-yl)methyl)benzoate (400 mg, 0.637 mmol, 1 equiv) in 4M hydrogen chloride solution in dioxane was stirred at ambient temperature for 3 h. The mixture was concentrated in vacuo and the crude residue was purified using preparatory high performance liquid chromatography to afford the acetate salt of the title compound as a white solid (130 mg, 35.7%); $^1$H NMR (400 MHz, DMSO-$d_6$): δ 1.62 (d, 2H, J=13.2 Hz); 1.89-1.93 (m, 2H); 2.27 (t, 2H, J=6.8 Hz); 2.59-2.72 (m, 8H); 2.95 (t, 2H, J=7.6 and 8 Hz); 3.57 (s, 3H); 4.19 (t, 2H, J=6.8 and 6.4 Hz); 4.59 (s, 2H); 4.61 (s, 2H); 6.76 (t, 1H, J=7.2 Hz); 6.87 (d, 2H, J=8 Hz); 6.97-7.01 (m, 1H); 7.07-7.11 (m, 1H); 7.17 (s, 1H); 7.20-7.24 (m, 2H); 7.46-7.54 (m, 4H); 7.86-7.88 (m, 2H); 13.01 (bs, 1H); MS for $C_{36}H_{40}N_4O_5$ m/z 609 (M+H)$^+$.

Preparation of tert-butyl 3-((8-(3-(3-(3-methoxy-3-oxopropyl)-1H-indol-1-yl)propyl)-4-oxo-1-phenyl-1,3,8-triazaspiro[4.5]decan-3-yl)methyl)benzoate

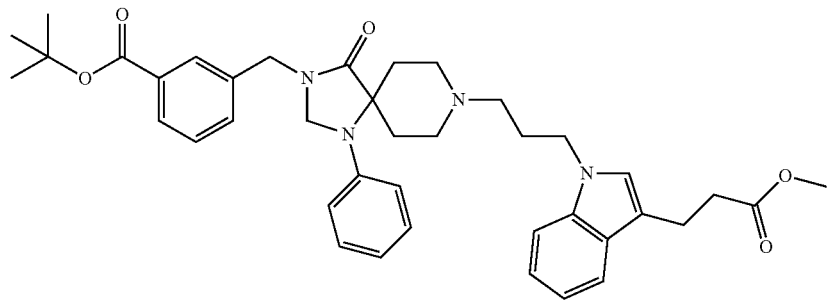 [SMILES: COC(=O)CCc1cn(CCCN2CCC3(CC2)C(=O)N(Cc2cccc(C(=O)OC(C)(C)C)c2)CN3c2ccccc2)c2ccccc12]

A mixture of tert-butyl 3-((4-oxo-1-phenyl-1,3,8-triazaspiro[4.5]decan-3-yl)methyl)benzoate (500 mg, 1.186 mmol, 1 equiv) and methyl 3-(1-(3-chloropropyl)-1H-indol-3-yl)propanoate (384.4 mg, 1.186 mmol, 1 equiv), sodium iodide (88.88 mg, 0.593 mmol, 0.5 equiv) and potassium carbonate (492 mg, 3.56 mmol, 3 equiv) in 2-butanone was stirred at 81° C. for 16 h. After cooling the reaction mixture, the crude mixture was partitioned between ethyl acetate and water. The organic layer was dried over MgSO$_4$, filtered, concentrated, and the crude residue was purified using preparative thin layer chromatography in 5% methanol in dichloromethane to afford the title compound as a white solid (442 mg, 56%); $^1$H NMR (400 MHz, DMSO-$d_6$): δ 1.52 (s, 9H); 1.63 (d, 2H, J=12 Hz); 1.90-1.96 (m, 2H); 2.24 (bs, 2H); 2.61-2.70 (m, 8H); 2.96 (t, 2H, J=7.6 Hz); 3.57 (s, 3H); 4.20 (t, 2H, J=6.4 and 6.8 Hz); 4.59 (s, 2H); 4.61 (s, 2H); 6.77 (t, 1H, J=7.2 and 7.6 Hz); 6.87 (d, 2H, J=8.4 Hz); 6.99 (t, 1H, J=7.6 Hz); 7.10 (t, 1H, J=7.6 and 6.8 Hz); 7.17 (s, 1H); 7.24 (t, 2H, J=7.2 and 8.4 Hz); 7.46-7.53 (m, 4H); 7.79-7.84 (m, 2H); MS for $C_{40}H_{48}N_4O_5$ m/z 665 (M+H)$^+$.

Preparation of methyl 3-(1-(3-chloropropyl)-1H-indol-3-yl)propanoate

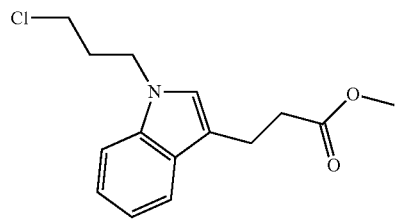 [SMILES: COC(=O)CCc1cn(CCCCl)c2ccccc12]

Sodium hydride (60% dispersion) (236 mg, 5.91 mmol, 1.2 equiv) was slowly added to a cold mixture of methyl 3-(1H-indol-3-yl)propanoate (2 g, 4.92 mmol, 1 equiv) in N,N-dimethylformamide. After all the sodium hydride has reacted, 1-bromo-3-chloropropane (1.94 ml, 19.68 mmol, 4 equiv) was added and the reaction stirred at 55° C. for 16 h. Upon cooling the reaction was partitioned between water and ethyl acetate. The organic layer was further washed with 1N hydrogen chloride, brine, dried over MgSO$_4$, filtered and concentrated in vacuo. The crude residue was purified using the Biotage flash chromatography system (SNAP 50 g cartridge, $R_f$=0.5, gradient—1%-10% ethyl acetate in hexanes) to afford the title compound as a yellow oil (1.154 g, 83%); $^1$H NMR (400 MHz, DMSO-$d_6$): δ 2.12-2.27 (m, 2H); 2.65-2.70 (m, 2H); 2.93-2.98 (m, 2H); 3.38-3.54 (m, 2H); 3.58 (s, 3H); 4.08-4.12 (m, 2H); 4.21-4.25 (m, 2H); 7.02 (t, 1H, J=7.6 Hz); 7.12-7.15 (m, 2H); 7.43 (dd, 1H, J=3.2 and 2.8 Hz); 7.52-7.55 (m, 1H); MS for $C_{15}H_{18}ClNO_2$ m/z 280 (M+H)$^+$.

Example 68

Compound 130

3-((4-oxo-8-(3-(2'-oxospiro[cyclopropane-1,3'-indoline]-1'-yl)propyl)-1-phenyl-1,3,8-triazaspiro[4.5]decan-3-yl)methyl)benzoic acid, hydrochloride salt

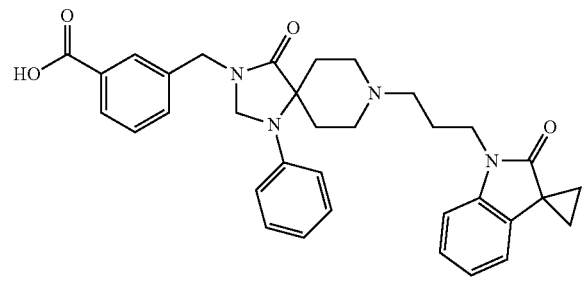 [SMILES: O=C(O)c1cccc(CN2CN(c3ccccc3)C3(CCN(CCCN4C(=O)C5(CC5)c5ccccc54)CC3)C2=O)c1]

tert-Butyl 3-((4-oxo-8-(3-(2'-oxospiro[cyclopropane-1,3'-indoline]-1'-yl)propyl)-1-phenyl-1,3,8-triazaspiro[4.5]decan-3-yl)methyl)benzoate (0.27 g, 0.435 mmol) and formic acid (4 mL) were stirred at room temperature for 20 hours. The reaction was evaporated to dryness and the residue purified by PTLC (10% methanol/dichloromethane) to give product as an oil; $^1$H NMR (DMSO-$d_6$); δ1.52 (m, 2H); 1.59 (m, 2H); 1.68 (d, J=13.6 Hz, 2H); 1.87 (m, 2H); 2.57-2.62 (m, 4H); 2.91 (m, 4H); 3.82 (t, J=6.4 Hz, 2H); 4.60 (s, 2H); 4.62 (s, 2H); 6.76 (t, J=7.2 Hz, 1H); 6.86 (d, J=8.4 Hz, 2H); 6.96-7.03 (m, 2H); 7.17-7.23 (m, 4H); 7.48-7.55 (m, 2H); 7.87-7.89 (m, 2H); 8.15 (s, 1H). The formate salt was dissolved in 4M hydrochloric acid in 1,4-dioxane (5 mL) and then evaporated under vacuum. The residue was dissolved in acetonitrile (5 mL) and water (5 mL) and lyophilized to give product as a white solid (0.17 g, 65%); HPLC rt 10.65 min; $^1$H NMR (DMSO-$d_6$); δ1.54 (m, 2H); 1.62 (m, 2H); 1.90 (d, J=14.4 hz, 2H); 2.11 (m, 2H); 2.92-2.98 (m, 2H); 3.22 (m, 2H); 3.46-3.70 (m, 4H); 3.85 (t, J=7.2 hz, 2H); 4.64 (s, 2H); 4.65 (s, 2H); 6.79 (t, J=7.6 hz, 1H); 7.00-7.06 (m, 4H); 7.19-7.29 (m, 4H); 7.49-7.58 (m, 2H); 7.87-7.89 (m, 2H); 10.6 (br s, 1H); 13.1 (br s, 1H); MS for $C_{34}H_{36}N_4O_4$ m/z 565 (M+H)$^+$.

Preparation of tert-butyl 3-((4-oxo-8-(3-(2'-oxospiro[cyclopropane-1,3'-indoline]-1'-yl)propyl)-1-phenyl-1,3,8-triazaspiro[4.5]decan-3-yl)methyl)benzoate

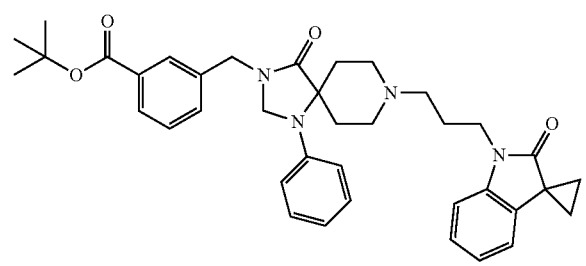 [SMILES: CC(C)(C)OC(=O)c1cccc(CN2CN(c3ccccc3)C3(CCN(CCCN4C(=O)C5(CC5)c5ccccc54)CC3)C2=O)c1]

tert-Butyl 3-((4-oxo-1-phenyl-1,3,8-triazaspiro[4.5]decan-3-yl)methyl)benzoate) (0.25 g, 0.593 mmol), 1'-(3-chloropropyl)spiro[cyclopropane-1,3'-indolin]-2'-one) (0.14 g, 0.593 mol), sodium iodide (0.027 g, 0.178 mmol), and potassium carbonate (0.12 g, 0.890 mmol) in 2-butanone (8 mL) were heated at 78° C. for 4 hours. The reaction was diluted with 10% methanol/dichloromethane, filtered, and evaporated. The residue was purified by PTLC (5% methanol/dichloromethane) to give product as a white solid (0.27 g, 72%); $^1$H NMR (DMSO-$d_6$); δ1.51 (s, 9H); 1.53-1.63 (m, 6H); 1.80 (m, 2H); 2.37 (m, 2H); 2.51-2.63 (m, 2H); 2.63-2.76 (m, 4H); 3.82 (t, J=6.8 Hz, 2H); 4.58 (s, 2H); 4.61 (s, 2H); 6.76 (t, J=7.2 Hz, 1H); 6.85 (d, J=8.4 Hz, 2H); 6.98-7.00 (m, 2H); 7.19-7.24 (m, 4H); 7.49-7.56 (m, 2H); 7.79 (s, 1H); 7.82-7.84 9M, 1H); MS for $C_{38}H_{44}N_4O_4$ m/z 621 (M+H)$^+$.

Example 69

Compound 131

3-((4-Oxo-8-(4-oxo-4-phenylbutyl)-1-phenyl-1,3,8-triazaspiro[4.5]decan-3-yl)methyl)benzoic acid

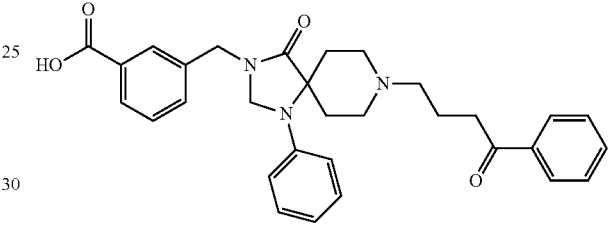

To tert-butyl 3-((4-oxo-8-(4-oxo-4-phenylbutyl)-1-phenyl-1,3,8-triazaspiro[4.5]decan-3-yl)methyl)benzoate (0.1 g, 0.18 mmol) was added 4M solution of HCl in dioxane (2 mL) and triethylsilane (0.1 mL). After stirring at room temperature for 4 hours, the reaction mixture was concentrated in vacuo and isolated by reverse phase HPLC to obtain the title compound as an acetate salt (0.044 g, 43%); $^1$H NMR (DMSO-$d_6$): δ 1.58 (d, 2H, J=13.6 Hz), 1.84 (t, 2H, J=6.8 Hz), 2.42-2.53 (m, 4H), 2.74-2.78 (m, 4H), 3.05 (t, 2H, J=7.2 Hz), 4.58 (d, 4H, J=13.2 Hz), 6.70-6.75 (m, 3H), 7.12 (t, 2H, J=7.2 Hz), 7.48-7.54 (m, 3H), 7.63 (t, 2H, J=7.6 Hz), 7.85 (d, 2H, J=2 Hz), 7.98 (dd, 2H, J=8 and 1.6 Hz); MS for $C_{31}H_{33}N_3O_4$ m/z 512.07 (M+H)$^+$.

Preparation of tert-butyl 3-((4-oxo-8-(4-oxo-4-phenylbutyl)-1-phenyl-1,3,8-triazaspiro[4.5]decan-3-yl)methyl)benzoate

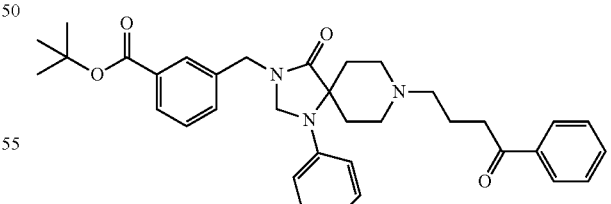

To a solution of tert-butyl 3-((4-oxo-1-phenyl-1,3,8-triazaspiro[4.5]decan-3-yl)methyl)benzoate (0.2 g, 0.47 mmol), potassium carbonate (0.097 g, 0.7 mmol) and sodium iodide (0.021 g, 0.14 mmol) in 2-butanone (5 mL), was added 4-chlorobutyrophenone (0.076 mL, 0.47 mmol, d=1.138). After stirring at 78° C. for 18 hours, the reaction mixture was filtered, concentrated and isolated by preparatory TLC (10% methanol/dichloromethane) to obtain the title compound (0.11 g, 41%); MS for $C_{35}H_{41}N_3O_4$ m/z 568.16 (M+H)$^+$.

Example 70

Compound 137

2-((8-(3-(3,3-Dimethyl-2-oxoindolin-1-yl)propyl)-4-oxo-1-phenyl-1,3,8-triazaspiro[4.5]decan-3-yl)methyl)benzoic acid

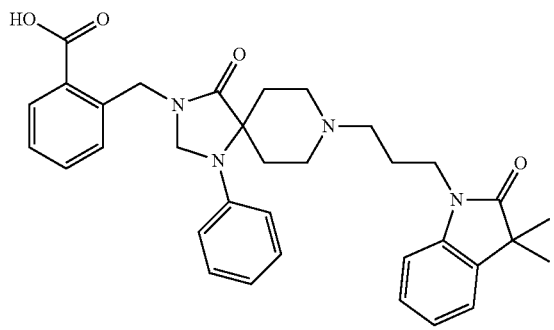 [SMILES: CC1(C)C(=O)N(CCCN2CCC3(CC2)C(=O)N(Cc2ccccc2C(=O)O)CN3c2ccccc2)c2ccccc21]

To tert-butyl 2-((8-(3-(3,3-dimethyl-2-oxoindolin-1-yl)propyl)-4-oxo-1-phenyl-1,3,8-triazaspiro[4.5]decan-3-yl)methyl)benzoate (0.17 g, 0.27 mmol) was added 4M solution of HCl in dioxane (3 mL) and triethylsilane (0.1 mL). After stirring at room temperature for 4 hours, the reaction mixture was concentrated in vacuo, washed with acetonitrile and lyophilized in acetonitrile/water (1:1) to obtain the title compound as a hydrochloride salt (0.8 g); $^1$H NMR (DMSO-$d_6$): δ 1.28 (s, 6H), 1.98 (d, 2H, J=10.4 Hz), 2.07 (t, 2H, J=6.4 Hz), 2.90-2.96 (m, 2H), 3.27 (br, 2H), 3.54-3.61 (m, 4H), 3.77 (t, 2H, J=6.8 Hz), 4.66 (s, 2H), 4.92 (s, 2H), 6.80 (t, 1H, J=7.2 Hz), 6.98 (d, 2H, J=8 Hz), 7.06 (t, 1H, J=7.6 Hz), 7.16 (d, 1H, J=7.6 Hz), 7.20-7.32 (m, 4H), 7.37 (d, 1H, J=7.2 Hz), 7.42 (t, 1H, J=8 Hz), 7.57 (t, 1H, J=7.6 Hz), 7.92 (d, 1H, J=8 Hz), 10.21 (br, 1H), 13.19 (br, 1H); MS for $C_{34}H_{38}N_4O_4$ m/z 567.22 (M+H)$^+$.

Preparation of tert-butyl 2-((8-(3-(3,3-dimethyl-2-oxoindolin-1-yl)propyl)-4-oxo-1-phenyl-1,3,8-triazaspiro[4.5]decan-3-yl)methyl)benzoate

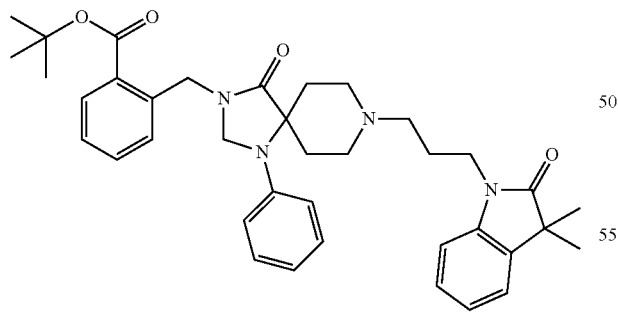

To a solution of benzyl 3-(2-(tert-butoxycarbonyl)benzyl)-4-oxo-1-phenyl-1,3,8-triazaspiro[4.5]decane-8-carboxylate (0.59 g, 1.06 mmol) in methanol (20 mL), was added 10 wt % palladium on carbon (0.1 g). After stirring under hydrogen at room temperature and atmospheric pressure for 2 hours, the reaction mixture was filtered, washed with methanol, concentrated in vacuo to obtain tert-butyl 2-((4-oxo-1-phenyl-1,3,8-triazaspiro[4.5]decan-3-yl)methyl)benzoate (0.4 g, 90%).

To a solution of tert-butyl 2-((4-oxo-1-phenyl-1,3,8-triazaspiro[4.5]decan-3-yl)methyl)benzoate (0.175 g, 0.42 mmol), sodium iodide (0.019 g, 0.13 mmol) and potassium carbonate (0.087 g, 0.63 mmol) in 2-butanone (5 mL), was added 1-(3-chloropropyl)-3,3-dimethylindolin-2-one (0.098 g, 0.42 mmol). After stirring at 78° C. for 18 hours, the reaction mixture was filtered and isolated by preparatory TLC (10% methanol/dichloromethane) to obtain the title compound (0.18 g, 69%); $^1$H NMR (DMSO-$d_6$): δ 1.26 (s, 6H), 1.57 (s, 9H), 1.67 (d, 2H, J=12.4 Hz), 1.75-1.76 (m, 2H), 2.32-2.33 (m, 2H), 2.50-2.72 (m, 6H), 3.74 (t, 2H, J=6.4 Hz), 4.61 (s, 2H), 4.84 (s, 2H), 6.76 (t, 1H, J=7.2 Hz), 6.84 (d, 2H, J=8 Hz), 7.02 (t, 1H, J=6.8 Hz), 7.13 (d, 1H, J=7.6 Hz), 7.23-7.31 (m, 4H), 7.34 (d, 1H, J=6.8 Hz), 7.41 (t, 1H, J=7.2 Hz), 7.57 (t, 1H, J=8.8 Hz), 7.82 (d, 1H, J=7.2 Hz); MS for $C_{38}H_{46}N_4O_4$ m/z 623.28 (M+H)$^+$.

Preparation of benzyl 3-(2-(tert-butoxycarbonyl)benzyl)-4-oxo-1-phenyl-1,3,8-triazaspiro[4.5]decane-8-carboxylate

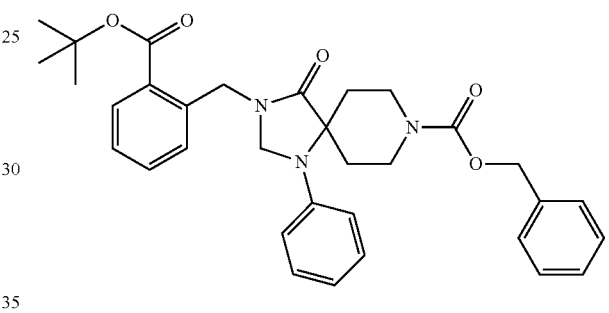

To a solution of benzyl 4-oxo-1-phenyl-1,3,8-triazaspiro[4.5]decane-8-carboxylate (1 g, 2.91 mmol) and potassium carbonate (0.6 g, 4.37 mmol) in N,N-dimethylformamide (20 mL), was added tert-butyl-2-(bromomethyl)benzoate (0.79 g, 2.91 mmol). After stirring at 55° C. for 18 hours, the reaction mixture was diluted with ethyl acetate (100 mL), washed with dilute citric acid, water and brine. The organic phase was dried over MgSO$_4$, filtered, and isolated by Biotage flash chromatography (10-60% ethyl acetate/hexanes) to obtain the title compound (0.59 g, 36%); $^1$H NMR (DMSO-$d_6$): δ 1.57 (s, 9H), 1.77 (d, 2H, J=13.6 Hz), 2.40-2.49 (m, 2H), 3.57 (br, 2H), 4.00-4.03 (m, 2H), 4.64 (s, 2H), 4.87 (s, 2H), 5.15 (br, 2H), 6.68 (d, 2H, J=8 Hz), 6.78 (t, 1H, J=6.8 Hz), 7.18 (t, 2H, J=7.6 Hz), 7.27-7.43 (m, 7H), 7.58 (t, 1H, J=8.4 Hz), 7.83 (dd, 1H, J=8 and 1.6 Hz); MS for $C_{33}H_{37}N_3O_5$ m/z 556.12 (M+H)$^+$.

Preparation of 1-(3-chloropropyl)-3,3-dimethylindolin-2-one

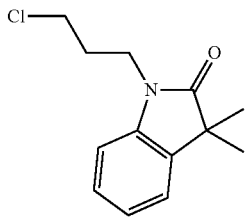 [SMILES: CC1(C)C(=O)N(CCCCl)c2ccccc21]

To a cooled (0° C.) solution of 3,3-dimethylindolin-2-one (2.15 g, 13.2 mmol) in N,N-dimethylformamide (15 mL), was added sodium hydride (0.332 g, 13.85 mmol), followed by addition of 1-bromo-3-chloropropane (2.6 mL, 26.4 mmol, d=1.6). After stirring at room temperature for 18 hours, the reaction mixture was diluted with ethyl acetate (100 mL), washed with dilute citric acid, water and brine. The organic phase was dried over $MgSO_4$, filtered and isolated by Biotage flash chromatography (10-75% ethyl acetate/hexanes) to obtain the title compound (2.6 g, 83%); MS for $C_{13}H_{16}ClNO$ m/z 237.99 $(M+H)^+$.

Example 71

Compound 138

3-((1-(4-Fluorophenyl)-4-oxo-8-(3-(2'-oxospiro[cyclopropane-1,3'-indoline]-1'-yl)propyl)-1,3,8-triazaspiro[4.5]decan-3-yl)methyl)benzoic acid

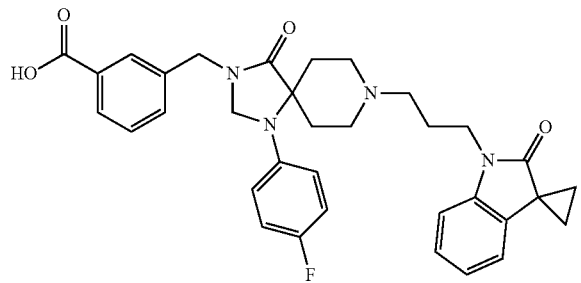 [SMILES: O=C(O)c1cccc(CN2CN(c3ccc(F)cc3)C3(CCN(CCCN4C(=O)C5(CC5)c5ccccc54)CC3)C2=O)c1]

To tert-butyl 3-((1-(4-fluorophenyl)-4-oxo-8-(3-(2'-oxospiro[cyclopropane-1,3'-indoline]-1'-yl)propyl)-1,3,8-triazaspiro[4.5]decan-3-yl)methyl)benzoate (2.84 g, 0.31 mmol, 1 equiv) was added concentrated formic acid. After stirring at room temperature for 16 hours, the reaction mixture was concentrated in vacuo and purified using the Biotage flash chromatography system (SNAP 50 g cartridge, $R_f$=0.5, gradient—1%-15% methanol in dichloromethane). The pure fractions were evaporated to dryness under reduced pressure. The pure residue was converted to the hydrogen chloride salt using 4M hydrogen chloride solution in dioxane. The resulting residue was lyophilized in acetonitrile/water (1:1) to obtain the title compound as a hydrogen chloride salt (1.8 g, 70%); $^1$H NMR (DMSO-$d_6$): δ 1.50 (t, 2H, J=7.6 Hz), 1.57 (t, 2H, J=7.6 Hz), 1.70 (d, 2H, J=14 Hz), 1.83 (t, 2H, J=6.8 Hz), 2.29-2.37 (m, 2H), 2.54 (t, 2H, J=6.4 Hz), 2.87-2.89 (m, 4H), 3.80 (t, 2H, J=6.8 Hz), 4.57 (d, 4H, J=12 Hz), 6.91-7.23 (m, 8H), 7.48-7.51 (m, 2H), 7.86-7.88 (m, 2H), 8.14 (s, 1H); MS for $C_{34}H_{35}FN_4O_4$ m/z 583.16 $(M+H)^+$.

Preparation of tert-butyl 3-((1-(4-fluorophenyl)-4-oxo-8-(3-(2'-oxospiro[cyclopropane-1,3'-indoline]-1'-yl)propyl)-1,3,8-triazaspiro[4.5]decan-3-yl)methyl)benzoate

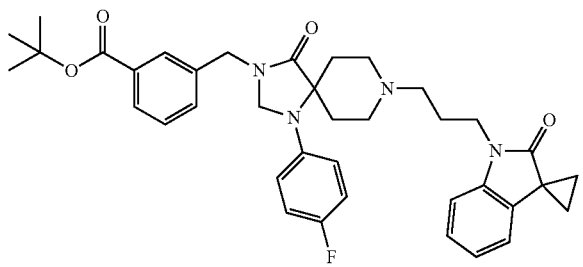 [SMILES: CC(C)(C)OC(=O)c1cccc(CN2CN(c3ccc(F)cc3)C3(CCN(CCCN4C(=O)C5(CC5)c5ccccc54)CC3)C2=O)c1]

To a solution of tert-butyl 3-((1-(4-fluorophenyl)-4-oxo-1,3,8-triazaspiro[4.5]decan-3-yl)methyl)benzoate (3 g, 6.81 mmol, 1 equiv), sodium iodide (0.408 g, 2.72 mmol, 0.4 equiv) and potassium carbonate (2.35 g, 13.62 mmol, 2 equiv) in 2-butanone (5 mL), was added 1'-(3-chloropropyl)spiro[cyclopropane-1,3'-indolin]-2'-one (1.61 g, 6.81 mmol, 1 equiv). After stirring at 78° C. for 16 hours, the reaction mixture was filtered and isolated using the Biotage flash chromatography system (SNAP 100 g cartridge, Rf=0.5, gradient 50%-100% ethyl acetate in hexanes) to obtain the title compound (2.84 g, 63%); $^1$H NMR (DMSO-$d_6$): δ 1.52 (s, 9H), 1.57-1.65 (m, 6H), 1.77 (t, 2H, J=6.4 Hz), 2.25-2.37 (m, 4H), 2.64-2.68 (m, 4H), 3.79 (t, 2H, J=6.8 Hz), 4.57 (d, 4H, J=13.2 Hz), 6.91-7.20 (m, 8H), 7.48-7.51 (m, 2H), 7.78 (s, 1H), 7.83 (d, 1H, J=7.2 Hz); MS for $C_{38}H_{43}FN_4O_4$ m/z 639.14 $(M+H)^+$.

Preparation of 1'-(3-chloropropyl)spiro[cyclopropane-1,3'-indolin]-2'-one

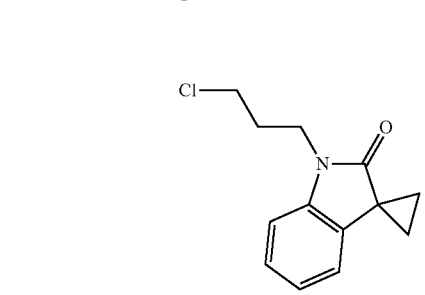 [SMILES: O=C1N(CCCCl)c2ccccc2C12CC2]

To a cooled (0° C.) solution of spiro[cyclopropane-1,3'-indolin]-2'-one (prepared according to methods described in J. Med. Chem. 1987, 824-829; J. Med. Chem. 1992, 163-172; U.S. Pat. No. 5,182,397) (1.0 g, 6.21 mmol) in N,N-dimethylformamide (5 mL), was added sodium hydride (0.149 g, 6.21 mmol), followed by addition of 1-bromo-3-chloropropane (0.733 mL, 7.45 mmol, d=1.6). After stirring at room temperature for 18 hours, the reaction mixture was diluted with ethyl acetate (100 mL), washed with dilute citric acid, water and brine. The organic phase was dried over $MgSO_4$, filtered and isolated by Biotage flash chromatography (10-40% ethyl acetate/hexanes) to obtain the title compound (1.1 g, 68%); $^1$H NMR (DMSO-$d_6$): δ 1.50-1.54 (m, 2H), 1.56-1.61 (m, 2H), 2.01-2.15 (m, 2H), 3.67 (t, 2H, J=6.4 Hz), 3.86 (t, 2H, J=6.8 Hz), 6.97-7.03 (m, 2H), 7.11 (d, 1H, J=8 Hz), 7.22-7.27 (m, 1H); MS for $C_{13}H_{14}ClNO$ m/z 236.04 $(M+H)^+$.

Example 72

Compound 142

3-((4-oxo-1-phenyl-8-(4-phenylbutyl)-1,3,8-triazaspiro[4.5]decan-3-yl)methyl)benzoic acid, formate

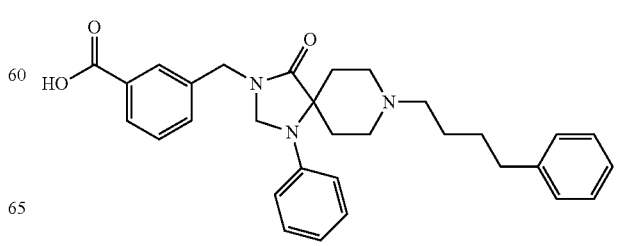

tert-Butyl 3-((4-oxo-1-phenyl-8-(4-phenylbutyl)-1,3,8-triazaspiro[4.5]decan-3-yl)methyl)benzoate (0.30 g, 0.542 mmol) and formic acid (8 mL) were stirred at room temperature for 20 hours. The reaction was evaporated to dryness and the residue purified by PTLC (10% methanol/dichloromethane). The product was dissolved in formic acid (5 mL) and then evaporated under vacuum. The residue was dissolved in acetonitrile (5 mL) and water (5 mL) and lyophilized to give product as a white solid (0.22 g, 80%); NMR (DMSO-d$_6$); δ1.54-1.63 (m, 4H); 1.67 (d, J=14 Hz, 2H); 2.57-2.69 (m, 6H); 2.97 (m, 4H); 4.59 (s, 2H); 4.62 (s, 2H); 6.72 (t, J=7.2 Hz, 1H); 6.84 (d, J=8.4 Hz, 2H); 7.12-7.21 (m, 5H), 7.25-7.28 (m, 2H); 7.47-7.51 (m, 2H); 7.88-7.89 (m, 2H); 8.21 (s, 1H). HPLC rt 11.66 min; MS for C$_{31}$H$_{35}$N$_3$O$_3$ m/z 498 (M+H)$^+$.

Preparation of tert-butyl 3-((4-oxo-1-phenyl-8-(4-phenylbutyl)-1,3,8-triazaspiro[4.5]decan-3-yl)methylbenzoate

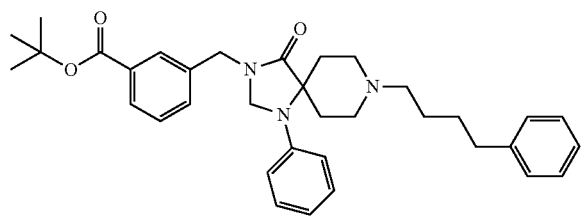 [SMILES: CC(C)(C)OC(=O)c1cccc(CN2CN(c3ccccc3)C3(CCN(CCCCc4ccccc4)CC3)C2=O)c1]

tert-Butyl 3-((4-oxo-1-phenyl-1,3,8-triazaspiro[4.5]decan-3-yl)methyl)benzoate (0.25 g, 0.593 mmol), 1-iodo-4-butylbenzene (0.15 g, 0.593 mmol), and potassium carbonate (0.12 g, 0.890 mmol) in N,N-dimethylformamide (8 mL) were stirred at 65° C. for 2 hours. The reaction was diluted with ethyl acetate, washed with water and brine, dried (MgSO$_4$), and evaporated. The residue was purified by PTLC (5% methanol/dichloromethane) to give product as an oil (0.30 g, 90%); MS for C$_{35}$H$_{43}$N$_3$O$_3$ m/z 554 (M+H)$^+$.

Example 73

Compound 143

3-((4-oxo-8-(4-oxo-4-(thiophen-2-yl)butyl)-1-phenyl-1,3,8-triazaspiro[4.5]decan-3-yl)methyl)benzoic acid, hydrochloride

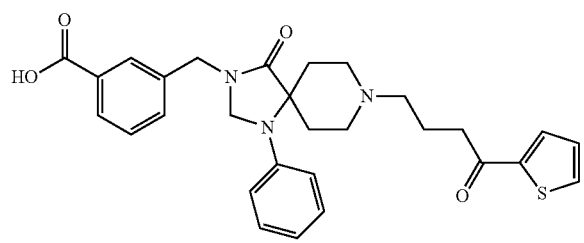 [SMILES: O=C(O)c1cccc(CN2CN(c3ccccc3)C3(CCN(CCCC(=O)c4cccs4)CC3)C2=O)c1]

tert-Butyl 3-((4-oxo-8-(4-oxo-4-(thiophen-2-yl)butyl)-1-phenyl-1,3,8-triazaspiro[4.5]decan-3-yl)methyl)benzoate (0.29 g, 0.505 mmol) and formic acid (6 mL) were stirred at room temperature for 20 hours. The reaction was evaporated to dryness and the residue purified by PTLC (10% methanol/dichloromethane) to give product as the formate salt; NMR (DMSO-d$_6$); δ1.63 (d, J=14 Hz, 2H); 1.87 (t, J=6.8 Hz, 2H); 2.52 (m, 4H); 2.88 (m, 4H); 3.01 (t, J=7.2 Hz, 2H); 4.58 (s, 2H); 4.61 (s, 2H); 6.75 (t, J=7.6 Hz, 1H); 6.80 (d, J=8 Hz, 2H); 7.17 (t, J=8.4 Hz, 2H); 7.24 (dd, J=3.6 Hz and 4.8 Hz, 1H); 7.48-7.54 (m, 2H); 7.87-7.89 (m, 2H); 7.95-7.99 (m, 2H); 8.18 (s, 1H). The formate salt was dissolved in 4M hydrochloric acid in dioxane (5 mL) and then evaporated under vacuum. The residue was dissolved in acetonitrile (5 mL) and water (5 mL) and lyophilized to give product as a white solid (0.22 g, 72%); HPLC rt 9.92 min; NMR (DMSO-d$_6$); δ1.90 (d, J=14.4 Hz, 2H); 2.10 (m, 2H); 3.03 (m, 2H); 3.17 (t, J=7.2 Hz, 4H); 3.58-3.69 (m, 4H); 4.65 (s, 2H); 4.66 (s, 2H); 6.80 (t, J=7.2 Hz, 1H); 7.07 (d, J=8.4 Hz, 2H); 7.21 (dd, J=7.2 Hz and 8.4 Hz, 2H); 7.27 (dd, J=3.6 Hz and 4.8 Hz, 1H); 7.52 (t, J=7.6 Hz, 1H); 7.57 (d, J=8 Hz, 1H); 7.88-7.90 (m, 2H); 7.99 (dd, J=1.6 Hz and 4 Hz, 1H); 8.02 (dd, J=1.2 Hz and 4.8 Hz, 1H); MS for C$_{29}$H$_{31}$N$_3$O$_4$S m/z 518 (M+H)$^+$.

Preparation of tert-butyl 3-((4-oxo-8-(4-oxo-4-(thiophen-2-yl)butyl)-1-phenyl-1,3,8-triazaspiro[4.5]decan-3-yl)methylbenzoate

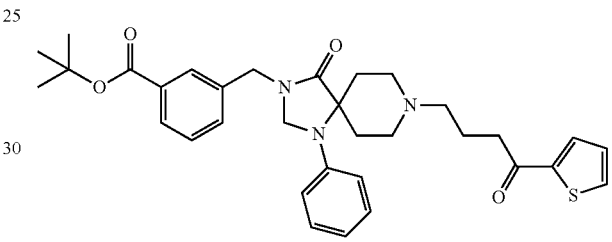

tert-Butyl 4-((4-oxo-1-phenyl-1,3,8-triazaspiro[4.5]decan-3-yl)methyl)benzoate (0.25 g, 0.593 mmol), 4-iodo-1-(thiophen-2-yl)butan-1-one (0.17 g, 0.593 mmol), and potassium carbonate (0.12 g, 0.890 mmol) in N,N-dimethylformamide (8 mL) were heated at 65° C. for 4 hours. The reaction was diluted with ethyl acetate, washed with water and brine, dried (MgSO$_4$), and evaporated. The residue was purified by PTLC (5% methanol/dichloromethane) to give product as an oil (0.29 g, 84%); NMR (DMSO-d$_6$); δ1.52 (s, 9H); 1.57 (m, 2H); 1.85 (m, 2H); 2.33-2.49 (m, 4H); 2.73 (m, 4H); 3.00 (m, 2H); 4.58 (s, 2H); 4.61 (m, 2H); 6.78 (m, 2H); 7.18-7.26 (m, 4H); 7.48-7.55 (m, 2H); 7.80-7.84 (m, 2H); 7.96-8.00 (m, 2H); MS for C$_{33}$H$_{39}$N$_3$O$_4$S m/z 574 (M+H)$^+$.

Preparation of 4-iodo-1-(thiophen-2-yl)butan-1-one

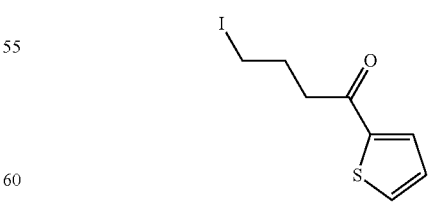

4-Chloro-2-butyrothienone (2.00 g, 0.0106 mol) and sodium iodide (2.38 g, 0.0159 mol) in acetone (30 mL) were refluxed overnight. The solvent was removed, the residue diluted with ether, washed with water and brine, dried (MgSO$_4$) and evaporated. The residue was purified by Biotage flash column chromatography (5% ethyl acetate/hexanes) to give product as an oil (2.84 g, 96%); MS for $C_8H_9IOS$ m/z 281 (M+H)$^+$.

Example 74

Compound 145

3-((1-(4-Fluorophenyl)-4-oxo-8-(3-(2-oxoindolin-1-yl)propyl)-1,3,8-triazaspiro[4.5]decan-3-yl)methyl)benzoic acid

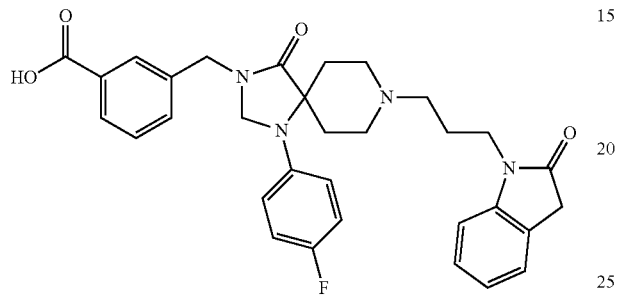

To a solution of tert-butyl 3-((1-(4-fluorophenyl)-4-oxo-1,3,8-triazaspiro[4.5]decan-3-yl)methyl)benzoate (0.2 g, 0.46 mmol), sodium iodide (0.021 g, 0.14 mmol) and potassium bicarbonate (0.069 g, 0.69 mmol) in 2-butanone (5 mL), was added 1-(3-chloropropyl)indolin-2-one (0.096 g, 0.46 mmol). After stirring at 78° C. for 2 hours, the reaction mixture was filtered and isolated by preparatory TLC (10% methanol/dichloromethane) to obtain tert-butyl 3-((1-(4-fluorophenyl)-4-oxo-8-(3-(2-oxoindolin-1-yl)propyl)-1,3,8-triazaspiro[4.5]decan-3-yl)methyl)benzoate (0.075 g, 27%).

To tert-butyl 3-((1-(4-fluorophenyl)-4-oxo-8-(3-(2-oxoindolin-1-yl)propyl)-1,3,8-triazaspiro[4.5]decan-3-yl)methyl)benzoate (0.07 g, 0.11 mmol) was added concentrated 4M HCl in dioxane (1.5 mL) and triethylsilane (0.05 mL). After stirring at room temperature for 18 hours, the reaction mixture was concentrated in vacuo and isolated by reverse phase HPLC to obtain the title compound as an acetate salt (0.035 g, 52%); $^1$H NMR (DMSO-d$_6$): δ 1.62 (d, 2H, J=13.6 Hz), 1.74 (t, 2H, J=6.4 Hz), 2.24-2.28 (m, 2H), 2.36 (t, 2H, J=6.4 Hz), 2.68 (d, 4H, J=6.8 Hz), 3.52 (s, 2H), 3.70 (t, 2H, J=6.8 Hz), 4.56 (d, 4H, J=14 Hz), 6.89-6.92 (m, 2H), 6.98 (t, 1H, J=7.2 Hz), 7.04-7.10 (m, 3H), 7.19-7.24 (m, 2H), 7.48-7.51 (m, 2H), 7.86 (d, 2H, J=3.2 Hz); MS for $C_{32}H_{33}FN_4O_4$ m/z 557.09 (M+H)$^+$.

Preparation of 1-(3-chloropropyl)indolin-2-one

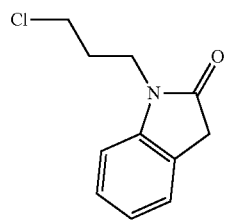 [SMILES: O=C1Cc2ccccc2N1CCCCl]

To a solution of oxindole (9.2 g, 69.1 mmol) and potassium carbonate (19.0 g, 138.2 mmol) in acetonitrile (100 mL), was added 1-bromo-3-chloropropane (13.6 mL, 138.2 mmol, d=1.6). After stirring at 80° C. for 18 hours, the reaction mixture was diluted with ethyl acetate (200 mL), washed with dilute citric acid, water and brine. The organic phase was dried over MgSO$_4$, filtered and isolated by Biotage flash chromatography (10-40% ethyl acetate/hexanes) to obtain the title compound (6.2 g, 43%); $^1$H NMR (DMSO-d$_6$): δ 1.98-2.05 (m, 2H), 3.54 (s, 2H), 3.67 (t, 2H, J=6.4 Hz), 3.77 (t, 2H, J=6.4 Hz), 6.98-7.03 (m, 2H), 7.24-7.28 (m, 2H); MS for $C_{11}H_{12}ClNO$ m/z 210.03 (M+H)$^+$.

Example 75

Compound 146

3-((8-(3-(3-methyl-2-oxoindolin-1-yl)propyl)-4-oxo-1-phenyl-1,3,8-triazaspiro[4.5]decan-3-yl)methyl)benzoic acid

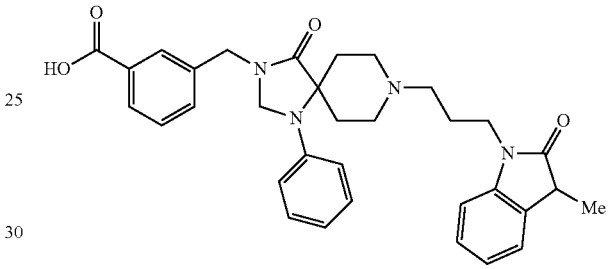

A solution of tert-butyl 3-((8-(3-(3-methyl-2-oxoindolin-1-yl)propyl)-4-oxo-1-phenyl-1,3,8-triazaspiro[4.5]decan-3-yl)methyl)benzoate (100 mg, 0.164 mmol, 1 equiv) in 4M hydrogen chloride solution in dioxane was stirred at ambient temperature for 16 h. The mixture was concentrated and dried in vacuo to afford the hydrogen chloride salt of the title compound as a white powder (12 mg, 14%); $^1$H NMR (400 MHz, DMSO-d$_6$): δ 1.34 (d, 3H, J=7.6 Hz); 1.63 (d, 2H, J=12.8 Hz); 1.79 (t, 2H, J=6.8 Hz); 2.49 (bs, 2H); 2.56 (bs, 2H); 2.67-2.77 (m, 4H); 3.45-3.51 (m, 1H); 3.7-3.75 (m, 2H); 4.59 (s, 2H); 4.61 (s, 2H); 6.77 (t, 1H, J=7.2 and 7.6 Hz); 6.86 (d, 2H, J=8.4 Hz); 7.01 (t, 1H, J=7.2 and 7.6 Hz); 7.10 (d, 1H, J=8 Hz); 7.19-7.25 (m, 3H); 7.31 (d, 1H, J=7.2 Hz); 7.48-7.52 (m, 2H); 7.86-7.88 (m, 1H); 13.01 (bs, 1H); MS for $C_{33}H_{36}N_4O_4$ m/z 553.11 (M+H)$^+$.

Preparation of tert-butyl 3-((8-(3-(3-methyl-2-oxoindolin-1-yl)propyl)-4-oxo-1-phenyl-1,3,8-triazaspiro[4.5]decan-3-yl)methyl)benzoate

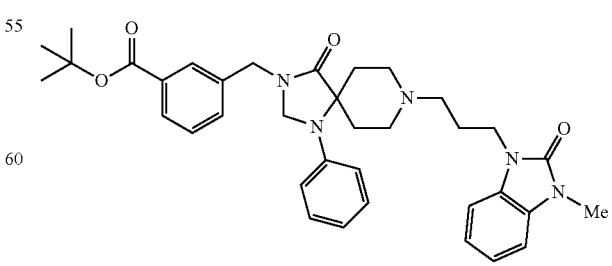

A mixture of tert-butyl 3-((4-oxo-1-phenyl-1,3,8-triazaspiro[4.5]decan-3-yl)methyl)benzoate (200 mg, 0.475 mmol, 1 equiv), 1-(3-chloropropyl)-3-methylindolin-2-one (155 mg, 0.665 mmol, 1.4 equiv), sodium iodide (28.5 mg, 0.19 mmol, 0.4 equiv) and potassium carbonate (71.4 mg, 0.7125 mmol, 1.5 equiv) in 2-butanone was stirred at 81° C. for 16 h. After cooling the reaction mixture, the crude mixture was partitioned between ethyl acetate and water. The organic layer was dried over $MgSO_4$, filtered, concentrated, and the crude residue was purified using preparative thin layer chromatography in 7% methanol in dichloromethane to afford the title compound (100 mg, ~30%); MS for $C_{37}H_{44}N_4O_4$ m/z 609.3 $(M+H)^+$.

Preparation of
1-(3-chloropropyl)-3-methylindolin-2-one

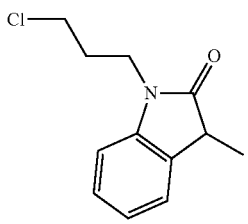

To a mixture of 3-methylindolin-2-one (1 g, 6.79 mmol, 1 equiv) in acetonitrile, potassium carbonate (1.877 g, 13.58 mmol, 2.5 equiv) followed by 1-bromo-3-chloropropane (2.01 ml, 20.38 mmol, 3 equiv) were added. The reaction was refluxed for 16 h. Upon cooling water was added and the mixture was extracted into ethyl acetate. The organic layer was further washed with brine, dried over $MgSO_4$, filtered and concentrated in vacuo. The crude residue was purified using the Biotage flash chromatography system (SNAP 100 g cartridge, $R_f$=0.5, gradient—2%-20% ethyl acetate in hexanes) to afford the title compound as a yellow oil (230 mg, 15%); $^1$H NMR (400 MHz, DMSO-$d_6$): δ 1.31 (d, 3H, J=7.6 Hz); 1.99-2.05 (m, 2H); 3.47-3.53 (m, 1H); 3.66 (t, 2H, J=6.4 Hz); 3.74-3.82 (m, 2H); 7.04 (d, 2H; J=7.6 Hz); 7.24-7.27 (m, 1H); 7.3-7.32 (m, 1H); MS for $C_{12}H_{14}ClNO$ m/z 211.06 $(M+H)^+$.

Example 76

Compound 148

2-((4-Oxo-8-(3-(2-oxoindolin-1-yl)propyl)-1-phenyl-1,3,8-triazaspiro[4.5]decan-3-yl)methyl)benzoic acid

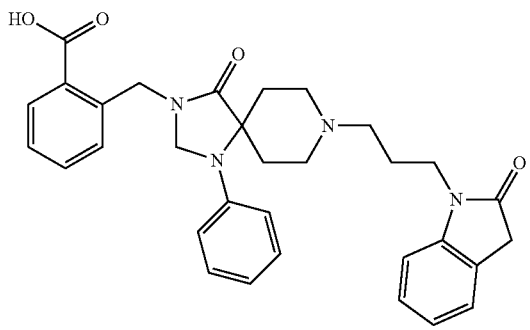 [SMILES: O=C(O)c1ccccc1CN1CN(c2ccccc2)C2(CCN(CCCN3C(=O)Cc4ccccc43)CC2)C1=O]

To a solution of tert-butyl 2-((4-oxo-1-phenyl-1,3,8-triazaspiro[4.5]decan-3-yl)methyl)benzoate (1.9 g, 4.5 mmol), sodium iodide (0.27 g, 1.8 mmol) and potassium carbonate (1.24 g, 9.0 mmol) in 2-butanone (20 mL), was added 1-(3-chloropropyl)indolin-2-one (0.945 g, 4.5 mmol). After stirring at 78° C. for 4 hours, the reaction mixture was filtered and isolated by Biotage flash chromatography (50-100% ethyl acetate/hexanes) to obtain tert-butyl 2-((4-oxo-8-(3-(2-oxoindolin-1-yl)propyl)-1-phenyl-1,3,8-triazaspiro[4.5]decan-3-yl)methyl)benzoate (0.45 g, 17%).

To tert-butyl 2-((4-oxo-8-(3-(2-oxoindolin-1-yl)propyl)-1-phenyl-1,3,8-triazaspiro[4.5]decan-3-yl)methyl)benzoate (0.45 g, 0.76 mmol) was added concentrated 4M HCl in dioxane (10 mL). After stirring at room temperature for 18 hours, the reaction mixture was concentrated in vacuo and washed with 1% methanol/dichloromethane to obtain the title compound as a hydrochloride salt (0.22 g, 50%); $^1$H NMR (DMSO-$d_6$): δ 1.97-2.06 (m, 4H), 2.92 (t, 2H, J=10 Hz), 3.20 (br, 2H), 3.53-3.57 (m, 6H), 3.76 (t, 2H, J=6.8 Hz), 4.66 (s, 2H), 4.92 (s, 2H), 6.80 (t, 1H, J=7.6 Hz), 6.98-7.04 (m, 3H), 7.12 (d, 1H, J=7.6 Hz), 7.20-7.32 (m, 5H), 7.42 (t, 1H, J=7.6 Hz), 7.57 (t, 1H, J=7.6 Hz), 7.92 (dd, 1H, J=7.6 and 1.2 Hz), 10.27 (br, 1H), 13.21 (s, 1H); MS for $C_{32}H_{34}N_4O_4$ m/z 539.15 $(M+H)^+$.

Example 77

Compound 149

2-((4-Oxo-8-(3-(2'-oxospiro[cyclopropane-1,3'-indoline]-1'-yl)propyl)-1-phenyl-1,3,8-triazaspiro[4.5]decan-3-yl)methyl)benzoic acid

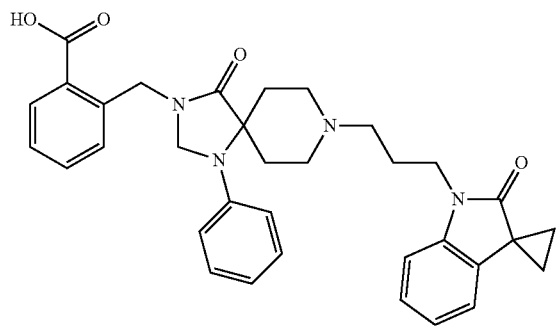 [SMILES: O=C(O)c1ccccc1CN1CN(c2ccccc2)C2(CCN(CCCN3C(=O)C4(CC4)c4ccccc43)CC2)C1=O]

To tert-butyl 2-((4-oxo-8-(3-(2'-oxospiro[cyclopropane-1,3'-indoline]-1'-yl)propyl)-1-phenyl-1,3,8-triazaspiro[4.5]decan-3-yl)methyl)benzoate (0.18 g, 0.29 mmol) was added concentrated formic acid (3 mL) and triethylsilane (0.05 mL). After stirring at room temperature for 18 hours, the reaction mixture was concentrated, taken in 4M HCl in dioxane and lyophilized to obtain the title compound as a hydrochloride salt (0.165 g, 95%); $^1$H NMR (DMSO-$d_6$): δ 1.52-1.63 (m, 4H), 1.98 (d, 2H, J=14.8 Hz), 2.08-2.10 (m, 2H), 2.92 (t, 2H, J=7.6 Hz), 3.21 (br, 2H), 3.45-3.71 (m, 4H), 3.84 (t, 2H, J=6.8 Hz), 4.68 (s, 2H), 4.92 (s, 2H), 6.80 (t, 1H, J=7.6 Hz), 6.98-7.05 (m, 4H), 7.20-7.32 (m, 5H), 7.42 (t, 1H, J=7.6 Hz), 7.57 (t, 1H, J=7.6 Hz), 7.92 (dd, 1H, J=8 and 1.6 Hz), 10.32 (br, 1H), 13.19 (s, 1H); MS for $C_{34}H_{36}N_4O_4$ m/z 565.14 $(M+H)^+$.

Preparation of tert-butyl 2-((4-oxo-8-(3-(2'-oxospiro [cyclopropane-1,3'-indoline]-1'-yl)propyl)-1-phenyl-1,3,8-triazaspiro[4.5]decan-3-yl)methyl)benzoate

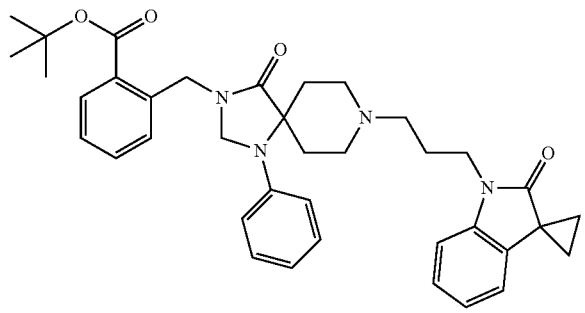 [SMILES: CC(C)(C)OC(=O)c1ccccc1CN1CN(c2ccccc2)C2(CCN(CCCN3C(=O)C4(CC4)c4ccccc43)CC2)C1=O]

To a solution of tert-butyl 2-((4-oxo-1-phenyl-1,3,8-triazaspiro[4.5]decan-3-yl)methyl)benzoate (0.2 g, 0.47 mmol), sodium iodide (0.021 g, 0.14 mmol) and potassium carbonate (0.097 g, 0.7 mmol) in 2-butanone (5 mL), was added 1'-(3-chloropropyl)spiro[cyclopropane-1,3'-indolin]-2'-one (0.112 g, 0.47 mmol). After stirring at 78° C. for 2 hours, the reaction mixture was filtered and isolated by Biotage flash chromatography (1-10% methanol/dichloromethane) to obtain the title compound (0.18 g, 62%); $^1$H NMR (DMSO-d$_6$): δ 1.51 (t, 4H, J=7.2 Hz), 1.57 (s, 9H), 1.67 (d, 2H, J=12.4 Hz), 1.79 (t, 2H, J=6.8 Hz), 2.36 (t, 2H, J=6.8 Hz), 2.54-2.74 (m, 6H), 3.81 (t, 2H, J=7.2 Hz), 4.62 (s, 2H), 4.84 (s, 2H), 6.76 (t, 1H, J=7.2 Hz), 6.84 (d, 2H, J=8 Hz), 6.96-7.02 (m, 2H), 7.17-7.27 (m, 5H), 7.41 (t, 1H, J=6.8 Hz), 7.57 (t, 1H, J=7.6 Hz), 7.83 (dd, 1H, J=8 and 1.2 Hz); MS for $C_{38}H_{44}N_4O_4$ m/z 621.12 (M+H)$^+$.

Example 78

Compound 150

3-((1-cyclohexyl-8-(4-(4-fluorophenyl)-4-oxobutyl)-4-oxo-1,3,8-triazaspiro[4.5]decan-3-yl)methyl)benzoic acid, hydrochloride

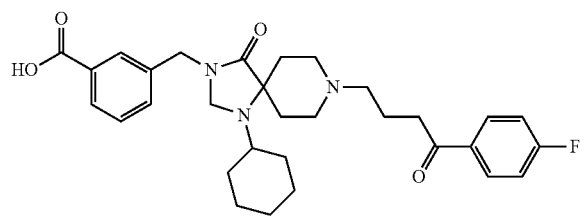 [SMILES: O=C(O)c1cccc(CN2CN(C3CCCCC3)C3(CCN(CCCC(=O)c4ccc(F)cc4)CC3)C2=O)c1]

tert-butyl 3-((1-cyclohexyl-8-(4-(4-fluorophenyl)-4-oxobutyl)-4-oxo-1,3,8-triazaspiro[4.5]decan-3-yl)methyl)benzoate (0.39 g, 0.659 mmol) and 4M hydrochloric acid/1% triethylsilane in 1,4-dioxane (6 mL) were stirred at room temperature for 4 hours. The reaction was evaporated and the residue purified by PTLC (10% methanol/dichloromethane). The product obtained from PTLC was redissolved in 4M hydrochloric acid in dioxane and evaporated. The residue was dissolved in acetonitrile (5 mL) and water (5 mL) and lyophilized to give product as a white solid (0.28 g, 75%); HPLC rt 10.92 min; NMR (DMSO-d$_6$); δ1.02-1.08 (m, 1H); 1.18-1.28 (m, 4H); 1.28-1.40 (m, 1H); 1.45-1.65 (m, 2H); 1.65- 1.78 (m, 3H); 1.85-2.10 (m, 3H); 2.33-2.50 (m, 2H); 3.10 (m, 2H); 3.22 (t, J=6.8 Hz, 2H); 3.49-3.56 (m, 5H); 4.52 (s, 2H); 7.35-7.40 (m, 2H); 7.50 (m, 2H); 7.85-7.86 (m, 2H); 8.05-8.09 (m, 2H); 10.6 (br s, 1H); 13.0 (br s, 1H); MS for $C_{31}H_{38}FN_3O_4$ m/z 536 (M+H)$^+$.

Preparation of tert-butyl 3-((1-cyclohexyl-8-(4-(4-fluorophenyl)-4-oxobutyl)-4-oxo-1,3,8-triazaspiro [4.5]decan-3-yl)methyl)benzoate

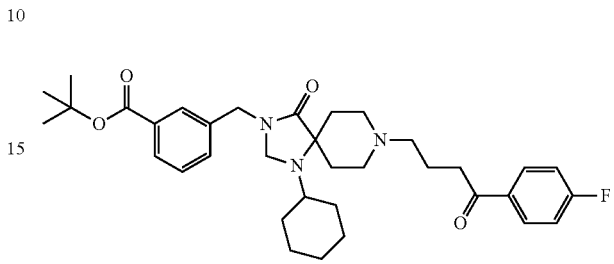

tert-Butyl 3-((1-cyclohexyl-4-oxo-1,3,8-triazaspiro[4.5] decan-3-yl)methyl)benzoate (0.353 g, 0.826 mmol), 4-iodo-4'-fluorobutyrophenone (0.27 g, 0.826 mmol), and potassium carbonate (0.17 g, 1.24 mmol) in N,N-dimethylformamide (8 mL) were heated at 65° C. for 2 hours. The reaction was diluted with ethyl acetate, washed with water and brine, dried (MgSO$_4$), and evaporated. The residue was purified by PTLC (5% methanol/dichloromethane) to give product as an oil (0.39 g, 80%); MS for $C_{35}H_{46}FN_3O_4$ m/z 592 (M+H)$^+$.

Example 79

Compound 153

2-((1-(4-Fluorophenyl)-4-oxo-8-(3-(2-oxoindolin-1-yl)propyl)-1,3,8-triazaspiro[4.5]decan-3-yl)methyl) benzoic acid

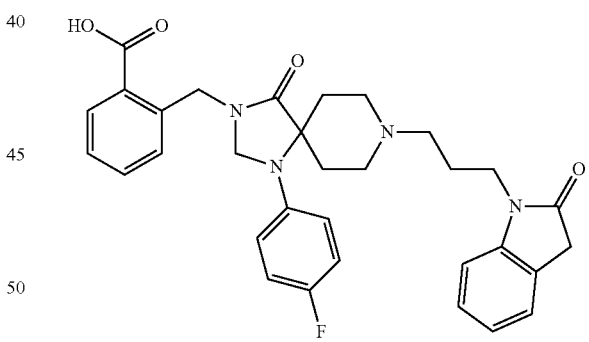

To tert-butyl 2-((1-(4-fluorophenyl)-4-oxo-8-(3-(2-oxoindolin-1-yl)propyl)-1,3,8-triazaspiro[4.5]decan-3-yl)methyl) benzoate (0.062 g, 0.1 mmol) was added concentrated 4M HCl in dioxane (1.0 mL) and triethylsilane (0.05 mL). After stirring at room temperature for 3 hours, the reaction mixture was concentrated in vacuo and lyophilized in acetonitrile: water (1:1) to obtain the title compound as a hydrochloride salt (0.035 g, 52%); $^1$H NMR (DMSO-d$_6$): δ 1.99-2.08 (m, 4H), 2.66 (t, 2H, J=12.4 Hz), 3.17-3.20 (m, 2H), 3.45-3.56 (m, 4H), 3.66-3.70 (m, 2H), 3.75 (t, 2H, J=6.8 Hz), 4.64 (s, 2H), 4.91 (s, 2H), 7.00-7.12 (m, 6H), 7.26-7.32 (m, 3H), 7.42 (t, 1H, J=7.2 Hz), 7.57 (t, 1H, J=7.6 Hz), 7.91 (dd, 1H, J=8 and 1.2 Hz), 10.05 (br, 1H), 13.18 (s, 1H); MS for $C_{32}H_{33}FN_4O_4$ m/z 557.06 (M+H)$^+$.

tert-Butyl 2-((1-(4-fluorophenyl)-4-oxo-8-(3-(2-ox-oindolin-1-yl)propyl)-1,3,8-triazaspiro[4.5]decan-3-yl)methylbenzoate

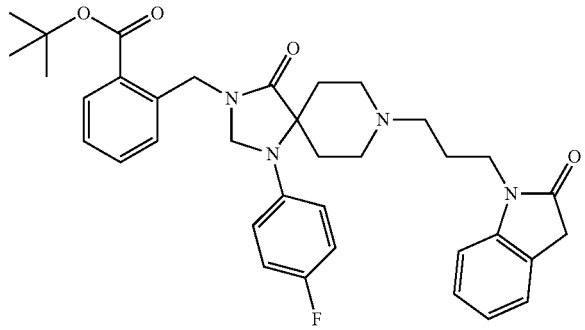 [SMILES: CC(C)(C)OC(=O)c1ccccc1CN1CN(c2ccc(F)cc2)C2(CCN(CCCN3C(=O)Cc4ccccc43)CC2)C1=O]

To a solution of benzyl 3-(2-(tert-butoxycarbonyl)benzyl)-1-(4-fluorophenyl)-4-oxo-1,3,8-triazaspiro[4.5]decane-8-carboxylate (1.5 g, 2.61 mmol) in methanol (25 mL), was added 10 wt % palladium on carbon (0.25 g). After stirring under hydrogen at room temperature and atmospheric pressure for 2 hours, the reaction mixture was filtered, washed with methanol, concentrated in vacuo to obtain tert-butyl 2-((1-(4-fluorophenyl)-4-oxo-1,3,8-triazaspiro[4.5]decan-3-yl)methyl)benzoate (1.1 g, 96%).

To a solution of tert-butyl 2-((1-(4-fluorophenyl)-4-oxo-1,3,8-triazaspiro[4.5]decan-3-yl)methyl)benzoate (0.175 g, 0.4 mmol), sodium iodide (0.018 g, 0.12 mmol) and potassium carbonate (0.083 g, 0.6 mmol) in 2-butanone (4 mL), was added 1-(3-chloropropyl)indolin-2-one (0.095 g, 0.4 mmol). After stirring at 78° C. for 18 hours, the reaction mixture was filtered and isolated by Biotage flash chromatography (1-10% methanol/dichloromethane) and preparatory TLC (10% methanol/dichloromethane) to obtain the title compound (0.077 g, 31%); $^1$H NMR (DMSO-d$_6$): δ 1.56 (s, 9H), 1.67 (d, 2H, J=12.4 Hz), 2.02 (br, 2H), 2.28-2.34 (m, 2H), 2.62-2.67 (m, 2H), 3.17-3.23 (m, 2H), 3.52-3.56 (m, 4H), 3.72 (t, 2H, J=6.4 Hz), 4.61 (s, 2H), 4.82 (s, 2H), 6.11-7.14 (m, 6H), 7.23-7.27 (m, 3H), 7.41 (t, 1H, J=7.6 Hz), 7.57 (t, 1H, J=7.6 Hz), 7.82 (d, 1H, J=8 Hz); MS for C$_{36}$H$_{41}$FN$_4$O$_4$ m/z 613.15 (M+H)$^+$.

Preparation of benzyl 3-(2-(tert-butoxycarbonyl)benzyl)-1-(4-fluorophenyl)-4-oxo-1,3,8-triazaspiro[4.5]decane-8-carboxylate

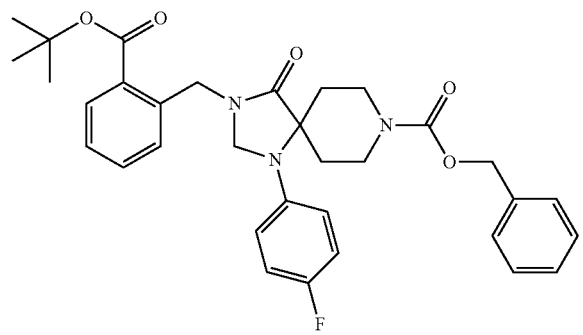 [SMILES: CC(C)(C)OC(=O)c1ccccc1CN1CN(c2ccc(F)cc2)C2(CCN(C(=O)OCc3ccccc3)CC2)C1=O]

To a solution of benzyl 1-(4-fluorophenyl)-4-oxo-1,3,8-triazaspiro[4.5]decane-8-carboxylate (1.6 g, 4.17 mmol) and potassium carbonate (0.86 g, 6.3 mmol) in N,N-dimethylformamide (20 mL), was added tert-butyl-2-(bromomethyl)benzoate (1.13 g, 4.17 mmol). After stirring at 60° C. for 24 hours, the reaction mixture was diluted with ethyl acetate (200 mL), washed with dilute citric acid, water and brine. The organic phase was dried over MgSO$_4$, filtered, and isolated by Biotage flash chromatography (10-100% ethyl acetate/hexanes) to obtain the title compound (1.5 g, 63%); $^1$H NMR (DMSO-d$_6$): δ 1.56 (s, 9H), 1.80 (d, 2H, J=14 Hz), 2.12 (t, 2H, J=10.8 Hz), 3.57 (br, 2H), 4.02 (d, 2H, J=6.8 Hz), 4.61 (s, 2H), 4.85 (s, 2H), 5.10 (s, 2H), 6.79-6.82 (m, 2H), 7.06 (t, 2H, J=9.2 Hz), 7.28-7.43 (m, 7H), 7.58 (t, 1H, J=7.6 Hz), 7.82 (dd, 1H, J=8 and 1.2 Hz); MS for C$_{33}$H$_{36}$FN$_3$O$_5$ m/z 596.12 (M+Na)$^+$.

Example 80

Compound 153

2-((8-(3-(3,3-Dimethyl-2-oxoindolin-1-yl)propyl)-1-(4-fluorophenyl)-4-oxo-1,3,8-triazaspiro[4.5]decan-3-yl)methyl)benzoic acid

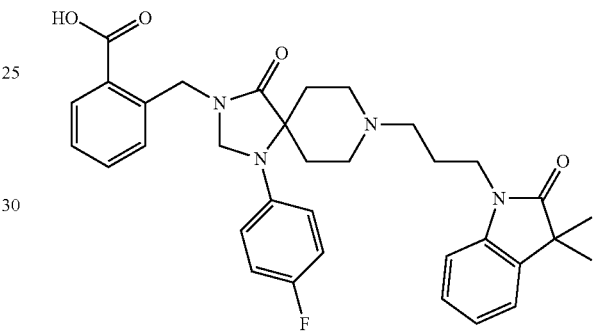

To tert-butyl 2-((8-(3-(3,3-dimethyl-2-oxoindolin-1-yl)propyl)-1-(4-fluorophenyl)-4-oxo-1,3,8-triazaspiro[4.5]decan-3-yl)methyl)benzoate (0.175 g, 0.27 mmol) was added concentrated 4M HCl in dioxane (3.0 mL) and triethylsilane (0.02 mL). After stirring at room temperature for 3 hours, the reaction mixture was concentrated in vacuo and lyophilized in acetonitrile:water (1:1) to obtain the title compound as a hydrochloride salt (0.16 g, 96%); $^1$H NMR (DMSO-d$_6$): δ 1.28 (s, 6H), 1.99-2.02 (m, 4H), 2.53-2.67 (m, 2H), 3.17 (br, 2H), 3.44-3.72 (m, 4H), 3.75 (t, 2H, J=7.2 Hz), 4.64 (s, 2H), 4.91 (s, 2H), 7.01-7.15 (m, 6H), 7.27 (dd, 1H, J=8 and 1.2 Hz), 7.31 (d, 1H, J=7.2 Hz), 7.36 (d, 1H, J=7.2 Hz), 7.42 (t, 1H, J=7.6 Hz), 7.57 (t, 1H, J=6.4 Hz), 7.92 (dd, 1H, J=8 and 1.2 Hz), 9.93 (br, 1H), 13.18 (s, 1H); MS for C$_{34}$H$_{37}$FN$_4$O$_4$ m/z 585.11 (M+H)$^+$.

Preparation of tert-butyl 2-((8-(3-(3,3-dimethyl-2-oxoindolin-1-yl)propyl)-1-(4-fluorophenyl)-4-oxo-1,3,8-triazaspiro[4.5]decan-3-yl)methyl)benzoate

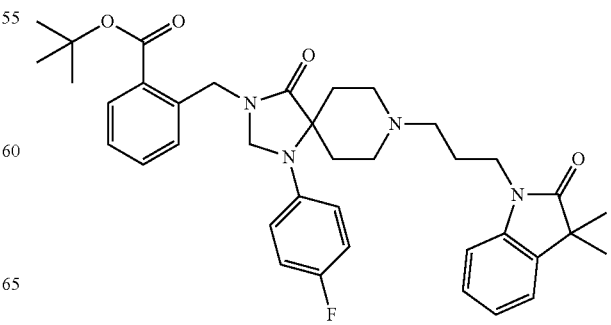

To a solution of tert-butyl 2-((1-(4-fluorophenyl)-4-oxo-1,3,8-triazaspiro[4.5]decan-3-yl)methyl)benzoate (0.15 g, 0.34 mmol), sodium iodide (0.015 g, 0.1 mmol) and potassium carbonate (0.081 g, 0.51 mmol) in 2-butanone (4 mL), was added 1-(3-chloropropyl)-3,3-dimethylindolin-2-one (0.081 g, 0.34 mmol). After stirring at 78° C. for 18 hours, the reaction mixture was filtered and isolated by Biotage flash chromatography (1-10% methanol/dichloromethane) and preparatory TLC (10% methanol/dichloromethane) to obtain the title compound (0.18 g, 83%); $^1$H NMR (DMSO-d$_6$): δ 1.25 (s, 6H), 1.56 (s, 9H), 1.67-1.75 (m, 4H), 2.31 (br, 4H), 2.64-2.66 (m, 4H), 3.72 (t, 2H, J=7.2 Hz), 4.58 (s, 2H), 4.82 (s, 2H), 6.90-6.91 (m, 2H), 7.02 (t, 1H, J=7.6 Hz), 7.08-7.12 (m, 3H), 7.19-7.27 (m, 2H), 7.33 (d, 1H, J=6.8 Hz), 7.40 (t, 1H, J=7.2 Hz), 7.57 (t, 1H, J=7.6 Hz), 7.82 (dd, 1H, J=7.2 and 1.2 Hz); MS for $C_{38}H_{45}FN_4O_4$ m/z 641.17 (M+H)$^+$.

Example 81

Compound 154

2-((4-oxo-8-(4-oxo-4-phenylbutyl)-1-phenyl-1,3,8-triazaspiro[4.5]decan-3-yl)methyl)benzoic acid

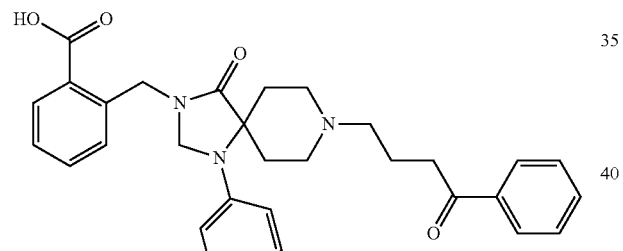

A solution of tert-butyl 2-((4-oxo-8-(4-oxo-4-phenylbutyl)-1-phenyl-1,3,8-triazaspiro[4.5]decan-3-yl)methyl)benzoate (268 mg, 0.472 mmol, 1 equiv) in 4M hydrogen chloride solution in dioxane was stirred at ambient temperature for 4 h. The mixture was concentrated in vacuo and purified using preparative thin layer chromatography in 7% methanol in dichloromethane. The pure extract was treated with 4M hydrogen chloride solution in dioxane to afford the hydrogen chloride salt of the title compound as a white powder (80 mg, 30%); $^1$H NMR (400 MHz, DMSO-d$_6$): δ 2.01 (d, 2H, J=14.4 Hz); 2.09 (t, 2H, J=7.2 and 7.6 Hz); 3.02 (t, 2H, J=12.4 and 10.4 Hz); 3.18 (bs, 2H); 3.23 (t, 2H, J=7.2 and 6.8 Hz); 3.65-3.7 (m, 4H); 4.69 (s, 2H); 4.94 (s, 2H); 6.81 (t, 1H, J=7.2 and 7.6 Hz); 7.04 (d, 2H, J=8.4 Hz); 7.24 (t, 2H, J=7.6 and 8 Hz); 7.33 (d, 1H, J=8 Hz); 7.43 (t, 2H, J=7.6 Hz); 7.53-7.61 (m, 3H); 7.66 (t, 1H, J=7.6 Hz); 7.93 (dd, 1H, J=1.2 and 1.6 Hz); 7.99-8.01 (m, 2H); 10.5 (bs, 1H); 13.2 (bs, 1H); MS for $C_{31}H_{33}N_3O_4$ m/z 512.4 (M+H)$^+$.

Preparation of tert-butyl 2-((4-oxo-8-(4-oxo-4-phenylbutyl)-1-phenyl-1,3,8-triazaspiro[4.5]decan-3-yl)methyl)benzoate

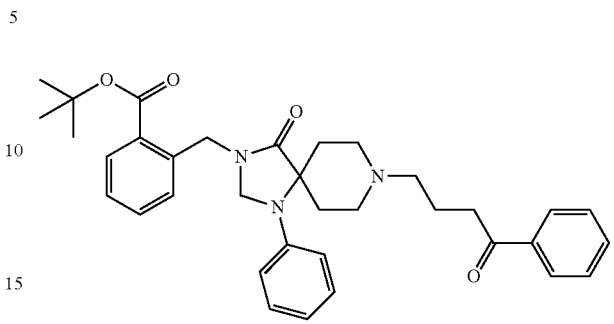

A mixture of tert-butyl 2-((4-oxo-1-phenyl-1,3,8-triazaspiro[4.5]decan-3-yl)methyl)benzoate (300 mg, 0.72 mmol, 1 equiv), 4-iodo-1-phenylbutan-1-one (198.5 mg, 0.72 mmol, 1 equiv) and potassium carbonate (199 mg, 1.44 mmol, 2 equiv) in N,N-dimethylformamide was stirred at 68° C. for 16 h. After cooling the reaction mixture, the crude mixture was partitioned between ethyl acetate and water. The organic layer was dried over MgSO$_4$, filtered, concentrated, and the crude residue was purified using the preparative thin layer chromatography in 8% methanol in dichloromethane to afford the title compound (268 mg, 65.5%); MS for $C_{35}H_{41}N_3O_4$ m/z 568.31 (M+H)$^+$.

Preparation of 4-iodo-1-phenylbutan-1-one

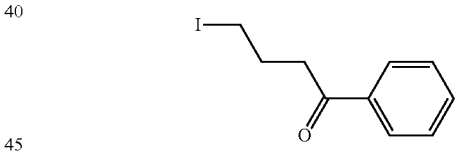

Sodium iodide (1.64 g, 10.95 mmol, 2 equiv) was added to a solution of 4-chloro-1-phenylbutan-1-one (1 g, 5.475 mmol, 1 equiv) in acetone. The reaction mixture was refluxed for 16 h. After cooling to ambient temperature, it was evaporated under reduced pressure to remove all the acetone. The residue was worked up using ethyl acetate and sodium bisulfite, followed by a wash with brine. The organic layer was dried over MgSO$_4$, filtered and concentrated in vacuo. The crude residue was purified using the Biotage flash chromatography system (SNAP 50 g cartridge, R$_f$=0.4, 5%-30% ethyl acetate in hexanes) to afford the title compound as white solid (880 mg, 59%). The bottle containing the compound was wrapped in aluminium foil to stored in the freezer to avoid further darkening of the mixture; $^1$H NMR (400 MHz, DMSO-d$_6$): δ 2.06-2.16 (m, 2H); 3.14 (t, 2H, J=3.2 and 4 Hz); 3.34 (t, 2H, J=6.8 and 7.2 Hz); 7.51-7.55 (m, 2H); 7.62-7.67 (m, 2H); 7.95-7.98 (m, 2H); MS for $C_{10}H_{11}IO$ m/z 274.99 (M+H)$^+$.

Example 82

Compound 155

2-((8-(3-(3-cyclopropyl-2-oxo-2,3-dihydro-1H-benzo[d]imidazol-1-yl)propyl)-4-oxo-1-phenyl-1,3,8-triazaspiro[4.5]decan-3-yl)methyl)benzoic acid

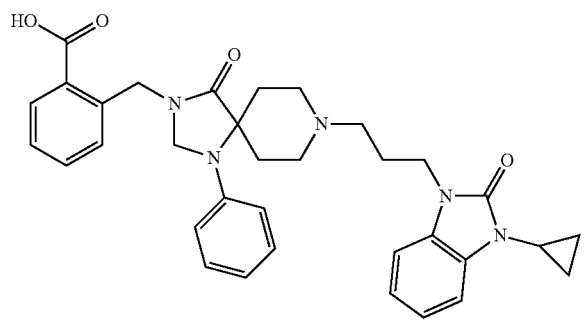 [SMILES: O=C(O)c1ccccc1CN1CN(c2ccccc2)C2(CCN(CCCn3c(=O)n(C4CC4)c4ccccc43)CC2)C1=O]

A solution of tert-butyl 2-((8-(3-(3-cyclopropyl-2-oxo-2,3-dihydro-1H-benzo[d]imidazol-1-yl)propyl)-4-oxo-1-phenyl-1,3,8-triazaspiro[4.5]decan-3-yl)methyl)benzoate (230 mg, 0.362 mmol, 1 equiv) in 4M hydrogen chloride solution in dioxane was stirred at ambient temperature for 5 h. The mixture was concentrated in vacuo and purified using preparative thin layer chromatography in 10% methanol in dichloromethane. The pure extract was treated with 4M hydrogen chloride solution in dioxane to afford the hydrogen chloride salt of the title compound as cream crystals (60 mg, 28.8%); $^1$H NMR (400 MHz, DMSO-d$_6$): δ 0.86-0.90 (m, 2H); 1.01-1.06 (m, 2H); 1.98 (d, 2H, J=14.4 Hz); 2.13 (bs, 2H); 2.88-2.99 (m, 3H); 3.2 (bs, 2H); 3.65-3.73 (m, 4H); 3.91 (t, 2H, J=6.8 Hz); 4.67 (s, 2H); 4.93 (s, 2H); 6.80 (t, 1H, J=7.2 Hz); 7.01 (d, 2H, J=8.4 Hz); 7.08-7.10 (m, 2H); 7.19-7.24 (m, 2H); 7.26-7.28 (m, 1H); 7.31 (d, 1H, J=7.6 Hz); 7.43 (t, 1H, J=6.8 and 7.6 Hz); 7.55-7.59 (m, 1H); 7.92 (dd, 1H, J=1.2 Hz); 10.50 (bs, 1H); 13.2 (bs, 1H); MS for C$_{34}$H$_{37}$N$_5$O$_4$ m/z 580.12 (M+H)$^+$.

Preparation of tert-butyl 2-((8-(3-(3-cyclopropyl-2-oxo-2,3-dihydro-1H-benzo[d]imidazol-1-yl)propyl)-4-oxo-1-phenyl-1,3,8-triazaspiro[4.5]decan-3-yl)methyl)benzoate

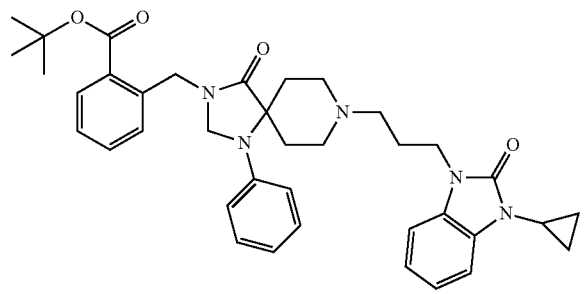 [SMILES: CC(C)(C)OC(=O)c1ccccc1CN1CN(c2ccccc2)C2(CCN(CCCn3c(=O)n(C4CC4)c4ccccc43)CC2)C1=O]

A mixture of tert-butyl 2-((4-oxo-1-phenyl-1,3,8-triazaspiro[4.5]decan-3-yl)methyl)benzoate (200 mg, 0.475 mmol, 1 equiv), 1-(3-chloropropyl)-3-cyclopropyl-1H-benzo[d]imidazol-2(3H)-one (118.75 mg, 0.475 mmol, 1 equiv), sodium iodide (28.5 mg, 0.19 mmol, 0.4 equiv) and potassium carbonate (131.3 mg, 0.95 mmol, 2 equiv) in 2-butanone was stirred at 81° C. for 16 h. After cooling the reaction mixture, the crude mixture was partitioned between ethyl acetate and water. The organic layer was dried over MgSO$_4$, filtered, concentrated, and the crude residue was purified using the Biotage flash chromatography system (SNAP 10 g cartridge, R$_f$=0.5, gradient—1%-10% methanol in dichloromethane) to afford the title compound (230 mg, 76%); $^1$H NMR (400 MHz, DMSO-d$_6$): δ 0.85-0.89 (m, 2H); 0.95-1.04 (m, 2H); 1.57 (s, 9H); 1.67 (d, 2H, J=12.4 Hz); 1.81 (t, 2H, J=6.4 and 6.8 Hz); 2.32-2.35 (t, 2H, J=6.8 Hz); 2.54-2.72 (m, 6H); 2.86-2.89 (m, 1H); 3.84-3.88 (t, 2H, J=6.8 and 6.4 Hz); 4.62 (s, 2H); 4.84 (s, 2H); 6.76-6.79 (t, 1H, J=7.2 Hz); 6.84-6.86 (d, 2H, J=8.4 Hz); 7.03-7.06 (t, 2H, J=5.6 and 6.8 Hz); 7.19-7.27 (m, 5H); 7.39-7.43 (t, 1H, J=7.6 and 7.2 Hz); 7.56-7.59 (t, 1H, J=8 and 6.4 Hz); 7.82-7.84 (d, 1H, J=7.6 Hz); MS for C$_{38}$H$_{45}$N$_5$O$_4$ m/z 636.12 (M+H)$^+$.

Example 83

Compound 156

3-((8-(3-(3-cyclopropyl-2-oxo-2,3-dihydro-1H-benzo[d]imidazol-1-yl)propyl)-1-(4-fluorophenyl)-4-oxo-1,3,8-triazaspiro[4.5]decan-3-yl)methyl)benzoic acid

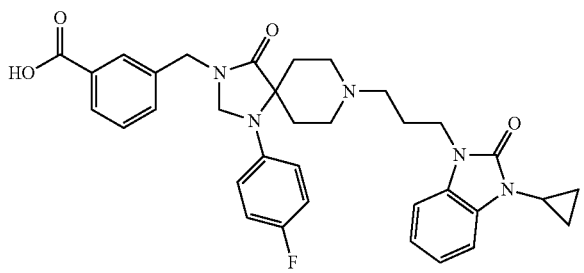 [SMILES: O=C(O)c1cccc(CN2CN(c3ccc(F)cc3)C3(CCN(CCCn4c(=O)n(C5CC5)c5ccccc54)CC3)C2=O)c1]

A solution of tert-butyl 3-((8-(3-(3-cyclopropyl-2,3-dihydro-1H-benzo[d]imidazol-1-yl)propyl)-1-(4-fluorophenyl)-4-oxo-1,3,8-triazaspiro[4.5]decan-3-yl)methyl)benzoate (166 mg, 0.254 mmol, 1 equiv) in 4M hydrogen chloride solution in dioxane was stirred at ambient temperature for 5 h. The mixture was concentrated in vacuo and purified using preparative thin layer chromatography in 10% methanol in dichloromethane. The pure extract was treated with 4M hydrogen chloride solution in dioxane to afford the hydrogen chloride salt of the title compound as cream crystals (55 mg, 36.4%); $^1$H NMR (400 MHz, DMSO-d$_6$): δ 0.86-0.90 (m, 2H); 1.01-1.06 (m, 2H); 1.93 (d, 2H, J=14 Hz); 2.06-2.11 (m, 2H); 2.58-2.73 (m, 2H); 2.88-2.89 (m, 1H); 3.19 (bs, 2H); 3.67-3.73 (m, 4H); 3.89 (t, 2H, J=6.8 Hz); 4.62 (s, 4H); 7.05-7.12 (m, 6H); 7.22-7.27 (m, 2H); 7.48-7.57 (m, 2H); 7.87-7.89 (m, 2H); 10.05 (bs, 1H); 13.03 (bs, 1H); MS for C$_{34}$H$_{36}$FN$_5$O$_4$ m/z 598.28 (M+H)$^+$.

127

Preparation of tert-butyl 3-((8-(3-(3-cyclopropyl-2-oxo-2,3-dihydro-1H-benzo[d]imidazol-1-yl)propyl)-1-(4-fluorophenyl)-4-oxo-1,3,8-triazaspiro[4.5]decan-3-yl)methyl)benzoate

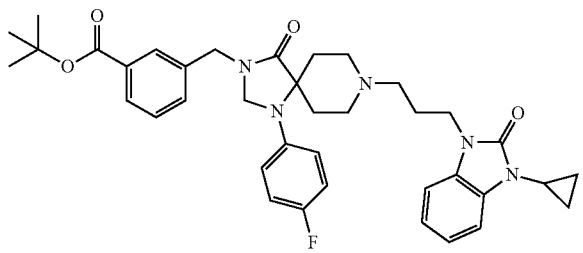 [SMILES: CC(C)(C)OC(=O)c1cccc(CN2CN(c3ccc(F)cc3)C3(CCN(CCCn4c(=O)n(C5CC5)c5ccccc54)CC3)C2=O)c1]

A mixture of tert-butyl 3-((1-(4-fluorophenyl)-4-oxo-1,3,8-triazaspiro[4.5]decan-3-yl)methyl)benzoate (163.5 mg, 0.372 mmol, 1 equiv), 1-(3-chloropropyl)-3-cyclopropyl-1H-benzo[d]imidazol-2(3H)-one (93 mg, 0.372 mmol, 1 equiv), sodium iodide (22.3 mg, 0.15 mmol, 0.4 equiv) and potassium carbonate (102.8 mg, 0.74 mmol, 2 equiv) in 2-butanone was stirred at 81° C. for 16 h. After cooling the reaction mixture, the crude mixture was partitioned between ethyl acetate and water. The organic layer was dried over MgSO$_4$, filtered, concentrated, and the crude residue was purified using the Biotage flash chromatography system (SNAP 10 g cartridge, R$_f$=0.5, gradient—1%-10% methanol in dichloromethane) to afford the title compound (166 mg, 68%); MS for C$_{38}$H$_{44}$FN$_5$O$_4$ m/z 654.24 (M+H)$^+$.

Example 84

Compound 157

3-((8-(4-(4-fluorophenyl)-4-(methoxyimino)butyl)-4-oxo-1-phenyl-1,3,8-triazaspiro[4.5]decan-3-yl)methyl)benzoic acid, hydrochloride

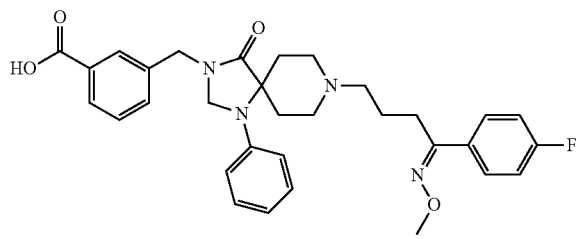 [SMILES: CO/N=C(/CCCN1CCC2(CC1)C(=O)N(Cc1cccc(C(=O)O)c1)CN2c1ccccc1)c1ccc(F)cc1]

tert-butyl 3-((8-(4-(4-fluorophenyl)-4-(methoxyimino)butyl)-4-oxo-1-phenyl-1,3,8-triazaspiro[4.5]decan-3-yl)methyl)benzoate (0.28 g, 0.455 mmol) and formic acid (6 mL) were stirred at room temperature for 20 hours. The reaction was evaporated to dryness and the residue purified by PTLC (10% methanol/dichloromethane) to give product as the formate salt; NMR (DMSO-d$_6$); δ1.62-1.69 (m, 4H); 2.51-2.62 (m, 4H); 2.73-2.84 (m, 6H); 3.73 and 3.81 (E & Z isomers, s, 3H); 4.59 (s, 2H); 4.61 (s, 2H); 6.75 (t, J=7.6 Hz, 1H); 6.83 (d, J=8.4 Hz, 2H); 7.16-7.22 (m, 4H); 7.48-7.54 (m, 2H); 7.73-7.76 (m, 2H); 7.87-7.88 (m, 2H); 8.17 (s, 1H). The formate salt was dissolved in 4M hydrochloric acid in dioxane (5 mL) and then evaporated under vacuum. The residue was dissolved in acetonitrile (5 mL) and water (5 mL) and lyophilized to give product as a white solid (0.22 g, 82%); HPLC rt 11.89 min; NMR (DMSO-d$_6$); δ1.90 (t, J=14.8 Hz, 2H); 2.07-2.12 (m, 1H); 2.78 (t, J=8 Hz, 1H); 2.97-3.07 (m, 2H); 3.17-3.24 (m, 2H); 3.52-3.70 (m, 6H); 3.76 and 3.94 (E & Z isomers, 3H); 4.64-4.66 (m, 4H); 6.79 (m, 1H); 7.03-7.09 (m, 2H); 7.18-7.29 (m, 3H); 7.38 (t, J=8.8 Hz, 1H); 7.49-7.53 (m, 1H); 7.56-7.59 (m, 1H); 7.75-7.79 (m, 1H); 7.88-7.90 (m, 2H); 8.06-8.10 (m, 1H); 10.9 (br s, 1H); 13.3 (br s, 1H); MS for C$_{32}$H$_{35}$FN$_4$O$_4$ m/z 559 (M+H)$^+$.

Preparation of tert-butyl 3-((8-(4-(4-fluorophenyl)-4-(methoxyimino)butyl)-4-oxo-1-phenyl-1,3,8-triazaspiro[4.5]decan-3-yl)methyl)benzoate

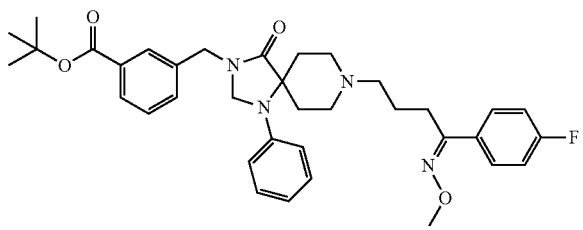 [SMILES: CO/N=C(/CCCN1CCC2(CC1)C(=O)N(Cc1cccc(C(=O)OC(C)(C)C)c1)CN2c1ccccc1)c1ccc(F)cc1]

tert-Butyl 3-((4-oxo-1-phenyl-1,3,8-triazaspiro[4.5]decan-3-yl)methyl)benzoate (0.25 g, 0.593 mmol), 1-(4-fluorophenyl)-4-iodobutan-1-one O-methyl oxime (0.19 g, 0.593 mmol), and potassium carbonate (0.12 g, 0.890 mmol) in N,N-dimethylformamide (8 mL) were stirred at 65° C. for 2 hours. The reaction was diluted with ethyl acetate, washed with water and brine, dried (MgSO$_4$), and evaporated. The residue was purified by PTLC (5% methanol/dichloromethane) to give product as an oil (0.28 g, 78%); MS for C$_{36}$H$_{43}$FN$_4$O$_4$ m/z 615 (M+H)$^+$.

Preparation of 1-(4-fluorophenyl)-4-iodobutan-1-one O-methyl oxime

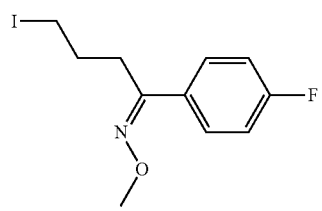

4-Chloro-1-(4-fluorophenyl)butan-1-one O-methyl oxime (0.78 g, 3.40 mmol) and sodium iodide (0.76 g, 5.09 mmol) in acetone (10 mL) were heated at reflux overnight. The mixture was evaporated, the residue diluted with ethyl acetate, washed with water and brine, dried (MgSO$_4$) and evaporated. The residue was purified by Biotage flash column chromatography (gradient to 10% ethyl acetate/hexanes) to give product as an oil (1.09 g, quant.); MS for C$_{11}$H$_{13}$FNO m/z 322 (M+H)$^+$.

129

Preparation of
4-chloro-1-(4-fluorophenyl)butan-1-one O-methyl oxime

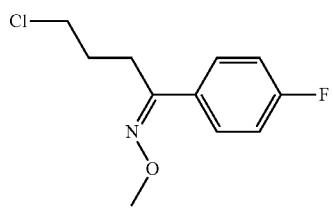

Methoxyamine hydrochloride (0.833 g, 9.97 mmol) was added portionwise to 4-chloro-4'-fluorobutyrophenone (2.00 g, 9.97 mmol) in pyridine (10 mL) and the mixture stirred at room temperature overnight and evaporated under vacuum. The residue was diluted with ethyl acetate, washed with 2N aqueous hydrochloric acid and brine, dried (MgSO$_4$) and evaporated to give product as an oil (2.29 g, quant.); MS for C$_{11}$H$_{13}$ClFNO m/z 230 (M+H)$^+$.

Example 85

Compound 158

3-((1-(4-fluorophenyl)-4-oxo-8-(4-oxo-4-phenylbutyl)-1,3,8-triazaspiro[4.5]decan-3-yl)methyl)benzoic acid

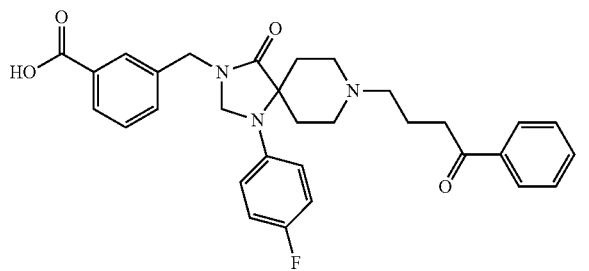 [SMILES: O=C(O)c1cccc(CN2CN(c3ccc(F)cc3)C3(CCN(CCCC(=O)c4ccccc4)CC3)C2=O)c1]

A solution of tert-butyl 3-((1-(4-fluorophenyl)-4-oxo-8-(4-oxo-4-phenylbutyl)-1,3,8-triazaspiro[4.5]decan-3-yl)methyl)benzoate (100 mg, 0.171 mmol, 1 equiv) in 4M hydrogen chloride solution in dioxane was stirred at ambient temperature for 5 h. The mixture was concentrated in vacuo and purified using preparative thin layer chromatography in 10% methanol in dichloromethane to afford the title compound as white powder (25 mg, 23%); $^1$H NMR (400 MHz, DMSO-d$_6$): δ 1.62 (d, 2H, J=14 Hz); 1.83 (t, 2H, J=6.8 and 7.2 Hz); 2.19-2.28 (m, 2H); 2.44 (t, 2H, J=6.8 Hz); 2.78 (bs, 4H); 3.03 (t, 2H, J=7.2 and 6.8 Hz); 4.54 (s, 2H); 4.59 (s, 2H); 6.81-6.85 (m, 2H); 6.99 (t, 2H, J=8.8 and 9.6 Hz); 7.49-7.53 (m, 4H); 7.62 (t, 1H, J=7.6 Hz); 7.86 (bs, 2H); 7.95-7.97 (m, 2H); 13.1 (bs, 1H); MS for C$_{31}$H$_{32}$FN$_3$O$_4$ m/z 530.4 (M+H)$^+$.

130

Preparation of tert-butyl 3-((1-(4-fluorophenyl)-4-oxo-8-(4-oxo-4-phenylbutyl)-1,3,8-triazaspiro[4.5]decan-3-yl)methyl)benzoate

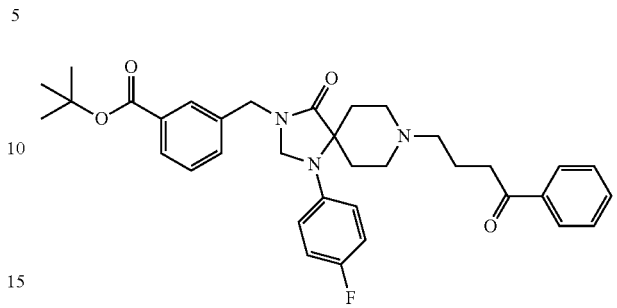

A mixture of tert-butyl 3-((1-(4-fluorophenyl)-4-oxo-1,3,8-triazaspiro[4.5]decan-3-yl)methyl)benzoate (250 mg, 0.57 mmol, 1 equiv), 4-chloro-1-phenylbutan-1-one (91.3 µl, 0.57 mmol, 1 equiv), sodium iodide (34 mg, 0.23 mmol, 0.4 equiv) and potassium carbonate (158 mg, 1.14 mmol, 2 equiv) in 2-butanone was stirred at 81° C. for 16 h. After cooling, the reaction mixture was filtered, concentrated in vacuo and was purified using the Biotage flash chromatography system (SNAP 10 g cartridge, R$_f$=0.45, gradient—1%-10% methanol in dichloromethane) to afford the title compound (100 mg, 46%); $^1$H NMR (400 MHz, DMSO-d$_6$): δ 1.53 (s, 9H); 1.59-1.63 (m, 2H); 1.82 (t, 2H, J=7.2 and 6.4 Hz); 2.19-2.23 (m, 2H); 2.37-2.39 (m, 2H); 2.70 (d, 4H, J=7.2 Hz); 3.02 (t, 2H, J=6.8 and 6.4 Hz); 4.54 (s, 2H); 4.59 (s, 2H); 6.84 (bs, 2H); 7.02 (t, 2H, J=9.6 and 8.8 Hz); 7.48-7.54 (m, 2H); 7.63 (t, 1H, J=8 Hz); 7.79-7.84 (m, 2H); 7.95-7.98 (m, 2H); MS for C$_{35}$H$_{40}$FN$_3$O$_4$ m/z 586.5 (M+H)$^+$.

Example 86

Compound 159

2-((8-(3-(3-cyclopropyl-2-oxo-2,3-dihydro-1H-benzo[d]imidazol-1-yl)propyl)-1-(4-fluorophenyl)-4-oxo-1,3,8-triazaspiro[4.5]decan-3-yl)methyl)benzoic acid

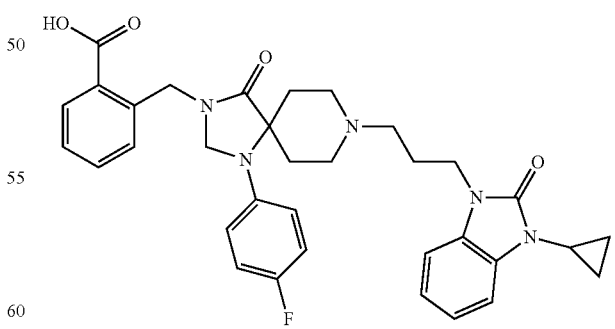

A solution of tert-butyl 2-((8-(3-(3-cyclopropyl-2-oxo-2,3-dihydro-1H-benzo[d]imidazol-1-yl)propyl)-1-(4-fluorophenyl)-4-oxo-1,3,8-triazaspiro[4.5]decan-3-yl)methyl)benzoate (240 mg, 0.367 mmol, 1 equiv) in 4M hydrogen chloride solution in dioxane was stirred at ambient temperature for 5 h. The mixture was concentrated in vacuo and purified using preparative thin layer chromatography in 10% methanol in dichloromethane to afford the title compound as a white powder (72 mg, 33%); $^1$H NMR (400 MHz, DMSO-d$_6$): δ 0.84-0.88 (m, 2H); 0.99-1.04 (m, 2H); 1.76 (d, 2H, J=13.6 Hz); 1.87 (bs, 2H); 2.41 (bs, 2H); 2.84-2.88 (m, 1H); 3.85 (t, 2H, J=6.8 Hz); 4.60 (s, 2H); 4.89 (s, 2H); 6.92-6.95 (m, 2H); 7.01-7.11 (m, 4H); 7.18-7.22 (m, 2H); 7.28 (d, 1H, J=7.6 Hz); 7.40 (t, 1H, J=7.6 Hz); 7.57 (t, 1H, J=8 and 7.2 Hz); 7.90 (d, 1H, J=6.8 Hz); 12.9 (bs, 1H); MS for C$_{34}$H$_{36}$FN$_5$O$_4$ m/z 598.4 (M+H)$^+$.

Preparation of tert-butyl 2-((8-(3-(3-cyclopropyl-2-oxo-2,3-dihydro-1H-benzo[d]imidazol-1-yl)propyl)-1-(4-fluorophenyl)-4-oxo-1,3,8-triazaspiro[4.5]decan-3-yl)methyl)benzoate

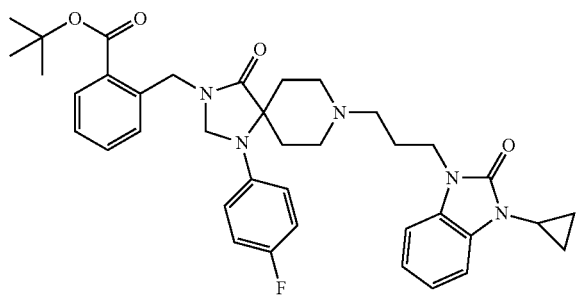 [SMILES: CC(C)(C)OC(=O)c1ccccc1CN1CN(c2ccc(F)cc2)C2(CCN(CCCn3c(=O)n(C4CC4)c4ccccc43)CC2)C1=O]

A mixture of tert-butyl 3-((1-(4-fluorophenyl)-4-oxo-1,3,8-triazaspiro[4.5]decan-3-yl)methyl)benzoate (163.5 mg, 0.372 mmol, 1 equiv), 1-(3-chloropropyl)-3-cyclopropyl-1H-benzo[d]imidazol-2(3H)-one (93 mg, 0.372 mmol, 1 equiv), sodium iodide (22.3 mg, 0.15 mmol, 0.4 equiv) and potassium carbonate (102.8 mg, 0.74 mmol, 2 equiv) in 2-butanone was stirred at 81° C. for 16 h. After cooling the reaction mixture, the crude mixture was partitioned between ethyl acetate and water. The organic layer was dried over MgSO$_4$, filtered, concentrated, and the crude residue was purified using preparative thin layer chromatography to afford the title compound as a cream powder (240 mg, 65%); MS for C$_{38}$H$_{44}$FN$_5$O$_4$ m/z 654.34 (M+H)$^+$.

Example 87

Compound 160

3-((4-oxo-8-(3-(2-oxoindolin-3-yl)propyl)-1-phenyl-1,3,8-triazaspiro[4.5]decan-3-yl)methyl)benzoic acid, hydrochloride

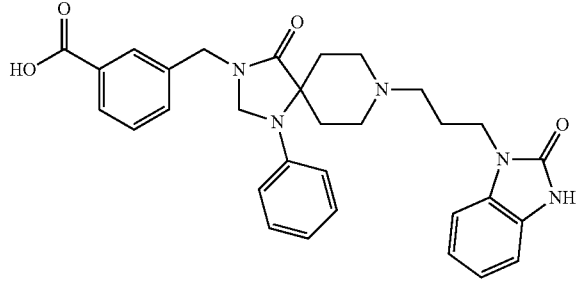 [SMILES: O=C(O)c1cccc(CN2CN(c3ccccc3)C3(CCN(CCCn4c(=O)[nH]c5ccccc54)CC3)C2=O)c1]

tert-Butyl 3-((4-oxo-8-(3-(2-oxoindolin-3-yl)propyl)-1-phenyl-1,3,8-triazaspiro[4.5]decan-3-yl)methyl)benzoate (0.29 g, 0.488 mmol) and 4M hydrochloric acid/1% triethylsilane in 1,4-dioxane (6 mL) were stirred at room temperature for 4 hours. The reaction was evaporated and the residue purified by PTLC (10% methanol/dichloromethane). The product obtained from PTLC was redissolved in 4M hydrochloric acid in dioxane and evaporated. The residue was dissolved in acetonitrile (5 mL) and water (5 mL) and lyophilized to give product as a white solid (0.25 g, 90%); HPLC rt 9.32 min; NMR (DMSO-d$_6$); δ1.82 (m, 4H); 1.89 (d, J=14 Hz, 2H); 2.94 (m, 2H); 3.16 (m, 2H); 3.44-3.54 (m, 5H); 4.64 (s, 4H); 6.79 (t, J=7.2 Hz, 1H); 6.84 (d, J=7.6 Hz, 1H); 6.97 (m, 1H); 7.01 (d, J=8.4 Hz, 2H); 7.17-7.23 (m, 3H); 7.32 (d, J=7.6 Hz, 1H); 7.49-7.58 (m, 2H); 7.87-7.89 (m, 2H); 10.38 (br s, 1H); 10.44 (s, 1H); 13.0 (br s, 1H); MS for C$_{32}$H$_{34}$N$_4$O$_4$ m/z 539 (M+H)$^+$.

Preparation of tert-butyl 3-((4-oxo-8-(3-(2-oxoindolin-3-yl)propyl)-1-phenyl-1,3,8-triazaspiro[4.5]decan-3-yl)methyl)benzoate

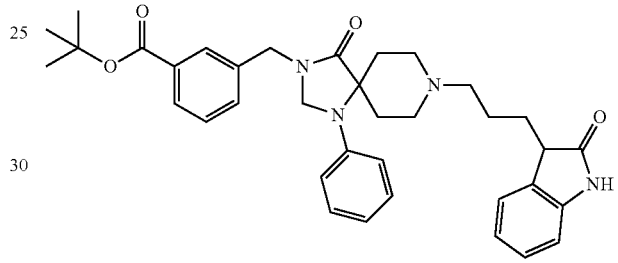

tert-Butyl 3-((4-oxo-1-phenyl-1,3,8-triazaspiro[4.5]decan-3-yl)methyl)benzoate (0.25 g, 0.593 mmol), 3-(2-oxoindolin-3-yl)propyl methanesulfonate (0.16 g, 0.593 mmolmmol), sodium iodide (0.027 g, 0.178 mmol) and potassium carbonate (0.12 g, 0.890 mmol) in 2-butanone (8 mL) were stirred at 78° C. for 2 hours. The reaction was diluted with ethyl acetate, washed with water and brine, dried (MgSO$_4$), and evaporated. The residue was purified by PTLC (5% methanol/dichloromethane) to give product as an oil (0.29 g, 82%); MS for C$_{36}$H$_{42}$N$_4$O$_4$ m/z 595 (M+H)$^+$.

3-(2-oxoindolin-3-yl)propyl methanesulfonate

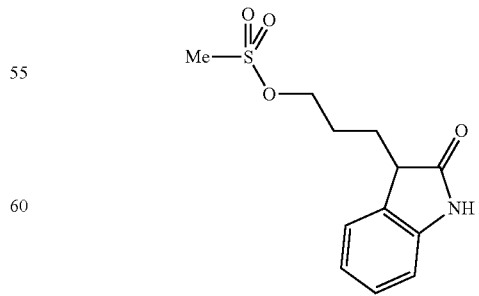

Methanesulfonyl chloride (0.42 mL, 5.39 mmol) was added dropwise at 0° C. to 3-(3-hydroxypropyl)indolin-2-one (1.03 g, 5.39 mmol) and triethylamine (1.13 mL, 8.09 mmol) in dichloromethane (20 mL). The mixture was allowed to warm to room temperature and stirred for 2 hours. The reaction was washed with 2M aqueous hydrochloric acid and brine, dried (MgSO$_4$), and evaporated. The residue was purified by Biotage flash column chromatography (30% ethyl acetate/hexanes) to give product as an oil (1.45 g, quant.); $^1$H NMR (DMSO-d$_6$); δ1.66-1.70 (m, 2H); 1.85-1.94 (m, 2H); 3.15 (s, 3H); 3.48 (t, J=6.4 Hz, 1H); 4.19 (t, J=6.4 Hz, 2H); 6.82 (d, J=8 Hz, 1H); 6.96 (m, 1H); 7.18 (m, 1H); 7.25 (d, J=7.6 Hz, 1H); 10.4 (s, 1H); MS for C$_{12}$H$_{15}$NO$_4$S m/z 270 (M+H)$^+$.

Preparation of 3-(3-hydroxypropyl)indolin-2-one

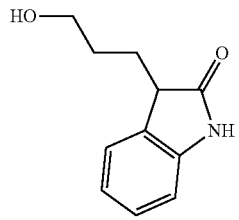 [SMILES: O=C1Nc2ccccc2C1CCCO]

Lithium aluminum hydride (0.5M solution in diglyme, 13.8 mL, 6.9 mmol) was added dropwise at 0° C. to methyl 3-(2-oxoindolin-3-yl)propanoate (1.51 g, 6.90 mmol) in tetrahydrofuran (30 mL). The mixture was allowed to warm to room temperature and then quenched with 2N aqueous hydrochloric acid. The reaction was extracted with ethyl acetate. The extract was washed with brine, dried (MgSO$_4$) and evaporated. The residue was purified by Biotage flash column chromatography (50% ethyl acetate/hexanes) to give product as a white solid (1.13 g, 86%); $^1$H NMR (DMSO-d$_6$); δ1.38 (m, 2H); 1.85 (m, 2H); 3.32-3.38 (t, J=6.4 Hz, 1H); 4.38 (t, J=5.2 Hz, 1H); 6.80 (d, J=8 Hz, 1H); 6.94 (m, 1H); 7.16 (m, 1H); 7.22 (d, J=7.2 Hz, 1H); 10.3 (s, 2H)

Preparation of methyl 3-(2-oxoindolin-3-yl)propanoate

A mixture of methyl 3-indolepropionate (5.00 g, 0.0246 mol), acetic acid (10 mL), dimethylsulfoxide (26 mL, 0.369 mol, 15 eq.) and concentrated hydrogen chloride (37%) (22 mL, 0.738 mol, 30 eq.) was stirred at ambient temperature for 2.5 h. Water was added to the mixture and the mixture was extracted with ethyl acetate. The organic layer was dried over MgSO$_4$, filtered and concentrated in vacuo. The crude residue was purified using the Biotage flash chromatography system (30% ethyl acetate in hexanes) to afford the title compound as an oil (5.28 g, 98%); $^1$H NMR (DMSO-d$_6$); 62.03-2.10 (m, 2H); 2.32-2.39 (m, 2H); 3.46 (t, J=6.4 Hz, 1H); 3.54 (s, 3H); 6.81 (d, J=7.6 Hz, 1H); 6.93-6.97 (m, 1H); 7.15-7.17 (m, 1H); 7.24 (d, J=7.6 Hz, 1H);

Example 88

Compound 161

2-((1-(4-Fluorophenyl)-4-oxo-8-(3-(2'-oxospiro[cyclopropane-1,3'-indoline]-1'-yl)propyl)-1,3,8-triazaspiro[4.5]decan-3-yl)methyl)benzoic acid

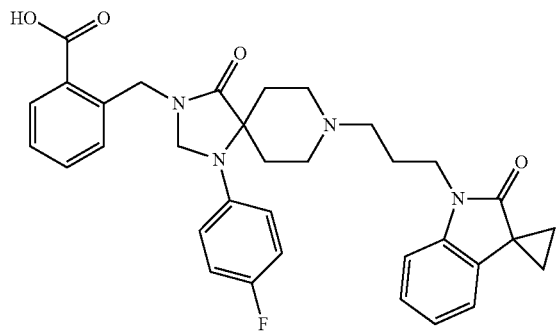 [SMILES: O=C(O)c1ccccc1CN1CN(c2ccc(F)cc2)C2(CCN(CCCN3C(=O)C4(CC4)c4ccccc43)CC2)C1=O]

To tert-butyl 2-((1-(4-fluorophenyl)-4-oxo-8-(3-(2'-oxospiro[cyclopropane-1,3'-indoline]-1'-yl)propyl)-1,3,8-triazaspiro[4.5]decan-3-yl)methyl)benzoate (0.12 g, 0.19 mmol) was added concentrated formic acid (2 mL) and triethylsilane (0.05 mL). After stirring at room temperature for 18 hours, the reaction mixture was concentrated, isolated by pTLC (10% methanol/dichloromethane) and lyophilized with 4M HCl in dioxane (0.5 mL) to obtain the title compound as a hydrochloride salt (0.038 g, 33%); $^1$H NMR (DMSO-d$_6$): δ 1.53 (t, 2H, J=3.6 Hz), 1.61 (t, 2H, J=3.6 Hz), 2.00 (d, 2H, J=14.4 Hz), 2.08 (t, 2H, J=8 Hz), 2.70 (t, 2H, J=13.6 Hz), 3.20 (br, 2H), 3.45-3.72 (m, 4H), 3.83 (t, 2H, J=7.2 Hz), 4.64 (s, 2H), 4.91 (s, 2H), 6.99-7.10 (m, 6H), 7.20-7.28 (m, 2H), 7.31 (d, 1H, J=7.6 Hz), 7.42 (t, 1H, J=7.6 Hz), 7.59 (t, 1H, J=6.8 Hz), 7.91 (dd, 1H, J=7.6 and 1.2 Hz), 10.26 (br, 1H), 13.18 (s, 1H); MS for C$_{34}$H$_{35}$FN$_4$O$_4$ m/z 583.3 (M+H)$^+$.

tert-Butyl 2-((1-(4-fluorophenyl)-4-oxo-8-(3-(2'-oxospiro[cyclopropane-1,3'-indoline]-1'-yl)propyl)-1,3,8-triazaspiro[4.5]decan-3-yl)methyl)benzoate

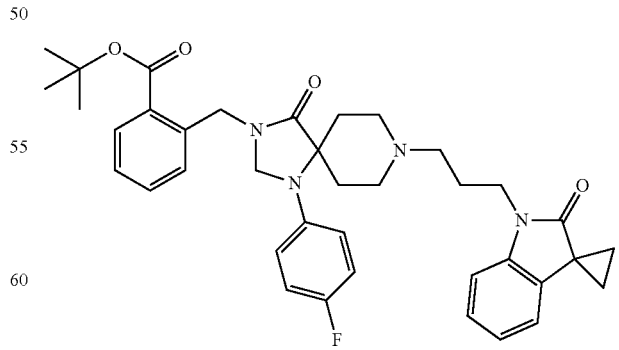

To a solution of tert-butyl 2-((1-(4-fluorophenyl)-4-oxo-1,3,8-triazaspiro[4.5]decan-3-yl)methyl)benzoate (0.2 g, 0.46 mmol), sodium iodide (0.021 g, 0.14 mmol) and potassium carbonate (0.095 g, 0.7 mmol) in 2-butanone (5 mL), was added 1'-(3-chloropropyl)spiro[cyclopropane-1,3'-indolin]-2'-one (0.107 g, 0.46 mmol). After stirring at 78° C. for 5 hours, the reaction mixture was filtered and isolated by Biotage flash chromatography (1-10% methanol/dichloromethane) and preparatory TLC (10% methanol/dichloromethane) to obtain the title compound (0.13 g, 44%); $^1$H NMR (DMSO-d$_6$): δ 1.50 (t, 2H, J=6.4 Hz), 1.56-1.60 (m, 11H), 1.69 (d, 2H, J=9.2 Hz), 1.75 (t, 2H, J=6.4 Hz), 2.32-2.34 (m, 4H), 2.64-2.67 (m, 4H), 3.79 (t, 2H, J=6.4 Hz), 4.58 (s, 2H), 4.82 (s, 2H), 6.91-6.92 (m, 2H), 6.97-6.99 (m, 2H), 7.08-7.15 (m, 3H), 7.19 (d, 1H, J=6.8 Hz), 7.25-7.31 (m, 1H), 7.41 (t, 1H, J=8 Hz), 7.57 (t, 1H, J=7.6 Hz), 7.82 (dd, 1H, J=8 and 1.2 Hz); MS for $C_{38}H_{43}FN_4O_4$ m/z 639.4 (M+H)$^+$.

Example 89

Compound 162

2-((8-(3-(3-Fluoro-3-methyl-2-oxoindolin-1-yl)propyl)-4-oxo-1-phenyl-1,3,8-triazaspiro[4.5]decan-3-yl)methyl)benzoic acid

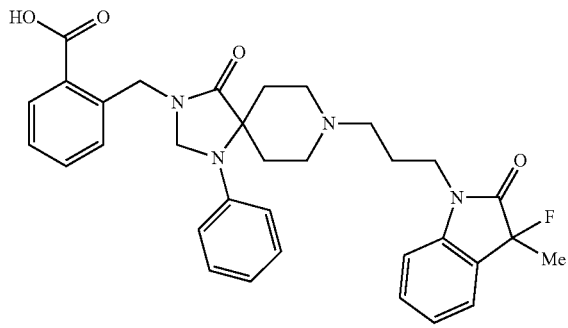 [SMILES: CC1(F)C(=O)N(CCCN2CCC3(CC2)C(=O)N(Cc2ccccc2C(=O)O)CN3c2ccccc2)c2ccccc21]

To tert-butyl 2-((8-(3-(3-fluoro-3-methyl-2-oxoindolin-1-yl)propyl)-4-oxo-1-phenyl-1,3,8-triazaspiro[4.5]decan-3-yl)methyl)benzoate (0.1 g, 0.16 mmol) was added concentrated 4M HCl in dioxane (1.6 mL) and triethylsilane (0.02 mL). After stirring at room temperature for 4 hours, the reaction mixture was concentrated, isolated by preparatory TLC (10% methanol/dichloromethane) and lyophilized with 4M HCl in dioxane (1 mL) to obtain the title compound as a hydrochloride salt (0.039 g, 40%); $^1$H NMR (DMSO-d$_6$): δ 1.72 (d, 3H, J=23.2 Hz), 1.97 (d, 2H, J=14 Hz), 2.07 (br, 2H), 2.93 (t, 2H, J=10 Hz), 3.17 (br, 2H), 3.44-3.79 (m, 8H), 4.64 (s, 2H), 4.92 (s, 2H), 6.80 (t, 1H, J=7.2 Hz), 6.99 (d, 1H, J=8.4 Hz), 7.07 (d, 1H, J=8 Hz), 7.15 (t, 1H, J=7.6 Hz), 7.20-7.26 (m, 2H), 7.31 (d, 1H, J=7.6 Hz), 7.40-7.48 (m, 2H), 7.57 (t, 1H, J=7.6 Hz), 7.92 (dd, 1H, J=8 and 1.2 Hz), 10.27 (br, 1H), 13.21 (s, 1H); MS for $C_{33}H_{35}FN_4O_4$ m/z 571.3 (M+H)$^+$.

Preparation of tert-butyl 2-((8-(3-(3-fluoro-3-methyl-2-oxoindolin-1-yl)propyl)-4-oxo-1-phenyl-1,3,8-triazaspiro[4.5]decan-3-yl)methyl)benzoate

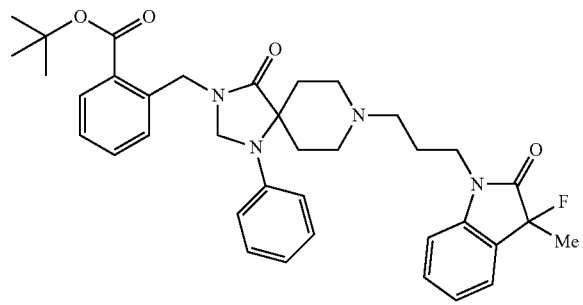 [SMILES: CC(C)(C)OC(=O)c1ccccc1CN1CN(c2ccccc2)C2(CCN(CCCN3C(=O)C(C)(F)c4ccccc43)CC2)C1=O]

To a solution of tert-butyl 2-((4-oxo-1-phenyl-1,3,8-triazaspiro[4.5]decan-3-yl)methyl)benzoate (0.17 g, 0.4 mmol), sodium iodide (0.018 g, 0.12 mmol) and potassium carbonate (0.083 g, 0.6 mmol) in 2-butanone (4 mL), was added 1-(3-chloropropyl)-3-fluoro-3-methylindolin-2-one (0.097 g, 0.4 mmol). After stirring at 78° C. for 5 hours, the reaction mixture was filtered and isolated by Biotage flash chromatography (1-10% methanol/dichloromethane) to obtain the title compound (0.11 g, 44%); $^1$H NMR (DMSO-d$_6$): δ 1.57 (s, 9H), 1.65-1.72 (m, 5H), 1.79 (t, 2H, J=6.8 Hz), 2.35 (t, 2H, J=6.4 Hz), 2.56-2.71 (m, 6H), 3.75 (t, 2H, J=6.4 Hz), 4.61 (s, 2H), 4.84 (s, 2H), 6.76 (t, 1H, J=7.6 Hz), 6.84 (d, 2H, J=8 Hz), 7.12 ((t, 1H, J=7.6 Hz), 7.21-7.26 (m, 4H), 7.38-7.42 (m, 2H), 7.57 (t, 2H, J=6.4 Hz), 7.82 (dd, 1H, J=7.6 and 1.2 Hz); MS for $C_{37}H_{43}FN_4O_4$ m/z 627.4 (M+H)$^+$.

Example 90

Compound 163

2-(((8-(3-(3-Fluoro-3-methyl-2-oxoindolin-1-yl)propyl)-1-(4-fluorophenyl)-4-oxo-1,3,8-triazaspiro[4.5]decan-3-yl)methyl)benzoic acid

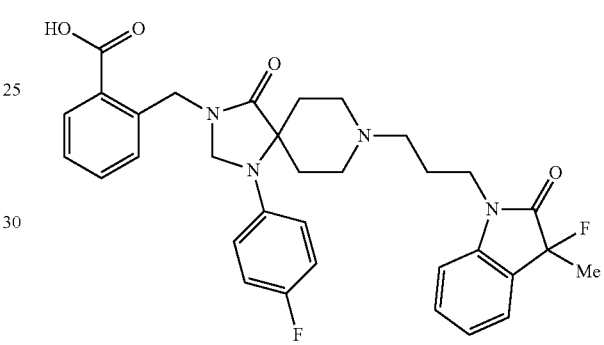

To tert-butyl 2-((8-(3-(3-fluoro-3-methyl-2-oxoindolin-1-yl)propyl)-1-(4-fluorophenyl)-4-oxo-1,3,8-triazaspiro[4.5]decan-3-yl)methyl)benzoate (0.2 g, 0.31 mmol) was added concentrated 4M HCl in dioxane (3 mL) and triethylsilane (0.05 mL). After stirring at room temperature for 4 hours, the reaction mixture was concentrated, isolated by preparatory TLC (10% methanol/dichloromethane) and lyophilized with 4M HCl in dioxane (1 mL) to obtain the title compound as a hydrochloride salt (0.073 g, 38%); $^1$H NMR (DMSO-d$_6$): δ 1.72 (d, 3H, J=23.2 Hz), 1.98-2.07 (m, 4H), 2.72 (t, 2H, J=10 Hz), 3.18 (br, 2H), 3.45-3.72 (m, 4H), 3.76 (t, 2H, J=6.8 Hz), 4.64 (s, 2H), 4.91 (s, 2H), 7.06-7.08 (m, 4H), 7.15 (t, 1H, J=7.6 Hz), 7.24 (d, 1H, J=7.6 Hz), 7.31 (d, 1H, J=7.2 Hz), 7.40-7.46 (m, 2H), 7.57 (t, 2H, J=7.6 Hz), 7.92 (d, 1H, J=8 Hz), 10.27 (br, 1H), 13.21 (s, 1H); MS for $C_{33}H_{34}F_2N_4O_4$ m/z 589.3 (M+H)$^+$.

Preparation of tert-butyl 2-((8-(3-(3-fluoro-3-methyl-2-oxoindolin-1-yl)propyl)-1-(4-fluorophenyl)-4-oxo-1,3,8-triazaspiro[4.5]decan-3-yl)methyl)benzoate

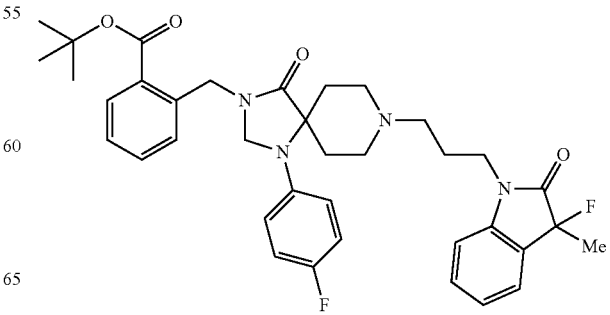

To a solution of tert-butyl 2-((1-(4-fluorophenyl)-4-oxo-1,3,8-triazaspiro[4.5]decan-3-yl)methyl)benzoate (0.15 g, 0.34 mmol), sodium iodide (0.015 g, 0.1 mmol) and potassium carbonate (0.070 g, 0.51 mmol) in 2-butanone (5 mL), was added 1-(3-chloropropyl)-3-fluoro-3-methylindolin-2-one (0.083 g, 0.34 mmol). After stirring at 78° C. for 18 hours, the reaction mixture was filtered and isolated by Biotage flash chromatography (1-10% methanol/dichloromethane) to obtain the title compound (0.2 g, 91%); $^1$H NMR (DMSO-$d_6$): δ 1.56 (s, 9H), 1.65-1.71 (m, 5H), 1.77 (t, 2H, J=7.2 Hz), 2.31-2.33 (m, 4H), 2.50-2.66 (m, 4H), 3.72 (t, 2H, J=6.8 Hz), 4.58 (s, 2H), 4.82 (s, 2H), 6.88-6.91 (m, 2H), 7.08-7.12 (m, 3H), 7.18 (d, 1H, J=8.4 Hz), 7.26 (d, 1H, J=7.6 Hz), 7.37-7.42 (m, 2H), 7.55-7.59 (m, 2H), 7.82 (d, 1H, J=6.4 Hz); MS for $C_{37}H_{42}F_2N_4O_4$ m/z 645.3 (M+H)$^+$.

Example 91

Compound 164

3-((8-(3-(3-Fluoro-3-methyl-2-oxoindolin-1-yl)propyl)-1-(4-fluorophenyl)-4-oxo-1,3,8-triazaspiro[4.5]decan-3-yl)methyl)benzoic acid

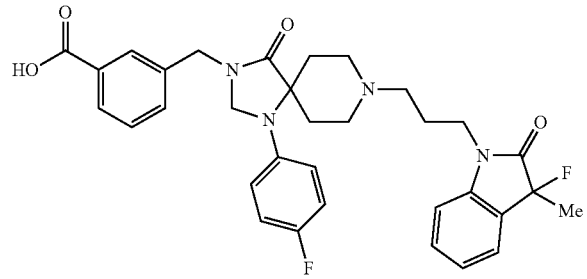

To tert-butyl 3-((8-(3-(3-fluoro-3-methyl-2-oxoindolin-1-yl)propyl)-1-(4-fluorophenyl)-4-oxo-1,3,8-triazaspiro[4.5]decan-3-yl)methyl)benzoate (0.26 g, 0.4 mmol) was added concentrated 4M HCl in dioxane (4 mL) and triethylsilane (0.05 mL). After stirring at room temperature for 4 hours, the reaction mixture was concentrated, isolated by preparatory TLC (10% methanol/dichloromethane) and lyophilized with 4M HCl in dioxane (1 mL) to obtain the title compound as a hydrochloride salt (0.16 g, 64%); $^1$H NMR (DMSO-$d_6$): δ 1.72 (d, 3H, J=22.4 Hz), 1.92 (d, 2H, J=13.6 Hz), 2.06 (br, 2H), 2.67 (t, 2H, J=10 Hz), 3.19 (br, 2H), 3.45-3.71 (m, 4H), 3.76 (t, 2H, J=7.2 Hz), 4.62 (s, 4H), 7.07 (d, 4H, J=6.4 Hz), 7.15 (t, 1H, J=8 Hz), 7.24 (d, 1H, J=8 Hz), 7.44-7.59 (m, 4H), 7.87 (dd, 2H, J=6.8 and 2 Hz), 10.27 (br, 1H), 13.03 (s, 1H); MS for $C_{33}H_{34}F_2N_4O_4$ m/z 589.3 (M+H)$^+$.

Preparation of tert-butyl 3-((8-(3-(3-fluoro-3-methyl-2-oxoindolin-1-yl)propyl)-1-(4-fluorophenyl)-4-oxo-1,3,8-triazaspiro[4.5]decan-3-yl)methyl)benzoate

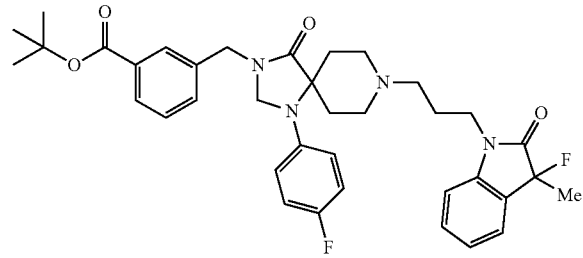 [SMILES: CC(C)(C)OC(=O)c1cccc(CN2CN(c3ccc(F)cc3)C3(CCN(CCCN4C(=O)C(C)(F)c5ccccc54)CC3)C2=O)c1]

To a solution of tert-butyl 3-((1-(4-fluorophenyl)-4-oxo-1,3,8-triazaspiro[4.5]decan-3-yl)methyl)benzoate (0.2 g, 0.46 mmol), sodium iodide (0.021 g, 0.14 mmol) and potassium bicarbonate (0.095 g, 0.69 mmol) in 2-butanone (5 mL), was added 1-(3-chloropropyl)-3-fluoro-3-methylindolin-2-one (0.11 g, 0.46 mmol). After stirring at 78° C. for 2 hours, the reaction mixture was filtered and isolated by Biotage flash chromatography (1-10% methanol/dichloromethane) to obtain the title compound (0.27 g, 91%); $^1$H NMR (DMSO-$d_6$): δ 1.52 (s, 9H), 1.65-1.71 (m, 5H), 1.77 (t, 2H, J=6.8 Hz), 2.32-2.34 (m, 4H), 2.66-2.68 (m, 4H), 3.72 (t, 2H, J=6.8 Hz), 4.57 (d, 4H, J=15.6 Hz), 6.88-6.91 (m, 2H), 7.07-7.13 (m, 3H), 7.18 (d, 1H, J=8 Hz), 7.39 (t, 1H, J=8 Hz), 7.47-7.56 (m, 3H), 7.78 (s, 1H), 7.82 (dt, 1H, J=6.8 and 2 Hz); MS for $C_{37}H_{42}F_2N_4O_4$ m/z 645.5 (M+H)$^+$.

Example 92

Compound 166

(R)-2-(4-oxo-8-(3-(2-oxoindolin-1-yl)propyl)-1-phenyl-1,3,8-triazaspiro[4.5]decan-3-yl)-2-phenylacetic acid

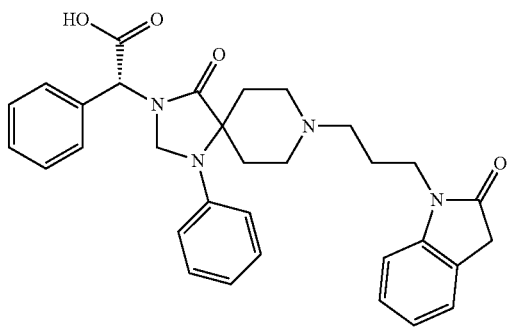 [SMILES: O=C(O)[C@@H](c1ccccc1)N1CN(c2ccccc2)C2(CCN(CCCN3C(=O)Cc4ccccc43)CC2)C1=O]

A solution of (R)-tert-butyl 2-(4-oxo-8-(3-(2-oxoindolin-1-yl)propyl)-1-phenyl-1,3,8-triazaspiro[4.5]decan-3-yl)-2-phenylacetate (257 mg, 0.453 mmol, 1 equiv) in 4M hydrogen chloride solution in dioxane was stirred at ambient temperature for 5 h. The mixture was concentrated in vacuo and purified using preparative thin layer chromatography in 10% methanol in dichloromethane. The purified mixture was treated with 4M hydrogen chloride solution in dioxane to afford the hydrogen chloride salt of the title compound as a cream powder (100 mg, 28%); $^1$H NMR (400 MHz, DMSO-$d_6$): δ 1.94 (m, 2H); 2.07 (m, 2H); 2.85 (m, 2H); 3.14 (m, 2H); 3.49-3.52 (m, 4H); 3.76 (t, 2H, J=6.8 Hz); 4.17 (d, 1H, J=5.2 Hz); 4.87 (d, 1H, J=4.8 Hz); 5.79 (s, 1H); 6.85 (m, 1H); 6.97-7.04 (m, 3H); 7.12 (d, 1H, J=7.6 Hz); 7.21 (t, 1H, J=7.6 and 8.4 Hz); 7.28 (dd, 2H, J=5.6 and 6 Hz); 7.42-7.45 (m, 6H) 10.6 (bs, 1H), 13.4 (bs, 1H); MS for $C_{32}H_{34}N_4O_4$ m/z 539 (M+H)$^+$.

Preparation of (R)-tert-butyl 2-(4-oxo-8-(3-(2-oxoindolin-1-yl)propyl)-1-phenyl-1,3,8-triazaspiro[4.5]decan-3-yl)-2-phenylacetate

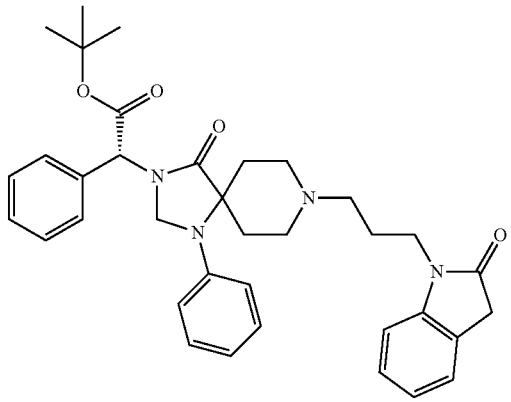 [SMILES: CC(C)(C)OC(=O)[C@@H](c1ccccc1)N1CN(c2ccccc2)C2(CCN(CCCN3C(=O)Cc4ccccc43)CC2)C1=O]

A mixture of (R)-tert-butyl 2-(4-oxo-1-phenyl-1,3,8-triazaspiro[4.5]decan-3-yl)-2-phenylacetate (250 mg, 0.60 mmol, 1 equiv), 1-(3-chloropropyl)-3-methylindolin-2-one (125.8 mg, 0.60 mmol, 1 equiv), sodium iodide (36 mg, 0.24 mmol, 0.4 equiv), and potassium carbonate (166 mg, 1.2 mmol, 2 equiv) in 2-butanone was stirred at 81° C. for 16 h. After cooling the reaction mixture, the crude mixture was partitioned between ethyl acetate and water. The organic layer was dried over MgSO$_4$, filtered, concentrated, and the crude residue was purified using preparative thin layer chromatography in 10% methanol in dichloromethane to afford the title compound as a cream solid (100 mg, 28%); MS for C$_{36}$H$_{42}$N$_4$O$_4$ m/z 595.32 (M+H)$^+$.

Example 93

Compound 167

(R)-2-(4-oxo-8-(4-oxo-4-phenylbutyl)-1-phenyl-1,3,8-triazaspiro[4.5]decan-3-yl)-2-phenylacetic acid

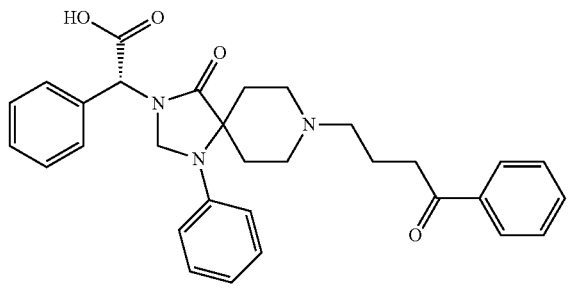 [SMILES: O=C(CCCN1CCC2(CC1)C(=O)N([C@@H](C(=O)O)c1ccccc1)CN2c1ccccc1)c1ccccc1]

To (R)-tert-butyl 2-(4-oxo-8-(4-oxo-4-phenylbutyl)-1-phenyl-1,3,8-triazaspiro[4.5]decan-3-yl)-2-phenylacetate (0.26 g, 0.4 mmol) was added concentrated 4M HCl in dioxane (4 mL). After stirring at room temperature for 18 hours, the reaction mixture was filtered, washed with dichloromethane and dried to obtain the title compound as a hydrochloride salt (0.17 g, 78%); $^1$H NMR (DMSO-d$_6$): δ 1.88 (t, 2H, J=13.6 Hz), 2.06-2.10 (m, 2H), 2.92 (br, 2H), 3.18-3.24 (m, 4H), 3.58 (br, 4H), 4.19 (d, 1H, J=4.8 Hz), 4.87 (d, 1H, J=4.8 Hz), 5.81 (s, 1H), 6.83 (t, 1H, J=7.2 Hz), 7.00 (d, 2H, J=8 Hz), 7.22 (t, 2H, J=8.4 Hz), 7.42-7.45 (m, 5H), 7.55 (t, 2H, J=7.6 Hz), 7.66 (t, 1H, J=7.2 Hz), 7.99 (d, 2H, J=7.2 Hz), 10.47 (br, 1H), 13.54 (s, 1H); MS for C$_{31}$H$_{33}$N$_3$O$_4$ m/z 512.3 (M+H)$^+$.

Preparation of (R)-tert-butyl 2-(4-oxo-8-(4-oxo-4-phenylbutyl)-1-phenyl-1,3,8-triazaspiro[4.5]decan-3-yl)-2-phenylacetate

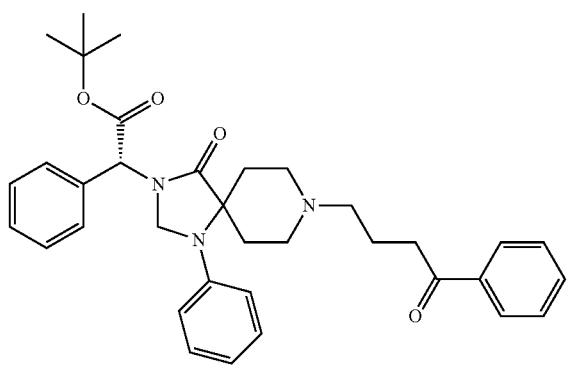 [SMILES: CC(C)(C)OC(=O)[C@@H](c1ccccc1)N1CN(c2ccccc2)C2(CCN(CCCC(=O)c3ccccc3)CC2)C1=O]

To a solution of benzyl (R)-tert-butyl 2-(4-oxo-1-phenyl-1,3,8-triazaspiro[4.5]decan-3-yl)-2-phenylacetate (0.33 g, 0.78 mmol) and potassium carbonate (0.22 g, 1.56 mmol) in N,N-dimethylformamide (7.5 mL), was added 4-iodo-1-phenylbutan-1-one (0.22 g, 0.78 mmol). After stirring at 60° C. for 18 hours, the reaction mixture was diluted with ethyl acetate (25 mL), washed with water and brine. The organic phase was dried over MgSO$_4$, filtered, and isolated by preparatory TLC (8% methanol/dichloromethane) to obtain the title compound (0.23 g, 52%); $^1$H NMR (DMSO-d$_6$): δ 1.42 (s, 9H), 1.55 (t, 2H, J=13.6 Hz), 1.82 (t, 2H, J=7.2 Hz), 2.31-2.40 (m, 4H), 2.50-2.72 (m, 4H), 3.32 (t, 2H, J=7.6 Hz), 4.08 (d, 1H, J=4.8 Hz), 4.74 (d, 1H, J=4.8 Hz), 5.75 (s, 1H), 6.72-6.79 (m, 3H), 7.14 (t, 2H, J=7.6 Hz), 7.34-7.47 (m, 5H), 7.52 (t, 2H, J=7.6 Hz), 7.63 (t, 1H, J=7.2 Hz), 7.97 (d, 2H, J=7.2 Hz); MS for C$_{35}$H$_{41}$N$_3$O$_4$ m/z 568.4 (M+H)$^+$.

Example 94

Compound 168

(S)-2-(4-oxo-8-(4-oxo-4-phenylbutyl)-1-phenyl-1,3,8-triazaspiro[4.5]decan-3-yl)-2-phenylacetic acid

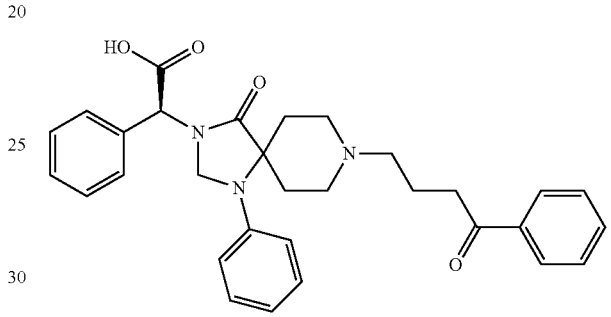

A solution of (R)-tert-butyl 2-(4-oxo-8-(3-(2-oxoindolin-1-yl)propyl)-1-phenyl-1,3,8-triazaspiro[4.5]decan-3-yl)-2-phenylacetate (257 mg, 0.453 mmol, 1 equiv) in 4M hydrogen chloride solution in dioxane was stirred at ambient temperature for 5 h. The mixture was concentrated in vacuo and purified using preparative thin layer chromatography in 10% methanol in dichloromethane. The pure extract was treated with 4M hydrogen chloride solution in dioxane to afford the hydrogen chloride salt of the title compound as a cream powder (100 mg, 28%); $^1$H NMR (400 MHz, DMSO-d$_6$): δ 1.88 (m, 2H); 2.05-2.09 (m, 2H); 2.85 (m, 2H); 3.15-3.24 (m, 2H); 3.56-3.59 (m, 4H); 4.19 (d, 1H, J=4.4 Hz); 4.89 (d, 1H, J=4.8 Hz); 5.81 (s, 1H); 6.84 (m, 1H); 6.99 (d, 2H, J=8.4 Hz); 7.23 (t, 2H, J=7.6 and 8.4 Hz); 7.45-7.47 (m, 5H); 7.55 (t, 2H, J=7.6 and 8 Hz); 7.64-7.68 (m, 1H); 7.98-8.01 (m, 2H); 10.4 (bs, 1H); 13.5 (bs, 1H); MS for C$_{31}$H$_{33}$N$_3$O$_4$ m/z 512.4 (M+H)$^+$.

Preparation of (S)-tert-butyl 2-(4-oxo-8-(4-oxo-4-phenylbutyl)-1-phenyl-1,3,8-triazaspiro[4.5]decan-3-yl)-2-phenylacetate

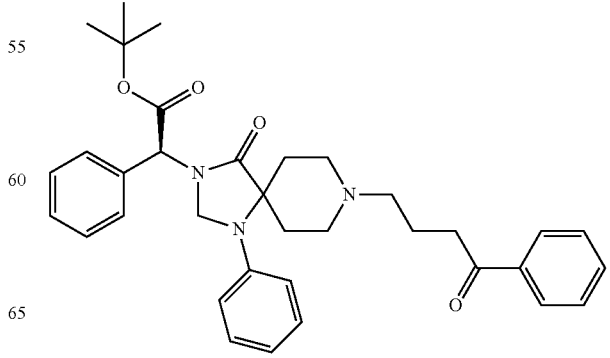

A mixture of (S)-tert-butyl 2-(4-oxo-1-phenyl-1,3,8-triazaspiro[4.5]decan-3-yl)-2-phenylacetate (300 mg, 0.71 mmol, 1 equiv), 4-chloro-1-phenylbutan-1-one (130 mg, 0.71 mmol, 1 equiv), sodium iodide (42.6 mg, 0.28 mmol, 0.4 equiv), and potassium carbonate (196.3 mg, 1.42 mmol, 2 equiv) in 2-butanone was stirred at 81° C. for 16 h. After cooling the reaction mixture, the crude mixture was partitioned between ethyl acetate and water. The organic layer was dried over $MgSO_4$, filtered, concentrated, and the crude residue was purified using the Biotage flash chromatography system (SNAP 10 g cartridge, $R_f$=0.5, gradient—1%-10% methanol in dichloromethane) to afford the title compound as an oil (200 mg, 50%); MS for $C_{35}H_{41}N_3O_4$ m/z 568.4 $(M+H)^+$.

Preparation of (S)-tert-butyl 2-(4-oxo-1-phenyl-1,3,8-triazaspiro[4.5]decan-3-yl)-2-phenylacetate

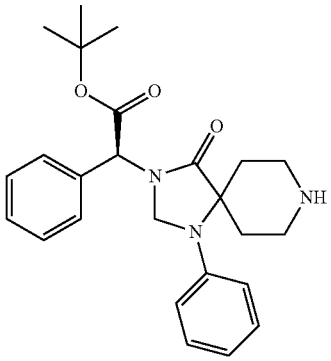 [SMILES: CC(C)(C)OC(=O)[C@H](c1ccccc1)N1CN(c2ccccc2)C2(CCNCC2)C1=O]

(R)-methyl 2-amino-2-phenylacetate (5 g, 24.8 mmol, 1 equiv) was dissolved in a mixture of 48% hydrogen bromide (13 ml, 198 mmol, 8 equiv) and water (19 ml). An aqueous solution of sodium nitrite (5.48 g, 79.36 mmol, 3.2 equiv) was added slowly and the mixture stirred at 0° C. for 1.5 h. The reaction was degassed in vacuo and extracted with ether. The organic layer was further washed with water and brine, dried over $MgSO_4$, and concentrated in vacuo. The resulting residue was purified using the Biotage flash chromatography system (SNAP 100 g cartridge, $R_f$=0.5, gradient—10% ethyl acetate/hexanes) to afford the (S)-methyl 2-bromo-2-phenylacetate as a light yellow oil (2.3 g, 40% yield); $^1$H NMR (400 MHz, DMSO-$d_6$): δ 3.72 (s, 3H); 5.95 (s, 1H); 7.36-7.42 (m, 3H); 7.53 (d, 2H, J=1.2 Hz); 7.56 (d, 1H, J=2 Hz). MS for $C_9H_9BrO_2$ m/z 229.98 $(M+H)^+$.

A mixture of benzyl 4-oxo-1-phenyl-1,3,8-triazaspiro[4.5]decane-8-carboxylate (2.4 g, 6.55 mmol, 1 equiv), 1 M lithium bis(trimethylsilyl)amide in tetrahydrofuran (7.86 ml, 7.86 mmol, 1.2 equiv), and (S)-methyl 2-bromo-2-phenylacetate (1.5 g, 6.55 mmol, 1 equiv) in N,N-dimethylformamide was stirred for 16 h at ambient temperature. Reaction was diluted with ethyl acetate and the organic layer was washed with water and brine. The combined organic layers were dried over $MgSO_4$ and concentrated in vacuo. The crude residue was purified using the Biotage flash chromatography system (SNAP 100 g cartridge, $R_f$=0.4, gradient—10%-50% ethyl acetate in hexanes) to afford (S)-benzyl 3-(2-methoxy-2-oxo-1-phenylethyl)-4-oxo-1-phenyl-1,3,8-triazaspiro[4.5]decane-8-carboxylates an orange solid (2.11 g, 63%); MS for $C_{30}H_{31}N_3O_5$ m/z 514.23 $(M+H)^+$.

A solution of (S)-benzyl 3-(2-methoxy-2-oxo-1-phenylethyl)-4-oxo-1-phenyl-1,3,8-triazaspiro[4.5]decane-8-carboxylate (2.16 g, 4.21 mmol, 1 equiv.) and lithium hydroxide (353 mg, 8.41 mmol, 2 equiv) in a 4:1 mixture of methanol and water (20 ml t/v) was stirred at ambient temperature for 16 hrs. The reaction was concentrated in vacuo and the mixture was partitioned between ethyl acetate and 10% citric acid. The organic layer was further washed with water and brine, dried over $MgSO_4$, filtered and concentrated. The resulting residue was dried thoroughly to afford (S)-2-(8-(benzyloxycarbonyl)-4-oxo-1-phenyl-1,3,8-triazaspiro[4.5]decan-3-yl)-2-phenylacetic acid as a white solid (2.05 g, quant); $^1$H NMR (400 MHz, DMSO-$d_6$): δ 1.67 (t, 2H, J=12.4 and 10.4 Hz); 2.25-2.33 (m, 2H); 3.56 (m, 2H); 3.98-4.05 (m, 2H); 4.14 (d, 1H, J=4.4 Hz); 4.86 (d, 1H, J=5.2 Hz); 5.14 (m, 2H); 5.81 (s, 1H); 6.67 (d, 2H, J=7.6 Hz); 6.81 (t, 1H, J=6.8 and 7.6 Hz); 7.17 (dd, 2H, J=7.6 and 7.2 Hz); 7.32-7.45 (m, 10H); 13.5 (s, 1H); MS for $C_{29}H_{29}N_3O_5$ m/z 500.21 $(M+H)^+$.

(S)-2-(8-(benzyloxycarbonyl)-4-oxo-1-phenyl-1,3,8-triazaspiro[4.5]decan-3-yl)-2-phenylacetic acid (2.05 g, 4.1 mmol, 1 equiv) was suspended in toluene and the mixture was heated to refluxing temperatures. N,N-dimethylformamide di-tert-butyl acetal (3.94 ml, 16.44 mmol, 4 equiv) was added dropwise to the refluxing mixture within 30 minutes. Refluxing was continued for an additional 30-45 minutes after which it was cooled and stirred at ambient temperature for 16 h. The reaction was diluted with ethyl acetate and the organic layer was washed with sodium bicarbonate (sat), water and brine. The ethyl acetate layer was dried over $MgSO_4$, filtered, concentrated in vacuo and purified using the Biotage flash chromatography system (SNAP 100 g cartridge, $R_f$=0.5, gradient—5%-30% ethyl acetate in hexanes) to afford the (S)-benzyl 3-(2-tert-butoxy-2-oxo-1-phenylethyl)-4-oxo-1-phenyl-1,3,8-triazaspiro[4.5]decane-8-carboxylate (1.75 g, 77%); $^1$H NMR (400 MHz, DMSO-$d_6$): δ 1.43 (s, 9H); 1.60 (m, 2H); 2.24-2.32 (m, 2H); 3.53 (bs, 2H); 3.96-4.05 (m, 2H); 4.11 (d, 1H, J=5.2 Hz); 4.77 (d, 1H, J=5.2 Hz); 5.13 (bs, 2H); 5.69 (s, 1H); 6.68 (d, 2H, J=8.4 Hz); 6.82 (t, 1H, J=7.2 Hz); 7.22 (dd, 2H, J=7.6 Hz); 7.32-7.46 (m, 10H); MS for $C_{33}H_{37}N_3O_5$ m/z 556.28 $(M+H)^+$.

A solution of (S)-benzyl 3-(2-tert-butoxy-2-oxo-1-phenylethyl)-4-oxo-1-phenyl-1,3,8-triazaspiro[4.5]decane-8-carboxylate (1.88 g, 3.39 mmol, 1 equiv) in a mixture of ethyl acetate and ethanol was charged with 10% palladium on carbon (1 g, 20%/wt) and the resulting mixture was hydrogenated at atmospheric pressure for 2 h. The reaction was filtered over Celite and the filtrate was concentrated and dried in vacuo to afford the title compound as a dark grey foam (1.24 g, 93%); MS for $C_{25}H_{31}N_3O_3$ m/z 422.24 $(M+H)^+$.

Example 95

Compound 170

(S)-2-(4-oxo-8-(3-(2-Oxoindolin-1-yl)propyl)-1-phenyl-1,3,8-triazaspiro[4.5]decan-3-yl)-2-phenylacetic acid

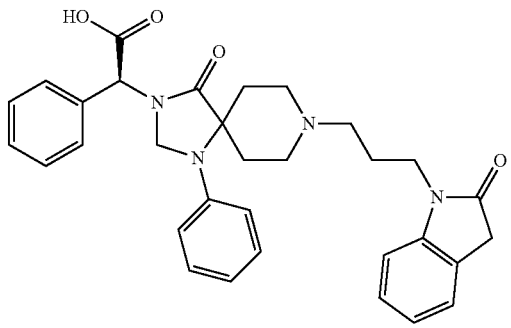 [SMILES: O=C(O)[C@H](c1ccccc1)N1CN(c2ccccc2)C2(CCN(CCCN3C(=O)Cc4ccccc43)CC2)C1=O]

To a solution of benzyl (S)-tert-butyl 2-(4-oxo-1-phenyl-1,3,8-triazaspiro[4.5]decan-3-yl)-2-phenylacetate (0.2 g, 0.48 mmol), sodium iodide (0.022 g, 0.14 mmol) and potassium carbonate (0.1 g, 0.72 mmol) in 2-butanone (5 mL), was added 1-(3-chloropropyl)indolin-2-one (0.101 g, 0.48 mmol). After stirring at 78° C. for 2 hours, the reaction mixture was filtered and isolated by Biotage flash chromatography (1-10% methanol/dichloromethane) and preparatory TLC (10% methanol/dichloromethane) to obtain (S)-tert-butyl 2-(4-oxo-8-(3-(2-oxoindolin-1-yl)propyl)-1-phenyl-1,3,8-triazaspiro[4.5]decan-3-yl)-2-phenylacetate (0.07 g, 25%).

To (S)-tert-butyl 2-(4-oxo-8-(3-(2-oxoindolin-1-yl)propyl)-1-phenyl-1,3,8-triazaspiro[4.5]decan-3-yl)-2-phenylacetate (0.07 g, 0.12 mmol) was added concentrated 4M HCl in dioxane (1.5 mL) and triethylsilane (0.015 mL). After stirring at room temperature for 5 hours, the reaction mixture was concentrated, purified by reverse phase HPLC and lyophilized with 4M HCl in dioxane (1 mL) to obtain the title compound as a hydrochloride salt (0.015 g, 22%); $^1$H NMR (DMSO-$d_6$): δ 1.86 (t, 2H, J=12 Hz), 2.09 (br, 2H), 2.77 (br, 2H), 3.19 (br, 2H), 3.45-3.57 (m, 6H), 3.76 (t, 2H, J=6.8 Hz), 4.17 (d, 1H, J=4.8 Hz), 4.86 (d, 1H, J=4.8 Hz), 5.78 (s, 1H), 6.83 (t, 1H, J=7.6 Hz), 6.94 (d, 2H, J=8.4 Hz), 7.02 (t, 1H, J=7.6 Hz), 7.11 (d, 1H, J=8.4 Hz), 7.22 (t, 2H, J=8 Hz), 7.28 (t, 2H, J=6.8 Hz), 7.40-7.46 (m, 5H), 10.08 (br, 1H), 13.50 (s, 1H); MS for $C_{32}H_{34}N_4O_4$ m/z 539.4 (M+H)$^+$.

Example 96

Compound 171

4-((8-(3-(3,3-dimethyl-2-oxoindolin-1-yl)propyl)-4-oxo-1-phenyl-1,3,8-triazaspiro[4.5]decan-3-yl)methyl)benzoic acid, hydrochloride

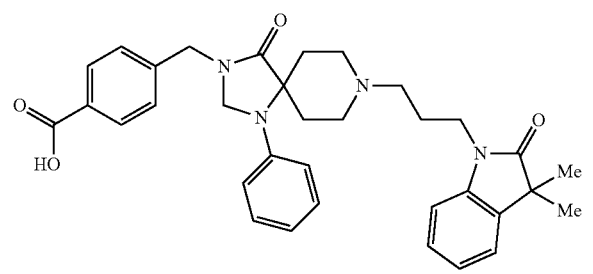 [SMILES: CC1(C)C(=O)N(CCCN2CCC3(CC2)C(=O)N(Cc2ccc(C(=O)O)cc2)CN3c2ccccc2)c2ccccc21]

tert-Butyl 4-((8-(3-(3,3-dimethyl-2-oxoindolin-1-yl)propyl)-4-oxo-1-phenyl-1,3,8-triazaspiro[4.5]decan-3-yl)methyl)benzoate (0.30 g, 0.482 mmol) and formic acid (6 mL) were stirred at room temperature for 20 hours. The reaction was evaporated to dryness and the residue purified by PTLC (10% methanol/dichloromethane). The product was dissolved in 4M hydrochloric acid in 1,4-dioxane (5 mL) and then evaporated under vacuum. The residue was dissolved in acetonitrile (5 mL) and water (5 mL) and lyophilized to give product as a white solid (0.21, 72%); HPLC rt 11.01 min; $^1$H NMR (DMSO-$d_6$); δ1.29 (s, 6H); 1.93 (d, J=14 Hz, 2H); 2.08-2.13 (m, 2H); 2.93-3.02 (m, 2H); 3.16-3.20 (m, 2H); 3.46-3.71 (m, 4H); 3.77 (t, J=7.2 Hz, 2H); 4.64 (s, 2H); 4.65 (s, 2H); 6.79 (t, J=7.2 Hz, 1H); 7.03-7.08 (m, 3H); 7.17-7.22 (m, 3H); 7.26-7.30 (m, 1H); 7.36-7.38 (m, 1H); 7.43 (d, J=8.4 Hz, 2H); 7.94 (m, 2H); 10.7 (br s, 1H); MS for $C_{34}H_{38}N_4O_4$ m/z 567 (M+H)$^+$.

Preparation of tert-butyl 4-((8-(3-(3,3-dimethyl-2-oxoindolin-1-yl)propyl)-4-oxo-1-phenyl-1,3,8-triazaspiro[4.5]decan-3-yl)methyl)benzoate

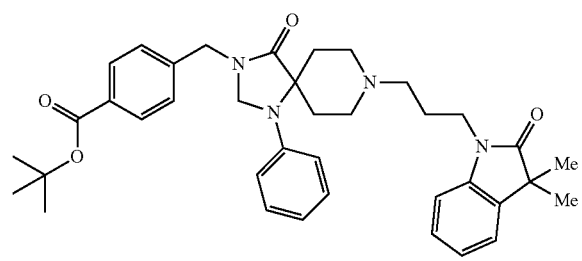 [SMILES: CC(C)(C)OC(=O)c1ccc(CN2CN(c3ccccc3)C3(CCN(CCCN4C(=O)C(C)(C)c5ccccc54)CC3)C2=O)cc1]

tert-Butyl 4-((4-oxo-1-phenyl-1,3,8-triazaspiro[4.5]decan-3-yl)methyl)benzoate (0.25 g, 0.593 mmol), 1-(3-chloropropyl)-3,3-dimethylindolin-2-one (0.14 g, 0.593 mmol), sodium iodide (0.026 g, 0.18 mmol), and potassium carbonate (0.12 g, 0.890 mmol) in 2-butanone (8 mL) were heated at 78° C. for 4 hours. The reaction was diluted with 10% methanol/dichloromethane, filtered, and evaporated. The residue was purified by PTLC (5% methanol/dichloromethane) to give product as an oil (0.31 g, 85%); MS for $C_{38}H_{46}N_4O_4$ m/z 623 (M+H)$^+$.

Preparation of tert-butyl 4-((4-oxo-1-phenyl-1,3,8-triazaspiro[4.5]decan-3-yl)methyl)benzoate

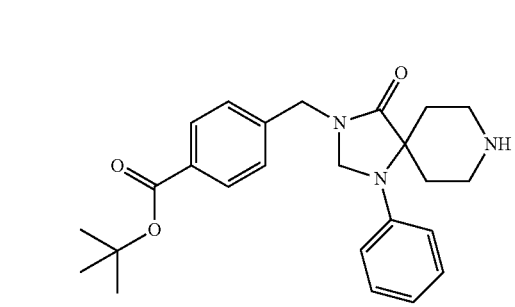 [SMILES: CC(C)(C)OC(=O)c1ccc(CN2CN(c3ccccc3)C3(CCNCC3)C2=O)cc1]

Benzyl 3-(4-(tert-butoxycarbonyl)benzyl)-4-oxo-1-phenyl-1,3,8-triazaspiro[4.5]decane-8-carboxylate (4.90 g, 8.82 mmol) and palladium on carbon (10 wt. %, wet, Degussa type E101 NE/W,) in ethyl acetate (50 mL) and methanol (50 mL) was stirred at room temperature under hydrogen (balloon) for 3 hours. The catalyst was removed by filtration and the filtrate evaporated and dried under vacuum to give product as foam (3.70 g, 99%); $^1$H NMR (DMSO-$d_6$); δ1.53 (s, 9H); 2.35-2.48 (m, 2H); 2.85-2.92 (m, 2H); 3.17-3.23 (m, 2H); 3.23-3.43 (m, 2H); 4.58 (s, 2H); 4.62 (s, 2H); 6.74 (t, J=6.8 Hz, 1H); 6.87 (d, J=8.4 Hz, 2H); 7.20 (dd, J=7.6 Hz and 8.8 Hz, 2H); 7.40 (d, J=8.4 Hz, 2H); 7.90 (m, 2H); MS for $C_{25}H_{31}N_3O_3$ m/z 422 (M+H)$^+$.

145

Preparation of benzyl 3-(4-(tert-butoxycarbonyl)benzyl)-4-oxo-1-phenyl-1,3,8-triazaspiro[4.5]decane-8-carboxylate

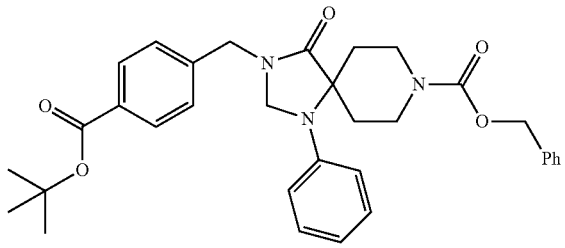 [SMILES: CC(C)(C)OC(=O)c1ccc(CN2CN(c3ccccc3)C3(CCN(C(=O)OCc4ccccc4)CC3)C2=O)cc1]

Sodium hydride (60% dispersion in oil, 0.46 g, 0.0114 mol) was added portionwise at 0° C. to benzyl 4-oxo-1-phenyl-1,3,8-triazaspiro[4.5]decane-8-carboxylate (4.00 g, 0.0109 mol) in N,N-dimethylformamide (40 mL) and the mixture stirred at 0° C. for 10 minutes. tert-Butyl 4-(bromomethyl)benzoate (3.27 g, 0.0120 mol) was added dropwise at 0° C., the mixture then allowed to warm to room temperature, and stirred for 2 hours. The reaction was quenched with 2M aqueous hydrochloric acid and extracted with ethyl acetate. The ethyl acetate extracts were washed with brine, dried (MgSO$_4$), and evaporated. The residue was purified by Biotage flash column chromatography (gradient 0 to 30% ethyl acetate/hexanes) to give product as an oil (4.97 g, 82%); $^1$H NMR (DMSO-d$_6$); δ1.53 (s, 9H); 1.72 (d, J=13.6 Hz, 2H); 2.34-2.42 (m, 2H); 3.57 (m, 2H); 3.99-4.03 (m, 2H); 4.61 (s, 2H); 4.63 (s, 2H); 6.69 (d, J=8 Hz, 2H); 6.78 (t, J=7.2 Hz, 1H); 7.18 (dd, J=7.2 Hz and 8.8 Hz, 2H); 7.32-7.39 (m, 5H); 7.42 (d, J=8.4 Hz, 2H); 7.90 (d, J=8.4 Hz, 2H);

Preparation of tert-Butyl 3-(bromomethyl)benzoate

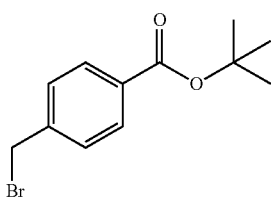

tert-butyl 4-methylbenzoate (31 g, 0.161 mol), N-bromosuccinimide (31.5 g, 0.177 mol), and benzoyl peroxide (0.39 g, 0.00161 mol) in carbon tetrachloride (200 mL) were heated at reflux for 20 hours. The mixture was allowed to cool to room temperature and succinimide filtered. The filtrate was evaporated and the residue purified by Biotage flash chromatography (gradient to 5% ethyl acetate/hexanes) to give product as an oil (27 g, 62%); NMR (DMSO-d$_6$); δ1.55 (s, 9H); 4.78 (s, 2H); 7.47-7.51 (m, 1H); 7.68-7.71 (m, 1H); 7.82-7.85 (m, 1H); 7.97 (t, J=1.6 Hz, 1H).

Preparation of tert-butyl 4-methylbenzoate

Lithium tert-butoxide (1M in hexanes, 178 mL, 0.178 mol) was added dropwise at room temperature to p-toluoyl chloride (25 g, 0.162 mol) in tetrahydrofuran (150 mL). The mixture was stirred at room temperature overnight and then diluted with water and extracted with ethyl acetate. The extract was washed with brine, dried (MgSO$_4$), and evaporated to give product as an oil which crystallized on standing (31 g, 98%)

Example 97

Compound 172

4-((4-oxo-8-(3-(2-oxoindolin-1-yl)propyl)-1-phenyl-1,3,8-triazaspiro[4.5]decan-3-yl)methyl)benzoic acid, hydrochloride

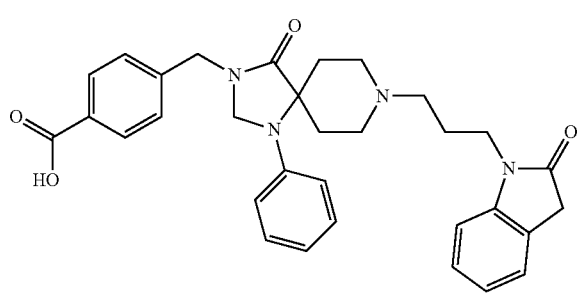 [SMILES: O=C(O)c1ccc(CN2CN(c3ccccc3)C3(CCN(CCCN4C(=O)Cc5ccccc54)CC3)C2=O)cc1]

tert-butyl 4-((4-oxo-8-(3-(2-oxoindolin-1-yl)propyl)-1-phenyl-1,3,8-triazaspiro[4.5]decan-3-yl)methyl)benzoate (0.088 g, 0.148 mmol) and formic acid (6 mL) were stirred at room temperature for 20 hours. The reaction was evaporated to dryness and the residue purified by PTLC (10% methanol/dichloromethane). The product was dissolved in 4M hydrochloric acid in 1,4-dioxane (5 mL) and then evaporated under vacuum. The residue was dissolved in acetonitrile (5 mL) and water (5 mL) and lyophilized to give product as a white solid (0.051 g, 60%); $^1$H NMR (DMSO-d$_6$); δ1.92 (d, J=15.2 Hz, 2H); 2.05-2.15 (m, 2H); 2.95-3.01 (m, 2H); 3.15-3.25 (m, 2H); 3.46-3.70 (m, 4H); 3.57 (s, 2H); 3.77 (t, J=7.2 Hz, 2H); 4.64 (s, 2H); 4.65 (s, 2H); 6.79 (t, J=7.6 Hz, 1H); 7.01-7.05 (m, 3H); 7.12-7.14 (m, 1H); 7.18-7.22 (m, 2H); 7.26-7.30 (m, 2H); 7.43 (d, J=8.4 Hz, 2H); 7.93 (m, 2H); 10.8 (br s, 1H); MS for $C_{32}H_{34}N_4O_4$ m/z 539 (M+H)$^+$.

Preparation of tert-butyl 4-((4-oxo-8-(3-(2-oxoindolin-1-yl)propyl)-1-phenyl-1,3,8-triazaspiro[4.5]decan-3-yl)methyl)benzoate

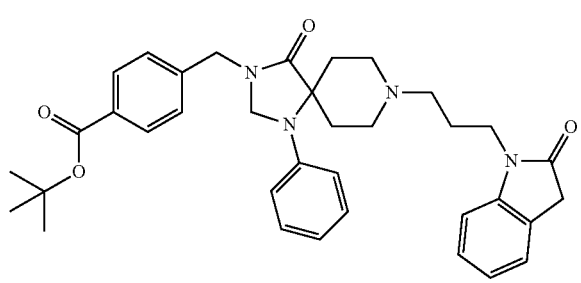 [SMILES: CC(C)(C)OC(=O)c1ccc(CN2CN(c3ccccc3)C3(CCN(CCCN4C(=O)Cc5ccccc54)CC3)C2=O)cc1]

tert-Butyl 4-((4-oxo-1-phenyl-1,3,8-triazaspiro[4.5]decan-3-yl)methyl)benzoate (0.25 g, 0.593 mmol), 1-(3-chloropropyl)indolin-2-one (0.12 g, 0.593 mmol), sodium iodide (0.026 g, 0.18 mmol), and potassium carbonate (0.12 g, 0.890 mmol) in 2-butanone (8 mL) were heated at 78° C. for 4 hours. The reaction was diluted with 10% methanol/dichloromethane, filtered, and evaporated. The residue was purified by PTLC (5% methanol/dichloromethane) to give product as an oil (0.088 g, 25%); MS for $C_{36}H_{42}N_4O_4$ m/z 595 (M+H)$^+$.

Example 98

Compound 173

3-((8-(4-hydroxy-4-phenylbutyl)-4-oxo-1-phenyl-1,3,8-triazaspiro[4.5]decan-3-yl)methyl)benzoic acid

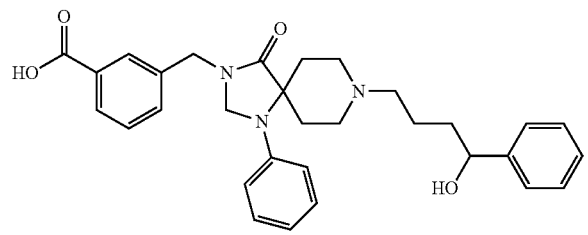

A solution tert-butyl 3-((8-(4-hydroxy-4-phenylbutyl)-4-oxo-1-phenyl-1,3,8-triazaspiro[4.5]decan-3-yl)methyl)benzoate (300 mg, 0.527 mmol, 1 equiv) in 4M hydrogen chloride solution in dioxane was stirred at ambient temperature for 5 h. The mixture was concentrated in vacuo and purified using preparative high performance liquid chromatography to afford the acetate salt of the title compound as a white solid (120 mg, 44.4%); $^1$H NMR (400 MHz, DMSO-d$_6$): δ 1.38-1.52 (m, 2H); 1.60 (d, 2H, J=13.2 Hz); 1.84-1.94 (m, 2H); 2.41 (t, 2H, J=7.2 and 7.6 Hz); 2.53-2.59 (m, 2H); 2.69-2.75 (m, 4H); 4.58 (s, 2H); 4.61 (s, 2H); 5.84 (t, 1H, J=6.8 and 6.4 Hz); 6.74 (t, 1H, J=7.6 and 7.2 Hz); 6.81 (s, 1H); 6.83 (s, 1H); 7.16-7.20 (m, 2H); 7.31-7.38 (m, 5H); 7.48-754 (m, 2H); 7.86-7.88 (m, 2H); 8.30 (S, 1H); 12.8 (bs, 1H); MS for $C_{31}H_{35}N_3O_4$ m/z 514.4 (M+H)$^+$.

Preparation of tert-butyl 3-((8-(4-hydroxy-4-phenylbutyl)-4-oxo-1-phenyl-1,3,8-triazaspiro[4.5]decan-3-yl)methyl)benzoate

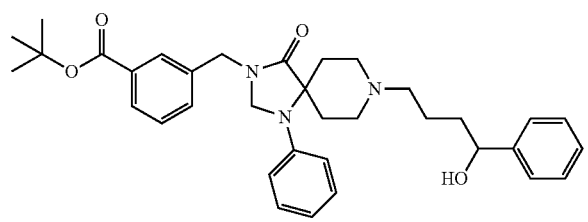 [SMILES: CC(C)(C)OC(=O)c1cccc(CN2CN(c3ccccc3)C3(CCN(CCCC(O)c4ccccc4)CC3)C2=O)c1]

A mixture of tert-butyl 3-((4-oxo-8-(4-oxo-4-phenylbutyl)-1-phenyl-1,3,8-triazaspiro[4.5]decan-3-yl)methyl)benzoate (1.45 g, 2.56 mmol, 1 equiv) in ethanol was warmed to 41° C. Sodium borohydride (194 mg, 5.13 mmol, 2 equiv) was slowly added and the reaction stirred as such for 30 minutes. It was stirred at room temperature for 16 h. The reaction was concentrated in vacuo and the mixture was partitioned between ethyl acetate and water, followed by a brine wash. The organic layer was dried over MgSO$_4$, filtered and concentrated. The residue was purified using the Biotage flash chromatography system (SNAP 50 g cartridge, R$_f$=0.45, gradient—1%-10% methanol in dichloromethane) to afford the title compound as a cream solid (1.2 g, 83%); $^1$H NMR (400 MHz, DMSO-d$_6$): δ 1.52 (s, 9H); 1.59-1.66 (m. 5H); 2.33-2.34 (m, 2H); 2.51-2.52 (m, 2H); 2.68-2.73 (m, 4H); 4.57-4.61 (m, 5H); 5.51 (d, 1H, J=3.6 Hz); 6.74-6.77 (m, 1H); 6.82 (s, 2H); 6.85 (s, 1H); 7.18-7.23 (m, 3H); 7.29-7.36 (m, 4H); 7.5-7.53 (m, 2H); 7.79 (bs, 1H); 7.82-7.84 (m, 1H); MS for $C_{35}H_{43}N_3O_4$ m/z 570.33 (M+H)$^+$.

Example 99

Compound 176

3-((1-cyclohexyl-4-oxo-8-(4-oxo-4-phenylbutyl)-1,3,8-triazaspiro[4.5]decan-3-yl)methyl)benzoic acid, hydrochloride

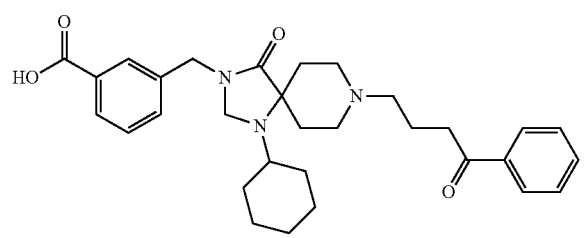 [SMILES: O=C(O)c1cccc(CN2CN(C3CCCCC3)C3(CCN(CCCC(=O)c4ccccc4)CC3)C2=O)c1]

tert-Butyl 3-((1-cyclohexyl-4-oxo-8-(4-oxo-4-phenylbutyl)-1,3,8-triazaspiro[4.5]decan-3-yl)methyl)benzoate (0.28 g, 0.488 mmol) and formic acid (6 mL) were stirred at room temperature for 20 hours. The reaction was evaporated to dryness and the residue purified by PTLC (10% methanol/dichloromethane). The product was dissolved in 4M hydrochloric acid in 1,4-dioxane (5 mL) and then evaporated under vacuum. The residue was dissolved in acetonitrile (5 mL) and water (5 mL) and lyophilized to give product as a white solid (0.18 g, 65%); $^1$H NMR (DMSO-d$_6$): δ1.05 (t, J=14.4 Hz, 2H); 1.20-1.40 (m, 4H); 1.45-1.63 (m, 2H); 1.63-1.78 (m, 3H); 1.83-1.98 (m, 2H); 1.98-2.10 (m, 3H); 2.20-2.40 (m, 2H); 3.12-3.17 (m, 2H); 3.19-3.24 (m, 2H); 3.45-3.55 (m, 2H); 4.19 (s, 2H); 4.52 (s, 2H); 7.48-7.57 (m, 4H); 7.64-7.68 (m, 1H); 7.85-7.89 (m, 2H); 7.98 (d, J=1.2 Hz, 1H); 8.00 (m, 1H); 10.9 (br s, 1H); MS for $C_{31}H_{39}N_3O_4$ m/z 518 (M+H)$^+$.

Preparation of tert-butyl 3-((1-cyclohexyl-4-oxo-8-(4-oxo-4-phenylbutyl)-1,3,8-triazaspiro[4.5]decan-3-yl)methyl)benzoate

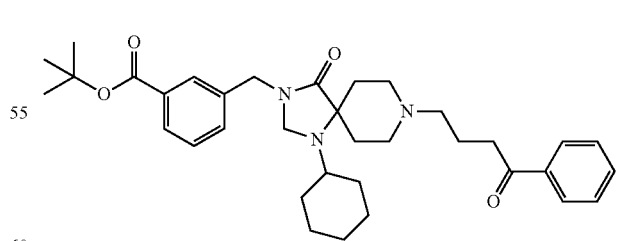

tert-Butyl 3-((1-cyclohexyl-4-oxo-1,3,8-triazaspiro[4.5]decan-3-yl)methyl)benzoate (0.30 g, 0.585 mmol), 4-iodobutyrophenone (0.17 g, 0.585 mmol), and potassium carbonate (0.12 g, 0.878 mmol) in N,N-dimethylformamide (8 mL) were stirred at 65° C. for 2 hours. The reaction was diluted with ethyl acetate, washed with water and brine, dried (MgSO$_4$), and evaporated. The residue was purified by PTLC (5% methanol/dichloromethane) to give product as an oil (0.28 g, 82%); MS for C$_{35}$H$_{47}$N$_3$O$_4$ m/z 574 (M+H)$^+$.

Example 100

Compound 177

3-(4-Cho-8-(4-oxo-4-phenylbutyl)-1-phenyl-1,3,8-triazaspiro[4.5]decan-3-yl)benzoic acid

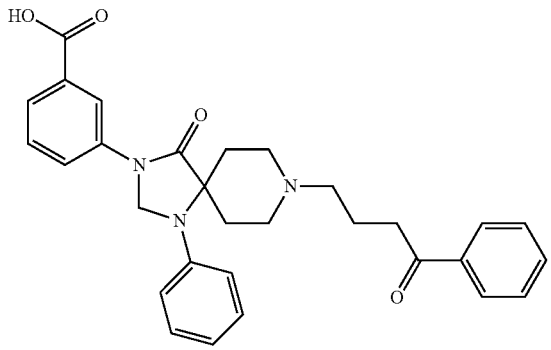 [SMILES: O=C(O)c1cccc(N2CN(c3ccccc3)C3(CCN(CCCC(=O)c4ccccc4)CC3)C2=O)c1]

To a solution of methyl 3-(4-oxo-8-(4-oxo-4-phenylbutyl)-1-phenyl-1,3,8-triazaspiro[4.5]decan-3-yl)benzoate (0.08 g, 0.16 mmol) in methanol (3 mL) was added lithium hydroxide monohydrate (0.013 g, 0.32 mmol) in water (1 mL). After stirring at 55° C. for 18 h, the reaction mixture was concentrated in vacuo, isolated by preparatory TLC (10% methanol/dichloromethane/0.1% acetic acid) and lyophilized with 4M HCl/dioxane (0.5 mL) to obtain the title compound as a hydrochloride salt (0.011 g, 13%); $^1$H NMR (DMSO-d$_6$): δ 2.07-2.16 (m, 4H), 2.91 (br, 2H), 3.21-3.24 (m, 4H), 3.56-3.62 (m, 4H), 5.25 (s, 2H), 6.90 (t, 1H, J=7.2 Hz), 7.24-7.34 (m, 4H), 7.53-7.68 (m, 4H), 7.81 (d, 1H, J=7.6 Hz), 7.92 (dd, 1H, J=8 and 1.6 Hz), 8.00 (d, 2H, J=8 Hz), 8.69 (s, 1H), 10.29 (br, 1H), 13.18 (br, 1H); MS for C$_{30}$H$_{31}$N$_3$O$_4$ m/z 498 (M+H)$^+$.

Example 101

Compound 179

Methyl 3-(4-oxo-8-(4-oxo-4-phenylbutyl)-1-phenyl-1,3,8-triazaspiro[4.5]decan-3-yl)benzoate

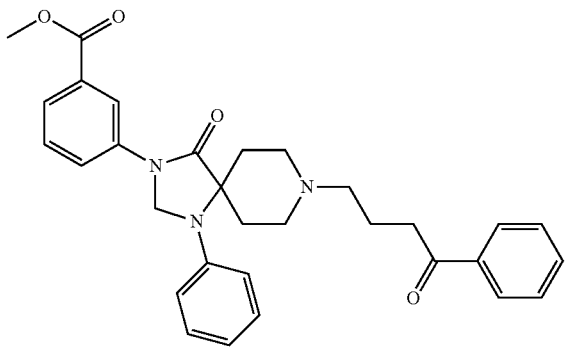 [SMILES: COC(=O)c1cccc(N2CN(c3ccccc3)C3(CCN(CCCC(=O)c4ccccc4)CC3)C2=O)c1]

To a solution of benzyl 3-(3-(methoxycarbonyl)phenyl)-4-oxo-1-phenyl-1,3,8-triazaspiro[4.5]decane-8-carboxylate (0.18 g, 0.36 mmol) in methanol (4 mL), was added 10 wt % palladium on carbon (0.036 g). After stirring under hydrogen at room temperature and atmospheric pressure for 18 hours, the reaction mixture was filtered, washed with methanol, concentrated in vacuo to obtain methyl 3-(4-oxo-1-phenyl-1,3,8-triazaspiro[4.5]decan-3-yl)benzoate (0.12 g).

To a solution of methyl 3-(4-oxo-1-phenyl-1,3,8-triazaspiro[4.5]decan-3-yl)benzoate (0.12 g, 0.33 mmol) and potassium carbonate (0.091 g, 0.66 mmol) in N,N-dimethylformamide (3 mL), was added 4-iodo-1-phenylbutan-1-one (0.09 g, 0.33 mmol). After stirring at 55° C. for 18 hours, the reaction mixture was diluted with ethyl acetate (50 mL), washed with water and brine. The organic phase was dried over MgSO$_4$, filtered, and isolated by Biotage flash chromatography (1-8% methanol/dichloromethane) to obtain the title compound (0.11 g, 65%); $^1$H NMR (DMSO-d$_6$): δ 1.75 (d, 2H, J=10.8 Hz), 1.83 (t, 2H, J=7.2 Hz), 2.35-2.41 (m, 4H), 2.67-2.74 (m, 4H), 3.04 (t, 2H, J=7.2 Hz), 3.88 (s, 3H), 5.19 (s, 2H), 6.87 (t, 1H, J=7.6 Hz), 7.02 (d, 2H, J=8 Hz), 7.24 (t, 2H, J=8.4 Hz), 7.52 (t, 2H, J=7.2 Hz), 7.57-7.65 (m, 2H), 7.79 (dt, 1H, J=8 and 1.2 Hz), 7.90-7.99 (m, 3H), 8.58 (t, 1H, J=1.6 Hz); MS for C$_{31}$H$_{33}$N$_3$O$_4$ m/z 512.3 (M+H)$^+$.

Preparation of benzyl 3-(3-(methoxycarbonyl)phenyl)-4-oxo-1-phenyl-1,3,8-triazaspiro[4.5]decane-8-carboxylate

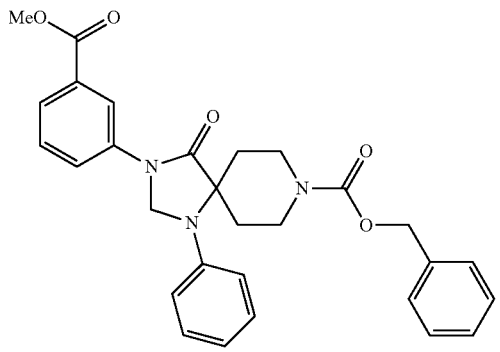 [SMILES: COC(=O)c1cccc(N2CN(c3ccccc3)C3(CCN(C(=O)OCc4ccccc4)CC3)C2=O)c1]

To a solution of benzyl 4-oxo-1-phenyl-1,3,8-triazaspiro[4.5]decane-8-carboxylate (0.2 g, 0.55 mmol), copper iodide (0.01 g, 0.055 mmol), N—N'-dimethylethylenediamine (0.012 mL, 0.11 mmol, d=0.819) and potassium carbonate (0.15 g, 1.1 mmol) in acetonitrile (5 mL), was added methyl 3-iodobenzoate (0.143 g, 0.55 mmol). After stirring at 75° C. for 18 hours, the reaction mixture was diluted with ethyl acetate (50 mL), washed with dilute citric acid, water and brine. The organic phase was dried over MgSO$_4$, filtered, and isolated by Biotage flash chromatography (10-75% ethyl acetate/hexanes) to obtain the title compound (0.15 g, 55%); $^1$H NMR (DMSO-d$_6$): δ 1.90 (d, 2H, J=14 Hz), 2.26-2.34 (m, 2H), 3.56 (br, 2H), 3.88 (s, 3H), 4.00 (d, 2H, J=12.8 Hz), 5.14-5.15 (m, 2H), 5.23 (s, 2H), 6.90 (t, 1H, J=7.2 Hz), 6.96 (d, 2H, J=8 Hz), 7.27 (t, 2H, J=8 Hz), 7.30-7.38 (m, 5H), 7.61 (t, 1H, J=8 Hz), 7.81 (dt, 1H, J=8.4 and 1.6 Hz), 7.93 (d, 1H, J=8.4 Hz), 8.58 (t, 1H, J=2 Hz).

Example 102

Compound 180

2-(4-oxo-8-(4-oxo-4-phenylbutyl)-1-phenyl-1,3,8-triazaspiro[4.5]decan-3-yl)benzoic acid

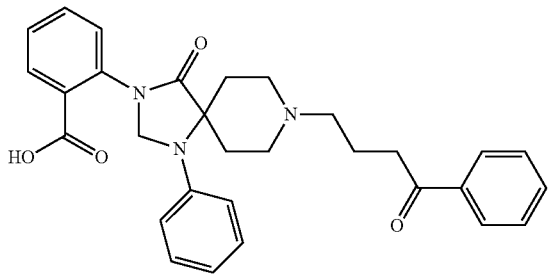 [SMILES: O=C(CCCN1CCC2(CC1)C(=O)N(c1ccccc1C(=O)O)CN2c1ccccc1)c1ccccc1]

A solution of tert-butyl 2-(4-oxo-8-(4-oxo-4-phenylbutyl)-1-phenyl-1,3,8-triazaspiro[4.5]decan-3-yl)benzoate (410 mg, 0.741 mmol, 1 equiv) in 4M hydrogen chloride solution in dioxane was stirred at ambient temperature for 5 h. The mixture was concentrated in vacuo and purified using preparative thin layer chromatography in 10% methanol in dichloromethane. The isolated mixture was treated with 4M hydrogen chloride solution in dioxane to afford the hydrogen chloride salt of the title compound as a white powder (160 mg, 43.5%); $^1$H NMR (400 MHz, DMSO-$d_6$): δ 2.05-2.08 (m, 4H); 3.04 (m, 2H); 3.16 (m, 2H); 3.22 (t, 2H, J=6.8 and 7.4 Hz); 3.56-3.71 (m, 4H); 5.10 (s, 2H); 6.84 (t, 1H, J=7.2 Hz); 7.14 (s, 1H); 7.16 (s, 1H); 7.25-7.29 (m, 2H); 7.52-7.57 (m, 3H); 7.63-7.68 (m, 2H); 7.71-7.75 (m, 1H); 7.94 (dd, 1H, J=1.2 Hz); 7.98-8.00 (m, 2H); 10.61 (bs, 1H); 13.22 (bs, 1H); MS for $C_{30}H_{31}N_3O_4$ m/z 498.3 (M+H)$^+$.

Preparation of tert-butyl 2-(4-oxo-8-(4-oxo-4-phenylbutyl)-1-phenyl-1,3,8-triazaspiro[4.5]decan-3-yl)benzoate

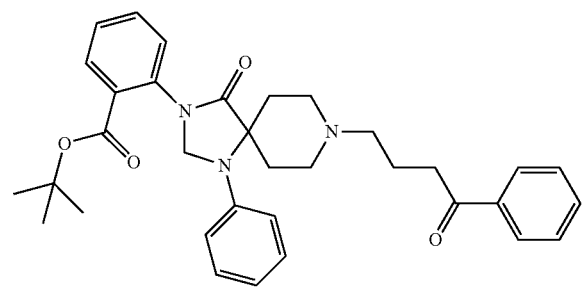 [SMILES: CC(C)(C)OC(=O)c1ccccc1N1CN(c2ccccc2)C2(CCN(CCCC(=O)c3ccccc3)CC2)C1=O]

A mixture of tert-butyl 2-(4-oxo-1-phenyl-1,3,8-triazaspiro[4.5]decan-3-yl)benzoate (370 mg, 0.909 mmol, 1 equiv), 4-iodo-1-phenylbutan-1-one (250 mg, 0.909 mmol, 1 equiv) and potassium carbonate (251 mg, 1.82 mmol, 2 equiv) in N,N-dimethylformamide was stirred at 68° C. for 16 h. After cooling the reaction mixture, the crude mixture was partitioned between ethyl acetate and water. The organic layer was dried over MgSO$_4$, filtered, concentrated, and the crude residue was purified using the Biotage flash chromatography system (SNAP 50 g cartridge, R$_f$=0.5, gradient—1%-10% methanol in dichloromethane) to afford the title compound as a white powder (410 mg, 82%); $^1$H NMR (400 MHz, DMSO-$d_6$): δ 1.49 (s, 9H); 1.74-1.83 (m, 4H); 2.37 (t, 2H, J=7.2 Hz); 2.61 (t, 2H, J=10 and 11.2 Hz); 2.726-2.73 (m, 4H); 3.05 (t, 2H, J=6.8 and 7.2 Hz); 5.06 (s, 2H); 6.79 (t, 1H, J=7.2 and 7.6 Hz); 6.87 (s, 1H); 6.89 (s, 1H); 7.20 (m, 2H); 7.46-7.69 (m, 6H); 7.76-7.78 (m, 1H); 7.95-7.99 (m, 2H); MS for $C_{34}H_{39}N_3O_4$ m/z 554.3 (M+H)$^+$.

Preparation of tert-butyl 2-(4-oxo-1-phenyl-1,3,8-triazaspiro[4.5]decan-3-yl)benzoate

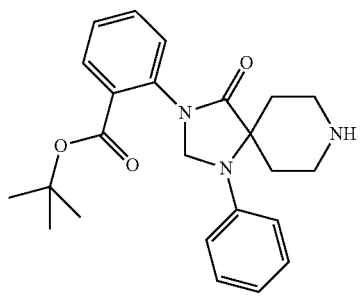 [SMILES: CC(C)(C)OC(=O)c1ccccc1N1CN(c2ccccc2)C2(CCNCC2)C1=O]

A solution of benzyl 3-(2-(tert-butoxycarbonyl)phenyl)-4-oxo-1-phenyl-1,3,8-triazaspiro[4.5]decane-8-carboxylate (1.86 g, 3.44 mmol, 1 equiv) in a mixture of ethyl acetate and ethanol was charged with 10% palladium on carbon (360 mg, 20%/wt) and the resulting mixture was hydrogenated at atmospheric pressure for 16 h. The reaction was filtered over Celite and the filtrate was concentrated and dried in vacuo to afford the title compound as a white foam (1.44 g, 96.4%); $^1$H NMR (400 MHz, DMSO-$d_6$): δ 1.49 (s, 9H); 1.71 (d, 2H, J=13.2 Hz); 2.41-2.49 (m, 2H); 2.84-2.88 (m, 2H); 3.08-3.13 (m, 2H); 5.07 (s, 2H); 6.78 (t, 1H, J=7.2 and 7.6 Hz); 6.98 (s, 1H); 7.00 (s, 1H); 7.23-7.27 (m, 2H); 7.46-7.49 (m, 1H); 7.60 (dd, 1H, J=1.2 and 1.6 Hz); 7.65-7.69 (m, 1H); 7.77 (dd, 1H, J=1.2 and 1.6 Hz); MS for $C_{24}H_{29}N_3O_3$ m/z 408.22 (M+H)$^+$.

Preparation of benzyl 3-(2-(tert-butoxycarbonyl)phenyl)-4-oxo-1-phenyl-1,3,8-triazaspiro[4.5]decane-8-carboxylate

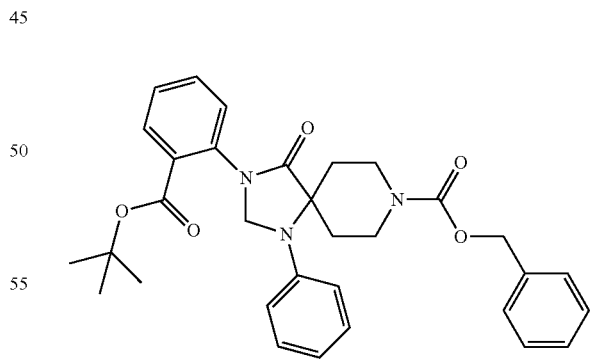

2-(8-(benzyloxycarbonyl)-4-oxo-1-phenyl-1,3,8-triazaspiro[4.5]decan-3-yl)benzoic acid (2.28 g, 4.69 mmol, 1 equiv) was suspended in toluene and the mixture was heated to refluxing temperatures. N,N-dimethylformamide di-tert-butyl acetal (4.5 ml, 18.76 mmol, 4 equiv) was added dropwise to the refluxing mixture within 30 minutes. Refluxing was continued for an additional 30-45 minutes after which it was cooled and stirred at ambient temperature for 16 h. The reaction was diluted with ethyl acetate and the organic layer was washed with sodium bicarbonate (sat), water and brine. The ethyl acetate layer was dried over MgSO$_4$, filtered, concentrated in vacuo and purified using the Biotage flash chromatography system (SNAP 100 g cartridge, R$_f$=0.5, gradient—5%-25% ethyl acetate in hexanes) to afford the title compound as a white solid (1.86 g, 73.3%); MS for C$_{32}$H$_{35}$N$_3$O$_5$ m/z 542.26 (M+H)$^+$.

Preparation of 2-(8-(benzyloxycarbonyl)-4-oxo-1-phenyl-1,3,8-triazaspiro[4.5]decan-3-yl)benzoic acid

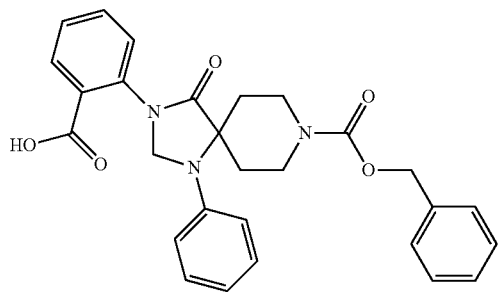 [SMILES: O=C(O)c1ccccc1N1CN(c2ccccc2)C2(CCN(C(=O)OCc3ccccc3)CC2)C1=O]

A solution of benzyl 3-(2-(methoxycarbonyl)phenyl)-4-oxo-1-phenyl-1,3,8-triazaspiro[4.5]decane-8-carboxylate (2.35 g, 4.7 mmol, 1 equiv.) and lithium hydroxide (394.4 mg, 9.4 mmol, 2 equiv) in a 3:1 mixture of methanol and water (20 ml t/v) was stirred at 60° C. for 16 hrs. Some dioxane was added to remove the turbidity in the reaction mixture and the stirring was continued for another 20 h. The reaction was concentrated in vacuo and the residue was partitioned between ethyl acetate and 10% citric acid. The organic layer was washed with water and brine, dried over MgSO$_4$, filtered and concentrated and dried in vacuo to afford the title compound as a cream solid (2.28 g, quant); $^1$H NMR (400 MHz, DMSO-d$_6$): δ 1.88 (d, 2H, J=14 Hz); 2.38-2.45 (m, 2H); 3.52 (bs, 2H); 3.97-4.05 (m, 2H); 5.08 (s, 2H); 5.15 (d, 2H, J=16.4 Hz); 6.79-6.84 (m, 3H); 7.20-7.24 (m, 2H); 7.33-7.39 (m, 5H); 7.49-7.53 (m, 1H); 7.61 (dd, 1H, J=0.8 Hz); 7.68-7.72 (m, 1H); 791 (dd, 1H, J=1.6 Hz); 13.1 (bs, 1H); MS for C$_{28}$H$_{27}$N$_3$O$_5$ m/z 486.3 (M+H)$^+$.

Preparation of benzyl 3-(2-(methoxycarbonyl)phenyl)-4-oxo-1-phenyl-1,3,8-triazaspiro[4.5]decane-8-carboxylate

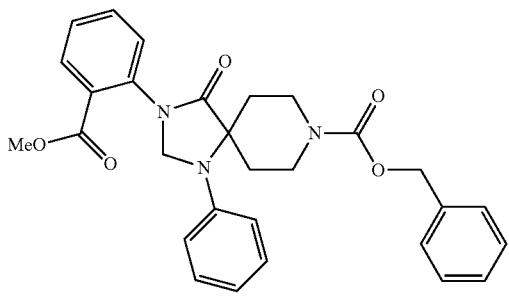 [SMILES: COC(=O)c1ccccc1N1CN(c2ccccc2)C2(CCN(C(=O)OCc3ccccc3)CC2)C1=O]

A mixture of benzyl 4-oxo-1-phenyl-1,3,8-triazaspiro[4.5] decane-8-carboxylate (2.79 g, 7.63 mmol, 1 equiv), methyl 2-iodobenzoate (2 g, 7.63 mmol, 1 equiv) potassium carbonate (2.11 g, 15.26 mmol, 2 equiv), copper(II) iodide (145.32 mg, 0.763 mmol, 0.1 equiv) and N,N'-dimethyl ethylenediamine (164.25 µl, 1.526 mmol, 0.2 equiv) in acetonitrile was heated at 75° C. for 16 h. Upon cooling 10% citric acid was added and the mixture was extracted with ethyl acetate. The organic layer was washed with water and brine, dried over MgSO4, filtered and concentrated. The residue was purified using the Biotage flash chromatography system (SNAP 100 g cartridge, R$_f$=0.3, gradient—5%-30% ethyl acetate in hexanes) to afford the title compound as a white powder (2.35 g, 61.57%); $^1$H NMR (400 MHz, DMSO-d$_6$): δ 1.85 (d, 2H, J=14 Hz); 2.35-2.51 (m, 2H); 3.49 (bs, 2H); 3.98-4.03 (m, 2H); 5.14 (s, 2H); 6.84-6.87 (m, 3H); 7.22-7.26 (m, 2H); 7.32-7.39 (m, 5H); 7.49-7.53 (m, 1H); 7.65 (dd, 1H, J=1.6 and 1.2 Hz); 7.70-7.75 (m, 1H); 7.86 (dd, 1H, J=1.2 and 1.6 Hz); MS for C$_{29}$H$_{29}$N$_3$O$_5$ m/z 500.21 (M+H)$^+$.

Example 103

Compound 182

4-(4-Cho-8-(4-oxo-4-phenylbutyl)-1-phenyl-1,3,8-triazaspiro[4.5]decan-3-yl)benzoic acid, hydrochloride

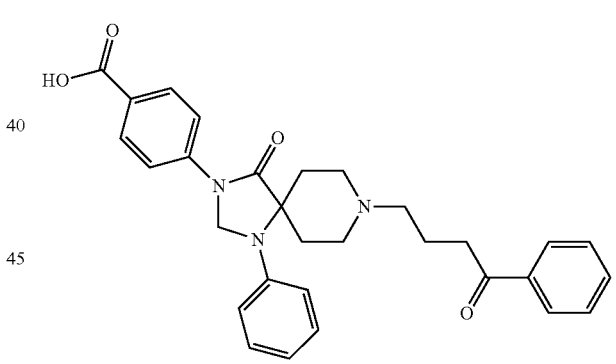

tert-Butyl 4-(4-oxo-8-(4-oxo-4-phenylbutyl)-1-phenyl-1,3,8-triazaspiro[4.5]decan-3-yl)benzoate (0.30 g, 0.542 mmol) and formic acid (6 mL) were stirred at room temperature for 20 hours. The reaction was evaporated to dryness and the residue purified by PTLC (10% methanol/dichloromethane). The product was dissolved in 4M hydrochloric acid in 1,4-dioxane (5 mL) and then evaporated under vacuum. The residue was dissolved in acetonitrile (5 mL) and water (5 mL) and lyophilized to give product as a white solid (0.19 g, 65%); HPLC rt 10.37 min; $^1$H NMR (DMSO-d$_6$); δ2.11-2.15 (m, 4H); 3.01 (m, 2H); 3.15-3.20 (m, 2H); 3.24 (t, J=7.2 hz, 2H); 3.46-3.49 (m, 2H); 3.56-3.71 (m, 2H); 5.26 (s, 2H); 6.90 (m, 1H); 7.29-7.31 (m, 4H); 7.55 (t, J=8 hz, 2H); 7.65 (t, J=7.2 hz, 1H); 7.99-8.04 (m, 6H); 10.83 (br s, 1H); 12.98 (br s, 1H); MS for C$_{30}$H$_{31}$N$_3$O$_4$ m/z 498 (M+H)$^+$.

Preparation of tert-butyl 4-(4-oxo-8-(4-oxo-4-phenylbutyl)-1-phenyl-1,3,8-triazaspiro[4.5]decan-3-yl)benzoate

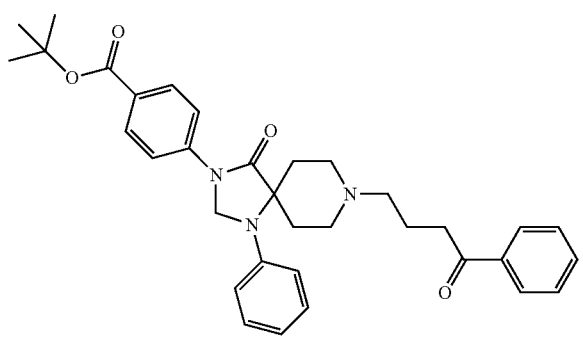 [SMILES: CC(C)(C)OC(=O)c1ccc(N2CN(c3ccccc3)C3(CCN(CCCC(=O)c4ccccc4)CC3)C2=O)cc1]

tert-Butyl 4-(4-oxo-1-phenyl-1,3,8-triazaspiro[4.5]decan-3-yl)benzoate (0.274 g, 0.672 mmol), 4-iodobutyrophenone (0.18 g, 0.672 mmol), and potassium carbonate (0.14 g, 1.01 mmol) in N,N-dimethylformamide (5 mL) were heated at 65° C. for 3 hours. The reaction was diluted with ethyl acetate, washed with water and brine, dried (MgSO$_4$), and evaporated. The residue was purified by PTLC (5% methanol/dichloromethane) to give product as an oil (0.30 g, 80%); MS for C$_{34}$H$_{39}$N$_3$O$_4$ m/z 554 (M+H)$^+$.

Preparation of tert-butyl 4-(4-oxo-1-phenyl-1,3,8-triazaspiro[4.5]decan-3-yl)benzoate

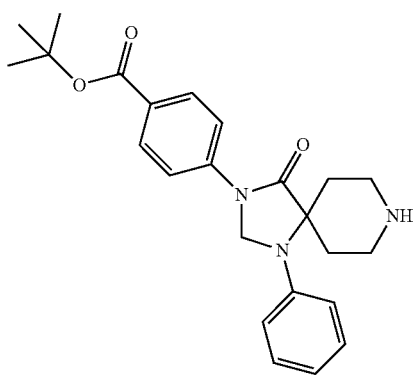 [SMILES: CC(C)(C)OC(=O)c1ccc(N2CN(c3ccccc3)C3(CCNCC3)C2=O)cc1]

Benzyl 3-(4-(tert-butoxycarbonyl)phenyl)-4-oxo-1-phenyl-1,3,8-triazaspiro[4.5]decane-8-carboxylate (0.62 g, 1.14 mmol) and palladium on carbon (10 wt. %, wet, Degussa type E101 NE/W,) (0.12 g) in ethyl acetate (5 mL) and methanol (5 mL) was stirred at room temperature under hydrogen (balloon) for 3 hours. The catalyst was removed by filtration and the filtrate evaporated and dried under vacuum to give product as foam (0.46 g, quant.); MS for C$_{24}$H$_{29}$N$_3$O$_3$ m/z 408 (M+H)$^+$.

Preparation of benzyl 3-(4-(tert-butoxycarbonyl)phenyl)-4-oxo-1-phenyl-1,3,8-triazaspiro[4.5]decane-8-carboxylate

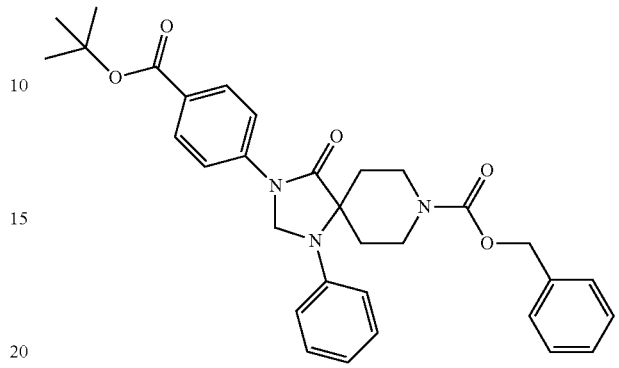

N,N-Dimethylformamide di-tert-butyl acetal (1.39 mL, 5.79 mmol) was added slowly dropwise to 4-(8-(benzyloxycarbonyl)-4-oxo-1-phenyl-1,3,8-triazaspiro[4.5]decan-3-yl)benzoic acid (0.703 g, 1.45 mmol) in toluene (10 mL) at reflux. The reaction was heated at reflux for 30 minutes and then evaporated under vacuum. The residue was purified by PTLC (30% ethyl acetate/hexanes) to give product as an oil (0.62 g, 79%); $^1$H NMR (DMSO-d$_6$); δ1.55 (s, 9H); 1.90 (d, 14.4 Hz, 2H); 2.24-2.32 (m, 2H); 3.55 (m, 2H); 3.98-4.03 (m, 2H); 5.14 (m, 2H); 5.22 (s, 2H); 6.92 (t, J=7.2 Hz, 1H), 6.97 (d, J=7.6 Hz, 2H); 7.28 (m, 2H); 7.33-7.38 (m, 5H); 7.96 (s, 4H); MS for C$_{32}$H$_{35}$N$_3$O$_5$ m/z 542 (M+H)$^+$.

Preparation of 4-(8-(benzyloxycarbonyl)-4-oxo-1-phenyl-1,3,8-triazaspiro[4.5]decan-3-ylbenzoic acid Benzyl 3-(4-(methoxycarbonyl)phenyl)-4-oxo-1-phenyl-1,3,8-triazaspiro[4.5]decane-8-carboxylate (1.16 g, 2.32 mmol) and lithium hydroxide (0.15 g, 3.48 mmol) in methanol (10 mL) and water (1 mL) were stirred at 45° C. for 20 h. The reaction was partially evaporated under vacuum, the residue acidified with 6M hydrochloric acid, and extracted with ethyl acetate. The extract was washed with brine, dried (MgSO$_4$), and evaporated to give product as a white solid (1.13 g, quant.); $^1$H NMR (DMSO-d$_6$); δ1.89 (d, J=14 Hz, 2H); 2.27-2.33 (m, 2H); 3.56 (m, 2H); 3.98-4.01 (m, 2H); 5.14 (d, 13.6 Hz, 2H); 5.23 (s, 2H); 6.91 (t, J=7.6 Hz, 1H); 6.96 (d, J=8 Hz, 2H); 7.27 (dd, J=7.6 Hz and 8.8 Hz, 2H); 7.32-7.38 (m, 5H); 7.96-8.02 (m, 4H); 12.9 (br s, 1H); MS for $C_{28}H_{27}N_3O_5$ m/z 486 (M+H)$^+$.

Preparation of benzyl 3-(4-(methoxycarbonyl)phenyl)-4-oxo-1-phenyl-1,3,8-triazaspiro[4.5]decane-8-carboxylate

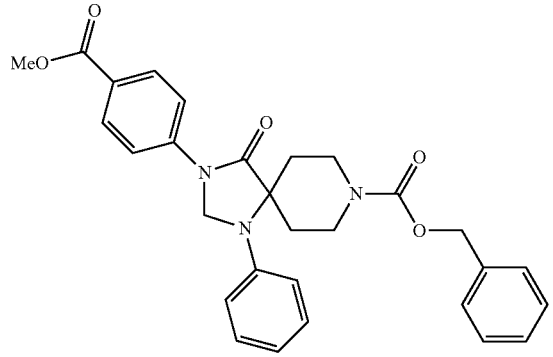 [SMILES: COC(=O)c1ccc(N2CN(c3ccccc3)C3(CCN(C(=O)OCc4ccccc4)CC3)C2=O)cc1]

Benzyl 4-oxo-1-phenyl-1,3,8-triazaspiro[4.5]decane-8-carboxylate (0.50 g, 1.37 mmol), methyl 4-fluorobenzoate (0.21 g, 1.37 mmol), and potassium carbonate (0.38 g, 2.74 mmol) in dimethyl sulfoxide were stirred at 100° C. for 3 days. The reaction was diluted with ethyl acetate, washed with water and brine, dried (MgSO$_4$), and evaporated. The residue was purified by Biotage flash chromatography (gradient from 0 to 30% ethyl acetate/hexanes) to give product as an oil (0.68 g, 21%); $^1$H NMR (DMSO-d$_6$); δ1.90 (d, 15.6 hz, 2H); 2.25-2.34 (m, 2H); 3.56 (m, 2H); 3.98-4.02 (m, 2H); 5.13 (m, 2H); 5.24 (s, 2H); 6.92 (t, J=8.4 hz, 1H); 6.98 (d, J=8.8 hz, 2H); 7.26-7.39 (m, 7H); 8.02 (dd, J=10 Hz and 17.6 Hz, 4H); MS for $C_{29}H_{29}N_3O_5$ m/z 500 (M+H)$^+$.

Example 104

Compound 186

N-(4-((4-oxo-8-(4-oxo-4-phenylbutyl)-1-phenyl-1,3,8-triazaspiro[4.5]decan-3-yl)methyl)phenyl)methanesulfonamide

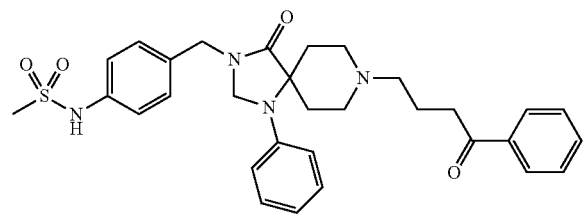 [SMILES: CS(=O)(=O)Nc1ccc(CN2CN(c3ccccc3)C3(CCN(CCCC(=O)c4ccccc4)CC3)C2=O)cc1]

N-(4-((4-oxo-1-phenyl-1,3,8-triazaspiro[4.5]decanyl)methyl)phenyl)methanesulfonamide, hydrochloride salt (0.35 g, 0.776 mmol), 4-iodobutyrophenone (0.21 g, 0.776 mmol), and potassium carbonate (0.21 g, 1.55 mmol) in N,N-dimethylformamide (10 mL) were stirred at 65° C. for 2 hours. The reaction was diluted with ethyl acetate, washed with water and brine, dried (MgSO$_4$), and evaporated. The residue was purified by PTLC (5% methanol/dichloromethane) to give product as a white solid (0.36 g, 82%); HPLC rt 12.97 min; $^1$H NMR (DMSO-d$_6$); δ1.58 (d, J=11.2 Hz, 2H); 1.85 (t, J=6 Hz, 2H); 2.44 (m, 4H); 2.73-2.76 (m, 4H); 2.97 (s, 3H); 3.06 (t, J=6.8 Hz, 2H); 4.49 (s, 2H); 4.55 (s, 2H); 6.72-6.77 (m, 3H); 7.13-7.26 (m, 6H); 7.51-7.55 (m, 2H); 7.62-7.66 (m, 1H); 7.98-8.00 (m, 2H); 9.75 (br s, 1H); MS for $C_{31}H_{36}N_4O_4S$ m/z 561 (M+H)$^+$.

Preparation of N-(4-((4-oxo-1-phenyl-1,3,8-triazaspiro[4.5]decan-3-yl)methyl)phenyl)methanesulfonamide, hydrochloride salt

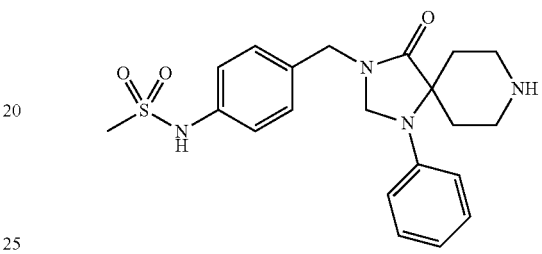

tert-Butyl 3-(4-(methylsulfonamido)benzyl)-4-oxo-1-phenyl-1,3,8-triazaspiro[4.5]decane-8-carboxylate (2.30 g, 4.47 mmol) and 4M hydrochloric acid in 1,4-dioxane (25 mL) were stirred at room temperature for 2 hours. The reaction was evaporated and dried under vacuum to give product as a light yellow solid (2.02 g, quant.); MS for $C_{21}H_{26}N_4O_3S$ m/z 415 (M+H)$^+$.

Preparation of tert-butyl 3-(4-(methylsulfonamido)benzyl)-4-oxo-1-phenyl-1,3,8-triazaspiro[4.5]decane-8-carboxylate

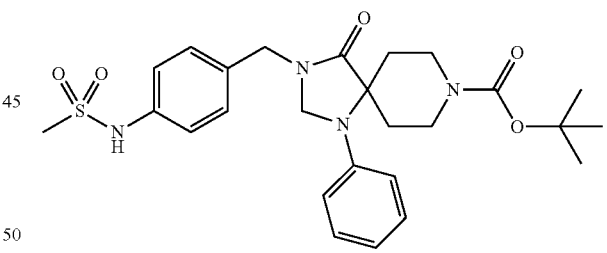

Methanesulfonyl chloride (0.39 mL, 5.02 mmol) was added dropwise at 0° C. to tert-butyl 3-(4-aminobenzyl)-4-oxo-1-phenyl-1,3,8-triazaspiro[4.5]decane-8-carboxylate (2.19 g, 5.02 mmol) and pyridine (0.61 mL, 7.53 mmol) in dichloromethane (10 mL). The reaction was allowed to warm to room temperature and stirred for 30 minutes. The mixture was diluted with dichloromethane, washed with 2M aqueous hydrochloric acid and brine, dried (MgSO$_4$) and evaporated. The residue was purified by PTLC (50% ethyl acetate/hexanes) to give product as an oil (2.38 g, 92%); $^1$H NMR (DMSO-d$_6$); δ1.45 (s, 9H); 1.63 (d, J=14 Hz, 2H); 2.18-2.23 (m, 2H); 2.98 (s, 3H); 3.30-3.55 (m, 2H); 3.80-3.95 (m, 2H); 4.52 (s, 2H); 4.59 (s, 2H); 6.67 (d, J=8 Hz, 2H); 6.76 (t, J=7.2 Hz, 2H); 7.15-7.21 (m, 4H); 7.26-7.28 (m, 2H); MS for $C_{26}H_{34}N_4O_5S$ m/z 515 (M+H)$^+$.

Preparation of tert-butyl 3-(4-aminobenzyl)-4-oxo-1-phenyl-1,3,8-triazaspiro[4.5]decane-8-carboxylate

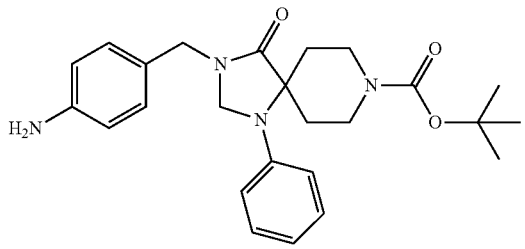 [SMILES: CC(C)(C)OC(=O)N1CCC2(CC1)C(=O)N(Cc1ccc([N+](=O)[O-])cc1)CN2c1ccccc1]

tert-Butyl 3-(4-nitrobenzyl)-4-oxo-1-phenyl-1,3,8-triazaspiro[4.5]decane-8-carboxylate (2.59 g, 5.55 mmol) and palladium on carbon (10 wt. %, wet, Degussa type E101 NE/W) (0.52 g) in ethyl acetate (30 mL) was stirred at room temperature under hydrogen (balloon) for 3 hours. The catalyst was removed by filtration and the filtrate evaporated and dried under vacuum to give product as an oil (2.42 g, quant.); $^1$H NMR (DMSO-$d_6$): δ1.45 (s, 9H); 1.57 (d, J=14 Hz, 2H); 2.39 (m, 2H); 3.45 (m, 2H); 3.88 (m, 2H); 4.36 (s, 2H); 4.52 (s, 2H); 5.09 (s, 2H); 6.53 (m, 2H); 6.64 (d, J=8 Hz, 2H); 6.75 (t, J=7.6 Hz, 1H); 6.96 (d, J=8.4 Hz, 2H); 7.16 (dd, J=7.2 Hz and 8.8 Hz, 2H); MS for $C_{25}H_{32}N_4O_3$ m/z 437 (M+H)$^+$.

Preparation of tert-butyl 3-(4-nitrobenzyl)-4-oxo-1-phenyl-1,3,8-triazaspiro[4.5]decane-8-carboxylate

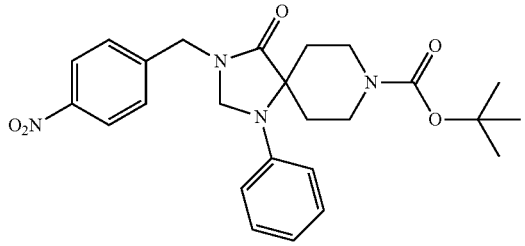

tert-Butyl 4-oxo-1-phenyl-1,3,8-triazaspiro[4.5]decane-8-carboxylate (2.00 g, 6.03 mmol), 4-nitrobenzyl bromide (1.30 g, 6.03 mmol), and potassium carbonate (1.25 g, 9.05 mmol) in N,N-dimethylformamide (20 mL) were heated at 65° C. for 4 hours. The reaction was diluted with ethyl acetate, washed with water and brine, dried (MgSO$_4$), and evaporated. The residue was purified by PTLC (50% ethyl acetate/hexanes) to give product as a light yellow solid (2.59, 92%); $^1$H NMR (DMSO-$d_6$): δ1.46 (s, 9H); 1.68 (d, J=13.6 Hz, 2H); 2.42 (m, 2H); 3.42 (m, 2H); 3.89 (m, 2H); 4.66 (s, 2H); 4.71 (s, 2H); 6.69 (d, J=8.4 Hz, 2H); 6.78 (t, J=6.8 Hz, 1H); 7.19 (dd, J=7.2 Hz and 8.8 Hz, 2H); 7.58 (d, J=8.8 Hz, 2H); 8.24 (m, 2H); MS for $C_{25}H_{30}N_4O_5$ m/z 467 (M+H)$^+$.

Example 105

Compound 211

N-(3-(4-(4-fluorophenyl)-4-oxobutyl)-4-oxo-1-phenyl-1,3,8-triazaspiro[4.5]decan-3-yl)methyl)phenyl)methanesulfonamide

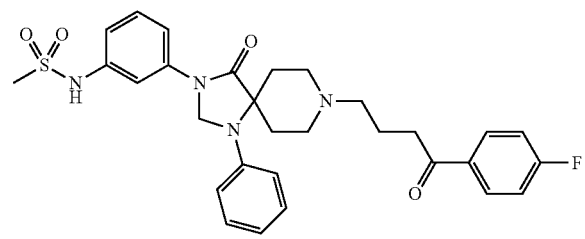 [SMILES: CS(=O)(=O)Nc1cccc(N2CN(c3ccccc3)C3(CCN(CCCC(=O)c4ccc(F)cc4)CC3)C2=O)c1]

To a solution of 3-(3-aminophenyl)-8-(4-(4-fluorophenyl)-4-oxobutyl)-1-phenyl-1,3,8-triazaspiro[4.5]decan-4-one (200 mg, 0.416 mmol, 1 equiv) in dichloromethane, maintained at 0° C., pyridine (66.6 μl, 0.823 mmol, 2 equiv) followed by the addition of methanesulfonyl chloride (28.7 μl, 0.3704 mmol, 0.9 equiv). The reaction was slowly warmed to room temperature and stirred for 16 h. It was diluted with dichloromethane and the organic layer was washed with 10%, citric acid followed by a brine wash. The organic layer was dried over MgSO$_4$, filtered and concentrated in vacuo. The residue was purified using preparatory thin layer chromatography in 7% methanol in dichloromethane to afford the title compound as a white powder (40 mg, 17%); $^1$H NMR (400 MHz, DMSO-$d_6$): δ 1.77 (bs, 2H); 1.85 (bs, 2H); 2.32-2.33 (m, 4H); 2.67-2.73 (m, 4H); 3.02 (s, 3H); 3.04 (m, 2H); 5.12 (s, 2H); 6.89 (dd, 1H, J=7.6 and 7.2 Hz); 7.02 (bs, 2H); 7.06-708 (m, 1H); 7.25-7.29 (m, 2H); 7.32-7.41 (m, 4H); 7.90-7.91 (m, 1H); 8.04-8.07 (m, 2H); 9.83 (s, 1H); MS for $C_{30}H_{33}FN_4O_4S$ m/z 565.3 (M+H)$^+$.

Example 106

Compound 212

N-(3-((4-Oxo-8-(3-(2'-oxospiro[cyclopropane-1,3'-indoline]-1'-yl)propyl)-1-phenyl-1,3,8-triazaspiro[4.5]decan-3-yl)methyl)phenyl)methanesulfonamide

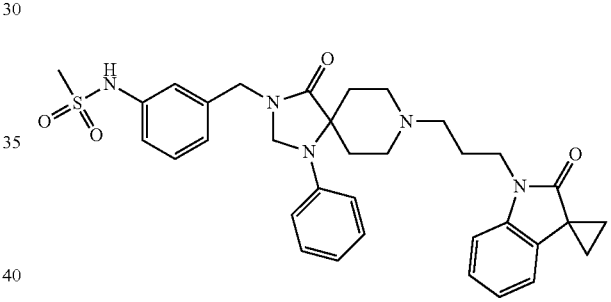

To a solution of benzyl 3-(3-(methylsulfonamido)benzyl)-4-oxo-1-phenyl-1,3,8-triazaspiro[4.5]decane-8-carboxylate (0.82 g, 1.49 mmol) in methanol (15 mL), was added 10 wt % palladium on carbon (0.15 g). After stirring under hydrogen at room temperature and atmospheric pressure for 18 hours, the reaction mixture was filtered, washed with methanol, concentrated in vacuo to obtain N-(3-((4-oxo-1-phenyl-1,3,8-triazaspiro[4.5]decan-3-yl)methyl)phenyl)methanesulfonamide (0.62 g, 99%).

To a solution of N-(3-((4-oxo-1-phenyl-1,3,8-triazaspiro[4.5]decan-3-yl)methyl)phenyl)methanesulfonamide (0.2 g, 0.48 mmol), sodium iodide (0.029 g, 0.19 mmol) and potassium carbonate (0.133 g, 0.96 mmol) in 2-butanone (5 mL), was added 1'-(3-chloropropyl)spiro[cyclopropane-1,3'-indolin]-2'-one (0.114 g, 0.48 mmol). After stirring at 78° C. for 18 hours, the reaction mixture was filtered and isolated by preparatory TLC (10% methanol/dichloromethane) to obtain the title compound (0.09 g, 31%); $^1$H NMR (DMSO-$d_6$): δ 1.51 (t, 2H, J=3.6 Hz), 1.58 (t, 2H, J=3.6 Hz), 1.64 (d, 2H, J=13.2 Hz), 1.80 (br, 2H), 2.37 (br, 2H), 2.51-2.57 (m, 2H), 2.68-2.73 (m, 4H), 2.96 (s, 3H), 3.82 (t, 2H, J=6.8 Hz), 4.52 (s, 2H), 4.58 (s, 2H), 6.76 (t, 1H, J=7.6 Hz), 6.84 (d, 2H, J=8.4 Hz), 6.96-7.02 (m, 3H), 7.09 (s, 1H), 7.12 (d, 1H, J=8 Hz), 7.17-7.24 (m, 4H), 7.32 (t, 1H, J=8 Hz), 9.81 (s, 1H); MS for $C_{34}H_{39}N_5O_4S$ m/z 614.4 (M+H)$^+$.

161

Preparation of benzyl 3-(3-(methylsulfonamido)benzyl)-4-oxo-1-phenyl-1,3,8-triazaspiro[4.5]decane-8-carboxylate

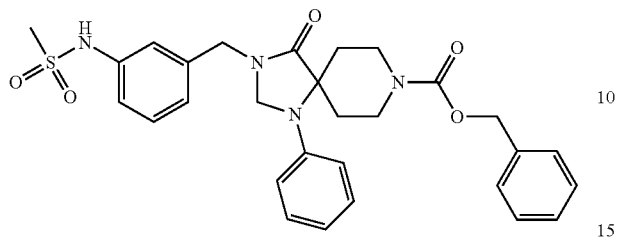

To a refluxing solution of benzyl 3-(3-nitrobenzyl)-4-oxo-1-phenyl-1,3,8-triazaspiro[4.5]decane-8-carboxylate (0.77 g, 1.53 mmol) and ammonium chloride (0.96 g, 18.0 mmol) in 2:1 mixture of ethanol/water (18 mL), was added iron powder (0.3 g, 5.4 mmol) over a period of 45 minutes. After refluxing for another hour, the reaction mixture was extracted with dichloromethane, washed the organic extracts with water and brine. The organic phase was dried over MgSO$_4$ and concentrated to obtain benzyl 3-(3-aminobenzyl)-4-oxo-1-phenyl-1,3,8-triazaspiro[4.5]decane-8-carboxylate (0.80 g, 95%).

To a cooled (0° C.) solution of benzyl 3-(3-nitrobenzyl)-4-oxo-1-phenyl-1,3,8-triazaspiro[4.5]decane-8-carboxylate (0.8 g, 1.7 mmol) and pyridine (0.275 mL, 3.4 mmol, d=0.978) in dichloromethane (20 mL), was added methanesulfonyl chloride (0.12 mL, 1.53 mmol, d=1.48). After stirring at room temperature for 18 hours, the reaction mixture was washed with dilute citric acid, water and brine. The organic phase was dried over MgSO$_4$, filtered, and isolated by Biotage flash chromatography (10-100% ethyl acetate/hexanes) to obtain the title compound (0.83 g, 89%); $^1$H NMR (DMSO-d$_6$): δ 1.73 (d, 2H, J=13.6 Hz), 2.35-2.43 (m, 2H), 2.97 (s, 3H), 3.57 (br, 2H), 4.00-4.05 (m, 2H), 4.55 (s, 2H), 4.61 (s, 2H), 5.13 (br, 2H), 6.88 (d, 2H, J=8 Hz), 6.76 (t, 1H, J=7.6 Hz), 7.03 (d, 1H, J=7.6 Hz), 7.10-7.20 (m, 4H), 7.31-7.39 (m, 6H), 9.80 (s, 1H); MS for C$_{29}$H$_{32}$N$_4$O$_5$S m/z 549.3 (M+H)$^+$.

Preparation of benzyl 3-(3-nitrobenzyl)-4-oxo-1-phenyl-1,3,8-triazaspiro[4.5]decane-8-carboxylate

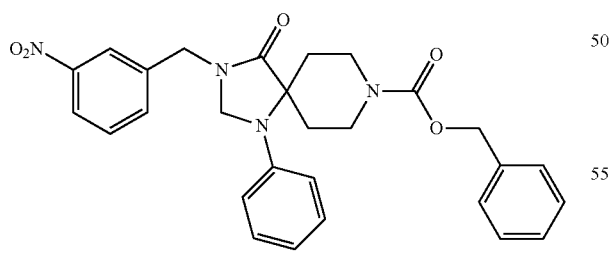

To a solution of benzyl 4-oxo-1-phenyl-1,3,8-triazaspiro[4.5]decane-8-carboxylate (1 g, 2.74 mmol) and potassium carbonate (0.76 g, 5.48 mmol) in N,N-dimethylformamide (25 mL), was added 3-nitrobenzyl bromide (0.59 g, 2.74 mmol). After stirring at 65° C. for 18 hours, the reaction mixture was diluted with ethyl acetate (200 mL), washed with dilute citric acid, water and brine. The organic phase was dried over MgSO$_4$, filtered, and isolated by Biotage flash chromatography (10-100% ethyl acetate/hexanes) to obtain the title compound (0.9 g, 66%); $^1$H NMR (DMSO-d$_6$): δ 1.73 (d, 2H, J=14 Hz), 2.35-2.40 (m, 2H), 3.57 (br, 2H), 4.02 (dd, 2H, J=8 and 3.6 Hz), 4.65 (s, 2H), 4.71 (s, 2H), 5.12-5.15 (m, 2H), 6.70 (d, 2H, J=8.4 Hz), 6.76 (t, 1H, J=7.2 Hz), 7.17 (t, 2H, J=8 Hz), 7.32-7.35 (m, 5H), 7.66-7.70 (m, 1H), 7.76 (d, 1H, J=8 Hz), 8.16-8.18 (m, 2H). MS for C$_{28}$H$_{28}$N$_4$O$_5$ m/z 501.3 (M+H)$^+$.

Example 107

Compound 213

N-(3-((4-Cho-8-(3-(2-oxoindolin-1-yl)propyl)-1-phenyl-1,3,8-triazaspiro[4.5]decan-3-yl)methyl)phenyl)methanesulfonamide

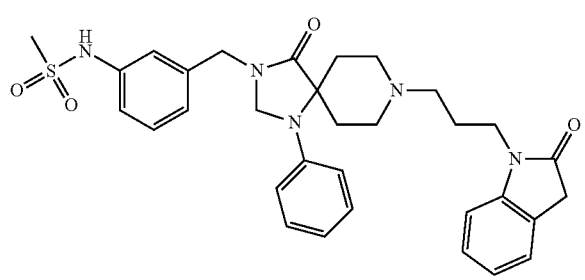 [SMILES: CS(=O)(=O)Nc1cccc(CN2CN(c3ccccc3)C3(CCN(CCCN4C(=O)Cc5ccccc54)CC3)C2=O)c1]

To a solution of N-(3-((4-oxo-1-phenyl-1,3,8-triazaspiro[4.5]decan-3-yl)methyl)phenyl)methanesulfonamide (0.22 g, 0.53 mmol), sodium iodide (0.032 g, 0.21 mmol) and potassium carbonate (0.146 g, 1.06 mmol) in 2-butanone (5 mL), was added 1-(3-chloropropyl)indolin-2-one (0.11 g, 0.53 mmol). After stirring at 78° C. for 3 hours, the reaction mixture was filtered and isolated by preparatory TLC (10% methanol/dichloromethane) to obtain the title compound (0.041 g, 13%); $^1$H NMR (DMSO-d$_6$): δ 1.66 (d, 2H, J=13.6 Hz), 1.78 (t, 2H, J=6.8 Hz), 2.33-2.47 (m, 2H), 2.50-2.56 (m, 2H), 2.76 (br, 4H), 2.96 (s, 3H), 3.54 (s, 2H), 3.73 (t, 2H, J=6.8 Hz), 4.52 (s, 2H), 4.58 (s, 2H), 6.77 (t, 1H, J=7.2 Hz), 6.85 (d, 2H, J=8.4 Hz), 6.97-7.02 (m, 2H), 7.08-7.13 (m, 3H), 7.20-7.26 (m, 4H), 7.32 (t, 1H, J=8 Hz), 9.80 (s, 1H); MS for C$_{32}$H$_{37}$N$_5$O$_4$S m/z 588.3 (M+H)$^+$.

Example 108

Compound 214

N-(4-(8-(4-(4-Fluorophenyl)-4-oxobutyl)-4-oxo-1-phenyl-1,3,8-triazaspiro[4.5]decan-3-yl)phenyl)methanesulfonamide

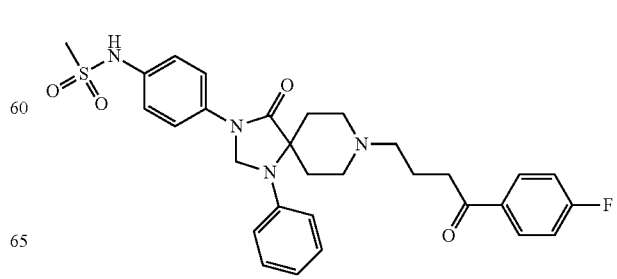

To tert-butyl 3-(4-(methylsulfonamido)phenyl)-4-oxo-1-phenyl-1,3,8-triazaspiro[4.5]decane-8-carboxylate (0.91 g, 1.82 mmol) was added 4M solution of HCl in dioxane (10 mL). After stirring at room temperature for 18 hours, the reaction mixture was concentrated in vacuo to obtain N-(4-(4-oxo-1-phenyl-1,3,8-triazaspiro[4.5]decan-3-yl)phenyl) methanesulfonamide as a hydrochloride salt (0.7 g).

To a solution of N-(4-(4-oxo-1-phenyl-1,3,8-triazaspiro[4.5]decan-3-yl)phenyl)methanesulfonamide (0.2 g, 0.46 mmol) and potassium carbonate (0.191 g, 1.38 mmol) in N,N-dimethylformamide (5 mL), was added 1-(4-fluorophenyl)-4-iodobutan-1-one (0.134 g, 0.46 mmol). After stirring at 65° C. for 18 hours, the reaction mixture was diluted with ethyl acetate (25 mL), washed with water and brine. The organic phase was dried over MgSO$_4$, filtered, concentrated and isolated by pTLC (10% methanol/dichloromethane) to obtain the product (0.03 g, 12%); $^1$H NMR (DMSO-d$_6$): δ 1.70-1.90 (m, 4H), 2.40-2.49 (m, 2H), 2.66-2.84 (m, 6H), 2.97 (s, 3H), 3.05 (br, 2H), 5.12 (s, 2H), 6.88 (t, 1H, J=7.6 Hz) 6.99-7.03 (m, 2H), 7.26 (d, 4H, J=9.2 Hz), 7.34 (t, 2H, J=8.4 Hz), 7.76 (d, 2H, J=8.8 Hz), 8.04-8.07 (m, 2H), 9.73 (s, 1H); MS for C$_{30}$H$_{33}$FN$_4$O$_4$S m/z 565.3 (M+H)$^+$.

Preparation of tert-butyl 3-(4-methylsulfonamido) phenyl)-4-oxo-1-phenyl-1,3,8-triazaspiro[4.5]decane-8-carboxylate

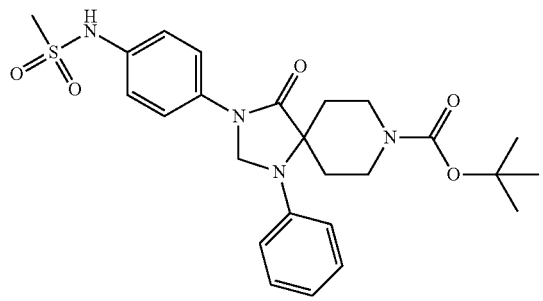 [SMILES: CC(C)(C)OC(=O)N1CCC2(CC1)C(=O)N(c1ccc(NS(C)(=O)=O)cc1)CN2c1ccccc1]

To a refluxing solution of tert-butyl 3-(4-nitrophenyl)-4-oxo-1-phenyl-1,3,8-triazaspiro[4.5]decane-8-carboxylate (1.0 g, 2.2 mmol) and ammonium chloride (1.18 g, 22.0 mmol) in 2:1 mixture of ethanol/water (21 mL), was added iron powder (0.37 g, 6.6 mmol) over a period of 45 minutes. After refluxing for another hour, the reaction mixture was extracted with dichloromethane, washed the organic extracts with water and brine. The organic phase was dried over MgSO$_4$ and concentrated to obtain tert-butyl 3-(4-aminophenyl)-4-oxo-1-phenyl-1,3,8-triazaspiro[4.5]decane-8-carboxylate (0.9 g, 97%).

To a cooled (0° C.) solution of tert-butyl 3-(4-aminophenyl)-4-oxo-1-phenyl-1,3,8-triazaspiro[4.5]decane-8-carboxylate (0.9 g, 1.99 mmol) and pyridine (0.322 mL, 3.98 mmol, d=0.978) in dichloromethane (20 mL), was added methanesulfonyl chloride (0.138 mL, 1.79 mmol, d=1.48). After stirring at room temperature for 18 hours, the reaction mixture was washed with dilute citric acid, water and brine. The organic phase was dried over MgSO$_4$, filtered, and isolated by Biotage flash chromatography (10-100% ethyl acetate/hexanes) to obtain the title compound (0.92 g, 92%); $^1$H NMR (DMSO-d$_6$): δ 1.45 (s, 9H), 1.78 (d, 2H, J=14 Hz), 2.32 (t, 2H, J=12.4 Hz), 2.97 (s, 3H), 3.44 (br, 2H), 3.87 (br, 2H), 5.15 (s, 2H), 6.87-6.91 (m, 3H), 7.24-7.28 (m, 4H), 7.78 (d, 2H, J=8.8 Hz), 9.73 (s, 1H); MS for C$_{25}$H$_{32}$N$_4$O$_5$S m/z 501.3 (M+H)$^+$.

Example 109

Compound 215

N-(4-(4-oxo-8-(3-(2-oxoindolin-1-yl)propyl)-1-phenyl-1,3,8-triazaspiro[4.5]decan-3-yl)phenyl)methanesulfonamide

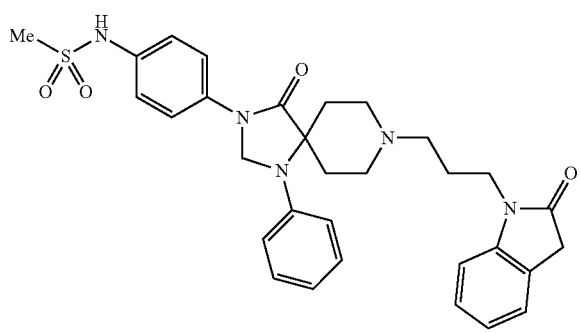 [SMILES: CS(=O)(=O)Nc1ccc(N2CN(c3ccccc3)C3(CCN(CCCN4C(=O)Cc5ccccc54)CC3)C2=O)cc1]

N-(4-((4-oxo-1-phenyl-1,3,8-triazaspiro[4.5]decanyl)methyl)phenyl)methanesulfonamide, hydrochloride salt (0.30 g, 0.665 mmol),), 1-(3-chloropropyl)indolin-2-one (0.14 g, 0.665 mmol), sodium iodide (0.030 g, 0.2 mmol), and potassium carbonate (0.14 g, 0.998 mmol) in 2-butanone (10 mL) were heated at 78° C. for 4 hours. The reaction was diluted with 10% methanol/dichloromethane, filtered, and evaporated. The residue was purified by PTLC (5% methanol/dichloromethane) to give product as a white solid (0.095 g, 25%); HPLC rt 11.99 min; $^1$H NMR (DMSO-d$_6$); δ1.95 (d, J=14.8 hz, 2H); 2.03 (m, 2H); 2.73 (m, 2H); 2.97 (s, 3H); 3.24 (m, 2H); 3.53-3.62 (m, 4H); 3.58 (s, 2H); 3.77 (t, J=6.8 hz, 2H); 4.51 (s, 2H); 4.61 (s, 2H); 6.83 (t, J=7.6 hz, 1H); 6.91 (d, J=8.4 hz, 2H); 7.04 (t, J=7.6 hz, 1H); 7.11 (d, J=8 hz, 1H); 7.18-7.29 (m, 8H); 9.78 (s, 1H); MS for C$_{31}$H$_{35}$N$_5$O$_4$S m/z 574 (M+H)$^+$.

Example 110

Compound 216

N-(4-(4-Oxo-8-(3-(2'-oxospiro[cyclopropane-1,3'-indoline]-1'-yl)propyl)-1-phenyl-1,3,8-triazaspiro[4.5]decan-3-yl)phenyl)methanesulfonamide

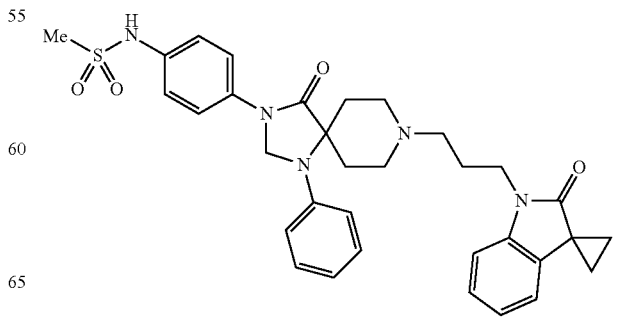

N-(4-((4-oxo-1-phenyl-1,3,8-triazaspiro[4.5]decanyl)methyl)phenyl)methanesulfonamide, hydrochloride salt (0.30 g, 0.665 mmol), 1'-(3-chloropropyl)spiro[cyclopropane-1,3'-indolin]-2'-one) (0.16 g, 0.665 mol), sodium iodide (0.030 g, 0.2 mmol), and potassium carbonate (0.14 g, 0.998 mmol) in 2-butanone (10 mL) were heated at 78° C. for 4 hours. The reaction was diluted with 10% methanol/dichloromethane, filtered, and evaporated. The residue was purified by PTLC (5% methanol/dichloromethane) to give product as a white solid (0.32 g, 80%); HPLC rt 13.43 min; $^1$H NMR (DMSO-d$_6$); δ1.54 (m, 2H); 1.63 (m, 2H); 1.95 (d, J=14.8 hz, 2H); 2.07 (m, 2H); 2.74 (m, 2H); 2.97 (s, 3H); 3.25 (m, 2H); 3.56-3.66 (m, 4H); 3.85 (t, J=6.8 hz, 2H); 4.52 (s, 2H); 4.61 (s, 2H); 6.83 (t, J=7.2 hz, 1H); 6.91 (d, J=8 hz, 2H); 7.01-7.06 (m, 2H); 7.18-7.29 (m, 8H); 9.78 (s, 1H); MS for $C_{33}H_{37}N_5O_4S$ m/z 600 (M+H)$^+$.

Example 111

Compound 217

N-(4-(8-(3-(3,3-Dimethyl-2-oxoindolin-1-yl)propyl)-4-oxo-1-phenyl-1,3,8-triazaspiro[4.5]decan-3-yl)phenyl)methanesulfonamide

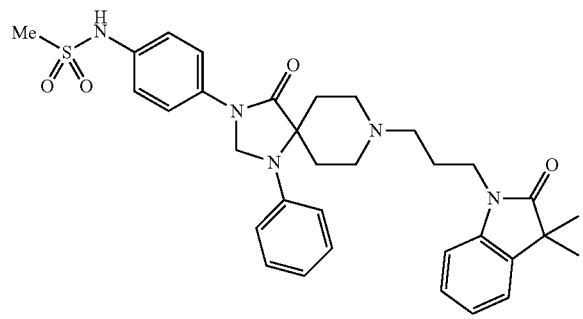 [SMILES: CC1(C)C(=O)N(CCCN2CCC3(CC2)C(=O)N(c2ccc(NS(C)(=O)=O)cc2)CN3c2ccccc2)c2ccccc21]

N-(4-((4-oxo-1-phenyl-1,3,8-triazaspiro[4.5]decanyl)methyl)phenyl)methanesulfonamide, hydrochloride salt (0.30 g, 0.665 mmol), 1-(3-chloropropyl)-3,3-dimethylindolin-2-one (0.16 g, 0.665 mmol), sodium iodide (0.030 g, 0.2 mmol), and potassium carbonate (0.14 g, 0.998 mmol) in 2-butanone (10 mL) were heated at 78° C. for 4 hours. The reaction was diluted with 10% methanol/dichloromethane, filtered, and evaporated. The residue was purified by PTLC (5% methanol/dichloromethane) to give product as a white solid (0.31 g, 78%); HPLC rt 14.12 min; $^1$H NMR (DMSO-d$_6$); δ1.27 (s, 6H), MS for $C_{33}H_{39}N_5O_4S$ m/z 602 (M+H)$^+$.

Example 112

Compound 218

2-((1-Cyclohexyl-4-oxo-8-(4-oxo-4-phenylbutyl)-1,3,8-triazaspiro[4.5]decan-3-yl)methyl)benzoic acid, hydrochloride

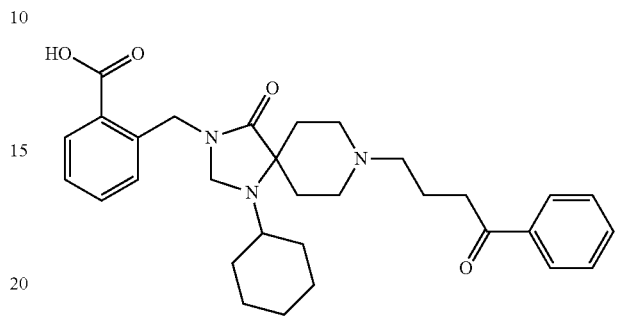

tert-Butyl 2-((1-cyclohexyl-4-oxo-8-(4-oxo-4-phenylbutyl)-1,3,8-triazaspiro[4.5]decan-3-yl)methyl)benzoate (0.22 g, 0.383 mmol) and formic acid (6 mL) were stirred at room temperature for 20 hours. The reaction was evaporated to dryness and the residue purified by PTLC (10% methanol/dichloromethane). The product was dissolved in 4M hydrochloric acid in 1,4-dioxane (5 mL) and then evaporated under vacuum. The residue was dissolved in acetonitrile (5 mL) and water (5 mL) and lyophilized to give product as a white solid (0.15 g, 70%); $^1$H NMR (DMSO-d$_6$); δ1.08 (t, J=14.4 Hz, 2H); 1.20-1.30 (m, 2H); 1.33-1.68 (m, 5H); 1.74 (d, J=12.4 Hz, 2H); 2.07 (m, 3H); 2.54 (m, 2H); 3.11-3.16 (m, 3H); 3.23 (t, J=6.8 Hz, 2H); 4.59 (s, 2H); 4.84 (s, 2H); 7.42 (m, 2H); 7.52-7.59 (m, 3H); 7.65 (m, 1H); 7.92 (d, J=7.2 Hz, 1H); 7.99 (dd, J=1.2 and 8 Hz, 2H); 11.0 (br s, 1H); 13.2 (br s, 1H); MS for $C_{31}H_{39}N_3O_4$ m/z 518 (M+H)$^+$.

Preparation of tert-Butyl 2-((1-cyclohexyl-4-oxo-8-(4-oxo-4-phenylbutyl)-1,3,8-triazaspiro[4.5]decan-3-yl)methyl)benzoate

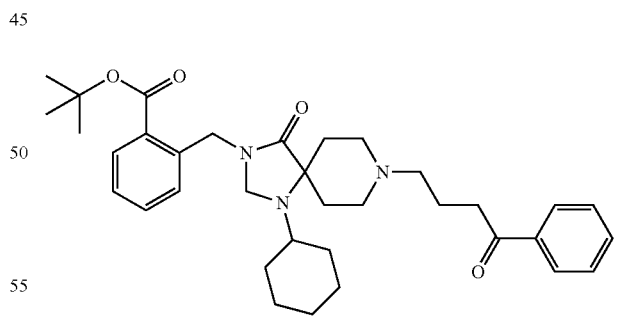

tert-Butyl 2-((1-cyclohexyl-4-oxo-1,3,8-triazaspiro[4.5]decan-3-yl)methyl)benzoate (0.30 g, 0.585 mmol), 4-iodobutyrophenone (0.17 g, 0.585 mmol), and potassium carbonate (0.12 g, 0.878 mmol) in N,N-dimethylformamide (8 mL) were stirred at 65° C. for 2 hours. The reaction was diluted with ethyl acetate, washed with water and brine, dried (MgSO$_4$), and evaporated. The residue was purified by PTLC (5% methanol/dichloromethane) to give product as an oil (0.22 g, 65%); MS for $C_{35}H_{47}N_3O_4$ m/z 574 (M+H)$^+$.

We claim:

1. A compound of formula I

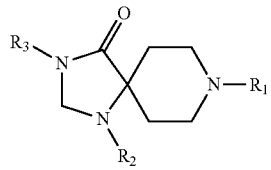

(I)

or a pharmaceutically acceptable salt thereof, or isomer thereof, wherein $R_1$ is chosen from the group consisting of (2-oxo-2,3-dihydro-1H-benzo[d]imidazol-1-yl)($C_2$-$C_4$alkyl) optionally substituted at the 3 position with cyclopropyl or at the 6 position with chlorine, (2-oxobenzo[d]oxazol-3(2H)-yl)($C_2$-$C_4$alkyl), (2-oxobenzo[d]thiazol-3(2H)-yl)($C_2$-$C_4$alkyl), (1H-benzo[d][1,2,3]triazol-1-yl)($C_2$-$C_4$alkyl), 2,3-dihydrobenzo[b][1,4]dioxine-2-($C_2$-$C_4$alkyl), 3-oxo-2H-benzo[b][1,4]oxazin-4-yl))($C_2$-$C_4$alkyl), (2-(cycloalkyl)-1H-benzo[d]imidazol-1-yl)($C_2$-$C_4$alkyl), ((3-(($C_1$-$C_6$alkyl)carbonyloxy(methyl))-2-oxo-2,3-dihydro-1H-benzo[d]imidazol-1-yl))($C_2$-$C_4$ alkyl), ((3-(methoxycarbonylethyl)-2-oxo-2,3-dihydro-1H-benzo[d]imidazol-1-yl))($C_2$-$C_4$ alkyl), ((2-(t-butoxycarbonyl)-2,3-dihydro-1H-benzo[d]imidazol-1-yl))($C_2$-$C_4$ alkyl), or 1H-indazol-3-yl($C_2$-$C_4$ alkyl), $R_2$ is phenyl optionally para-substituted with chloro, fluoro or methoxy, or $R_2$ is cycloalkyl of three to seven carbon atoms optionally substituted with one to six halogens;

$R_3$ is

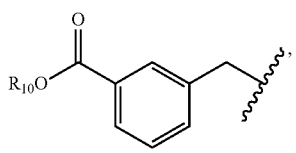

(A)

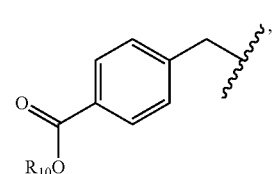

(B)

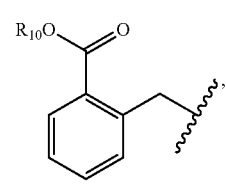

(C)

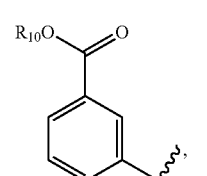

(D)

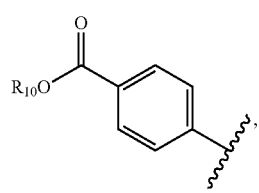

(E)

-continued

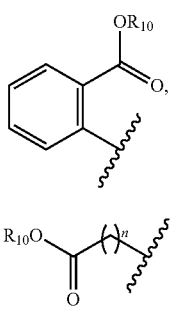  (F)

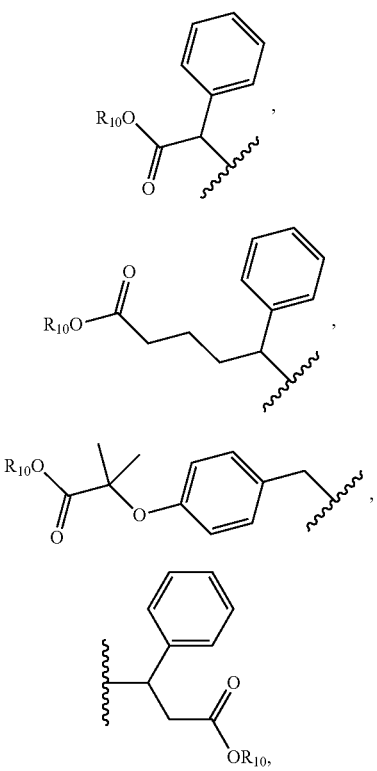

wherein n is 3-5, and $R_{10}$ is H or alkyl of one to six carbons.

2. The compound of claim 1, wherein $R_3$ is represented by formula A, C, D, or F and $R_{10}$ is H.

3. The compound of claim 2, wherein $R_3$ is represented by formula A or D.

4. The compound of claim 1, wherein $R_2$ is phenyl or cyclohexyl.

5. The compound of claim 4, wherein $R_2$ is cyclohexyl.

6. The compound of claim 4, wherein $R_2$ is phenyl.

7. The compound of claim 1, wherein $R_2$ is phenyl or cyclohexyl; and $R_3$ is represented by formula A, C, D, or F and $R_{10}$ is H.

8. The compound of claim 7, wherein $R_2$ is cyclohexyl.

9. The compound of claim 8, wherein $R_3$ is represented by formula A.

10. A compound chosen from the group consisting of

3((4-Oxo-8-(3-(2-oxo-2,3-dihydro-1H-benzo[d]imidazol-1-yl)propyl)-1-phenyl-1,3,8-triazaspiro[4.5]decan-3-yl)methyl)benzoic acid

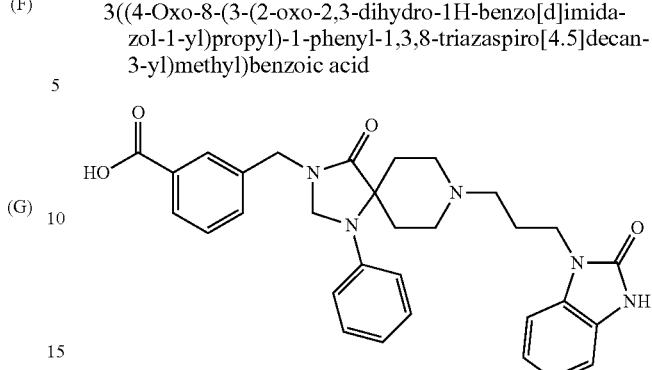

(R)-2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetic acid

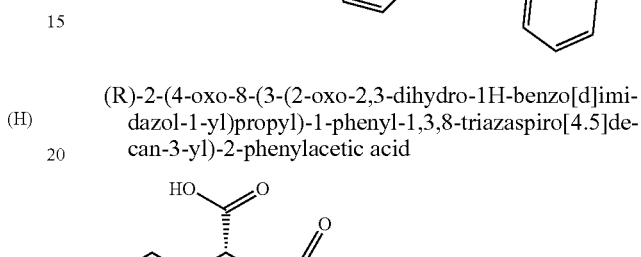

(S)-2-(4-oxo-8-(3-(2-oxo-2,3-dihydro-1H-benzo[d]imidazol-1-yl)propyl)-1-phenyl-1,3,8-triazaspiro[4.5]decan-3-yl)-2-phenylacetic acid

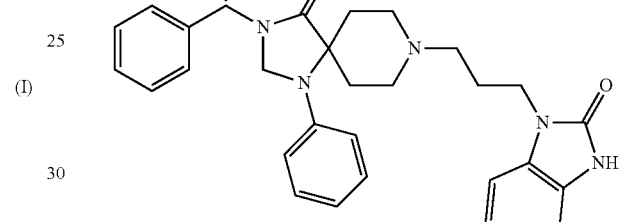

3-((1-(4-Fluorophenyl)-4-oxo-8-(3-(2-oxo-2,3-dihydro-1H-benzo[d]imidazol-1-yl)propyl)-1,3,8-triazaspiro[4.5]decan-3-yl)methyl)benzoic acid

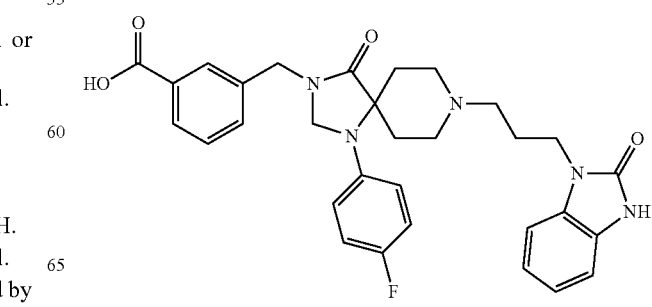

| 171 | 172 |

3-((1-cyclohexyl-4-oxo-8-(3-(2-oxo-2,3-dihydro-1H-benzo[d]imidazol-1-yl)propyl)-1,3,8-triazaspiro[4.5]decan-3-yl)methyl)benzoic acid, formate

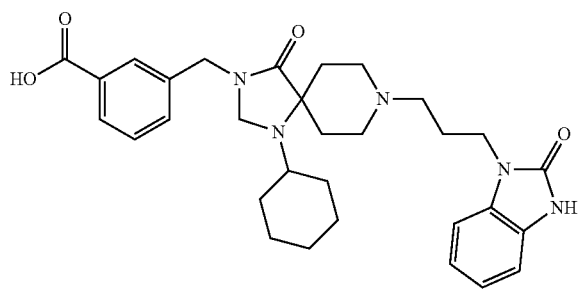 [SMILES: O=C(O)c1cccc(CN2CN(C3CCCCC3)C3(CCN(CCCn4c(=O)[nH]c5ccccc54)CC3)C2=O)c1]

3-((4-oxo-8-(3-(2-oxoindolin-1-yl)propyl)-1-phenyl-1,3,8-triazaspiro[4.5]decan-3-yl)methyl)benzoic acid, hydrochloride

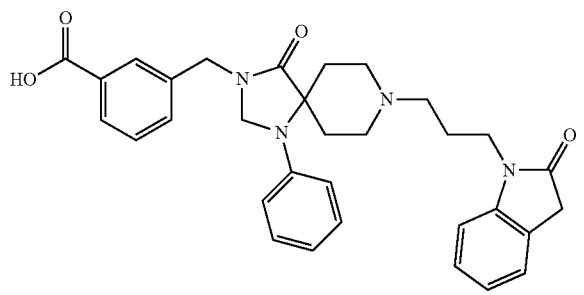

3-((4-oxo-8-(3-(2'-oxospiro[cyclopropane-1,3'-indoline]-1'-yl)propyl)-1-phenyl-1,3,8-triazaspiro[4.5]decan-3-yl)methyl)benzoic acid, hydrochloride salt

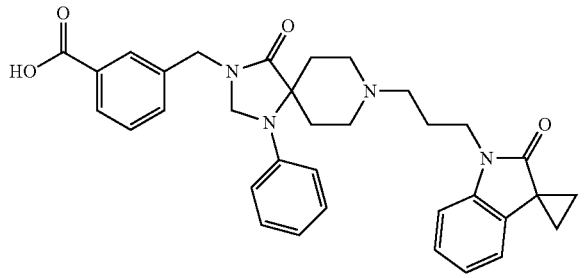 [SMILES: O=C(O)c1cccc(CN2CN(c3ccccc3)C3(CCN(CCCN4C(=O)C5(CC5)c5ccccc54)CC3)C2=O)c1]

3-((1-(4-Fluorophenyl)-4-oxo-8-(3-(2'-oxospiro[cyclopropane-1,3'-indoline]-1'-yl)propyl)-1,3,8-triazaspiro[4.5]decan-3-yl)methyl)benzoic acid

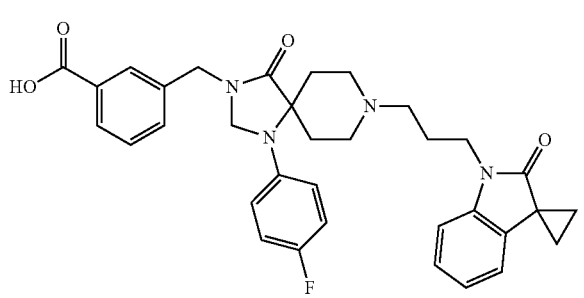 [SMILES: O=C(O)c1cccc(CN2CN(c3ccc(F)cc3)C3(CCN(CCCN4C(=O)C5(CC5)c5ccccc54)CC3)C2=O)c1]

3-((1-(4-Fluorophenyl)-4-oxo-8-(3-(2-oxoindolin-1-yl)propyl)-1,3,8-triazaspiro[4.5]decan-3-yl)methyl)benzoic acid

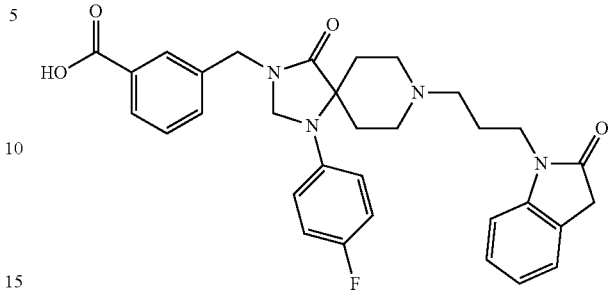

2((4-Oxo-8-(3-(2-oxoindolin-1-yl)propyl)-1-phenyl-1,3,8-triazaspiro[4.5]decan-3-yl)methyl)benzoic acid

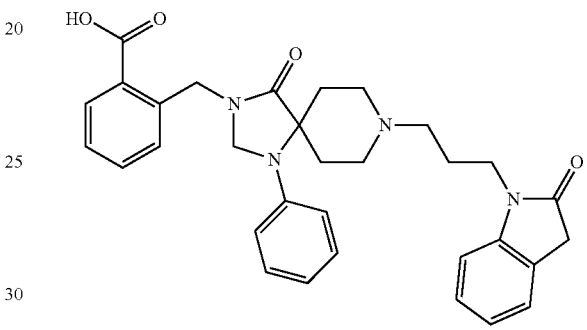

2((4-Oxo-8-(3-(2'-oxospiro[cyclopropane-1,3'-indoline]-1'-yl)propyl)-1-phenyl-1,3,8-triazaspiro[4.5]decan-3-yl)methyl)benzoic acid

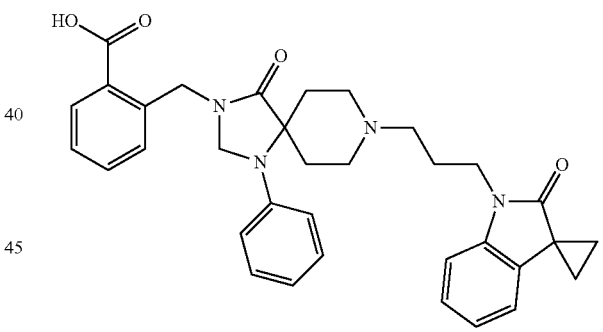

2-((1-(4-Fluorophenyl)-4-oxo-8-(3-(2-oxoindolin-1-yl)propyl)-1,3,8-triazaspiro[4.5]decan-3-yl)methyl)benzoic acid

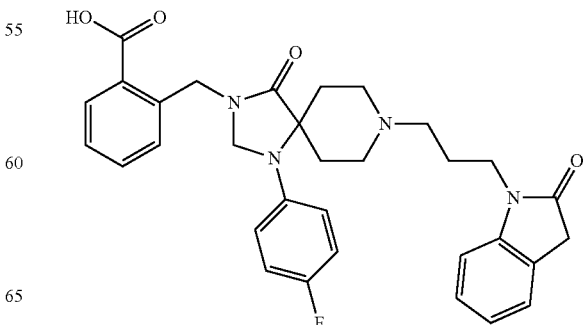

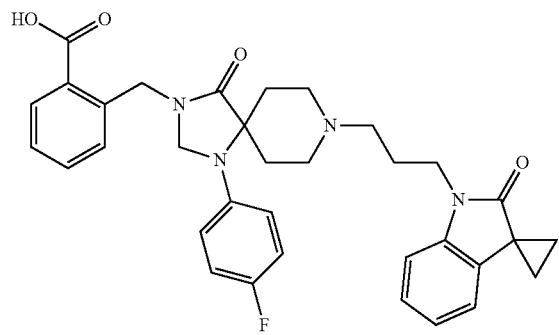 [SMILES: O=C(O)c1ccccc1CN1CN(c2ccc(F)cc2)C2(CCN(CCCN3C(=O)C4(CC4)c4ccccc43)CC2)C1=O]

2-((1-(4-Fluorophenyl)-4-oxo-8-(3-(2'-oxospiro[cyclopropane-1,3'-indoline]-1'-yl)propyl)-1,3,8-triazaspiro[4.5]decan-3-yl)methyl)benzoic acid 2-((8-(3-(3-Fluoro-3-methyl-2-oxoindolin-1-yl)propyl)-1-(4-fluorophenyl)-4-oxo-1,3,8-triazaspiro[4.5]decan-3-yl)methyl)benzoic acid

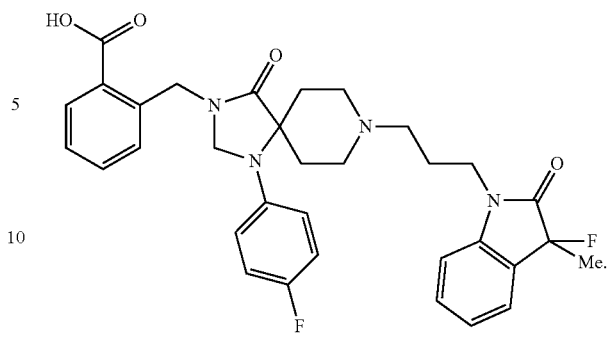

11. A composition comprising a compound of claim 1 and at least one pharmaceutically acceptable excipient.

12. The compound of claim 1, wherein the pharmaceutically acceptable salt is a maleic acid salt.

13. A composition comprising a compound of claim 10 and at least one pharmaceutically acceptable excipient.

* * * * *